(12) United States Patent
Nebuloni et al.

(10) Patent No.: US 11,839,594 B2
(45) Date of Patent: *Dec. 12, 2023

(54) EUTECTIC FORMULATIONS OF CYCLOBENZAPRINE HYDROCHLORIDE AND AMITRIPTYLINE HYDROCHLORIDE

(71) Applicant: TONIX PHARMA HOLDINGS LIMITED, Dublin (IE)

(72) Inventors: Marino Nebuloni, Rho (IT); Patrizia Colombo, Trezzano sul Naviglio (IT)

(73) Assignee: Tonix Pharma Holdings Limited, Dublin (IE)

( * ) Notice: Subject to any disclaimer, the term of this patent is extended or adjusted under 35 U.S.C. 154(b) by 121 days.

This patent is subject to a terminal disclaimer.

(21) Appl. No.: 17/082,949

(22) Filed: Oct. 28, 2020

(65) Prior Publication Data

US 2021/0038538 A1 Feb. 11, 2021

Related U.S. Application Data

(60) Division of application No. 16/140,090, filed on Sep. 24, 2018, now Pat. No. 10,864,175, which is a continuation of application No. 14/776,624, filed as application No. PCT/US2014/029872 on Mar. 14, 2014, now Pat. No. 10,117,936.

(60) Provisional application No. 61/792,757, filed on Mar. 15, 2013.

(51) Int. Cl.
| | | |
|---|---|---|
| A61K 31/135 | (2006.01) | |
| A61K 31/047 | (2006.01) | |
| A61K 31/137 | (2006.01) | |
| A61K 9/14 | (2006.01) | |
| A61K 9/16 | (2006.01) | |
| A61K 47/10 | (2017.01) | |
| A61K 47/02 | (2006.01) | |
| A61K 47/12 | (2006.01) | |
| A61K 47/26 | (2006.01) | |
| A61K 31/55 | (2006.01) | |

(52) U.S. Cl.
CPC ............ *A61K 31/135* (2013.01); *A61K 9/145* (2013.01); *A61K 9/1623* (2013.01); *A61K 9/1688* (2013.01); *A61K 9/1694* (2013.01); *A61K 31/047* (2013.01); *A61K 31/137* (2013.01); *A61K 47/02* (2013.01); *A61K 47/10* (2013.01); *A61K 47/12* (2013.01); *A61K 47/26* (2013.01); *A61K 31/55* (2013.01)

(58) Field of Classification Search
CPC .. A61K 31/135; A61K 31/137; A61K 31/047; A61K 9/145
See application file for complete search history.

(56) References Cited

U.S. PATENT DOCUMENTS

| | | |
|---|---|---|
| 4,788,063 A | 11/1988 | Fisher |
| 4,968,507 A | 11/1990 | Zentner |
| 5,073,543 A | 12/1991 | Marshall |
| 5,120,548 A | 6/1992 | McClelland |
| 5,439,686 A | 8/1995 | Desai |
| 5,498,421 A | 3/1996 | Grinstaff |
| 5,591,731 A | 1/1997 | Kennedy |
| 5,591,767 A | 1/1997 | Mohr |
| 5,639,476 A | 6/1997 | Oshlack |
| 5,674,533 A | 10/1997 | Santus |
| 5,733,566 A | 3/1998 | Lewis |
| 6,096,331 A | 8/2000 | Desai |
| 6,248,363 B1 | 6/2001 | Patel |
| 6,267,985 B1 | 7/2001 | Chen |
| 6,309,663 B1 | 10/2001 | Patel |
| 6,358,944 B1 | 3/2002 | Lederman |
| 6,383,471 B1 | 5/2002 | Chen |
| 6,395,788 B1 | 5/2002 | Iglehart |
| 6,506,405 B1 | 1/2003 | Desai |
| 6,537,579 B1 | 3/2003 | Desai |
| 6,541,523 B2 | 4/2003 | Iglehart |
| 6,649,186 B1 | 11/2003 | Robinson |
| 6,720,001 B2 | 4/2004 | Chen |
| 6,749,868 B1 | 6/2004 | Desai |
| 6,753,006 B1 | 6/2004 | Desai |
| 6,761,903 B2 | 7/2004 | Chen |
| 7,105,486 B2 | 9/2006 | Mickle |
| 7,223,735 B2 | 5/2007 | Mickle |
| 7,532,935 B2 | 5/2009 | Maschino |
| 7,655,630 B2 | 2/2010 | Mickle |
| 7,658,945 B2 | 2/2010 | Singh |
| 7,659,253 B2 | 2/2010 | Mickle |
| 7,659,254 B2 | 2/2010 | Mickle |

(Continued)

FOREIGN PATENT DOCUMENTS

| DE | 4439858 | 5/1996 |
|---|---|---|
| EP | 1842436 | 10/2007 |

(Continued)

OTHER PUBLICATIONS

Bennet et al., "An internet survey of 2,596 people with fibromyaliga," Bmc Muscluloskeletal Disorders, 8(27):2-12 (2007).
PTSD, Japanese Journal of Molecular Psychiatry, 2(3):39-45 (2002) (no translation).
Razaghi et al., "Investigation of cyclobenzaprine hydrochloride release from oral osmotic delivery systems containing a water-swellable polymer," Drug Development and Industrial Pharmacy, 28(6):631-639 (2002).
Razaghi et al., "Release of cyclobenzaprine hydrochloride from osmotically rupturable tablets," Drug Development and Industrial Pharmacy, 28(6):695-701 (2002).
Riumachi byougaku text [Rheumatology text], Japan, Shindan to Chiryo Sha, Inc., Sep. 10, 2010, pp. 410-412.

(Continued)

*Primary Examiner* — Kevin E Weddington
(74) *Attorney, Agent, or Firm* — HALEY GUILIANO LLP; James F. Haley, Jr.; Stacey W. Chung

(57) ABSTRACT

The present invention relates to pharmaceutical compositions and methods of manufacturing the same, comprising a eutectic of Cyclobenzaprine HCl and mannitol or Amitriptyline HCl and mannitol.

7 Claims, 120 Drawing Sheets

(56) References Cited

U.S. PATENT DOCUMENTS

| | | | |
|---|---|---|---|
| 7,662,787 | B2 | 2/2010 | Mickle |
| 7,662,788 | B2 | 2/2010 | Mickle |
| 7,671,030 | B2 | 3/2010 | Mickle |
| 7,671,031 | B2 | 3/2010 | Mickle |
| 7,674,774 | B2 | 3/2010 | Mickle |
| 7,678,770 | B2 | 3/2010 | Mickle |
| 7,678,771 | B2 | 3/2010 | Mickle |
| 7,682,628 | B2 | 3/2010 | Singh |
| 7,687,466 | B2 | 3/2010 | Mickle |
| 7,687,467 | B2 | 3/2010 | Mickle |
| 7,700,561 | B2 | 4/2010 | Mickle |
| 7,713,936 | B2 | 5/2010 | Mickle |
| 7,718,619 | B2 | 5/2010 | Mickle |
| 7,723,305 | B2 | 5/2010 | Mickle |
| RE41,884 | E | 10/2010 | Garavilla |
| 7,820,788 | B2 | 10/2010 | Desai |
| 7,923,536 | B2 | 4/2011 | Desai |
| 8,093,300 | B2 | 1/2012 | Lederman |
| 8,137,734 | B2 | 3/2012 | Venkatesh |
| 8,138,229 | B2 | 3/2012 | Desai |
| 8,586,103 | B2 | 11/2013 | Li |
| 9,474,728 | B2 | 10/2016 | Lederman |
| 9,636,408 | B2 | 5/2017 | Nebuloni |
| 9,918,948 | B2 | 3/2018 | Lederman |
| 10,117,936 | B2 * | 11/2018 | Nebuloni ............ A61K 9/1694 |
| 10,322,094 | B2 | 6/2019 | Nebuloni |
| 10,357,465 | B2 * | 7/2019 | Lederman ............ A61P 21/02 |
| 10,736,859 | B2 | 8/2020 | Nebuloni |
| 11,026,898 | B2 * | 6/2021 | Lederman ............ A61K 9/2018 |
| 2001/0046988 | A1 | 11/2001 | Iglehart |
| 2003/0077227 | A1 | 4/2003 | Dugger |
| 2003/0077297 | A1 | 4/2003 | Chen |
| 2005/0059656 | A1 | 3/2005 | Kristal et al. |
| 2005/0096327 | A1 | 5/2005 | Caprathe |
| 2005/0181041 | A1 | 8/2005 | Goldman |
| 2006/0073189 | A1 | 4/2006 | Pinney |
| 2007/0141144 | A1 | 6/2007 | Roberts |
| 2008/0146672 | A1 | 6/2008 | Denton |
| 2009/0054403 | A1 | 2/2009 | Woiwode |
| 2009/0098200 | A1 | 4/2009 | Krayz |
| 2009/0275541 | A1 | 11/2009 | Sullivan |
| 2010/0021507 | A1 | 1/2010 | Bunick |
| 2010/0098832 | A1 | 4/2010 | Venkatesh |
| 2010/0247586 | A1 | 9/2010 | Hugerth |
| 2010/0247649 | A1 | 9/2010 | Palaparthi |
| 2010/0266682 | A1 | 10/2010 | Davar |
| 2011/0068511 | A1 | 3/2011 | Sowden |
| 2011/0124656 | A1 | 5/2011 | Lederman |
| 2011/0319389 | A1 | 12/2011 | Lederman |
| 2012/0101154 | A1 | 4/2012 | Lederman |
| 2012/0232159 | A1 | 9/2012 | Lederman |
| 2013/0165511 | A1 | 6/2013 | Lederman |
| 2014/0171515 | A1 | 6/2014 | Lederman |
| 2014/0336264 | A1 | 11/2014 | Nebuloni |
| 2015/0065581 | A1 | 3/2015 | Lederman |
| 2016/0030576 | A1 | 2/2016 | Nebuloni |
| 2017/0239195 | A1 | 8/2017 | Nebuloni |
| 2017/0281568 | A1 | 10/2017 | Lederman |
| 2018/0344668 | A1 | 12/2018 | Nebuloni |
| 2019/0022030 | A1 | 1/2019 | Nebuloni |
| 2019/0022031 | A1 | 1/2019 | Nebuloni |
| 2019/0282517 | A1 | 9/2019 | Nebuloni |
| 2019/0358177 | A1 | 11/2019 | Lederman |

FOREIGN PATENT DOCUMENTS

| | | |
|---|---|---|
| EP | 2233134 | 9/2010 |
| FR | 2635461 | 2/1990 |
| WO | WO1999018937 | 4/1999 |
| WO | WO1999058115 | 11/1999 |
| WO | WO2001012174 | 2/2001 |
| WO | WO20010012175 | 2/2001 |
| WO | WO2001089476 | 11/2001 |
| WO | WO2004035021 | 4/2004 |
| WO | WO2004039320 | 5/2004 |
| WO | WO2005051297 | 6/2005 |
| WO | WO2007038620 | 4/2007 |
| WO | WO2009002770 | 12/2008 |
| WO | WO2009089494 | 7/2009 |
| WO | WO2011062614 | 5/2011 |
| WO | WO2012137054 | 10/2012 |
| WO | WO2013020021 | 2/2013 |
| WO | WO2013188847 | 12/2013 |
| WO | WO2014145156 | 9/2014 |
| WO | 2020039256 | 2/2020 |

OTHER PUBLICATIONS

Ullmann's Encyclopedia of Industrial Chemistry, 6th Edition, Weinheim, vol. 10, Chapter 2 (16 Pages) (2003).

Aaronson et al., "Defining and measuring fatigue," Image J. Nurs. Sch, 31:45-50 (1999).

Abd el-Fattah et al., "Enhancement of dissolution rate of hydrochlorothiazide via solid dispersion," Pharmazie., 41:790-793 (1986).

Abernethly et al., "Absolute bioavailability of imipramine: influence of food," Psychopharmacology (Berl), 83:104-106 (1984).

Amin et al., "Indion 414 as superdisinte grant in formulation of mouth dissolve tablets," Indian Journal of Pharmaceutical Sciences, 68:117-119 (2006).

Amitai et al., "Distribution of amitriptyline and nortriptyline in blood: role of alpha-1-glycoprotein," Ther. Drug Monit., 15:267-273 (1993).

Arnold et al., "Antidepressant treatment of fibromyalgia. A meta-analysis and review," Psychosomatics, 41(2): 104-113 (2000).

Bagul, "Current status of table disintegrants: a review," retrieved from [http://www.pharmainfo.net/reviews/current-status-tablet-disintegrantsa-review] (2006) 13 pages.

Balant et al., "Prodrugs for the improvement of drug absorption via different routes of administration," European Journal of Drug Metabolism and Pharmacokinetics,15(2):143-153 (1990).

Balasubramaniam et al., "Effects of superdisintegrants on dissolution of cationic drugs," Dissolution Technologies, 18-25 (2008).

Barker et al., "Identification of a single amino acid, phenylalanine 586, that is responsible for high affinity interactions of tricyclic antidepressants with the human serotonin transporter," Mol. Pharmacol., 50:957-965 (1996).

Barnes et al., "Brainstem noradrenergic system depression by cyclobenzaprine," Neuropharmacology, 19:221-224 (1980).

Bartoli et al., "An atypical case of reverse Takotsubo cardiomyopathy during general anesthesia in a 30-year-old male with post-traumatic stress disorder," J. Cardiothorac Vasc. Anesth., 25:1116-1118 (2011).

Baumann et al., "Amitriptyline pharmacokinetics and clinical response: I. Free and total plasma amitriptyline and nortriptyline," Int. Clin. Psychopharmacol., 1:89-101 (1986).

Bennett et al., "A comparision of cyclobenzaprine and placebo in the management of fibrositis: A double-blind controlled study," Arthiritis Rheum., 31:1535-1542 (1988).

Berezhkovskiy et al., "Prediction of the possibility of the second peak of drug plasma concentration time curve after iv bolus administration from the standpoint of the traditional multi-compartmental linear pharmacokinetics," J. Pharm. Sci., 97:2385-2393 (2008).

Bhatt et al., "Development and validation of amitriptyline and its metabolite in human plasma by ultra performance liquid chromatography—tandem mass spectrometry and its application to a bioequivalence study," Biomedical Chromatography, 24:1247-1254 (2010).

Bhowmik et al., "Fast dissolving tablet: an overview," Journal of Chemical and Pharmaceutical Research, 1:163-177 (2009).

Bi et al., "Mechanism of eutectic formation upon compaction and its effects on tablet properties," Thermochimica Acta, 404:213-226 (2003).

Bickel et al., "Buccal absorption and other properties of pharmacokinetic importance of imipramine and its metabolites," J. Pharm Pharmacol., 21:160-168 (1969).

Blake et al.,"The development of a clinician-administered PTSD scale," Journal of Traumatic Stress, 8:75-90 (1995).

(56) References Cited

OTHER PUBLICATIONS

Braithwaite et al., "Plasma concentration of amitriptyline and clinical response," Lancet., 17:1297-1300 (1972).
Breyer-Pfaff et al., "Comparative N-glucuronidation kinetics of ketotifen and amitriptyline by expressed human UDP-glucuronosyltransferases and liver microsomes," Drug Metab. Dispos., 28:869-872 (2000).
Brittain, "A summary of the scholarly activities associated with Center for Pharmaceutical Physics," Journal of Pharmaceutical Physics, vol. 11 (2009) 24 pages.
Brittain, "Profiles of Drug Substances, Excipients, and Related Methodology," Journal of Pharmaceutical Physics, vol. 12 (2010) 14 pages.
Cai et al., "A humanized UGT1 mouse model expressing the UGT1A1*28 allele for assessing drug clearance by UGT1A1-dependent glucuronidation," Drug Metab. Dispos., 38:879-886 (2010).
Caillé et al., "Pharmacokinetics of two lorazepam formulations, oral and sublingual, after multiple doses," Biopharmaceutics and Drug Disposition, 4(1):31-42 (1983).
Calandre et al., "Monotherapy or combination therapy for fibromyalgia treatment?," Current Rheumatology Reports, 14(6):568-575 (2012).
Campbell-Roberts et al., "Quantitative analysis of mannitol polymorphs. X-ray powder diffractometry—exploring preferred orientation effects," J. Pharm. Biomed. Anal., 28:1149-1159 (2002).
Commissiong et al., "Cyclobenzaprine: a possible mechanism of action for its muscle relaxant effect," Canadian Journal of Physiology and Pharmacology, 59(1):37-44 (1981).
Cotton et al., "Cyclobenzaprine hydrochloride," Anal Profiles Drug Subs, 17:41-72 (1988).
Davies et al., "Multiple peaking phenomena in pharmacokinetic disposition," Clinical Pharmacokinetics, 49:351-377 (2010).
Descamps et al., "Transformation of pharmaceutical compounds upon milling and comilling: The role of T(g)," J. Pharm. Sci., 96:1398-1407 (2007).
Dobrinska, "Enterohepatic circulation of drugs," J. Clin. Pharmacol., 29:577-580 (1989).
El-Banna et al., "Physicochemical study of drug binary systems. Part 3: Tolbutamide-urea and tolbutamide-mannitol systems," Pharmazie., 30:788-792 (1975).
El-Banna et al., "The application of solid dispersion technique in the preparation of therapeutic tablets. Part 1: Paracetamol, amylobarbitone, and caffeine tablets," Pharmazie, 32:511-515 (1977).
Ereshefsky et al., "Pharmacokinetic factors affecting antidepressant drug clearance and clinical effect: evaluation of doxepin and imipramine—new data and review," Clin. Chem., 34:863-880 (1988).
Experimental Report, Batch No. #CYB_GAL_001, dated Aug. 24, 2020 (13 pages).
FDA guidance for industry, bioavailability and bioequivalence studies for orally administered drug products—general considerations, US Dept. of Health and Human Services, FDA, Center for Drug Evaluation and Research (2003) 26 pages.
Fleisher, et al., "Clinical predictors of progression to Alzheimer disease in amnestic mild cognitive impairment," Neurology, 68(19):1588-1595 (2007).
Folstein et al., "Mini-mental state. A practical method for grading the cognitive state of patients for the clinician," Journal of Psychiatric Research, 12(3):189-198 (1975).
Fossaluzza et al., "Combined therapy with cyclobenzaprine and ibuprofen in primary fibromyalgia syndrome," International Journal of Pharmacology Research, 12:99-102 (1992).
Fronczek et al., "Three polymorphs (alpha, beta, and delta) of D-mannitol at 100 K," Acta Crystallographica Section C, 59:o567-o570 (2003).
Fujiwara et al., "Developmental hyperbilirubinemia and CNS toxicity in mice humanized with the UDP glucuronosyltransferase 1 (UGT1) locus," Proc. Natl. Acad. Sci., USA, 107:5024-5029 (2010).
Gai et al., "Bioavailability of a controlled-release cyclobenzaprine tablet and influence of a high fat meal on bioavailability," International Journal of Clinical Pharmacology and Therapeutics, 47(4):269-274 (2009).

Gibson, "Pharmaceutial Preformulation and Formulation", 2nd Edition, New York, 231-234 (2009) (8 pages).
Godfrey, "A guide to the understanding and use of tricyclic antidepressants in the overall management of fibromyalgia and other chronic pain syndromes," Archives of Internal Medicine, 156:1047-1052 (1996).
Green et al., "Glucuronidation of amine substrates by purified and expressed UDP-glucuronosyltransferase proteins," Drug Metab. Dispos., 26:860-867 (1998).
Greenblatt et al., "Use of Antipsychotics for the Treatment of Behavioral Symptoms of Dementia," Journal of Clinical Pharmacology, 56(9):1048-57 (2016).
Grof et al., "Preliminary comparative trial of proheptatriene and imipramine in the treatment of depressions (An intensive and controlled study)," Activitas Nervosa Superior, 7:288-289 (1965).
Guo et al., "Liquid chromatography-tandem mass spectrometry method for measurement of nicotine N-glucuronide: a marker for human UGT2B10 inhibition," J. Pharm. Biomed. Anal., 55:964-971 (2011).
Halvani et al., "The relation between shift work, sleepiness, fatigue and accidents in Iranian Industrial Mining Group workers," Industrial Health, 47(2), 134-138 (2009).
Havlikova et al., "Fatigue in Parkinson's disease is not related to excessive sleepiness or quality of sleep," Journal of the Neurological Sciences, 270(1-2), 107-113 (2008).
Hawes, "N+-glucuronidation, a common pathway in human metabolism of drugs with a tertiary amine group," Drug Metab. Dispos., 26:830-837 (1998).
Higashi et al., "Validation of the hospital anxiety and depression scale in a gastro-intestinal clinic," Japanese Journal of Gastroenterological Surgery, 93(12):884-892 (1996).
Hiller et al., "Retigabine N-glucuronidation and its potential role in enterohepatic circulation," Drug Metab. Dispos., 27:605-612 (1999).
Honda et al., "Tricyclic analogs cyclobenzaprine, amitriptyline and cyproheptadine inhibit the spinal reflex transmission through 5-HT(2) receptors," European Journal of Pharmacology, 458(1-2):91-99 (2003).
Hucker et al., "Metabolism of cyclobenzaprine in the dog," Drug Metabolism & Disposition, 6(2):184-192 (1978).
Hucker et al., Physiological disposition and metabolism of cyclobenzaprine in the rat, dog, rhesus monkey, and man Drug Metabolism & Disposition, 6:659-672 (1978).
Hucker et al., "Plasma levels and bioavailability of cyclobenzaprine in human subjects," Journal of Clinical Pharmacology, 17:719-727 (1977).
Jorgensen et al., "Pharmacokinetics of amitriptyline infused intravenously in man," European. Journal of Clinical Pharmacology, 10:337-341 (1976).
Journal of Japan Society of Pain Clinicians, 12(4):380-384 (2005).
Kaivosaari et al., "N-glucuronidation of drugs and other xenobiotics by human and animal UDP-glucuronosyltransferases," Xenobiotica., 41:652-669 (2011).
Kar, "Behavioral and psychological symptoms of dementia and their management," Indian Journal of Psychiatry, 51(Suppl 1):S77-D86 (2009).
Katz et al., "Cyclobenzaprine in the treatment of acute muscle spasm: review of a decade of clinical experience," Clinical Therapeutics, 10(2):216-228 (1988).
Kerner et al., "Obstructive Sleep Apnea is Linked to Depression and Cognitive Impairment: Evidence and Potential Mechanisms," American Journal of Geriatric Psychiatry, 24(6):496-508 (2016).
Kobayashi et al., "Cyclobenzaprine, a centrally acting muscle relaxant, acts on descending serotonergic systems," European Journal of Clinical Pharmacology, 311:29-35 (1996).
Kornhuber et al., "Identification of new functional inhibitors of acid sphingomyelinase using a structure-property-activity relation model," J. Med. Chem., 51:219-237 (2008).
Krishnan et al., "The molecular neurobiology of depression," Nature, 455:894-902 (2008).
Kubo et al., "Improvement of dissolution rate and oral bioavailability of a sparingly water-soluble drug, (+/−)-5[[2-(2-

(56) References Cited

OTHER PUBLICATIONS naphthalenylmethyl)-5-benzoxazolyl]-methyl]- 2,4-thiazolidinedione, in co-ground mixture with D-mannitol," Biol. Pharm. Bull., 20:460-463 (1997).
Lee et al., "Transinactivation of the epidermal growth factor receptor tyrosine kinase and focal adhesion kinase phosphorylation by dietary flavonoids: effect on invasive potential of human carcinoma cells," Biochem. Pharmacol., 67:2103-0114 (2004).
Link et al., "Cardiovascular regulation in mice lacking alpha2-adrenergic receptor subtypes b and c," Science, 273:803-805 (1996).
Lower et al., "Armodafinil for sarcoidosis-associated fatigue: a double-blind, placebo-controlled, crossover trial." Journal of Pain and Symptom Management, 45(2), 159-169 (2013).
Mansfield, J.C. (1991) Instruction Manual for the Cohen Mansfield Agitation Inventory.
Miles et al., "An investigation of human and rat liver microsomal mycophenolic acid glucuronidation: evidence for a principal role of UGT1A enzymes and species differences in UGT1A specificity," Drug Metab. Dispos., 33:1513-1520 (2005).
Miller et al., "Management of fibromyalgia, a distinct rheumatologic syndrome," Clinical Pharmacy, 6(10):778-786 (1987).
Moldofsky et al., "Effects of bedtime very low dose cyclobenzaprine on symptoms and sleep physiology in patients with fibromyalgia syndrome: a double-blind randomized placebo-controlled study," Journal of Rheumatology, 38(12):2653-2663 (2011).
Mullin, "Crystallization and Precipitation," Ullman's Encyclopedia of Industrial Chemistry, 6th Edition, vol. 10, London 424-428 (2009) (16 pages).
Narang et al., "Sublingual mucosa as a route for systemic drug delivery," International Journal of Pharma Sciences, 3:18-22 (2011).
Ohshima et al., "Tissue distribution and metabolism of amitriptyline after repeated administration in rats," Metabolism and Disposition, 22:21-25 (1994).
Overo et al., "Kinetics of nortriptyline in man according to a two compartment model," European Journal of Clinical Pharmacology, 8:343-347 (1975).
Pae, et al., "The relationship between fibromyalgia and major depressive disorder: a comprehensive review," Current Medical Research and Opinion, 24(8):2359-2371 (2008).
Price et al., "Single-dose pharmacokinetics of sublingual versus oral administration of micronized 17 beta-estradiol," Obstetrics and Gynecology, 89(3):340-345 (1997).
Pritchard et al., "Role of serotonin transporter polymorphisms in the behavioural and psychological symptoms in probable Alzheimer disease patients," Dementia and Geriatric Cognitive Disorders, 24(3):201-206 (2007).
Proitsi et al., "Association of serotonin and dopamine gene pathways with behavioral subphenotypes in dementia," Neurobiology of aging, 33(4):791-803 (2012).
Protocol Registration Receipt Jun. 26, 2012, "Comparative bioavailability of sublingual TNX-102, oral and intravenous cyclobenzaprine in healthy adults" 4 pages.
Razaghi et al., "Investigation of cyclobenzaprine hydrochloride release from oral osmotic delivery systems containing a water-swellable polymer," Drug Dev. Ind. Pharma., 28:631-639.
Razaghi et al., "Investigation of cyclobenzaprine hydrochloride release from oral osmotic delivery systems containing a water-swellable polymer," Drug Development and Industrial Pharmacy, 28(6):695-701 (2002).
Rizzi et al.,"Cyclic alternating pattern: a new marker of sleep alteration in patients with fibromyalgia?," Journal of Rheumatology, 31:1193-1199 (2004).
Rosa et al, "Automatic detection of cyclic alternating pattern (CAP) sequences in sleep: preliminary results," Clinical Neurophysiology, 110:585-592 (1999).
Rosa et al., "Somatic treatments for mood disorders," Neuropsychopharmacology, 37(1):102-116 (2012).
Rowe et al., "Handbook of Pharmaceutical Excipients," 6th Edition, London 424-428 (2009)(7 pages).
RX-s.net, https://web.archive.org/web/20060516153148/http:l/rx-s.net/weblog/more/cyclobenzaprine_flexerilreg/ [retrieved on Mar. 12, 2013], from 2006 (2 pages).
Santandrea et al., "A double-blind crossover study of two cyclobenzaprine regimens in primary fibromyalgia syndrome," Journal of International Medical Research, 21:74-80 (1993).
Schneider et al., "Risk of death with atypical antipsychotic drug treatment for dementia: meta-analysis of randomized placebo-controlled trial," JAMA, 294(15):1934-43 (2005).
Shen et al., "Distinguishing sleepiness and fatigue: focus on definition and measurement," Sleep Medicine Review, 10:63-76 (2006).
Sheng et al. "Efficacy of Modafinil on Fatigue and Excessive Daytime Sleepiness Associated with Neurological Disorders: A Systematic Review and Meta-Analysis," PLoS One, 8(12), e81802 (2013).
Shih et al., "Sundown Syndrome, Sleep Quality, and Walking Among Community-Dwelling People With Alzheimer Disease," Journal of the American Medical Directors Association, 18(5), 396-401 (2017).
Shukla et al., "Mouth dissolving tablets I: an overview of formulation," Technology Scientia Pharmaceutica, 76:309-326 (2009).
Siddegowda et al., "Cyclo-benzaprinium chloride," Acta Crystallographica, Sect. E Struct. Rep. Online. Jul. 1, 2011; 67(Pt 7): o1846 (Abstract only) (2 pages).
Singh et al., "Tablet disintegrants: an Overview," American Journal of Pharmtech Research (2012) (10 pages).
Stankoff et al., Modafinil for fatigue in MS: a randomized placebo-controlled double-blind study. Neurology, 64(7), 1139-1143 (2005).
Sura et al., "Dysphagia in the elderly: management and nutritional considerations," Clinical Interventions in Aging, 7:287-298 (2012).
Sutfin et al., "The analysis and disposition of imipramine and its active metabolites in man," Psychopharmacology (Berl.), 82:310-317 (1984).
Telang et al., "Crystallization of D-mannitol in binary mixtures with NaCl: phase diagram and polymorphism," Pharmaceutical Research, 20:1939-1945 (2003).
Terzano et al., "Atlas, rules, and recording techniques for the scoring of cyclic alternating pattern sleep," Sleep Medicine, 3:187-199 (2002).
Terzano et al., "Polysomnographic analysis of arousal responses in obstructive sleep apnea syndrome by means of the cyclic alternating pattern," Journal of Clinical Neurophysiology, 13:145-155 (1996).
Thomas et al., "Sleep as a window into the world of fibromyalgia syndrome," Journal of Rheumatology, 38:2499-2500 (2011).
Tieleman et al., "Poor sleep quality and fatigue but no excessive daytime sleepiness in myotonic dystrophy type 2," Journal of Neurology, Neurosurgery, and Psychiatry, 81(9), 963-967 (2010).
Till et al., "Evidence for route dependent biotransformation of cyclobenzaprine hydrochloride," Biopharmaceutics & Drug Disposition, 3:19-28 (1982).
Trzepacz et al., "Validation of the Delirium Rating Scale-revised-98: comparison with the delirium rating scale and the cognitive test for delirium," Journal of Neuropsychiatry and Clinical Neuroscience, 13(2):229-242 (2001).
Tukey et al., "Human UDP-glucuronosyltransferases: metabolism, expression, and disease," Annu. Rev. Pharmacol. Toxicol., 40:581-616 (2000).
Vaddady et al., "In vitro pharmacokinetic/pharmacodynamic models in anti-infective drug development: focus on Tb," Future Medicinal Chemistry, 2:1355-1369 (2010).
Vinar et al., "Proheptatriene in depression (extensive study)," Activitas Nervosa Superior, 7:290 (1965).
Wang et al., "Identification of human liver cytochrome P450 isoforms involved in the in vitro metabolism of cyclobenzaprine," Drug Metabolism and Disposition, 24:786-791 (1996).
Wang et al., "Prazosin for the treatment of behavioral symptoms in patients with Alzheimer disease with agitation and aggression," American Journal of Geriatric Psychiatry, 17(9):744-751 (2009).
Way et al., "Isotope dilution gas chromatographic-mass spectrometric measurement of tricyclic antidepressant drugs. Utility of the 4-carbethoxyhexafluorobutyryl derivatives of secondary amines," Journal of Analytical Toxicology, 22:374-382 (1998).

(56) References Cited

OTHER PUBLICATIONS

Weintraub et al., "Pharmacologic interventions for psychosis and agitation in neurodegenerative diseases: evidence about efficacy and safety," Psychiatric Clinicals in North America, 28(4):941-983 (2005).
Williamson et al., "Pharmacological interventions for agitation in patients with traumatic brain injury: protocol for a systematic review and meta-analysis," Systemic Review, 5(1):193 (2016).
Winchell et al., "Cyclobenzaprine pharmacokinetics, including the effects of age, gender, and hepatic insufficiency," Journal of Clinical Pharmacology, 42:61-69 (2002).
Wong et al., "Potential interference of cyclobenzaprine and norcyclobenzaprine with HPLC measurement of amitriptyline and nortriptyline: resolution by GC-MS analysis," Journal of Analytical Toxicology, 19:218-224 (1995).
Xie et al., "Sleep drives metabolite clearance from the adult brain," Science, 342(6156):373-377 (2013).
Yan et al., "Absolute bioavailability and stereoselective pharmacokinetics of doxepin," Xenobiotica., 32:615-623 (2002).
Zajc et al., "Physical properties and dissolution behaviour of nifedipine/mannitol solid dispersions prepared by hot melt method," International Journal of Pharmaceutics, 291:51-58 (2004).
Zelapar Full Prescribing Information, Cardinal Health, Inc., Valeant Pharmaceuticals North America, Jul. 2006 (2 pages).
Zhang et al., "Concepts and challenges in quantitative pharmacology and model-based drug development," AAPS J., 10:552-559 (2008).
Alamo et al., "Evaluation of a patient-centred approach in generalized musculoskeletal chronic pain/fibromyalgia patients in primary care," Patient Education and Counseling, 48(1):23-31 (2002).
Anderson et al., "Evidence-based guidelines for treating depressive disorders with antidepressants: A revision of the 2000 British Association for Psychopharmacology guidelines," Journal of Psychopharmacology, 22(4):343-396 (2008).
Anonymous, "Guideline on clinical investigation of medicinal products in the treatment of depression," European Medical Agency Science Medicines Health, (May 30, 2013) (19 pages).
Aulton, "Pharmaceutics—The Science of Dosage Form Design," Second Edition, Churchill Livingstone, De Montfort University, Leicester, UK (2007).
Baru et al., "Cyclobenzaprine drug assay and cyclobenzaprine-excipient interaction study by chromatography, thermal and spectral analysis," Journal of Pharmaceutical Chemistry & Chemical Science, 1(1):1-9 (2017).
Caley et al., "SSRI efficacy-finding the right dose," Journal of Psychiatric Practice, 8(1):33- 40 (2002).
Carette et al., "Comparison of amitriptyline, cyclobenzaprine, and placebo in the treatment of fibromyalgia. A randomized, double-blind clinical trial," Arthritis and Rheumatism, 37(1):32-40 (1994)
Elsner et al., "Newer generation fentanyl transmucosal products for breakthrough pain in opioid-tolerant cancer patients," Clinical Drug Investigation, 31(9): 605-618 (2011).
European Patent Office Apr. 1, 2022, Written Decision for European Patent Application No. 12755254.5 (33 pages).
Experimental report prepared by the inventor of the Patent, Professor Marino Nebuilni, Dec. 17, 2021 (9 pages).
Experimental Report, Nov. 10, 2021 (6 pages).
Experimental Report, Nov. 11, 2021 (7 pages).
Giron et al., "Thermal Analysis of Drugs and Drug Products", Encyclopedia of Pharmaceutical Technology, Third Edition, vol. 1, PharmaceuTech, Inc., Informa Healthcare (5 pages) (2007).
Gramaglia et al., "High speed DSC (hyper-DSC) as a tool to measure the solubility of a drug within a solid or semi-solid matrix," International Journal of Pharmaceutics, 301(1-2):1-5 (2005).
Hu Xian Feng et al., "Overview of fibromyalgia syndrome treatment," Chinese Medical Journal of Metallurgical Industry, 23(4):454-456(2006) (Machine Translation).
IUPAC Gold Book E02225: "eutectic reaction" (1 page) (2014).
Katz et al., "A study of sublingual absorption. II. Striated muscle relaxants and neurovegetative blocking agents," Journal of the American Pharmaceutical Association, 44(8):472-476 (1955).
Kim et al., "Tablet Formulation of Eutectic Mixture: Preparation of Tablet Containing Aspirin and Isopropylantipyrine," Yakhak Joeji, 29(4):193-198 (1985) (with English Translation).
Kovaleski et al., "Impurities in generic pharmaceutical development," Advanced Drug Delivery Reviews, 59(1):56-63 (2007).
Li Xinzhong et al., Handbook of Practical Drug for Residents, the 1st edition, (2009) (Machine Translation).
Lok et al., "The Performance of the Hospital Anxiety and Depression Scale for Screening of Depressive and Anxiety Disorders in Patients with Rheumatoid Arthritis (RA)," Arthritis and Rheumatology, 62(10S):Abstract 1777 (2010) (2 pages).
*Merck & Co., Inc.* v. *Danbury Pharmacal, Inc.*, Civil Action No. 86-588 MMS, U.S. District Court of Delaware, Opinion (Aug. 31, 1988) (32 pages).
Product monograph for Elavil® Amitriptyline Hydrochloride Tablets USP (Jul. 23, 2010) (17 pages).
Second Declaration of Dr. Gregory M. Sullivan, M.D. (Dec. 21, 2021) (3 pages).
Shen et al, "The Advance on Studies of Fibromyalgia syndrome," Chinese Journal of Clinical Neurosciences, 20(3):329-334 (2012).
Taniguchi et al., "Microenvironmental pH-modification to improve dissolution behavior and oral absorption for drugs with pH-dependent solubility," Expert Opinion on Drug Delivery, 11(4):505-516 (2014).
Weiner, "What Are Excipients?," Excipient Toxicity and Safety, Marcel Decker, Inc. (2 pages) (2000).
U.S. Appl. No. 17/121,547, filed Dec. 14, 2020, Pending.
Li Jianhong, "New Drug Handbook," Jiangxi Science and Technology Press, 2nd Edition, pp. 81-82 (2005) (3 pages) (English Translation).
U.S. Appl. No. 13/918,692, filed Jun. 14, 2013, Pending.
U.S. Appl. No. 12/948,828, filed Nov. 18, 2010, Issued, U.S. Pat. No. 9,918,948.
U.S. Appl. No. 15/915,688, filed Mar. 8, 2018, Abandoned.
U.S. Appl. No. 17/951,723, filed Sep. 23, 2022, Pending.
U.S. Appl. No. 13/157,270, filed Jun. 9, 2011, Abandoned.
U.S. Appl. No. 14/477,981, filed Sep. 5, 2014, Issued, U.S. Pat. No. 9,474,728.
U.S. Appl. No. 15/266,035, filed Sep. 15, 2016, Abandoned.
U.S. Appl. No. 16/537,170, filed Aug. 9, 2019, Issued, U.S. Pat. No. 10,722,478.
U.S. Appl. No. 16/903,965, filed Jun. 17, 2020, Pending.
U.S. Appl. No. 13/412,571, filed Mar. 5, 2012, Pending.
U.S. Appl. No. 14/214,433, filed Mar. 14, 2014, Issued, U.S. Pat. No. 9,636,408.
U.S. Appl. No. 15/459,093, filed Mar. 15, 2017, Issued, U.S. Pat. No. 9,956,188.
U.S. Appl. No. 15/941,484, filed Mar. 30, 2018, Issued, U.S. Pat. No. 10,322,094.
U.S. Appl. No. 16/429,852, filed Jun. 3, 2019, Issued, U.S. Pat. No. 10,736,859.
U.S. Appl. No. 14/776,624, filed Sep. 14, 2015, Issued, U.S. Pat. No. 10,117,936.
U.S. Appl. No. 15/511,287, filed Mar. 15, 2017, Issued, U.S. Pat. No. 10,357,465.
U.S. Appl. No. 16/140,090, filed Sep. 24, 2018, Issued, U.S. Pat. No. 10,864,175.
U.S. Appl. No. 16/140,105, filed Sep. 24, 2018, Issued, U.S. Pat. No. 10,864,176.
U.S. Appl. No. 16/518,338, filed Jul. 22, 2019, Pending.
U.S. Appl. No. 17/121,547, filed Dec. 14, 2020, Allowed.
U.S. Appl. No. 16/215,952, filed Dec. 11, 2018, Pending.
U.S. Appl. No. 17/269,106, filed Feb. 17, 2021, Pending.
U.S. Appl. No. 17/226,058, filed Apr. 8, 2021, Pending.
U.S. Appl. No. 18/265,525, filed Jun. 6, 2023, Pending.
Anonymous, "History of Changes for Study: NCT04172831; A Study to Evaluate the Efficacy and Safety of TNX-102 SL in Patients With Fibromyalgia (RELIEF)", ClinicalTrails.gov (2020) (10 pages).

(56) References Cited

OTHER PUBLICATIONS

Celik et al., "Efficacy of Paroxetine and Amitriptyline in Post-traumatic Stress Disorder: An Open-label Comparative Study," Bulletin of Clinical :sychopharmacology, 21(3):179-185 (2011).

Sullivan et al., "Abstract No. 0477: TNX-102 SL (Sublingual Cyclobenzaprine) for the Treatment of Fibromyalgia in the RELIEF Study: Positive Results of a Phase 3 Randomized, Double-Blind, Placebo-Controlled Multicenter Efficacy and Safety Trial," Arthritis and Rheumatology, 73(9) (2021) (3 pages).

Sullivan et al., "Abstract No. 0827: A phase 3 randomized, double-blind, placebo-controlled trial of bedtime sublingual cyclobenzaprine (TNX-102 SL) for the treatment of fibromyalgia (FM): Evidence for a broad spectrum of activity on the fm syndrome", Arthritis and Rheumatology, 2019 ACR/ARP Annual Meeting, 71(10) (2019) (1 page).

\* cited by examiner

Peak Search

Sample: Cyclobenzaprine HCl  File: Cyclobenzaprine  HDate: January-24-13 13:02:20  Operator: Redox
Comment: FT 0.02 deg-1.0 s  Memo: Cyclobenzaprine HCl micro
Method: 2nd differential  Typical width: 0.100 deg.  Min. height: 100.00 cps

| Peak no. | 2theta | Flex Width | d-value | Intensity | I/Io | Peak no. | 2theta | Flex Width | d-value | Intensity | I/Io |
|---|---|---|---|---|---|---|---|---|---|---|---|
| 1 | 5.440 | 0.141 | 16.2319 | 331 | 10 | 31 | 25.640 | 0.141 | 3.4715 | 977 | 28 |
| 2 | 7.720 | 0.141 | 11.4423 | 318 | 10 | 32 | 26.380 | 0.235 | 3.3783 | 1411 | 41 |
| 3 | 8.820 | 0.141 | 10.0176 | 363 | 11 | 33 | 26.820 | 0.165 | 3.3214 | 433 | 13 |
| 4 | 10.400 | 0.165 | 8.4990 | 613 | 18 | 34 | 27.700 | 0.165 | 3.2178 | 1850 | 53 |
| 5 | 12.200 | 0.165 | 7.2134 | 617 | 18 | 35 | 27.960 | 0.141 | 3.1885 | 1106 | 32 |
| 6 | 12.980 | 0.141 | 6.8148 | 2196 | 63 | 36 | 28.400 | 0.141 | 3.1401 | 500 | 15 |
| 7 | 13.300 | 0.165 | 6.6519 | 262 | 8 | 37 | 29.540 | 0.212 | 3.0214 | 243 | 8 |
| 8 | 13.920 | 0.165 | 6.3567 | 332 | 10 | 38 | 30.600 | 0.118 | 2.9191 | 451 | 13 |
| 9 | 15.140 | 0.141 | 5.8471 | 1306 | 38 | 39 | 30.780 | 0.165 | 2.9025 | 615 | 18 |
| 10 | 15.480 | 0.165 | 5.7194 | 898 | 26 | 40 | 31.140 | 0.165 | 2.8697 | 518 | 16 |
| 11 | 16.120 | 0.118 | 5.4938 | 460 | 14 | 41 | 32.640 | 0.188 | 2.7412 | 458 | 14 |
| 12 | 16.500 | 0.165 | 5.3681 | 3015 | 90 | 42 | 34.220 | 0.259 | 2.6182 | 493 | 14 |
| 13 | 17.400 | 0.165 | 5.0924 | 3523 | 100 | 43 | 34.660 | 0.188 | 2.5859 | 263 | 8 |
| 14 | 17.920 | 0.141 | 4.9458 | 2138 | 61 | 44 | 35.080 | 0.259 | 2.5539 | 291 | 9 |
| 15 | 18.780 | 0.165 | 4.7262 | 1128 | 33 | 45 | 37.680 | 0.188 | 2.3853 | 278 | 8 |
| 16 | 19.020 | 0.118 | 4.6622 | 237 | 7 | 46 | 38.220 | 0.259 | 2.3528 | 390 | 12 |
| 17 | 19.560 | 0.188 | 4.5347 | 758 | 22 | 47 | 38.720 | 0.259 | 2.3236 | 325 | 10 |
| 18 | 19.380 | 0.165 | 4.4668 | 729 | 21 | 48 | 39.790 | 0.165 | 2.2641 | 282 | 9 |
| 19 | 19.500 | 0.188 | 4.3667 | 1063 | 31 | 49 | 42.730 | 0.212 | 2.1120 | 267 | 8 |
| 20 | 20.320 | 0.165 | 4.3121 | 691 | 20 | 50 | 44.160 | 0.188 | 2.0492 | 281 | 8 |
| 21 | 20.580 | 0.188 | 4.2149 | 2070 | 59 | 51 | 44.860 | 0.118 | 2.0171 | 265 | 8 |
| 22 | 21.660 | 0.188 | 4.0958 | 1530 | 44 | 52 | 48.540 | 0.165 | 1.8740 | 230 | 7 |
| 23 | 21.880 | 0.165 | 4.0225 | 1414 | 41 | | | | | | |
| 24 | 22.080 | 0.165 | 3.9853 | 1139 | 33 | | | | | | |
| 25 | 22.400 | 0.212 | 3.9438 | 735 | 21 | | | | | | |
| 26 | 22.700 | 0.165 | 3.8340 | 1242 | 36 | | | | | | |
| 27 | 23.190 | 0.141 | 3.7985 | 2304 | 66 | | | | | | |
| 28 | 23.400 | 0.165 | 3.7479 | 1516 | 44 | | | | | | |
| 29 | 23.720 | 0.165 | 3.6391 | 358 | 11 | | | | | | |
| 30 | 24.440 | 0.188 | 3.5985 | 800 | 23 | | | | | | |

February-06-2013  12:25:17  Page 2

FIG. 68

Peak Search

Sample : Mannitol  
Comment : FT 0.02 deg 1.0 s  
Method : 2nd differential  
File : Mannitolo.raw  
Memo : Mannitolo  
Typical width : 0.100 deg.  
Date : January-24-13 12:00:25  
Min. height : 300.00 cps  
Operator : Redox

| Peak no. | 2theta | Flex Width | d-value | Intensity | I/Io | Peak no. | 2theta | Flex Width | d-value | Intensity | I/Io |
|---|---|---|---|---|---|---|---|---|---|---|---|
| 1 | 9.260 | ***** | 9.5425 | 322 | 5 | 31 | 34.880 | ***** | 2.5701 | 415 | 7 |
| 2 | 10.340 | 0.165 | 8.5481 | 54 | 0 | 32 | 35.420 | 0.212 | 2.5322 | 635 | 10 |
| 3 | 10.800 | ***** | 8.1850 | 282 | 4 | 33 | 35.960 | 0.329 | 2.4954 | 1541 | 24 |
| 4 | 11.340 | ***** | 7.7965 | 256 | 4 | 34 | 36.500 | 0.329 | 2.4597 | 700 | 11 |
| 5 | 13.540 | 0.165 | 6.5342 | 1169 | 18 | 35 | 38.620 | 0.259 | 2.3294 | 1157 | 18 |
| 6 | 14.500 | 0.165 | 6.1037 | 2439 | 37 | 36 | 39.400 | 0.212 | 2.2817 | 599 | 9 |
| 7 | 16.680 | 0.165 | 5.3106 | 1812 | 28 | 37 | 40.680 | ***** | 2.2161 | 435 | 7 |
| 8 | 17.160 | 0.165 | 5.1631 | 3268 | 49 | 38 | 41.700 | 0.165 | 2.1642 | 476 | 8 |
| 9 | 18.640 | 0.188 | 4.7563 | 6688 | 100 | 39 | 43.320 | 0.188 | 2.0869 | 557 | 9 |
| 10 | 19.720 | 0.188 | 4.4982 | 2186 | 33 | 40 | 43.840 | ***** | 2.0634 | 1437 | 22 |
| 11 | 20.300 | 0.188 | 4.3710 | 4237 | 64 | 41 | 45.460 | 0.212 | 1.9935 | 458 | 7 |
| 12 | 21.020 | 0.188 | 4.2229 | 4246 | 64 | 42 | 47.100 | 0.259 | 1.9279 | 560 | 9 |
| 13 | 21.580 | 0.188 | 4.1145 | 1551 | 24 | | | | | | |
| 14 | 23.280 | 0.188 | 3.8178 | 4700 | 71 | | | | | | |
| 15 | 24.620 | 0.165 | 3.6129 | 870 | 14 | | | | | | |
| 16 | 25.020 | 0.188 | 3.5561 | 1183 | 18 | | | | | | |
| 17 | 25.820 | 0.306 | 3.4477 | 856 | 13 | | | | | | |
| 18 | 26.480 | 0.165 | 3.3632 | 536 | 9 | | | | | | |
| 19 | 26.880 | 0.188 | 3.3141 | 1024 | 16 | | | | | | |
| 20 | 27.400 | 0.235 | 3.2524 | 657 | 10 | | | | | | |
| 21 | 28.020 | 0.188 | 3.1818 | 1976 | 30 | | | | | | |
| 22 | 29.380 | 0.188 | 3.0375 | 1669 | 25 | | | | | | |
| 23 | 30.400 | ***** | 2.9379 | 389 | 6 | | | | | | |
| 24 | 31.200 | 0.188 | 2.8590 | 611 | 10 | | | | | | |
| 25 | 31.620 | 0.212 | 2.8273 | 542 | 9 | | | | | | |
| 26 | 32.580 | 0.188 | 2.7461 | 595 | 9 | | | | | | |
| 27 | 33.040 | 0.188 | 2.7089 | 1075 | 17 | | | | | | |
| 28 | 33.480 | 0.188 | 2.6743 | 1100 | 17 | | | | | | |
| 29 | 33.820 | 0.212 | 2.6482 | 1467 | 22 | | | | | | |
| 30 | 34.200 | 0.188 | 2.6196 | 1231 | 19 | | | | | | |

February-06-2013 12:24:19 Page 2

EUTECTIC FORMULATIONS OF CYCLOBENZAPRINE HYDROCHLORIDE AND AMITRIPTYLINE HYDROCHLORIDE

RELATED APPLICATION

This application is a division of U.S. patent application Ser. No. 16/140,090, filed Sep. 24, 2018 (pending), which is a continuation of U.S. patent application Ser. No. 14/776,624, filed Sep. 14, 2015, now U.S. Pat. No. 10,117,936, which is a national stage application under 35 U.S.C. § 371 of International Application PCT/US2014/029872, filed on Mar. 14, 2014, which claims priority and benefit from U.S. Provisional Patent Application 61/792,757, filed Mar. 15, 2013 (expired), the contents and disclosures of which are incorporated by reference in their entireties.

BACKGROUND OF THE INVENTION

Cyclobenzaprine, or 3-(5H-dibenzo[a,d]cyclohepten-5-ylidene)-N,N-dimethyl-1-propanamine, was first approved by the U.S. Food and Drug Administration in 1977 for the treatment of acute muscle spasms of local origin. (Katz, W., et al., Clinical Therapeutics 10:216-228 (1988)). Amitriptyline, or 3-(10,11-dihydro-5H-dibenzo [a,d] cycloheptene-5-ylidene)-N,N-dimethyl-1-propanamine, was first approved by the U.S. Food and Drug Administration for the treatment of depression.

Subsequent studies have shown cyclobenzaprine to also be effective in the treatment of fibromyalgia syndrome, post-traumatic stress disorder (PTSD), traumatic brain injury (TBI), generalized anxiety disorder and depression. Furthermore, the utility of cyclobenzaprine as an agent for improving the quality of sleep, as a sleep deepener, or for treating sleep disturbances has been investigated. However, while FDA-approved therapeutics address pain and mood, there are currently no FDA-approved treatments that address the disturbed sleep and fatigue associated with fibromyalgia syndrome. Treatment with cyclobenzaprine may be particularly useful in treating sleep disturbances caused by, exacerbated by, or associated with fibromyalgia syndrome, prolonged fatigue, chronic fatigue, chronic fatigue syndrome, a sleep disorder, a psychogenic pain disorder, chronic pain syndrome (type II), the administration of a drug, autoimmune disease, stress or anxiety, or for treating an illness caused by or exacerbated by sleep disturbances, and symptoms of such illness. See, for example, U.S. Pat. Nos. 6,395,788 and 6,358,944, incorporated herein by reference.

Cyclobenzaprine HCl or Amitriptyline HCl Active Pharmaceutical Ingredients (or APIs) are stable in pill, tablet or capsule formulations for oral administration when combined with certain excipients. However, Cyclobenzaprine HCl or Amitriptyline HCl have slow absorption when ingested by mouth (per oral, or po). To speed absorption, tablets containing Cyclobenzaprine HCl or Amitriptyline HCl have been formulated in various sublingual (SL) preparations. However, both sublingual and oral formulations can have issues with the stability of the APIs and the physical compositions themselves, especially when a basifying agent (a chemical compound that increases the pH of solutions after dissolution of Cyclobenzaprine HCl or Amitriptyline HCl) is present. Therefore, a method or composition that increases stability of Cyclobenzaprine HCl or Amitriptyline HCl (with or without the presence of a basifying agent) in a formulation would be useful.

SUMMARY OF THE INVENTION

Some embodiments of the invention are:
1. A pharmaceutical composition comprising a eutectic of mannitol and Cyclobenzaprine HCl.
2. The pharmaceutical composition of embodiment 1, comprising 60%-90% Cyclobenzaprine HCl and 40%-10% mannitol by weight.
3. The pharmaceutical composition of embodiment 2, comprising amounts of Cyclobenzaprine HCl and mannitol selected from: 60%±2% Cyclobenzaprine HCl and 40%±2% mannitol, 65%±2% Cyclobenzaprine HCl and 35%±2% mannitol, 70%±2% Cyclobenzaprine HCl and 30%±2% mannitol, 75%±2% Cyclobenzaprine HCl and 25%±2% mannitol, 80%±2% Cyclobenzaprine HCl and 20%±2% mannitol, 85%±2% Cyclobenzaprine HCl and 15%±2% mannitol, and 90%±2% Cyclobenzaprine HCl and 10%±2% mannitol by weight.
4. The pharmaceutical composition of embodiment 3, comprising 75%±2% Cyclobenzaprine HCl and 25%±2% mannitol by weight.
5. The pharmaceutical composition of any one of embodiments 1-4, wherein the Cyclobenzaprine HCl:mannitol molar ratio is 1.76±0.1.
6. The pharmaceutical composition of any one of embodiments 1-5, wherein the Cyclobenzaprine HCl is micronized Cyclobenzaprine HCl.
7. The pharmaceutical composition of any one of embodiments 1-6, further comprising a basifying agent.
8. The pharmaceutical composition of embodiment 7, wherein the basifying agent is $K_2HPO_4$.
9. The pharmaceutical composition of embodiment 7, wherein the basifying agent is $Na_2HPO_4$.
10. The pharmaceutical composition of embodiment 7, wherein the basifying agent is trisodium citrate, anhydrous.
11. A method of manufacturing a eutectic composition of any one of embodiments 1-10, comprising mixing Cyclobenzaprine HCl and mannitol or milling Cyclobenzaprine HCl and mannitol.
12. The method of embodiment 11, comprising milling Cyclobenzaprine HCl and mannitol.
13. The method of embodiment 12, wherein, the Cyclobenzaprine HCl and mannitol are milled in a high shear granulator.
14. The method of embodiment 11, comprising mixing Cyclobenzaprine HCl and mannitol.
15. The method of embodiment 14, wherein the Cyclobenzaprine HCl and mannitol are mixed via compression.
16. The method of embodiment 15, wherein the Cyclobenzaprine HCl and mannitol are compressed via roller compaction.
17. A method of manufacturing a eutectic composition of any one of embodiments 1-10, comprising spray drying Cyclobenzaprine HCl and mannitol.
18. The method of any one of embodiments 11-17, wherein the Cyclobenzaprine HCl is micronized Cyclobenzaprine HCl.
19. The method of any one of embodiments 11-18, wherein the pharmaceutical composition comprises a basifying agent.
20. The method of embodiment 19, wherein the basifying agent is $K_2HPO_4$.
21. The method of embodiment 19, wherein the basifying agent is $Na_2HPO_4$.
22. The method of embodiment 19, wherein the basifying agent is trisodium citrate, anhydrous.

23. A pharmaceutical composition comprising a eutectic of mannitol and Amitriptyline HCl.
24. The pharmaceutical composition of embodiment 23, wherein the eutectic mixture melts at 133±3° C.
25. The pharmaceutical composition of embodiment 23, comprising 60%-90% Amitriptyline HCl and 40%-10% mannitol by weight.
26. The pharmaceutical composition of embodiment 25, comprising amounts of Amitriptyline HCl and mannitol selected from: 40%±2% Amitriptyline HCl and 60%±2% mannitol, 45%±2% Amitriptyline HCl and 55%±2% mannitol, 50%±2% Amitriptyline HCl and 50%±2% mannitol, 55%±2% Amitriptyline HCl and 45%±2% mannitol, 60%±2% Amitriptyline HCl and 40%±2% mannitol, 65%±2% Amitriptyline HCl and 35%±2% mannitol, 70%±2% Amitriptyline HCl and 30%±2% mannitol, 75%±2% Amitriptyline HCl and 25%±2% mannitol, 80%±2% Amitriptyline HCl and 20%±2% mannitol, 85%±2% Amitriptyline HCl and 15%±2% mannitol, and 90%±2% Amitriptyline HCl and 10%±2% mannitol by weight.
27. The pharmaceutical composition of embodiment 26, comprising 75%±2% Amitriptyline HCl and 25%±2% mannitol by weight.
28. The pharmaceutical composition of embodiment 26, comprising 50%±2% Amitriptyline HCl and 50%±2% mannitol by weight.
29. The pharmaceutical composition of any one of embodiments 23-28, wherein the Amitriptyline HCl is micronized Amitriptyline HCl.
30. The pharmaceutical composition of any one of embodiments 23-29, further comprising a basifying agent.
31. The pharmaceutical composition of embodiment 30, wherein the basifying agent is $K_2HPO_4$.
32. The pharmaceutical composition of embodiment 30, wherein the basifying agent is $Na_2HPO_4$.
33. The pharmaceutical composition of embodiment 30, wherein the basifying agent is trisodium citrate, anhydrous.
34. The pharmaceutical composition of any one of embodiments 1-10 and 23-33, wherein the mannitol is β mannitol.
35. The pharmaceutical composition of embodiment 34, wherein the composition comprises Cyclobenzaprine HCl and the eutectic melts at 143.6±3° C.
36. The pharmaceutical composition of any one of embodiments 1-10 and 23-33, wherein the mannitol is δ mannitol.
37. The pharmaceutical composition of embodiment 36, wherein the composition comprises Cyclobenzaprine HCl and the eutectic melts at 134° C.±3° C.
38. A method of manufacturing a eutectic composition of any one of embodiments 23-35, comprising mixing Amitriptyline HCl and mannitol or milling Amitriptyline HCl and mannitol.
39. The method of embodiment 38, comprising milling Amitriptyline HCl and mannito 1.
40. The method of embodiment 39, wherein, the Amitriptyline HCl and mannitol are milled in a high shear granulator.
41. The method of embodiment 38, comprising mixing Amitriptyline HCl and mannitol.
42. The method of embodiment 41, wherein the Amitriptyline HCl and mannitol are mixed via compression.
43. The method of embodiment 42, wherein the Amitriptyline HCl and mannitol are compressed via roller compaction.
44. A method of manufacturing a eutectic composition of any one of embodiments 23-34 and 36, comprising spray drying Amitriptyline HCl and mannitol.
45. The method of any one of embodiments 38-44, wherein the Amitriptyline HCl is micronized Amitriptyline HCl.
46. The method of any one of embodiments 38-45, wherein the pharmaceutical composition comprises a basifying agent.
47. The method of embodiment 46, wherein the basifying agent is $K_2HPO_4$.
48. The method of embodiment 46, wherein the basifying agent is $Na_2HPO_4$.
49. The method of embodiment 46, wherein the basifying agent is trisodium citrate, anhydrous.
50. The method of any one of embodiments 11-22 and 38-49, wherein the eutectic composition comprises 13 mannitol.
51. The method of embodiment 50, wherein the composition comprises Cyclobenzaprine HCl and the eutectic melts at 143.6±3° C.
52. The method of any one of embodiments 11-22 and 38-49, wherein the eutectic composition comprises δ mannitol.
53. The method of embodiment 52, wherein the composition comprises Cyclobenzaprine HCl and the eutectic melts at 134° C.±3° C.

BRIEF DESCRIPTION OF THE DRAWINGS

FIG. 68: XRPD peaks of Cyclobenzaprine HCl (table).

FIG. 70: XRPD peaks of Mannitol, beta form (table).

DETAILED DESCRIPTION OF THE INVENTION

Figure 1:
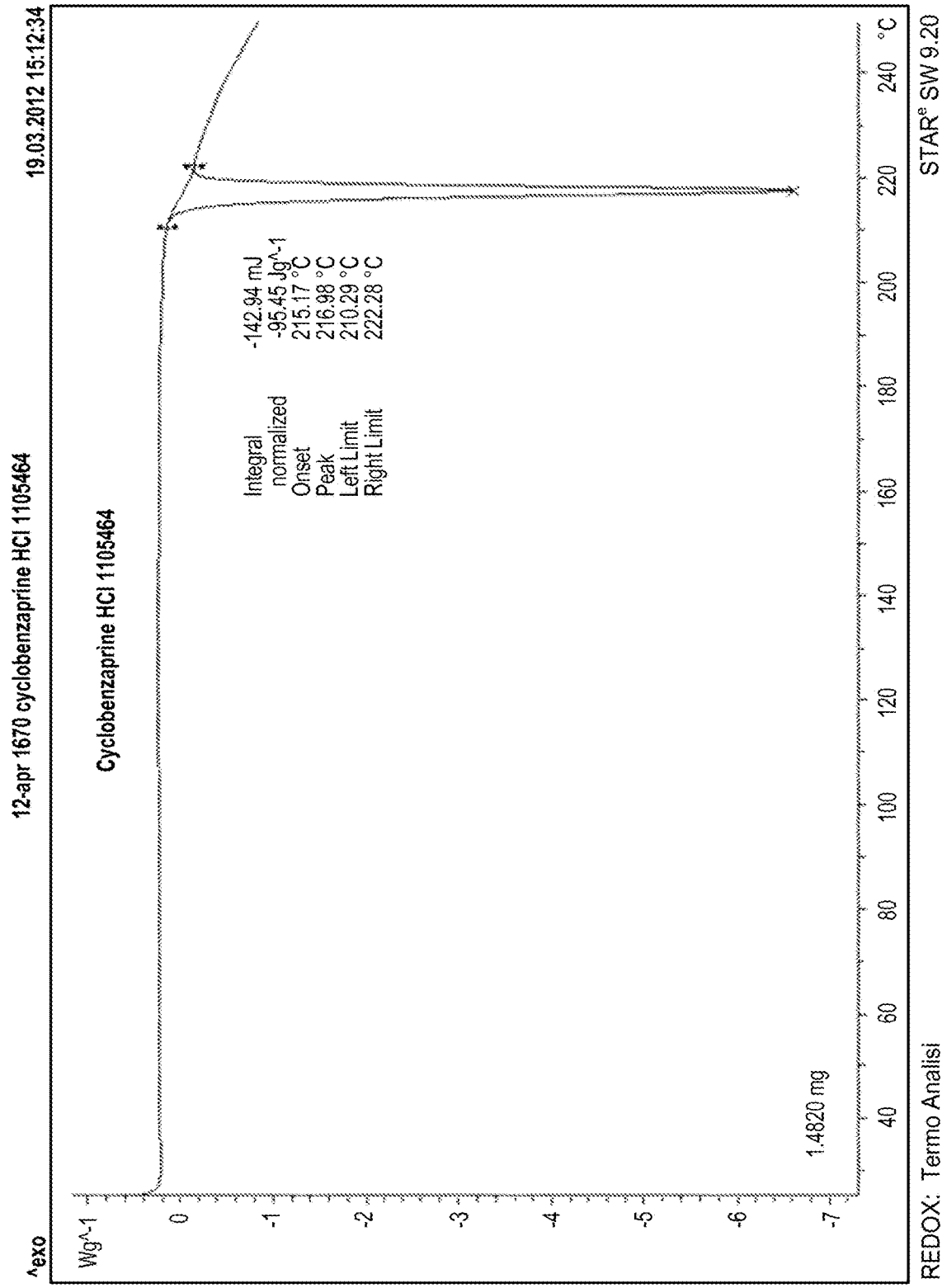
FIG. 1: DSC heating curve of Cyclobenzaprine HCl.

Unless otherwise defined herein, scientific and technical terms used in this application shall have the meanings that are commonly understood by those of ordinary skill in the art. Generally, nomenclature used in connection with, and techniques of, pharmacology, cell and tissue culture, molecular biology, cell and cancer biology, neurobiology, neurochemistry, virology, immunology, microbiology, genetics and protein and nucleic acid chemistry, described herein, are those well known and commonly used in the art.

The methods and techniques of the present invention are generally performed, unless otherwise indicated, according to conventional methods well known in the art and as described in various general and more specific references that are cited and discussed throughout this specification.

Chemistry terms used herein are used according to conventional usage in the art, as exemplified by "The McGraw-Hill Dictionary of Chemical Terms", Parker S., Ed., McGraw-Hill, San Francisco, CA. (1985).

All of the above, and any other publications, patents and published patent applications referred to in this application are specifically incorporated by reference herein. In case of conflict, the present specification, including its specific definitions, will control.

Throughout this specification, the word "comprise" or variations such as "comprises" or "comprising" will be understood to imply the inclusion of a stated integer (or components) or group of integers (or components), but not the exclusion of any other integer (or components) or group of integers (or components).

The singular forms "a," "an," and "the" include the plurals unless the context clearly dictates otherwise.

The term "including" is used to mean "including but not limited to." "Including" and "including but not limited to" are used interchangeably.

A "patient", "subject", or "individual" are used interchangeably and refer to either a human or a non-human animal. These terms include mammals, such as humans, primates, livestock animals (including bovines, porcines, etc.), companion animals (e.g., canines, felines, etc.) and rodents (e.g., mice and rats).

"Treating" a condition or patient refers to taking steps to obtain beneficial or desired results, including clinical results. Beneficial or desired clinical results include, but are not limited to, alleviation or amelioration of one or more symptoms associated with a disease or condition as described herein.

"Administering" or "administration of" a substance, a compound or an agent to a subject can be carried out using one of a variety of methods known to those skilled in the art. For example, a compound or an agent can be administered sublingually or intranasally, by inhalation into the lung or rectally. Administering can also be performed, for example, once, a plurality of times, and/or over one or more extended periods. In some aspects, the administration includes both direct administration, including self-administration, and indirect administration, including the act of prescribing a drug. For example, as used herein, a physician who instructs a patient to self-administer a drug, or to have the drug administered by another and/or who provides a patient with a prescription for a drug is administering the drug to the patient.

In solid drug product formulation, the knowledge of possible interactions between the drug substance and the excipients is a crucial point for the prediction of chemical and physical stability.

Very often the excipients can modify the biological activity and chemical stability of the API because the dissolution or chemical structures are changed. In some cases, the excipient can improve the chemical stability profile over time and avoid undesirable physical behavior of the final dosage form.

A eutectic system is a mixture of chemical compounds or elements that has a single chemical composition that melts at a lower temperature than any other composition made up of the same ingredients. A composition comprising a eutectic is known as the eutectic composition and its melting temperature is known as the eutectic temperature. To define a eutectic composition, a binary phase diagram should be built by analyzing different compounds ratios.

The effect of a eutectic on tablet properties shows that compaction provides the intimate contact and mutual solubility sufficient for eutectic formation. Eutectic compositions often have higher stability and/or dissolution rates than their non-eutectic counterparts. Because eutectics enhance dissolution, they can be employed to increase permeability in solid dispersions and dispersion systems. However, in the development of certain tableted dosage forms, undesired eutectic formation (during manufacturing operation such as wet granulation), can lead to unwanted changes in physical or chemical characteristics of the tablet, such as low eutectic melting temperature, sticking, unpredictable hardness, instability or difficulties in accelerated assessment of stability.

Mannitol and Sorbitol are excipients commonly used in solid drug products. Mannitol and Sorbitol are 6-carbon sugar alcohols isomers. Sugar alcohols are hydrogenated carbohydrates whose carbonyl group has been reduced to a primary or secondary hydroxyl group. Other 6-carbon sugar alcohols include Inositol, Galactitol, Fucitol, and Iditol.

Although Mannitol and Sorbitol can be included in pharmaceutical compositions, it is typically because they provide qualitative benefits such as sweet taste or a cooling effect in the mouth, but are physically inert. Thus, it was surprising to discover that mannitol formed a eutectic composition with Cyclobenzaprine HCl and with Amitriptyline HCl. By contrast, sorbitol dissolved Cyclobenzaprine HCl and did not form a eutectic, underscoring the unpredictability of eutectic formation and the protective effect of the eutectic formed with mannitol. Without wishing to be bound by theory, it is possible that the two co-penetrating crystal lattices of mannitol and Cyclobenzaprine HCl provide protection of the Cyclobenzaprine HCl from hydration and other chemical interactions.

Compounds

The compounds useful in embodiments of the present invention include Cyclobenzaprine HCl and Amitriptyline HCl. In some embodiments, the compounds are micronized. In alternative embodiments, the compounds are not micronized. In some embodiments, the compounds may be present in one or more crystal isoforms.

As used herein, "Cyclobenzaprine HCl" refers to the pharmaceutically acceptable cyclobenzaprine hydrochloride salt of cyclobenzaprine.

As used herein, "Amitriptyline HCl" refers to the pharmaceutically acceptable amitriptyline hydrochloride salt of amitriptyline.

Eutectic compositions

In some embodiments, the invention provides a pharmaceutical composition comprising a eutectic mixture of mannitol and an active pharmaceutical ingredient. In certain embodiments, the active pharmaceutical ingredient is Cyclobenzaprine HCl or Amitriptyline HCl.

In some embodiments, the invention provides a pharmaceutical composition comprising a eutectic mixture of mannitol and Cyclobenzaprine HCl. In certain embodiments (for example, when the composition comprises a δ mannitol eutectic), the eutectic has a melting temperature of 143.6±3° C. In certain embodiments, a melting temperature of the eutectic is approximately 135.6° C., 136.6° C., 137.6° C., 138.6° C., 139.6° C., 140.6° C., 141.6° C., 142.6° C., 143.6° C., 144.6° C., 145.6° C., 146.6° C., 147.6° C., 148.6° C., 149.6° C., 150.6° C., 151.6° C., 152.6° C., or 153.6° C. In certain embodiments (for example, when the composition comprises a δ mannitol eutectic), the eutectic has a melting temperature of 134±3° C. In certain embodiments (for example, when the composition comprises a δ mannitol eutectic), a melting temperature of the eutectic is approximately 124° C., 125° C., 126° C., 127° C., 128° C., 129° C., 130° C., 131° C., 132° C., 133° C., 134° C., 135° C., 136° C., 137° C., 138° C., 139° C., 140° C., 141° C., 142° C., 143° C., or 144° C. In particular embodiments, the melting temperature of the eutectic is the temperature at which melting begins. In alternative embodiments, the melting temperature of the eutectic is the temperature at which maximum melting is observed. In certain embodiments, the composition comprises greater than 5% Cyclobenzaprine HCl and less than 95% mannitol by weight. In certain embodiments, the composition comprises 1%-5% Cyclobenzaprine HCl and 99%-95% mannitol by weight. In certain embodiments, the composition comprises 5%-10% Cyclobenzaprine HCl and 95%-90% mannitol by weight. In certain embodiments, the composition comprises 10%-20% Cyclobenzaprine HCl and 90%-80% mannitol by weight. In certain embodiments, the composition comprises 10%-90% Cyclobenzaprine HCl and 90%-10% mannitol by weight, for example, 60%-90% Cyclobenzaprine HCl and 40%-10% mannitol or 70%-80% Cyclobenzaprine HCl and 30%-20% mannitol by weight. Exemplary compositions comprise 60%±2% Cyclobenzaprine HCl and 40%±2% mannitol, 65%±2% Cyclobenzaprine HCl and 35%±2% mannitol, 70%±2% Cyclobenzaprine HCl and 30%±2% mannitol, 75%±2% Cyclobenzaprine HCl and 25%±2% mannitol, 80%±2% Cyclobenzaprine HCl and 20%±2% mannitol, 85%±2% Cyclobenzaprine HCl and 15%±2% mannitol, and 90%±2% Cyclobenzaprine HCl and 10%±2% mannitol by weight. In certain embodiments, a composition comprises 75%±10% Cyclobenzaprine HCl and 25%±10% mannitol by weight. In certain embodiments, a composition comprises 75%±2% Cyclobenzaprine HCl and 25%±2% mannitol by weight. In certain embodiments, a composition comprises 75% Cyclobenzaprine HCl and 25% mannitol by weight. In certain embodiments, the composition comprises Cyclobenzaprine HCl and mannitol in a Cyclobenzaprine HCl:mannitol molar ratio of 1.70±0.1 to 1.80±0.1. In certain embodiments, the molar ratio is about 1.6 to 2.0. In particular embodiments, the molar ration is 1.70±0.1, 1.71±0.1, 1.72±0.1, 1.73±0.1, 1.74±0.1, 1.75±0.1, 1.76±0.1, 1.77±0.1, 1.78±0.1, 1.79±0.1, or 1.80±0.1. In certain embodiments, the molar ratio is 1.60±0.5, 1.65±0.5, 1.70±0.5, 1.75±0.5, 1.80±0.5, 1.85±0.5, 1.90±0.5, 1.95±0.5, or 2.0±0.5. In certain embodiments the molar ratio is 1.76±0.1. In certain embodiments the molar ratio is 1.76±0.5.

In some embodiments, the invention provides a pharmaceutical composition comprising a eutectic mixture of mannitol and Amitriptyline HCl. In certain embodiments, the composition has a melting temperature of 133±3° C. In certain embodiments, a melting temperature of the composition is approximately 125° C., 126° C., 127° C., 128° C., 129° C., 130° C., 131 ° C., 132° C., 133 ° C., 134° C., 135 ° C., 136 ° C., 137° C., 138° C., 139° C., 140° C., 141° C., 142° C., or 143° C. In particular embodiments, the melting temperature of the eutectic is the temperature at which melting begins. In alternative embodiments, the melting temperature of the eutectic is the temperature at which maximum melting is observed. In certain embodiments, the composition comprises greater than 5% Amitriptyline HCl and less than 95% mannitol by weight. In certain embodiments, the composition comprises 1%-5% Amitriptyline HCl and 99%-95% mannitol by weight. In certain embodiments, the composition comprises 5%-10% Amitriptyline HCl and 95%-90% mannitol by weight. In certain embodiments, the composition comprises 10%-20% Amitriptyline HCl and 90%-80% mannitol by weight. In certain embodiments, the composition comprises 10%-90% Amitriptyline HCl and 90%-10% mannitol by weight, for example, 60%-90% Amitriptyline HCl and 40%-10% mannitol or 70%-80% Amitriptyline HCl and 30%-20% mannitol by weight. Exemplary compositions comprise 60%±2% Amitriptyline HCl and 40%±2% mannitol, 65%±2% Amitriptyline HCl and 35%±2% mannitol, 70%±2% Amitriptyline HCl and 30%±2% mannitol, 75%±2% Amitriptyline HCl and 25%±2% mannitol, 80%±2% Amitriptyline HCl and 20%±2% mannitol, 85%±2% Amitriptyline HCl and 15%±2% mannitol, and 90%±2% Amitriptyline HCl and 10%±2% mannitol by weight. In certain embodiments, a composition comprises 75%±10% Amitriptyline HCl and 25%±10% mannitol by weight. In certain embodiments, a composition comprises 75%±2% Amitriptyline HCl and 25%±2% mannitol by weight. In certain embodiments, a composition comprises 75% Amitriptyline HCl and 25% mannitol by weight. In certain embodiments, the composition comprises Amitriptyline HCl and mannitol in an Amitriptyline HCl:mannitol molar ratio 1.70±0.1 to 1.80±0.1. In certain embodiments, the molar ratio is of 1.70±0.1, 1.71±0.1, 1.72±0.1, 1.73±0.1, 1.74±0.1, 1.75±0.1, 1.76±0.1, 1.77±0.1, 1.78±0.1, 1.79±0.1, or 1.80±0.1. In certain embodiments the molar ratio is 1.76±0.1.

Another benefit of the eutectic compositions of the invention is increased stability of a tablet containing Cyclobenzaprine HCl. In some embodiments, the invention provides a pharmaceutical composition comprising Cyclobenzaprine HCl and mannitol or Amitriptyline HCl and mannitol, wherein the composition has an increased stability in tablet form as compared to the same tablet without mannitol, e.g., to a tablet comprising sorbitol but not mannitol. Indeed, a tablet containing Cyclobenzaprine HCl, $K_2HPO_4$, and mannitol was stable for three months at 40° C. and 75% relative humidity. By contrast, a tablet containing Cyclobenzaprine HCl, $K_2HPO_4$, and sorbitol stored at the same conditions disintegrated before reaching even reaching one week.

In some embodiments, the invention provides a pharmaceutical composition comprising Cyclobenzaprine HCl and mannitol or Amitriptyline HCl and mannitol, wherein the composition has an increased dissolution rate of a stable tablet compared to Cyclobenzaprine HCl or Amitriptyline HCl alone or in a formulation containing one or more excipients that are not basifying agents. For example, the composition at 5 minutes can exhibit greater than 55%, greater than 50%, greater than 45%, greater than 40%, greater than 35%, greater than 30%, or greater than 25% dissolution when mixed with 100 mL of 50 mM Citrate pH 4 at 37.0±0.5° C. For example, the composition at 10 minutes can exhibit greater than 80%, greater than 75%, greater than 65%, greater than 60%, greater than 55%, greater than 50%, dissolution when mixed with 100 mL of 50 mM Citrate pH 4 at 37.0±0.5 ° C. For example, the composition at 240 minutes can exhibit greater than 80%, greater than 75%, greater than 65%, greater than 60%, greater than 55%, greater than 50%, dissolution when mixed with 100 mL of 50 mM Citrate pH 4 at 37.0±0.5° C.

Mannitol is capable of crystallizing in three polymorphic states: α, β, and δ. These three forms can be distinguished by X-ray powder diffraction, and each polymorph has a different melting point. See, e.g., Sharma and Kalonia, AAPS PharmaSciTech 5(1):E10 (2004). Even more surprising than the observation of a first eutectic with Cyclobenzaprine HCl and mannitol (β polymorph) was the observation of a second eutectic with a different polymorphic form of mannitol (δ polymorph). The eutectic comprising δ mannitol and Cyclobenzaprine HCl or Amitriptyline HCl (also referred to herein as the "β mannitol eutectic") has several advantages over the eutectic comprising β mannitol and Cyclobenzaprine HCl or Amitriptyline HCl (also referred to herein as the "β mannitol eutectic"). Prime among these are a lower melting point than the β mannitol eutectic and enhanced dissolution over the β mannitol eutectic.

In some embodiments, the invention provides a eutectic pharmaceutical composition comprising Cyclobenzaprine HCl and mannitol or Amitriptyline HCl and mannitol, wherein the mannitol is in its β polymorphic state. In some embodiments, the invention provides a eutectic pharmaceutical composition comprising Cyclobenzaprine HCl and mannitol or Amitriptyline HCl and mannitol, wherein the mannitol is in its δ polymorphic state. In certain embodiments, the pharmaceutical composition comprising the mannitol in its β polymorphic state is a sublingual composition. In certain embodiments, the pharmaceutical composition comprising the mannitol in its β polymorphic state is an oral composition. In certain embodiments, the pharmaceutical composition comprising the mannitol in its δ polymorphic state is a sublingual composition. In certain embodiments, the pharmaceutical composition comprising the mannitol in its δ polymorphic state is an oral composition. In particular embodiments wherein the composition is an oral composition, the oral composition is bioequivalent to 5 mg Cyclobenzaprine HCl oral tablets (e.g., Flexeril 5 mg). In particular embodiments wherein the composition is an oral composition, the oral composition is bioequivalent to 10 mg Cyclobenzaprine HCl oral tablets (e.g., Flexeril 10 mg). Flexeril tablets are composed of hydroxypropyl cellulose, hydroxypropyl methylcellulose, iron oxide, lactose, magnesium stearate, starch, and titanium dioxide. Dosing 10 mg t.i.d. in normal healthy volunteers, the AUC at steady state (after 4 days of dosing) was 177 ng.hr/mL (range, 80-319 ng.hr/mL) and the Cmax was 25.9 ng/mL (range, 12.8-46.1 ng/mL). Additional pharmacokinetic properties of orally administered Cyclobenzaprine can be found, for example, in Winchell et al., J Clin Pharmacol. 42(1):61-9 (2002) and Hucker et al., J Clin Pharmacol. 17(11-12):719-27 (1977).

In some embodiments, the invention provides a composition comprising eutectic of mannitol and Cyclobenzaprine HCl. In some embodiments, the invention provides a composition comprising eutectic of mannitol and Amitriptyline HCl. The skilled worker will understand that these compositions may be suitable for administration in a variety of ways, such as those described herein. For example, a composition may be suitable for administration orally (administration wherein the Cyclobenzaprine or Amitriptyline is absorbed in the gastrointestinal tract), or for transmucosal absorption (e.g., sublingual, buccal, or intranasal absorption, or by inhalation).

Methods of Manufacturing Eutectic Compositions

The skilled worker will appreciate that a eutectic composition of the invention can be manufactured according to any of a number of known methods. In some embodiments, the invention provides methods for producing a eutectic composition of the invention comprising milling an API (Cyclobenzaprine HCl or Amitriptyline HCl) with mannitol, mixing an API (Cyclobenzaprine HCl or Amitriptyline HCl) with mannitol, or a combination thereof. For example, the APT and mannitol can be milled in an agate mortar or mixed in a high shear granulator. High shear mixing combines dry powders using a high speed impellor and chopper blades to uniformly mix the ingredients. Some particle size reduction is possible due to the shear force and the high speed of the mixing blades. The API and mannitol also can be milled and mixed in a Turbula® Shaker-Mixer. In certain embodiments, the API and mannitol can be mixed via compression, for example, via roller compaction. Roller compaction forces fine powders between two counter-rotating rolls and presses the raw materials into a solid compact or sheet (referred to as flakes). The flakes are reduced in size until they reach a desired grain size. In certain embodiments, mannitol can be melted and mixed with Cyclobenzaprine HCl or Amitriptyline HCl to form a eutectic composition. In certain embodiments, the API is a micronized API (e.g., micronized Cyclobenzaprine HCl or micronized Amitriptyline HCl).

In some embodiments, the invention provides methods for producing a eutectic composition of the invention comprising spray drying a solution of an API (Cyclobenzaprine HCl or Amitriptyline HCl) with mannitol. The skilled worker will appreciate that spray drying is routine, and parameters for spray drying can be determined without undue experimentation. For example, spray drying can be performed under any of the following conditions:

T Inlet (° C.): 120
T Outlet (° C.): 73-76
Feed rate (ml/min): 4
Flow Rate (L/h): 600
Aspiration (100%): 100
delta Pressure (mbar): 2-10

These conditions also may be scaled up to provide higher throughput manufacturing.

Methods of Detecting Eutectic Compositions

Methods of detecting eutectic compositions are well known. The skilled worker will appreciate that eutectic compositions can be detected by any of these methods. For example, rapid differential scanning calorimetry ("DSC") can be used to detect a eutectic melting point by evaluating the amount of heat recorded from eutectic melting and comparing it with the melting heat of the eutectic composition. During a slow scan of DSC, the increased temperature in the crucible facilitates the formation of the eutectic even when the two components (such as Mannitol and cyclobenzaprine HCl may not have been mixed before the start of the experiment.) In contrast, a rapid DSC scan reduces the time during which eutectic compositions can form in the crucible because the temperature inside the crucible rapidly increases during the analysis and rapidly reaches the values at which the mannitol melts. Another useful method is measuring compaction force vs. DSC eutectic melting point. In this method, mixtures are prepared with known ratios and then submitted to well-defined compaction forces. DSC analyses are then performed and the heat of the eutectic melting versus the forces is then recorded and plotted. These values are compared with those obtained with the eutectic ratio, providing the percentage of eutectic in the formulation.

An additional method that can be used to detect the amount of eutectic in a composition is to compare tensile strength and compression force. In this method, tablets are prepared with only mannitol and API at different compression forces. For each tablet prepared, the percentage of eutectic formed versus tensile strength of the tablets is correlated. There is a proportionally linear correlation between the tensile strength and the intimate contact area. The slope of this correlation provides the percentage of the eutectic formed.

There is a linear correlation between the percentage of eutectic composition in a preparation and the porosity of powders in a composition. In this method, a standard curve can be generated by preparing samples with different ratios of components in which at least one of the components has a variety of different particle sizes, measuring the specific surface area and the porosity of the powders and plotting porosity against the percentage of eutectic. Because there is a linear correlation between the two parameters, the slope of this correlation with what is recorded for the eutectic mixture provides the percentage of the eutectic formed Dissolution rate also can be used to detect the percent of eutectic because a eutectic may have higher dissolution and higher bioavailability. In this method, the intrinsic dissolution rate (using disk sample holder in a defined and appropriate medium) of the single components is calculated, followed by the dissolution rate of the eutectic mixture. Based on the thermodynamic parameters (entropy), the eutectic should have a more rapid dissolution rate than the other mixtures. By these analyses, it is also possible to obtain information on the performance of a tablet in terms of bioavailability. This approach also can evaluate the higher bioavailability of a eutectic versus mixtures of the individual components.

Scanning Electron Microscopy (SEM) can be used by performing a scanning EM of each pure component, on the eutectic, and on the mixtures, and observing the different crystal morphology by pointing out the differently shaped particles.

Methods of Administering Eutectic Compositions

Appropriate methods of administering a pharmaceutical composition of the invention to a subject will depend, for example, on the age of the subject, whether the subject is active or inactive at the time of administering, whether the subject is experiencing symptoms of a disease or condition at the time of administering, the extent of the symptoms, and the chemical and biological properties of the API (e.g. solubility, digestibility, bioavailability, stability and toxicity). In some embodiments, the pharmaceutical composition is administered for oral or transmucosal absorption.

Methods of administering compositions for oral absorption are well known in the art. For example, a composition may be administered orally through tablets, capsules, pills, or powders. In these embodiments, the compositions are absorbed by the gastrointestinal tract after swallowing. In certain embodiments, the composition lacks a film or membrane (e.g., a semipermeable membrane).

Methods of administering compositions for transmucosal absorption are well known in the art. For example, a composition may be administered for buccal absorption through buccal tablets, lozenges, buccal powders, and buccal spray solutions. A composition may be administered for sublingual absorption through sublingual tablets, sublingual films, liquids, sublingual powders, and sublingual spray solutions. In certain embodiments, the composition lacks a film or membrane (e.g., a semipermeable membrane). A composition may be administered for intranasal absorption through nasal sprays. A composition may be administered for pulmonary absorption through aerosolized compositions and inhalable dried powders. Because mannitol powder is an inhalation product in the U.S. (trade name: Aridol®; Pharmaxis Ltd.), inhalation may be an especially beneficial form of administration. When administered via sprays or aerosolized compositions, a composition may be prepared with saline as a solution, employ benzyl alcohol or other suitable preservatives, or include absorption promoters to enhance bioavailability, fluorocarbons, and/or other solubilizing or dispersing agents.

Doses and dosing regimens can be determined by one of skill in the art according to the needs of a subject to be treated. The skilled worker may take into consideration factors such as the age or weight of the subject, the severity of the disease or condition being treated, and the response of the subject to treatment. A composition of the invention can be administered, for example, as needed or on a daily basis. In some embodiments, a composition can be administered immediately prior to sleep or several hours before sleep. Administration prior to sleep may be beneficial by providing the therapeutic effect before the onset of the symptoms of the disease or condition being treated. Dosing may take place over varying time periods. For example, a dosing regimen may last for 1 week, 2 weeks, 3 weeks, 4 weeks, 5 weeks, 6 weeks, 7 weeks, 8 weeks, 9 weeks, 10 weeks, 11 weeks, 12 weeks, or longer. In some embodiments, a dosing regimen will last 1 month, 2 months, 3 months, 4 months, 5 months, 6 months, 7 months, 8 months, 9 months, 10 months, 11 months, 12 months, or longer.

Therapeutic Uses

The pharmaceutical compositions of the invention may be employed for treating or preventing the development of fibromyalgia syndrome, also known as fibrositis (see, e.g., Moldofsky et al,. J Rheumatol 38(12):2653-2663 (2011) and Thomas, J Rheumatol 38(12):2499-2500 (2011)). Fibromyalgia is a chronic, non-inflammatory rheumatic disorder. The American College of Rheumatology (ACR) published classification criteria for fibromyalgia in 1990 (Wolfe, F., et al., Arthritis and Rheumatism 33:160-172 (1990)). Subsequently, a modification to the ACR criteria been published (Wolfe et al., J Rheumatol 38(6):1113-22 (2011)). Diagnostic criteria have also been published by an international network of working groups called, "Outcome Measures in Rheumatology" clinical trials or OMERACT (Mease P, et al. J Rheumatol. 2009;36(10):2318-29.). Fibromyalgia is traditionally characterized by stiffness or diffuse pain, aches, muscle soreness, sleep disturbances or fatigue. The pain is generally widespread and generally localized at specific "tender points," which may bring on widespread pain and muscle spasm when touched. Other symptoms include mental and emotional disturbances such as poor concentration and irritability, neuropsychiatric symptoms such as depression and anxiety, joint swelling, headache, numbness. Fibromyalgia is associated with nonrefreshing sleep, tiredness, sleepiness, reflux, mental fog and cognitive impairments including difficulty multi-tasking. Fibromyalgia also is often comorbid with sleep disorders, fatigue, non-restorative sleep, anxiety, and depression. The compositions and methods of the invention can be used to treat any one of the above-identified conditions, and any combination thereof.

Some practitioners further classify fibromyalgia into two categories—primary or secondary-concomitant fibromyalgia. Generally, primary fibromyalgia syndrome can be considered fibromyalgia occurring in the absence of another significant condition whereas secondary-concomitant fibromyalgia can be considered fibromyalgia occurring in the presence of another significant medical disorder, which may have been caused by or is merely associated with the patient's fibromyalgia. Secondary or concomitant fibromyalgia can include fibromyalgia in patients with classical or definite rheumatoid arthritis, osteoarthritis of the knee or hand, low back pain syndromes, cervical pain syndromes, cancer pain syndromes, temporomandibular joint disorders, migraine headaches, menopause, post-traumatic stress disorder and interstitial cystitis or painful bladder syndrome (or combinations thereof).

The compositions of the invention also may be employed for treating or preventing the development (either the initiation, consolidation or perpetuation) of a PTSD symptom following a traumatic event. A traumatic event is defined as a direct personal experience that involves actual or threatened death or serious injury, or other threat to one's physical integrity, or witnessing an event that involves death, injury, or a threat to the physical integrity of another person; or learning about unexpected or violent death, serious harm, or threat of death or injury experienced by a family member or other close associate. Traumatic events that are experienced directly include, but are not limited to, military combat, violent personal assault (sexual assault, physical attack, robbery, mugging), being kidnapped, being taken hostage, terrorist attack, torture, incarceration as a prisoner of war or in a concentration camp, natural or manmade disasters, severe automobile accidents, or being diagnosed with a life-threatening illness. For children, sexually traumatic events may include developmentally inappropriate sexual experiences without threatened or actual violence or injury. Witnessed events include, but are not limited to, observing the serious injury or unnatural death of another person due to violent assault, accident, war, or disaster or unexpectedly witnessing a dead body or body parts. Events experienced by others that are learned about may include, but are not limited to, violent personal assault, serious accident, or serious injury experienced by a family member or a close friend, learning about the sudden, unexpected death of a family member or a close friend, or learning that one's child has a life-threatening disease. The disorder may be especially severe or long lasting when the stressor is of human design (e.g., torture or rape). The initiation of a PTSD symptom typically occurs immediately following the traumatic event, during which the symptoms of PTSD appear and become increasingly severe. One theory of how PTSD develops is that there is a type of "learning" or reinforcement process during which the memories of the trauma are engrained in the mind. As these memories become more fixed (a process called consolidation), symptoms such as flashbacks and nightmares grow in severity and frequency. Interventions during this critical time may prevent some patients from developing full-blown PTSD. The consolidation of a PTSD symptom typically occurs during the weeks and months following a traumatic event. A person's memories of that event become consolidated into highly vivid and concrete memories that are re-experienced with increasing frequency either as flashbacks or nightmares. During this time, hyperarousal symptoms and avoidant behavior can become increasingly severe and disabling. The perpetuation of a PTSD symptom occurs once traumatic memories are consolidated, and the re-experienced symptoms (flashbacks and nightmares) and hyperarousal symptoms become persistent and remain at a level that is functionally disabling to the patient.

The compositions of the invention may be used to treat different phases of PTSD development at various time intervals after a traumatic event. For example, treating the initiation phase of PTSD may require the administration of a composition of the invention soon after the traumatic event, for example within the first week, within the second week, within the third week, or within the fourth week or later. By contrast, when treating the consolidation phase of PTSD, the skilled worker may be able to administer a composition of the invention later after the traumatic event and later during the development of the symptoms, for example, within the first month, within the second month, or within the third month or later. The perpetuation phase of PTSD may be treated with a composition of the invention administered 3 months or longer after the traumatic event, for example within the third month, within the fourth month, within the fifth month, or later. As a result of treatment at the initiation, consolidation, or perpetuation phase, PTSD symptoms will be ameliorated or be eliminated.

The compositions of the invention also can be used to treat traumatic brain injury (TBI). TBI is associated with sleep disorders, sleep disturbances, fatigue, non-restorative sleep, anxiety, and depression. The compositions and methods of the invention also can be used to treat any of the above conditions, in combination with or independently of treating TBI.

The compositions of the invention also can be used to chronic traumatic encephalopathy (CTE). CTE is associated with sleep disorders, sleep disturbances, fatigue, non-restorative sleep, anxiety, and depression. The compositions and methods of the invention also can be used to treat any of the above conditions, in combination with or independently of treating CTE.

The compositions and methods of the invention may be used to treat sleep disorders or sleep disturbances. A "sleep disorder" may be any one of four major categories of sleep dysfunction (DSM-IV, pp. 551-607; see also The International Classification of Sleep Disorders: (ICSD) Diagnostic and Coding Manual, 1990, American Sleep Disorders Association). One category, primary sleep disorders, comprises sleep disorders that do not result from another mental disorder, a substance, or a general medical condition. They include without limitation primary insomnia, primary hypersomnia, narcolepsy, circadian rhythm sleep disorder, nightmare disorder, sleep terror disorder, sleepwalking disorder, REM sleep behavior disorder, sleep paralysis, day/night reversal and other related disorders; substance-induced sleep disorders; and sleep disorders due to a general medical condition. Primary insomnia non-restorative sleep is described by the DSM-IV-TR as a type of primary insomnia wherein the predominant problem is waking up feeling unrefreshed or nonrefreshed. A second category comprises those sleep disorders attributable to substances, including medications and drugs of abuse. A third category comprises sleep disturbances arising from the effects of a general medical condition on the sleep/wake system. A fourth category of sleep disorders comprises those resulting from an identifiable mental disorder such as a mood or anxiety disorder. A fifth category of sleep disorders comprises those described as non-restorative sleep. One definition of non-restorative sleep is in the DSM-IV-TR as a type of primary insomnia (A1.3) wherein the predominant problem is waking up feeling unrefreshed or nonrefreshed. Symptoms of each category of sleep disorder are known in the art. A "sleep disturbance" may be an impairment in refreshing sleep. Such a clinical diagnosis may be made based on a patient's self described feeling of fatigue upon waking or the patient's report of poor quality sleep. Such impediments to good quality sleep may be described as shallow sleep or frequent awakenings which may be associated with an increase in the Cyclic Alternating Pattern (CAP) A2 or A3 rate or cycle duration or an increase in the normalized CAP A2+A3 which is determined by CAP (A2+A3)/CAP (A1+A2+A3) in non-REM sleep (see, e.g., Moldofsky et al,. J Rheumatol 38(12): 2653-2663 (2011) and Thomas, J Rheumatol 38(12):2499-2500 (2011)), alpha rhythm contamination in non-REM sleep, or absence of delta waves during deeper physically restorative sleep. Such "sleep disturbances" may or may not rise to the level of a "sleep disorder" as defined in the DSM-IV, although they may share one or more symptom in common. Symptoms of sleep disturbances are known in the art. Among the known symptoms are groggy or spacey feelings, tiredness, feelings of being run down, and having difficulty concentrating during waking hours. Among the sleep-related conditions that may be treated with the methods and compositions of the invention are dyssomnias (e.g., intrinsic sleep disorders such as sleep state misperception, psychophysiological insomnia, idiopathic insomnia, obstructive sleep apnea syndrome, central sleep apnea syndrome, central alveolar hypoventilation syndrome, restless leg syndrome, and periodic limb movement disorder; extrinsic sleep disorders such as environmental sleep disorder, adjustment sleep disorder, limit-setting sleep disorder, stimulant-dependent sleep disorder, alcohol-dependent sleep disorder, toxin-induced sleep disorder, sleep onset association disorder, hypnotic dependent sleep disorder, inadequate sleep hygiene, altitude insomnia, insufficient sleep syndrome, nocturnal eating syndrome, and nocturnal drinking syndrome; and circadian rhythm sleep disorders such as jet lag syndrome, delayed sleep phase syndrome, advanced sleep phase syndrome, shift work sleep disorder, non-24 hour sleep-wake disorder, and irregular sleep-wake patterns), parasomnias (e.g., arousal disorders such as sleepwalking, confusional arousals, and sleep terrors and sleep-wake transition disorders such as rhythmic movement disorder, sleep talking and sleep starts, and nocturnal leg cramps), and sleep disorders associated with medical or psychiatric conditions or disorders. The compositions of the invention also can be used to treat muscle spasms. Muscle spasms can be associated with muscle pain, e.g., back pain. The compositions and methods of the invention also can be used to treat any of the above conditions, in combination with or independently of treating muscle spasms.

Basifying Agents

The compositions of the invention may include a basifying agent. As used herein, a "basifying agent" refers to an agent (e.g., a substance that increases the local pH of a liquid comprising Cyclobenzaprine HCl or Amitriptyline HCl, including potassium dihydrogen phosphate (monopotassium phosphate, monobasic potassium phosphate, $KH_2PO_4$), dipotassium hydrogen phosphate (dipotassium phosphate, dibasic potassium phosphate, $K_2HPO_4$), tripotassium phosphate ($K_3PO_4$), sodium dihydrogen phosphate (monosodium phosphate, monobasic sodium phosphate, $NaH_2PO_4$), disodium hydrogen phosphate (disodium phosphate, dibasic sodium phosphate, $Na_2HPO_4$), trisodium phosphate ($Na_3PO_4$), trisodium citrate anhydrous, bicarbonate or carbonate salts, borate, hydroxide, silicate, nitrate, dissolved ammonia, the conjugate bases of some organic acids (including bicarbonate), and sulfide) that raises the pH of a solution containing Cyclobenzaprine HCl or Amitriptyline HCl. Without wishing to be bound by theory, a basifying agent, while providing beneficial pharmacokinetic attributes to pharmaceutical compositions comprising Cyclobenzaprine HCl or Amitriptyline HCl, also may destabilize the Cyclobenzaprine HCl or Amitriptyline HCl due to interactions between the HCl and basifying agent. Thus, a eutectic composition as described herein may be especially useful in compositions comprising a basifying agent.

Excipients

In some embodiments, a composition of the invention is useful as a medicament. In some embodiments, the invention provides for the use of a composition of the invention in the manufacture of a medicament. In some embodiments, it may be beneficial to include one or more excipients in the compositions of the invention. One of skill in the art would appreciate that the choice of any one excipient may influence the choice of any other excipient. For example, the choice of a particular excipient may preclude the use of one or more additional excipient because the combination of excipients would produce undesirable effects. One of skill in the art would be able to empirically determine which additional excipients, if any, to include in the formulations of the invention. For example, Cyclobenzaprine HClor Amitriptyline HCl can be combined with at least one pharmaceutically acceptable carrier such as a solvent, bulking agents, binder, humectant, disintegrating agent, solution retarder, disintegrant, glidant, absorption accelerator, wetting agent, solubilizing agent, lubricant, sweetening agent, or flavorant agent. A "pharmaceutically acceptable carrier" refers to any diluent or excipient that is compatible with the other ingredients of the formulation, and which is not deleterious to the recipient. A pharmaceutically acceptable carrier can be selected on the basis of the desired route of administration, in accordance with standard pharmaceutical practices.

Bulking Agents

In some embodiments, it may be beneficial to include a bulking agent in the compositions of the invention. Bulking agents are commonly used in pharmaceutical compositions to provide added volume to the composition. Bulking agents are well known in the art. Accordingly, the bulking agents described herein are not intended to constitute an exhaustive list, but are provided merely as exemplary bulking agents that may be used in the compositions and methods of the invention.

Exemplary bulking agents may include carbohydrates, sugar alcohols, amino acids, and sugar acids. Bulking agents include, but are not limited to, mono-, di-, or poly-, carbohydrates, starches, aldoses, ketoses, amino sugars, glyceraldehyde, arabinose, lyxose, pentose, ribose, xylose, galactose, glucose, hexose, idose, mannose, talose, heptose, glucose, fructose, methyl a-D-glucopyranoside, maltose, lactone, sorbose, erythrose, threose, arabinose, allose, altrose, gulose, idose, talose, erythrulose, ribulose, xylulose, psicose, tagatose, glucosamine, galactosamine, arabinans, fructans, fucans, galactans, galacturonans, glucans, mannans, xylans, inulin, levan, fucoidan, carrageenan, galactocarolose, pectins, amylose, pullulan, glycogen, amylopectin, cellulose, microcrystalline cellulose, pustulan, chitin, agarose, keratin, chondroitin, dermatan, hyaluronic acid, xanthin gum, sucrose, trehalose, dextran, lactose, alditols, inositols, sorbitol, mannitol, glycine, aldonic acids, uronic acids, aldaric acids, gluconic acid, isoascorbic acid, ascorbic acid, glucaric acid, glucuronic acid, gluconic acid, glucaric acid, galacturonic acid, mannuronic acid, neuraminic acid, pectic acids, maize starch, and alginic acid.

Disintegrants

In some embodiments, it may be beneficial to include a disintegrant in the compositions of the invention. Disintegrants aid in the breakup of solid compositions, facilitating delivery of an active pharmaceutical composition. Disintegrants are well known in the art. Some disintegrants have been referred to as superdisintegrants because they have fast properties, and may be used as disintegrants in the context of the invention. Accordingly, the disintegrants described herein are not intended to constitute an exhaustive list, but are provided merely as exemplary disintegrants that may be used in the compositions and methods of the invention. Exemplary disintegrants include crospovidone, microcrystalline cellulose, sodium carboxymethyl cellulose, methyl cellulose, sodium starch glycolate, calcium carboxymethyl croscarmellose sodium, polyvinylpyrrolidone, lower alkyl-substituted hydroxypropyl cellulose, Indion 414, starch, pre-gelatinized starch, calcium carbonate, gums, sodium alginate, and Pearlitol Flash®. Pearlitol Flash® (Roquette) is a mannitol-maize starch disintegrant that is specifically designed for orally dispersible tablets (ODT). Certain disintegrants have an effervescent quality.

Glidants

In some embodiments, it may be beneficial to include a glidant in the cosmpositions of the invention. Glidants aid in the ability of a powder to flow freely. Glidants are well known in the art. Accordingly, the glidants described herein are not intended to constitute an exhaustive list, but are provided merely as exemplary glidants that may be used in the compositions and methods of the invention. Exemplary glidants include colloidal silica (silicon dioxide), magnesium stearate, starch, talc, glycerol behenate, DL-leucine, sodium lauryl sulfate, calcium stearate, and sodium stearate.

Lubricants

In some embodiments, it may be beneficial to include a lubricant in the compositions of the invention. Lubricants help keep the components of a composition from clumping. Lubricants are well known in the art. Accordingly, the lubricants described herein are not intended to constitute an exhaustive list, but are provided merely as exemplary lubricants that may be used in the compositions and methods of the invention. Exemplary lubricants include calcium stearate, magnesium stearate, stearic acid, sodium stearyl fumarate, vegetable based fatty acids, talc, mineral oil, light mineral oil, hydrogenated vegetable oil (e.g., peanut oil, cottonseed oil, sunflower oil, sesame oil, olive oil, corn oil, safflower oil, canola oil, coconut oil and soybean oil), silica, zinc stearate, ethyl oleate, ethyl laurate.

Sweeteners

In some embodiments, it may be beneficial to include a sweetener in the compositions of the invention. Sweeteners help improve the palatability of the composition by conferring a sweet taste to the composition. Sweeteners are well known in the art. Accordingly, the sweeteners described herein are not intended to constitute an exhaustive list, but are provided merely as exemplary sweeteners that may be used in the compositions and methods of the invention. Exemplary sweeteners include, without limitation, compounds selected from the saccharide family such as the mono-, di-, tri-, poly-, and oligosaccharides; sugars such as sucrose, glucose (corn syrup), dextrose, invert sugar, fructose, maltodextrin and polydextrose; saccharin and salts thereof such as sodium and calcium salts; cyclamic acid and salts thereof; dipeptide sweeteners; chlorinated sugar derivatives such as sucralose and dihydrochalcone; sugar alcohols such as sorbitol, sorbitol syrup, mannitol, xylitol, hexaresorcinol, and the like, and combinations thereof. Hydrogenated starch hydrolysate, and the potassium, calcium, and sodium salts of 3,6-dihydro-6-methyl-1-1,2,3-oxathiazin-4-one-2,2-dioxide many also be used.

Flavorants

In some embodiments, it may be beneficial to include a flavorant in the compositions of the invention. Flavorants help improve the palatability of the composition by conferring a more desirable taste to the composition. Flavorants are well known in the art. Accordingly, the flavorants described herein are not intended to constitute an exhaustive list, but are provided merely as exemplary flavorants that may be used in the compositions and methods of the invention. Exemplary flavorants include, without limitation, natural and/or synthetic (i.e., artificial) compounds such as mint, peppermint, spearmint, wintergreen, menthol, anise, cherry, strawberry, watermelon, grape, banana, peach, pineapple, apricot, pear, raspberry, lemon, grapefruit, orange, plum, apple, lime, fruit punch, passion fruit, pomegranate, chocolate (e.g., white, milk, dark), vanilla, caramel, coffee, hazelnut, cinnamon, combinations thereof, and the like.

Coloring Agents

Coloring agents can be used to color code the composition, for example, to indicate the type and dosage of the therapeutic agent therein. Coloring Agents are well known in the art. Accordingly, the coloring agents described herein are not intended to constitute an exhaustive list, but are provided merely as exemplary coloring agents that may be used in the compositions and methods of the invention. Exemplary coloring agents include, without limitation, natural and/or artificial compounds such as FD & C coloring agents, natural juice concentrates, pigments such as titanium oxide, silicon dioxide, and zinc oxide, combinations thereof, and the like.

Combination Therapy

As described above, the compositions and methods of the invention may be used to treat PTSD, depression, fibromyalgia, traumatic brain injury, sleep disorder, non-restorative sleep, chronic pain, and anxiety disorder. Any of the methods of treatment described also may be combined with a psychotherapeutic intervention to improve the outcome of the treatment. Exemplary psychotherapeutic interventions directed at either modifying traumatic memories or reducing emotional responses to traumatic memories, including psychological debriefing, cognitive behavior therapy and eye movement desensitization and reprocessing, systematic desensitization, relaxation training, biofeedback, cognitive processing therapy, stress inoculation training, assertiveness training, exposure therapy, combined stress inoculation training and exposure therapy, combined exposure therapy, and relaxation training and cognitive therapy. In each case, the goal of the intervention involves either modifying traumatic memories or reducing emotional responses to traumatic memories. The intended result is generally an improvement in the symptoms of PTSD or the reduction of occurrences of symptoms, as evidenced in terms of physiological responding, anxiety, depression, and feelings of alienation.

In some embodiments of the invention, a composition is combined with a drug which may further alleviate the symptoms of PTSD, depression, fibromyalgia, traumatic brain injury, sleep disorder, non-restorative sleep, chronic pain, or anxiety disorder. The drugs include an alpha-1-adrenergic receptor antagonist, a beta-adrenergic antagonist, an anticonvulsant, a selective serotonin reuptake inhibitor, a serotonin-norepinephrine reuptake inhibitor, and an analgesic. Exemplary anticonvulsants include carbamazepine, gabapentin, lamotrigine, oxcarbazepine, pregabalin, tiagabine, topiramate, and valproate. An exemplary alpha-1-adrenergic receptor antagonist is prazosin. Exemplary selective serotonin reuptake inhibitors or serotonin-norepinephrine reuptake inhibitors include, bupropion, citalopram, desvenlafaxine, duloxetine, escitalopram, fluoxetine, escitalopram, fluvoxamine, milnacipran, paroxetine, sertraline, trazodone, and venlafaxine. Exemplary analgesics include pregabalin, gabapentin, acetaminophen, tramadol, and non-steroidal anti-inflammatory drugs (e.g., ibuprofen and naproxen sodium). Additional drugs that can be used in combination with the compositions of the invention include sodium oxybate, zolpidem, pramipexole, modafinil, temazepam, zaleplon, and armodafinil.

It is to be understood that the embodiments of the present invention which have been described are merely illustrative of some of the applications of the principles of the present invention. Numerous modifications may be made by those skilled in the art based upon the teachings presented herein without departing from the true spirit and scope of the invention.

The following examples are set forth as being representative of the present invention. These examples are not to be construed as limiting the scope of the invention as these and other equivalent embodiments will be apparent in view of the present disclosure, figures, and accompanying claims.

EXAMPLES

Example 1

Thermal analytical techniques were used to assess the compatibility of a drug product (tablet) containing Cyclobenzaprine HCl (API). The compatibility assessment was carried out between the API and a number of possible excipients in a 1:1 ratio. Based on the thermal events recorded for each component and for the mixtures, the analyses were carried out by investigating the peaks recorded by differential scanning calorimetry (DSC) in mixture between API and the excipients. Differences in thermal profiles between the single compound and the related mixture obtained after milling the products in an agate mortar were evaluated. Stability and compatibility also were also assessed on the final drug product after stress conditions at 40° C. and 50° C. for one month.

The following raw materials were used:
Cyclobenzaprine HCl
Sodium stearyl fumarate
Potassium Phosphate Bibasic
Crospovidone (Kollidon CL)
Silicon Colloidal
Pearlitol flash
Opadry 03F190003 Clear
Opadryll 85F19000 Clear A "formulation ratio" mixture was made with the following composition: 2.40 mg Cyclobenzaprine HCl, 31.55 mg Mannitol and Maize starch, 2.00 Crospovidone, 0.50 mg colloidal silica, 0.050 mg Sodium Stearyl Fumarate, and 1.05 Potassium hydrogen phosphate.

Aliquots of API and each excipient were weighed in a ratio of 1:1 (unless specified otherwise) and ground in an agate mortar. The homogeneous mixtures then were analyzed.

Differential Scanning Calorimetry (DSC)

The DSC heating curves were obtained with a TA 821 DSC Mettler instrument under the following conditions:
Heating rate: 10° C./min
Ambient: Nitrogen 30 mL/min
Sample holder: normal open aluminum pan
Temperature range: from 25° C. to 250° C.
Instrument calibration: Indium sample purity 99.999%

With Cyclobenzaprine HCl alone, melting with decomposition was detected between 210° C. and 223° C. (onset at 215.2° C., ΔH=−96.5 J/g) (FIG. 1).

Figure 2:
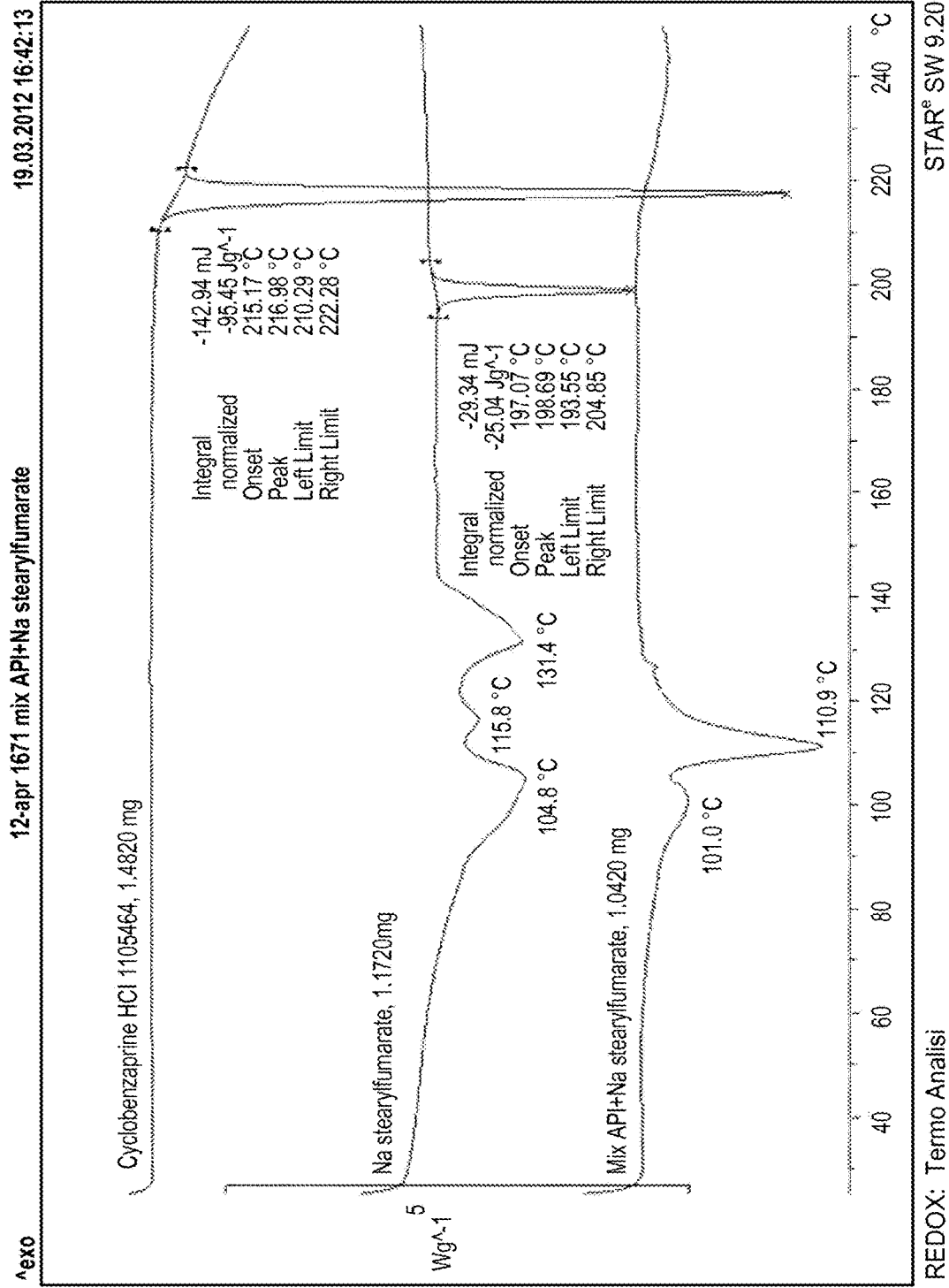
FIG. 2: DSC heating curve of Cyclobenzaprine HCl+ Sodium stearyl Fumarate 1:1.

In a 1:1 mixture of Cyclobenzaprine HCl and Sodium Stearyl fumarate, the endothermic transitions of sodium stearyl fumarate were recorded in the range of 100° C. to 120° C. (FIG. 2). No API transition peak was detected, but a physical interaction was observed.

Figure 3:
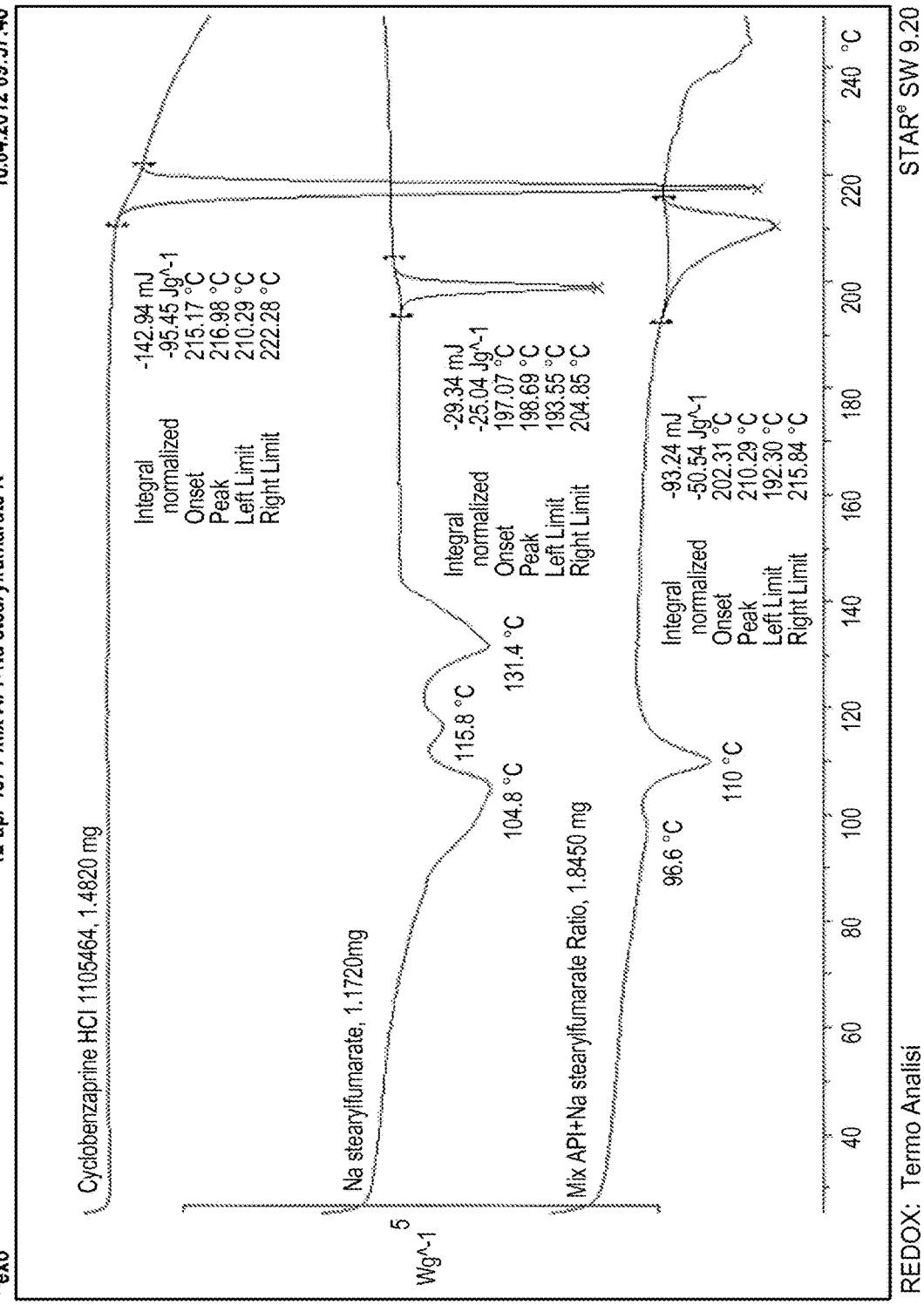
FIG. 3: DSC heating curve of Cyclobenzaprine HCl+ Sodium stearyl Fumarate, formulation ratio.

In a 1:1 mixture of Cyclobenzaprine HCl and Sodium Stearyl fumarate, the endothermic transitions of sodium stearyl fumarate were recorded in the range of 90° C. to 120° C. (FIG. 3). The API transition peak was detected between 192° C. and 216° C. (onset at 202.31° C., ΔH=−50.5J/g). A small physical interaction was observed. This interaction likely occurred during tablet compression when a possible rise in temperature can induce changes in the API.

Figure 4:
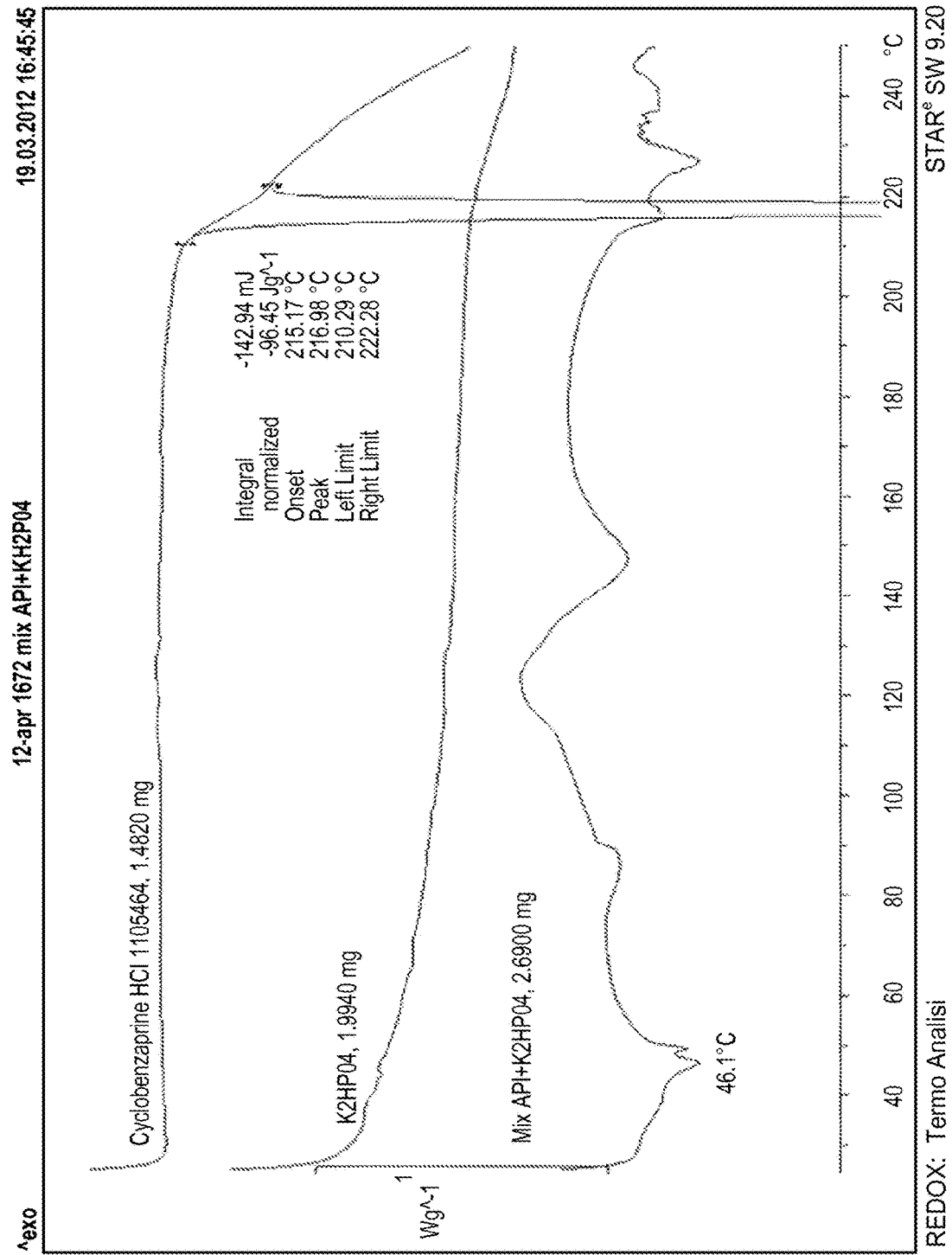
FIG. 4: DSC heating curve of Cyclobenzaprine HCl+ Potassium Phosphate dibasic 1:1.

In a 1:1 mixture of Cyclobenzaprine HCl and Potassium phosphate bibasic, a chemical interaction (acid-base) was observed between API and excipient. A transition between 40° C. and 60° C. was observed (FIG. 4), while, at high temperatures, the API melting peak was slightly visible.

Figure 5:
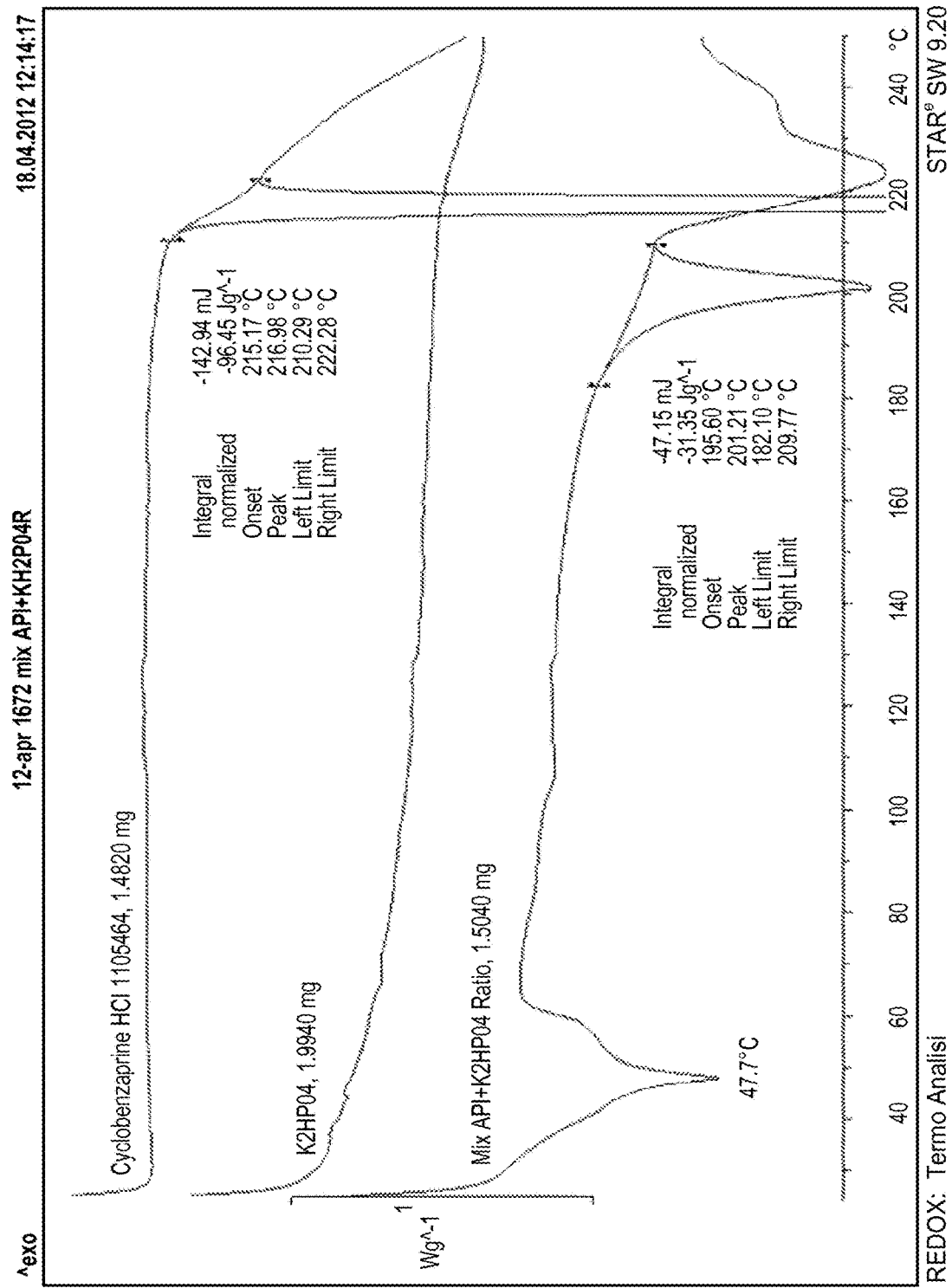
FIG. 5: DSC heating curve of Cyclobenzaprine HCl+ Potassium Phosphate dibasic, formulation ratio.

In the formulation ratio, a peak was observed at 47° C., likely due to water absorption by $K_2HPO_4$ while the API melting peak was detected between 182° C. and 210° C. (onset at 195.6° C., ΔH=−31.4/g) (FIG. 5). A small interaction was observed at higher temperatures.

Figure 6:
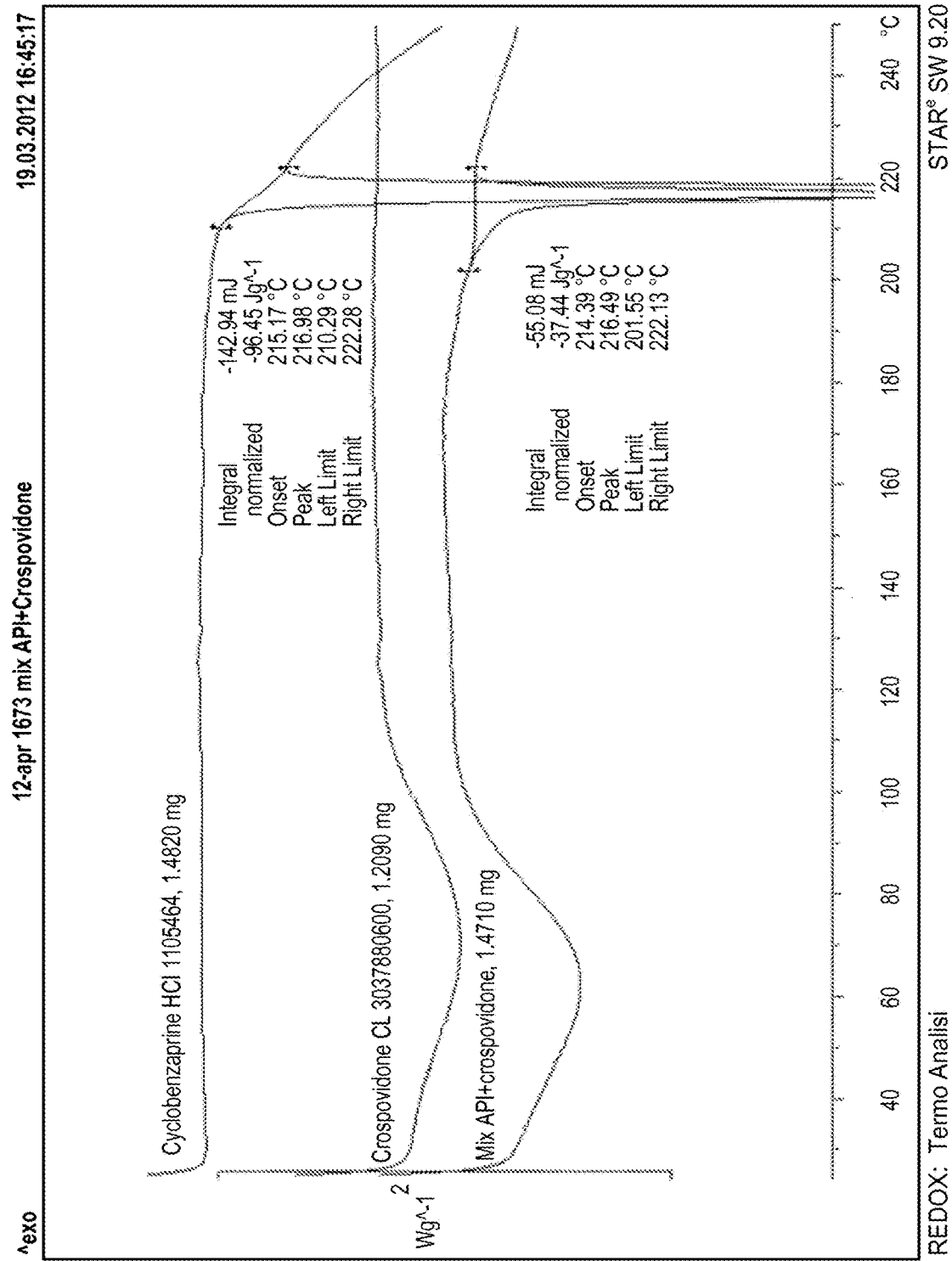
FIG. 6: DSC heating curve of Cyclobenzaprine HCl+ Crospovidone (Kollidon CL) 1:1.

In a 1:1 mixture of Cyclobenzaprine HCl and Crospovidone (Kollidon CL), the release of imbibition water was recorded between 30° C. and 110° C., followed by the melting/decomposition of API between 210° C. and 223° C. (onset at 214.4° C., ΔH=−37.4 J/g) (FIG. 6). No interaction was detected.

Figure 7:
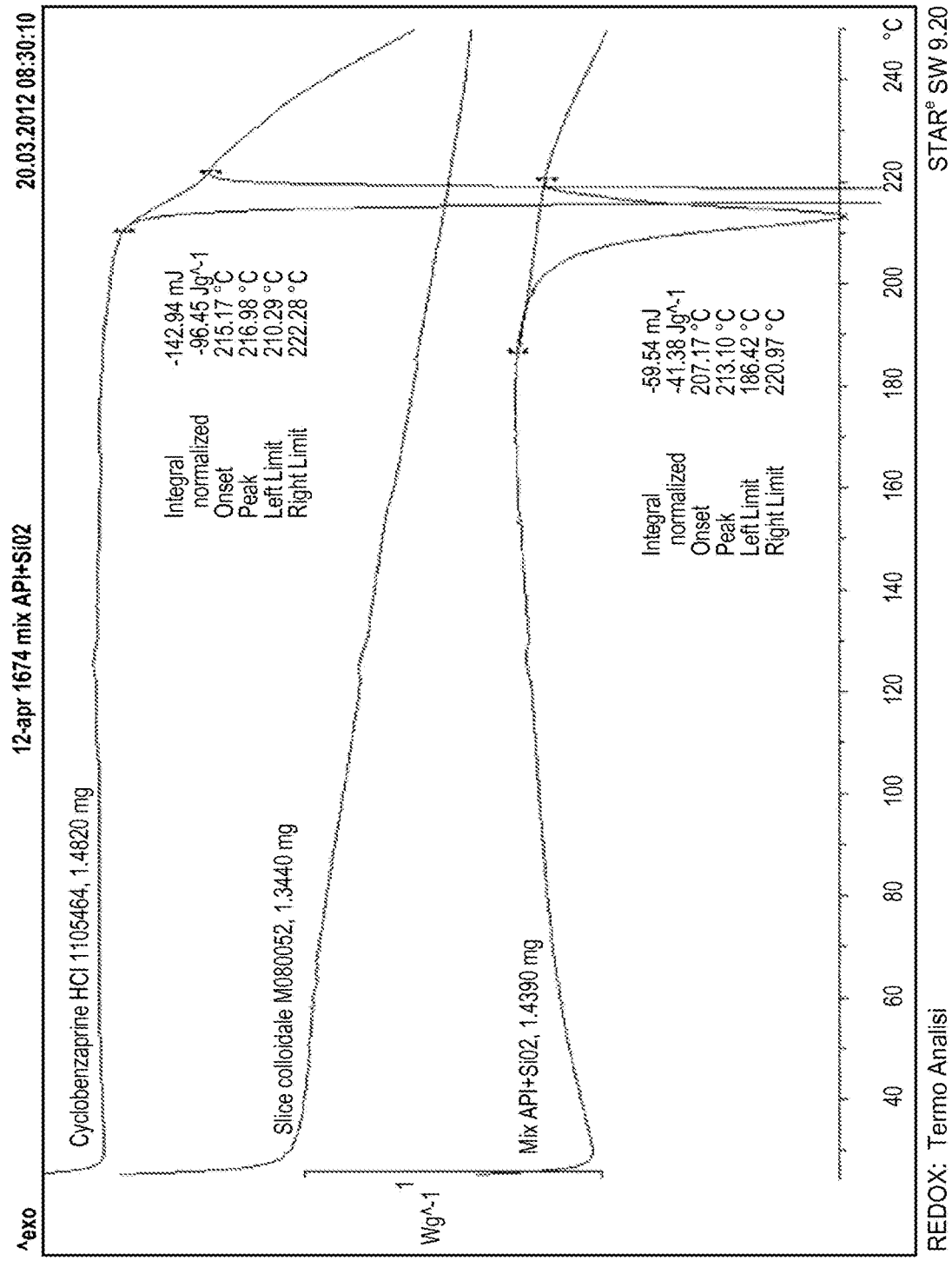
FIG. 7: DSC heating curve of Cyclobenzaprine HCl+ Silicon (colloidal) 1:1.

In a 1:1 mixture of Cyclobenzaprine HCl and Silicon (colloidal), the API melting/decomposition peak was recorded between 186° C. and 221° C. (onset at 207.2° C., ΔH=−41.4 J/g) (FIG. 7). No interaction was detected, only a lowering of the degree of crystallinity.

Figure 8:
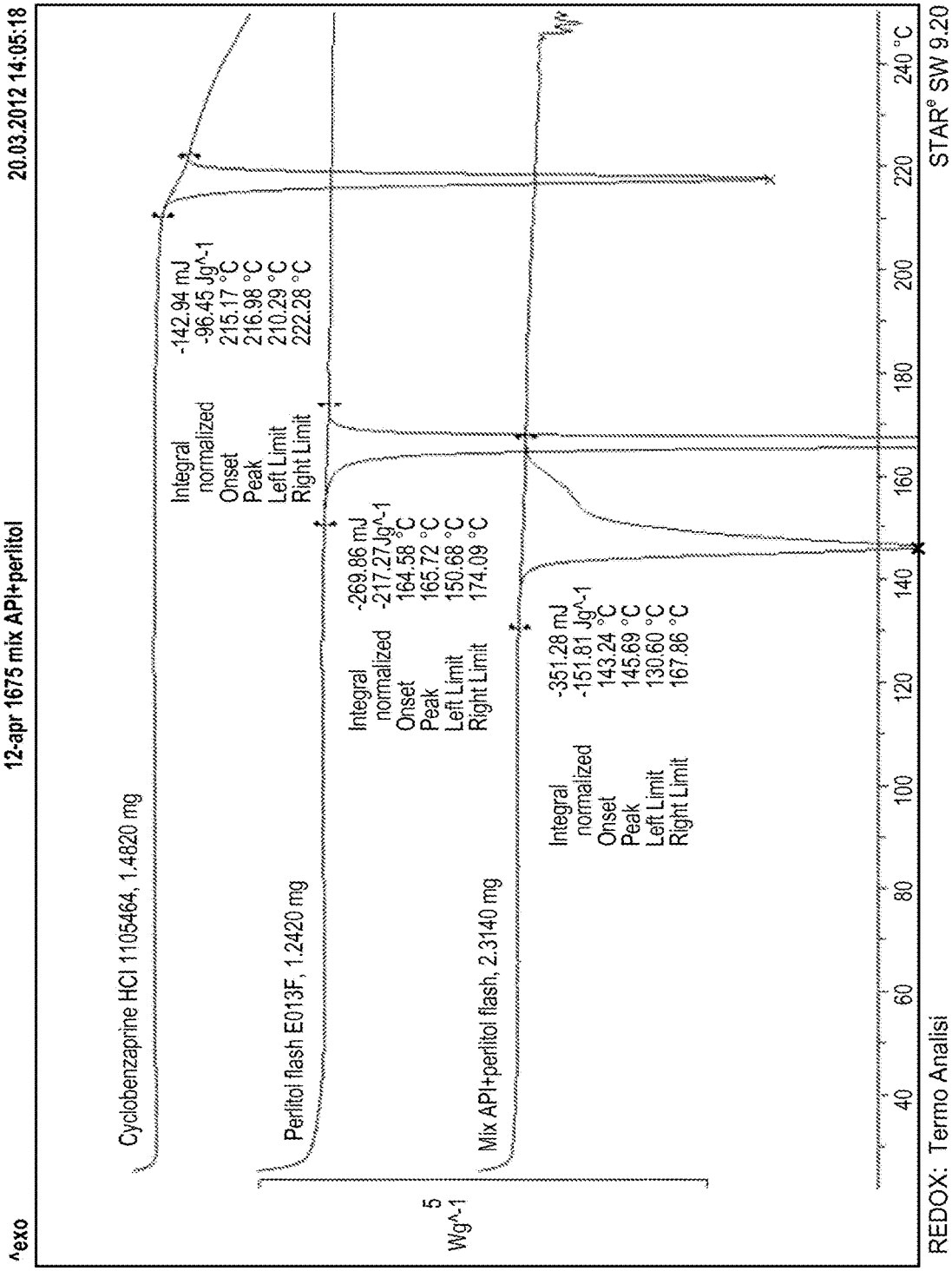
FIG. 8: DSC heating curve of Cyclobenzaprine HCl+ Pearlitol Flash® 1:1.

In a 1:1 mixture of Cyclobenzaprine HCl and Pearlitol Flash®, a physical complex interaction peak (eutectic) was surprisingly observed in the range of 130° C. to 168° C. (onset at 143.2° C., ΔH=−151.8 J/g) (FIG. 8). No API transition melting was detected, only a physical complex fusion at lower temperatures.

Figure 9:
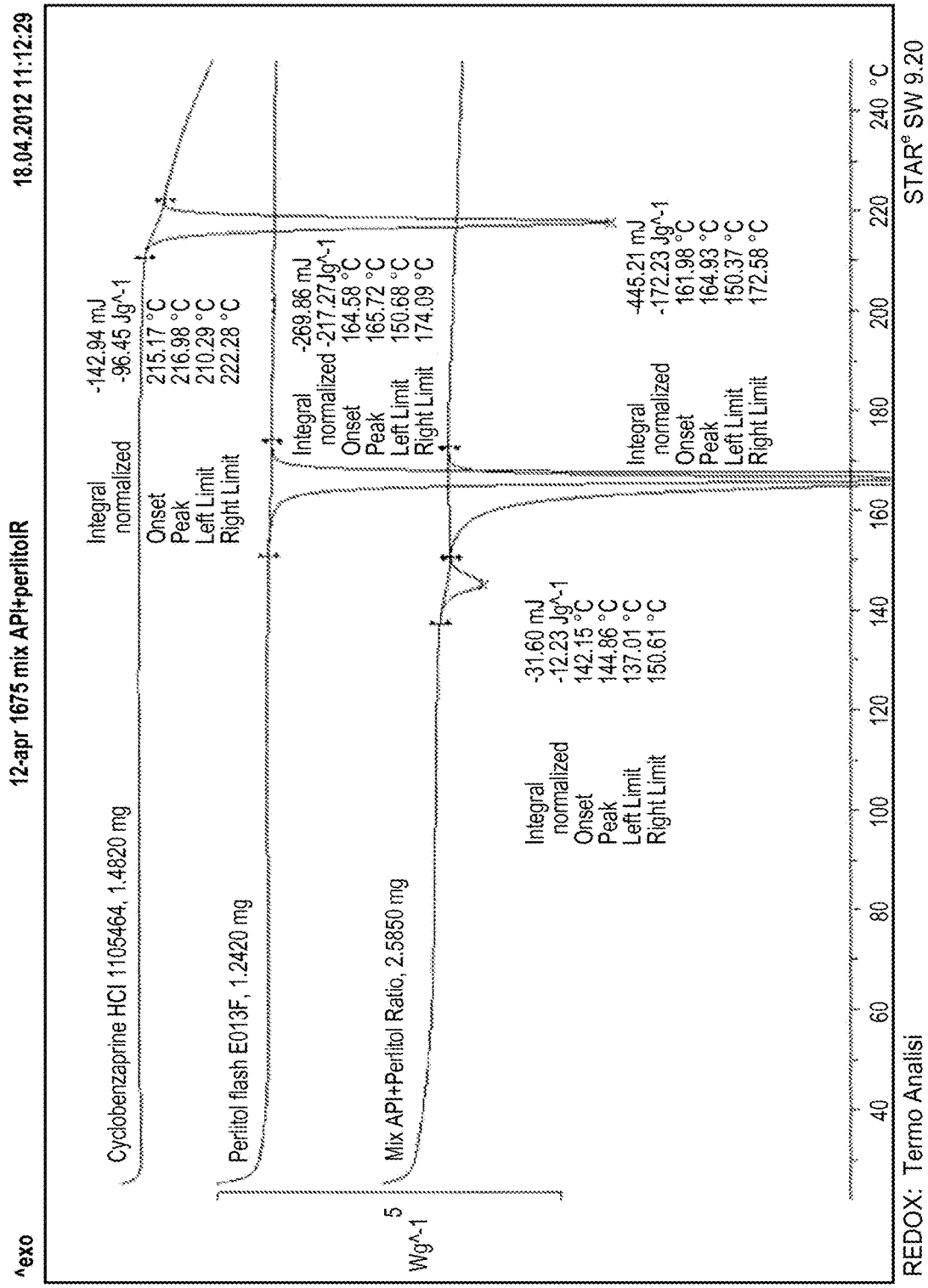
FIG. 9: DSC heating curve of Cyclobenzaprine HCl+ Pearlitol Flash®, formulation ratio.

In the formulation mixture, because the ratio is about 13:1 Pearlitol®:API, the melting peak of Pearlitol® was detected between 150° C. and 173° C. (onset at 162.0° C., ΔH=−172.2 J/g) (FIG. 9), preceded by a small peak at 137° C. to 151° C. (onset at 142.2° C., ΔH=−12.2 J/g) due to the eutectic between the two components. The same behavior was observed in the 1:1 mixture.

Figure 10:
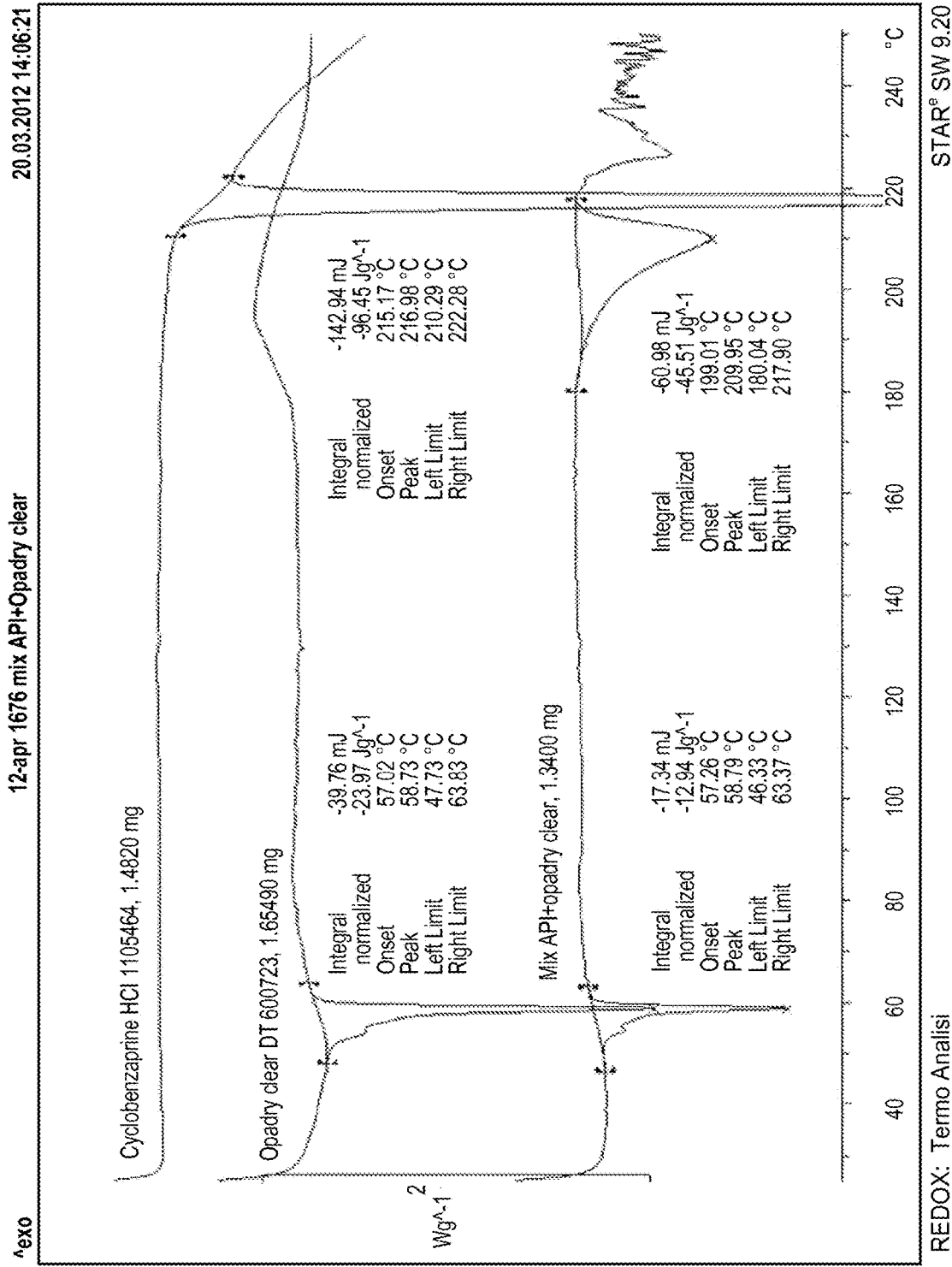
FIG. 10: DSC heating curve of Cyclobenzaprine HCl+ Opadry Clear 1:1.

In a 1:1 mixture of Cyclobenzaprine HCl and Opadry Clear, the PEG transitions were easily visible between 46° C. and 64° C., followed by an API melting/decomposition peak between 180° C. and 218° C. (onset at 199.0 ° C., ΔH=−45.5 J/g) (FIG. 10). The interaction is due to the melted Opadry.

Figure 11:
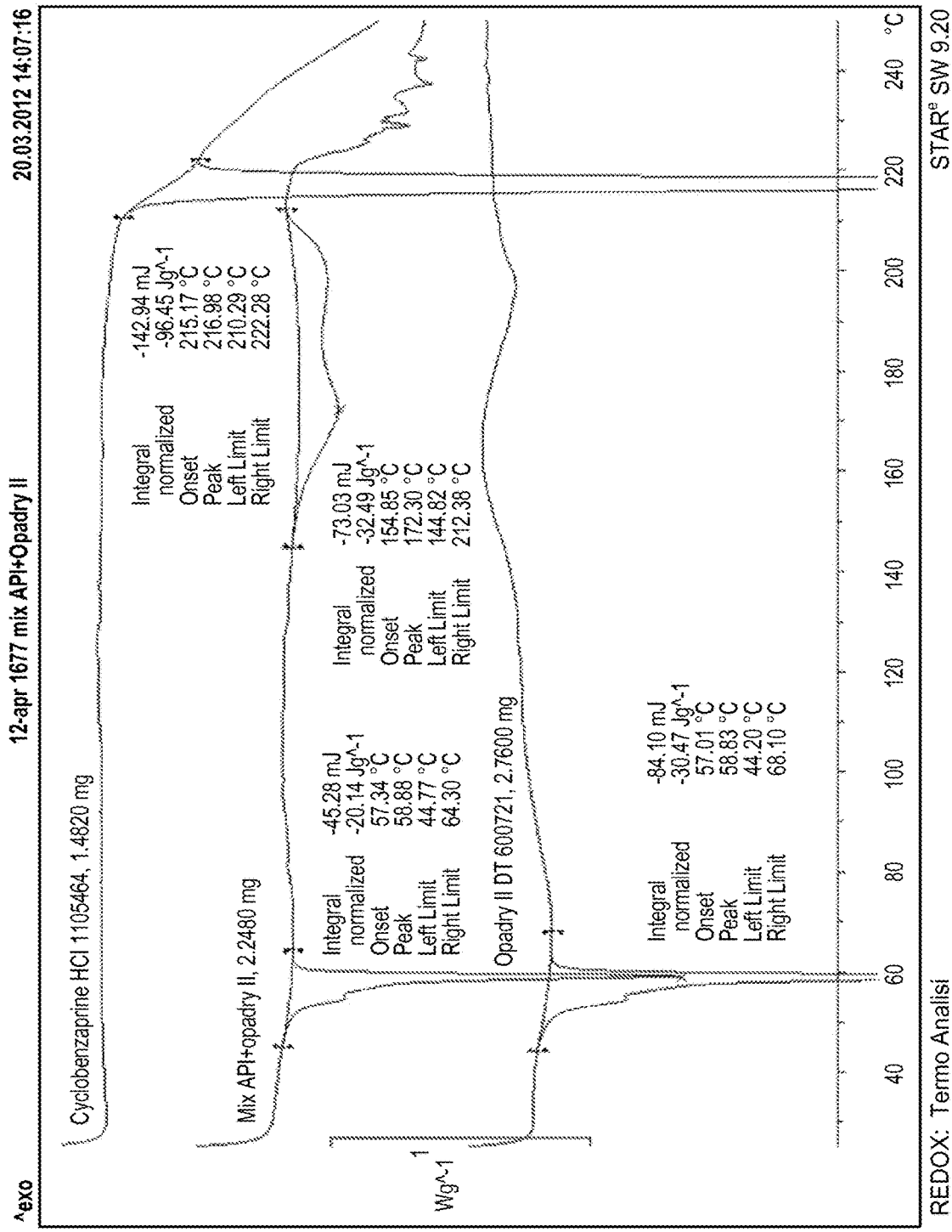
FIG. 11: DSC heating curve of Cyclobenzaprine HCl+ Opadry II Clear 1:1.

In a 1:1 mixture of Cyclobenzaprine HCl and Opadry II Clear, the PEG transitions were easily visible between 44° C. and 65° C., followed by the interaction peak between PVA (Polyvinyl Alcohol) and API, in the range of 44° C. to 213° C. (onset at 154.9° C., ΔH=-32.5 Jig) (FIG. 11) that could be due to the partial solubilization of the API by the excipients.

Figure 12:
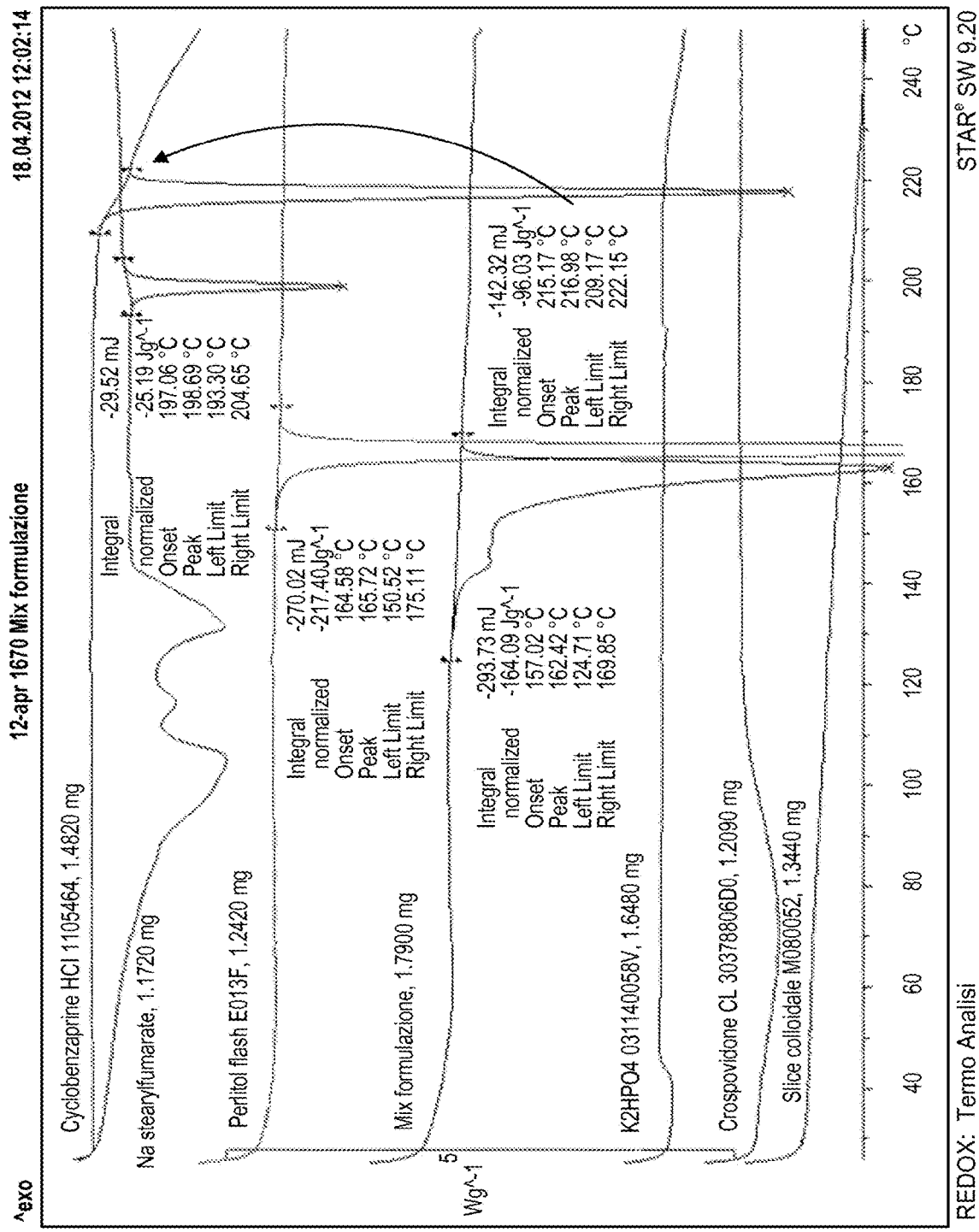
FIG. 12: DSC heating curve relative to final, formulation mixture.

In the formulation mixture, only one thermal event was recorded between 124° C. and 170° C. (onset at 157.0° C., ΔH=-164.1 Jig) (FIG. 12). The event was cause by Pearlitol Flash® which, due to its amount, covered all the other transitions. Moreover, the API with Pearlitol gave a eutectic (physical interaction at the solid state) that was detected at 142° C. This physical interaction can stabilize the formula and prevent other interactions with excipients (e.g., Opadry I, Opadray II, and $K_2HPO_4$).

Figure 13:
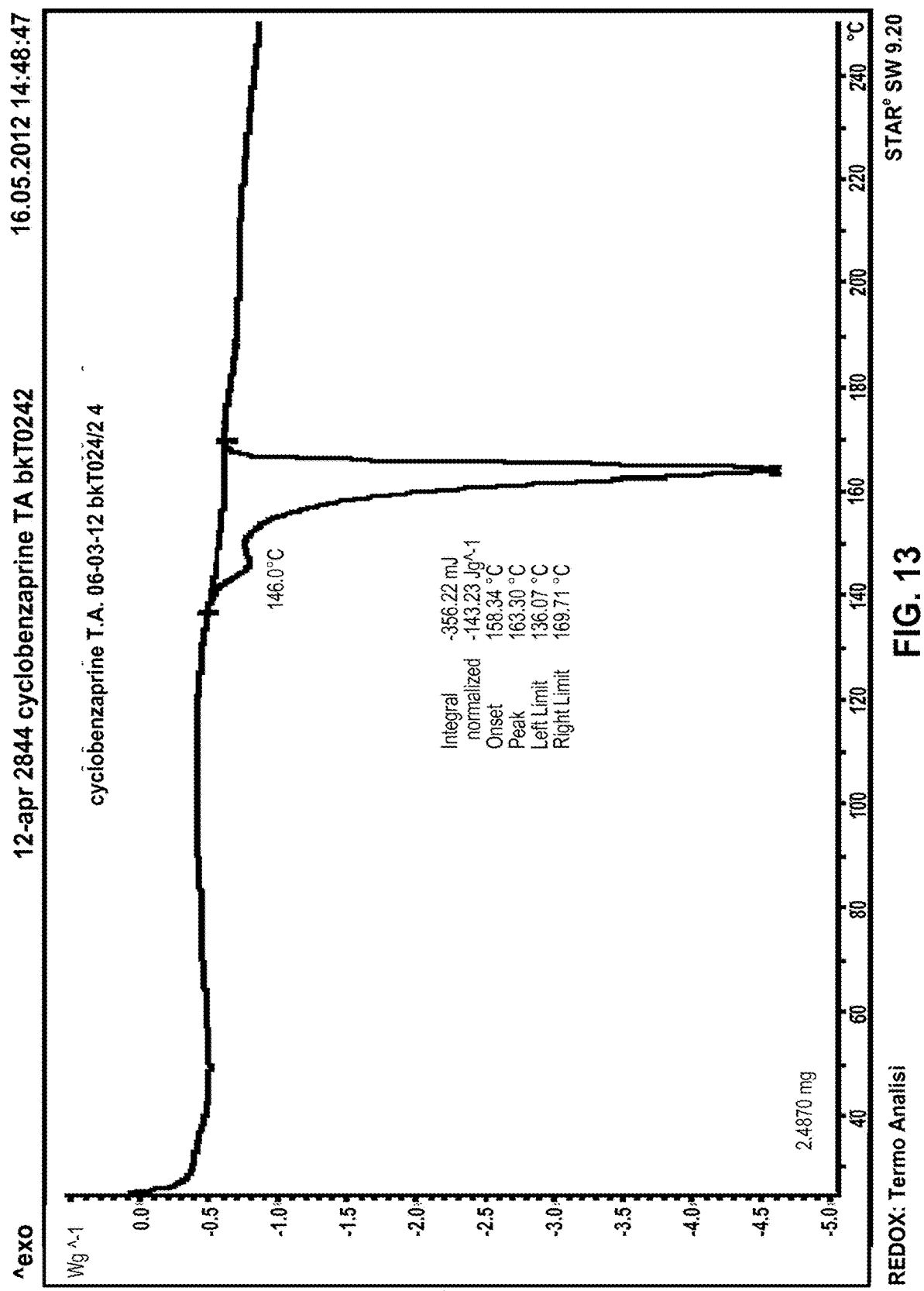
FIG. 13: DSC heating curve relative to the tablet at time zero of Cyclobenzaprine HCl.

To evaluate the interaction between the API and the excipient, thermal investigations were conducted on a tablet stored for 1 month at 40° and 50° C. The data recorded were compared with the thermal profile of the same batch analyzed at time zero. Two thermal events for Cyclobenzaprine HCl were recorded: a first of a small entity at 146.0° C., and a second between 136° C. and 170° C. (onset at 158.3° C., ΔH=-143.2 J/g) (FIG. 13), mainly due to melting of Pearlitol flash.

Figure 14:
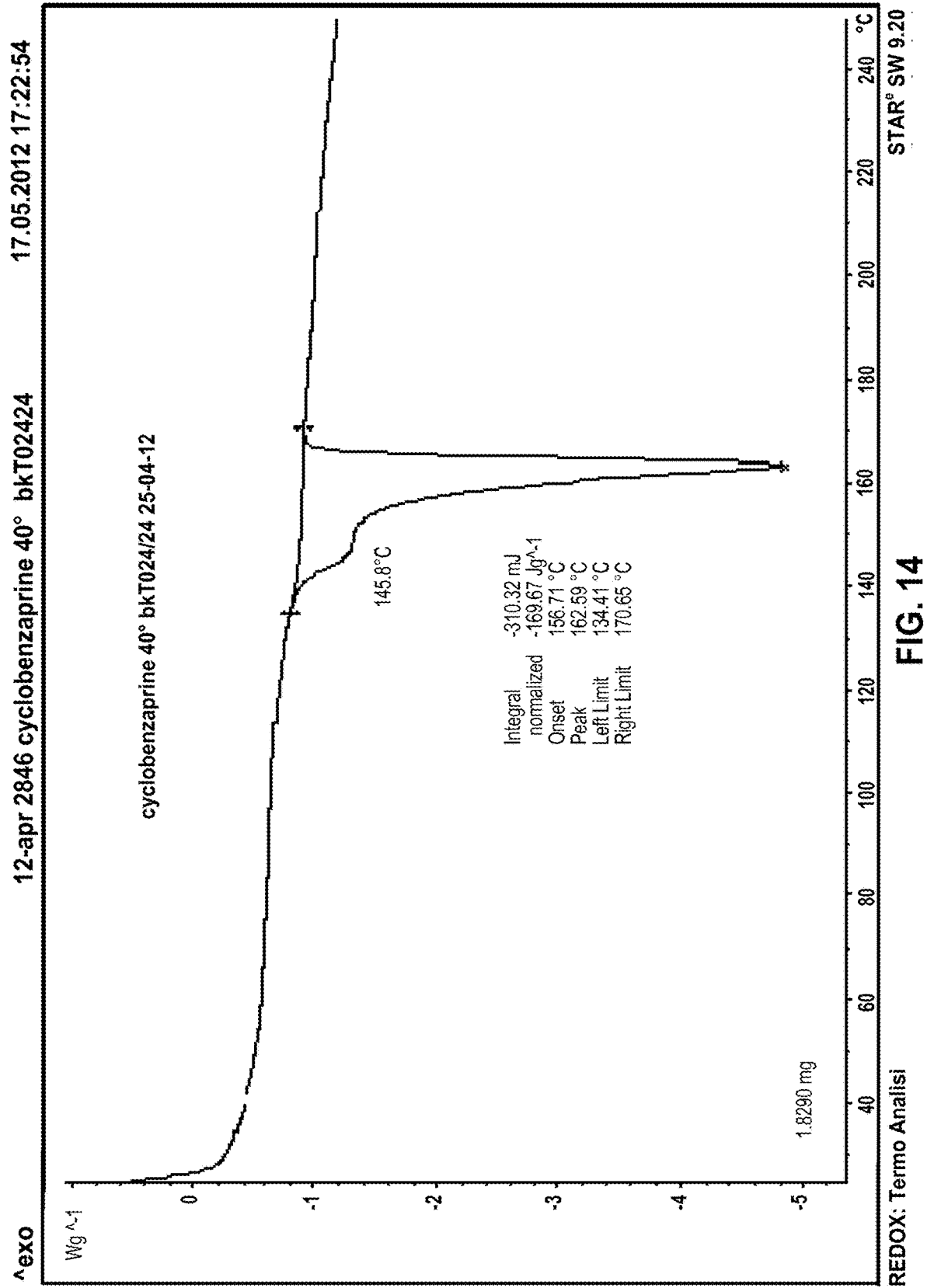
FIG. 14: DSC heating curve relative to the tablet of Cyclobenzaprine HCl at 40° C.
Figure 15:
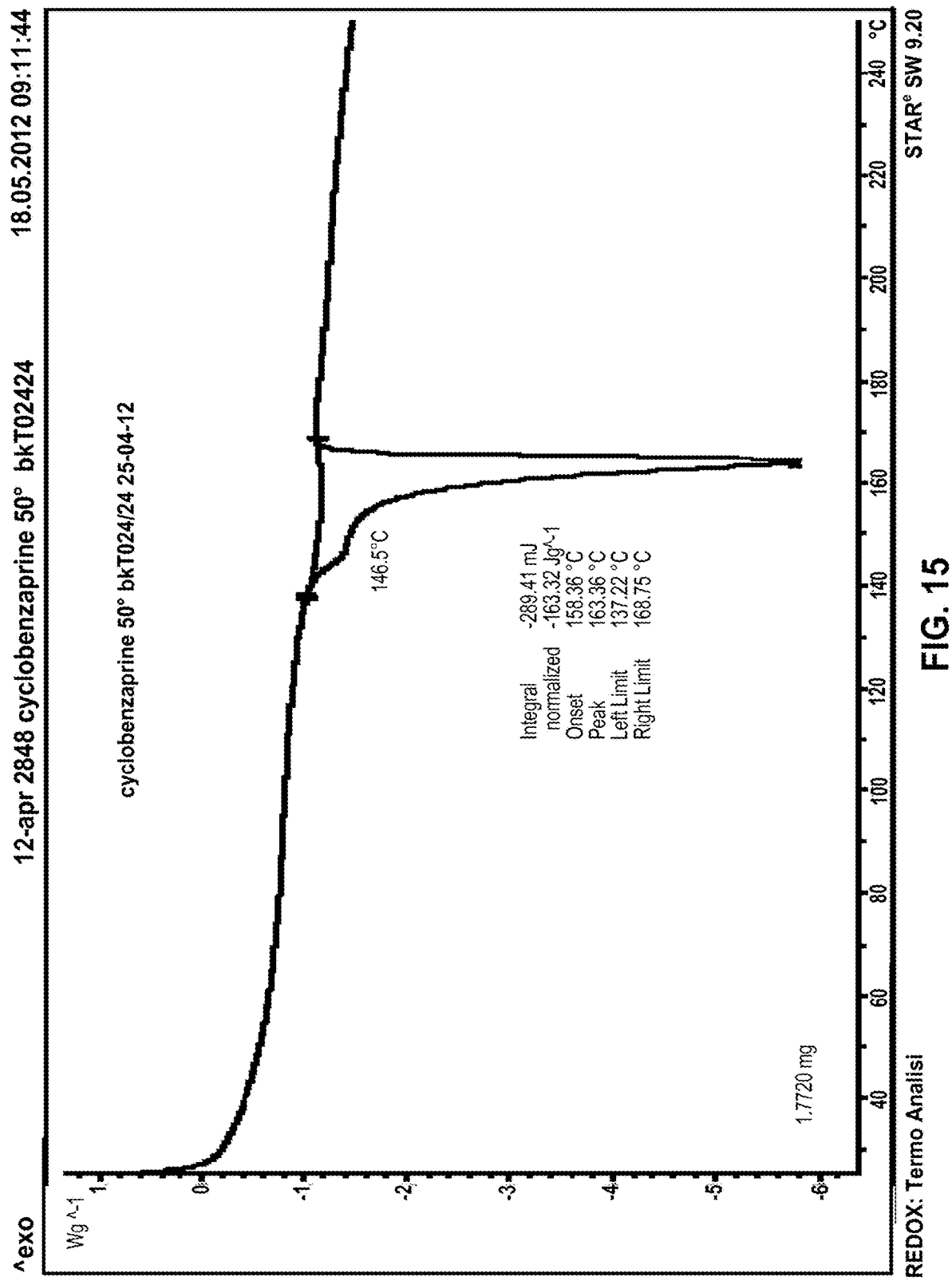
FIG. 15: DSC heating curve relative to tablet Cyclobenzaprine HCl after storage at 50° C.

Two thermal events were recorded for Cyclobenzaprine HCl at 40 ° C.: the first one of small entity at 145.8° C., and the second between 134° C. and 171° C. (onset at156.7° C., ΔH=-169.7 J/g) (FIG. 14), mainly due to melting of Pearlitol Flash®. Two thermal events also were recorded for Cyclobenzaprine HCl at 50° C.: the first one of small entity at 146.5° C., and the second between 137° C. and 179 ° C. (onset at 158.4° C., ΔH=-163.3 J/g) (FIG. 15), mainly due to melting of Pearlitol Flash®. The thermal behaviors recorded were similar, and no interactions were observed in the tablet after storage at 40° C. and 50° C. The interaction recorded for the binary mixtures was no longer observed, likely due to the dilution of the API by the Pearlitol Flash® excipient and reduced contact between API and the lubricant sodium stearyl fumarate.

In summary, different types of interaction were observed among the excipients and the API. A physical interaction was observed with Sodium Stearyl fumarate, especially in the 1:1 ratio, likely due to partial API solubilization or reactions at the particles' surfaces between the $Cl^-$ and $Na^+$ counter ions. In the formulation ratio, this incompatibility disappears. Even in a formulation tested for stability at 40° C. and 50° C. for one month, this interaction was not seen. A chemical (acid-base) interaction was observed with Potassium phosphate bibasic, both in 1:1 and in formulation ratios. No interaction was observed with Silicon (colloidal) and Kollidon. A eutectic interaction was observed with Pearlitol Flash®, due to the presence of mannitol. In the formulation ratio (about 13:1 excipient:API), the thermal transition of the API was completely shifted by excipient complex formation (eutectic). The interaction with Opadry Clear is small and is due to PEG contributions that preceded the API Transition. The interaction with Opadry II Clear is evident and could be due to the presence of PVA (Polyvinyl Alcohol) that partially solubilizes the API. Table 1 summarizes the observations of the various excipients with Cyclobenzaprine HCl API.

TABLE 1

Excipient reactions with API

| Excipient | Mixture 1:1 | Mixture in formulation ratio |
|---|---|---|
| Sodium stearyl fumarate | Physical interaction | No interaction |
| Potassium phosphate dibasic | Acid-base interaction | Low chemical interaction |

TABLE 1-continued

Excipient reactions with API

| Excipient | Mixture 1:1 | Mixture in formulation ratio |
|---|---|---|
| Crospovidone (Kollidon CL) | No | ND |
| Silicon (colloidal) | No | ND |
| Pearlitol Flash ® | Eutectic | Eutectic |
| Opadry Clear | Chemical (small) | ND |
| Opadry II Clear | Chemical | ND |

ND: Not determined

Example 2

As described above, thermal analytical techniques were further used to assess the compatibility of a drug product (tablet) containing Cyclobenzaprine HCl (API). The compatibility assessment was carried out between the API and additional excipients in a 1:1 ratio. The 1:1 API-excipient mixtures were formed in two different ways: first, by mixing only, and second, by strong milling in an agate mortar. The thermal behavior recorded in the two different mixtures were compared with those of the single components. On the basis of thermal events recorded for each component and for the mixtures, the analyses were carried out by investigating the meanings of the peaks recorded by differential scanning calorimetry (DSC) in mixtures between the API and the excipients. Furthermore, in order to define the nature of the interaction, the Fourier Transform Infra Red Spectroscopy with Total Attenuated Reflectance (FT-IR/ATR) and X-ray powder diffraction (XRPD) of some samples (API, excipient, and mixed and milled mixtures) was carried out and compared.

The following raw materials were used:
Cyclobenzaprine HCl
Di Sodium phosphate anhydrous
Di Sodium phosphate dihydrate
Di Sodium phosphate heptahydrate
Trisodium citrate dihydrate
Effersoda®
Sorbitol
Mannitol
Mix API+Di Sodium phosphate anhydrous
Mix API+Di Sodium phosphate dihydrate
Mix API+Di Sodium phosphate heptahydrate
Mix API+Trisodium citrate dihydrate
Mix API+Effersoda®
Mix API+Sorbitol
Mix API+Mannitol
Trisodium citrate anhydrous
Disodium Glycine Carbonate
Mix API+Trisodium citrate anhydrous
Mix API+Disodium Glycine Carbonate Aliquots of API and each excipient were weighed in a ratio of 1:1 and ground in an agate mortar. Then, the homogeneous mixtures were analyzed. These sample mixtures were labeled "B", while the mechanical-only mixtures were labeled "A."

Differential Scanning Calorimetry (DSC)
The DSC heating curves were obtained by TA 821 DSC Mettler instrument under the following conditions:
Heating rate: 10° C./min
Ambient: Nitrogen 30 mL/min
Sample holder: normal open aluminum pan
Temperature range: from 25° C. to 250° C.
Instrument calibration: Indium sample purity 99.999%
Fourier Transform Infra Red Spectroscopy with Total Attenuated Reflectance (FT-IR/ATR)

The FT-IR spectra were collected with a Perkin Elmer spectrum Two instrument with air as background and 4 cm$^{-1}$ resolution.

X-Ray Powder Diffraction (XRPD)

X-ray powder diffraction (XRPD) tests were performed with the ULTIMA IV instrument (Rigaku), laying the sample on a static sample holder. The X-ray focusing slit has a variable width, interlocked with the q value. The X-ray tube has a Copper target, with a current intensity of 40 mA and a voltage of 40 kV. Radiation was generated by the Cockcroft-Walton method, and was constituted by $K_{\alpha 1}$ (1.540562 Å) and $K_{\alpha 2}$ (1.544398 Å). The analytical conditions were:

Fixed Time; sampling width 0.02 deg, scanning rate 1.3 s/step, 2 q range 3.35 deg and sample holder; amorphous glass equiangular 9200/2G, 0.2 mm deep. The sample was pressed with a glass plate.

Figure 16:
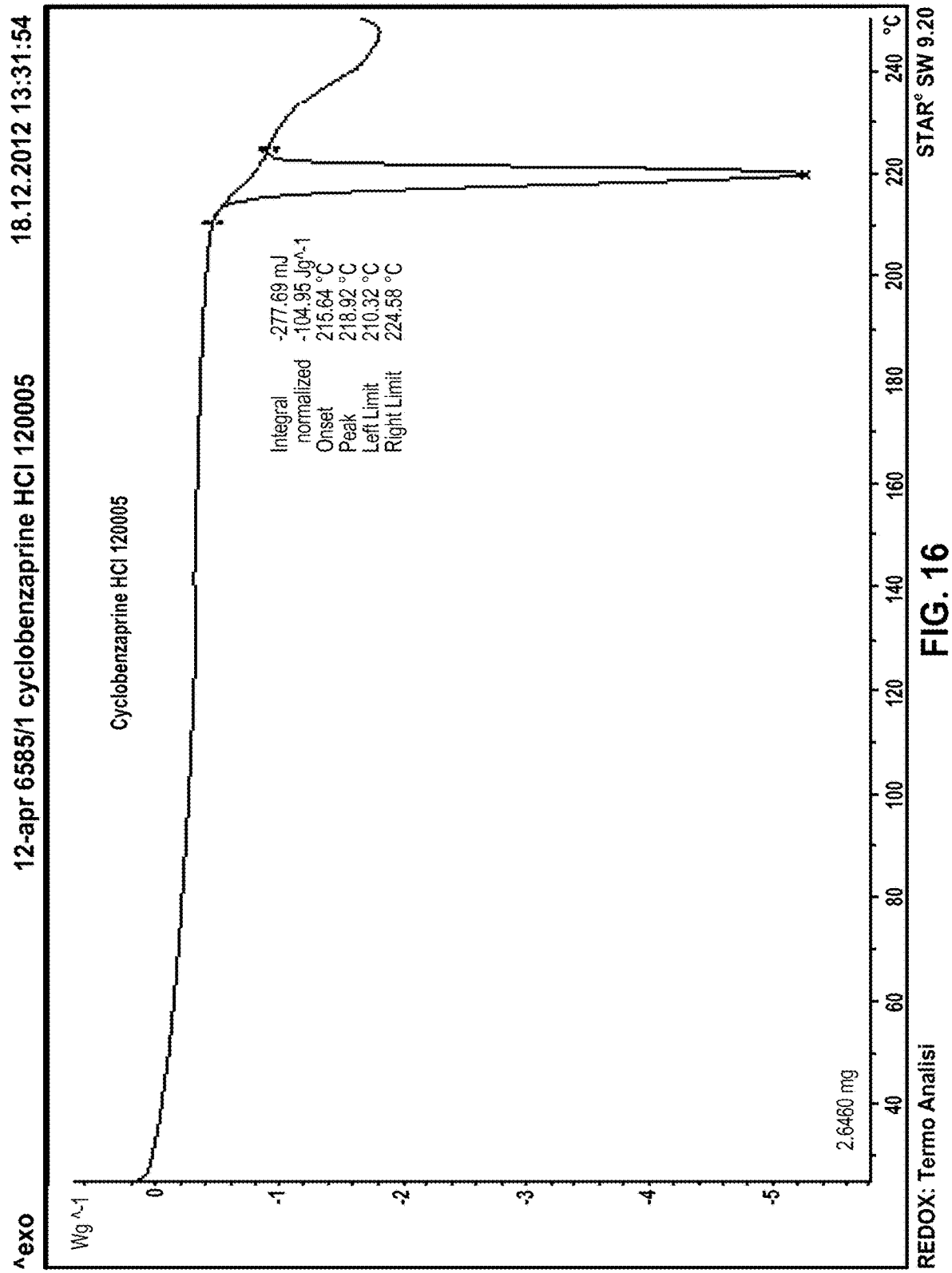
FIG. 16: DSC heating curve of Cyclobenzaprine HCl.
Figure 17:
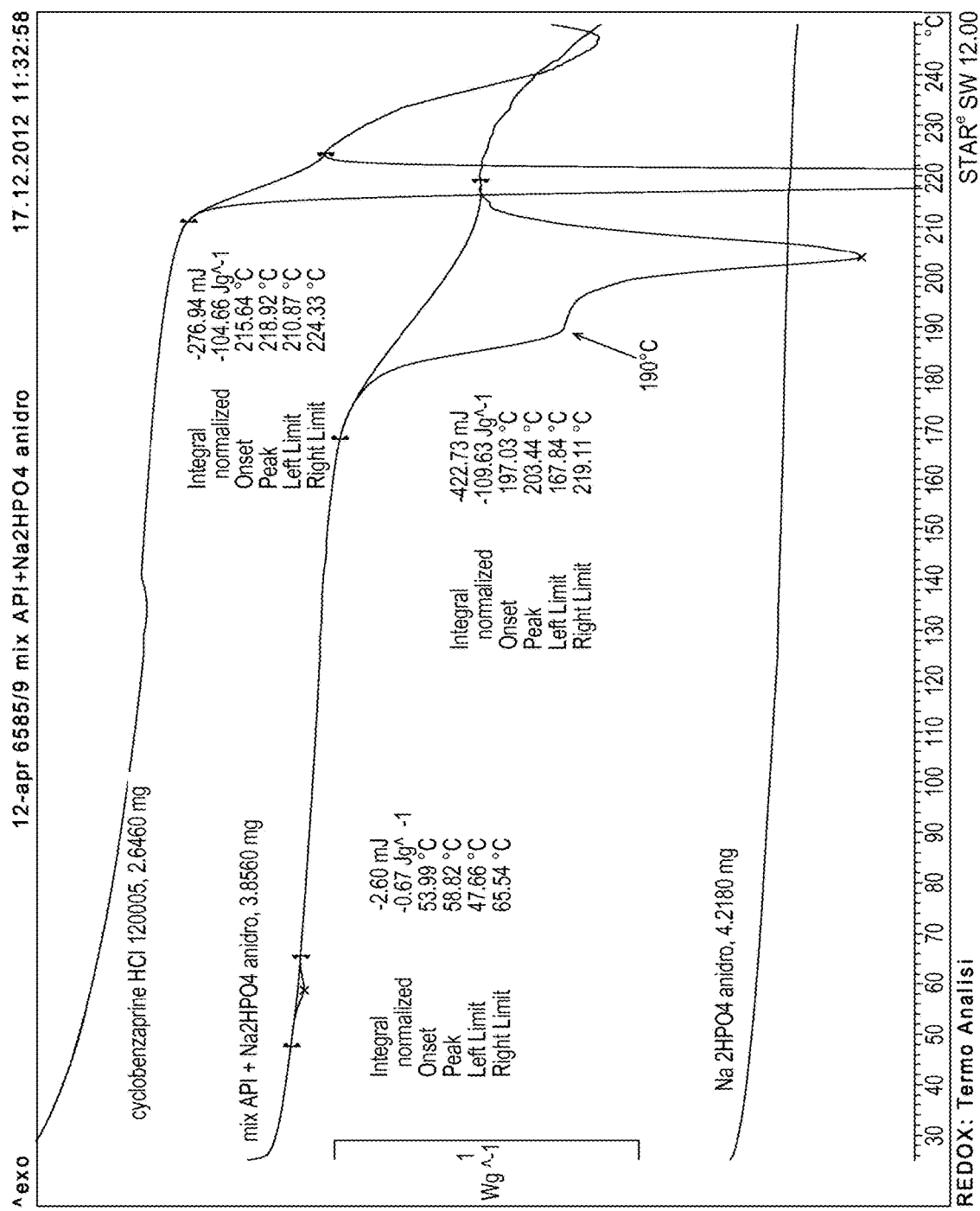
FIG. 17: DSC heating curve of Cyclobenzaprine HCl+ Sodium phosphate anhydrous 1:1 (mixture A).
Figure 18:
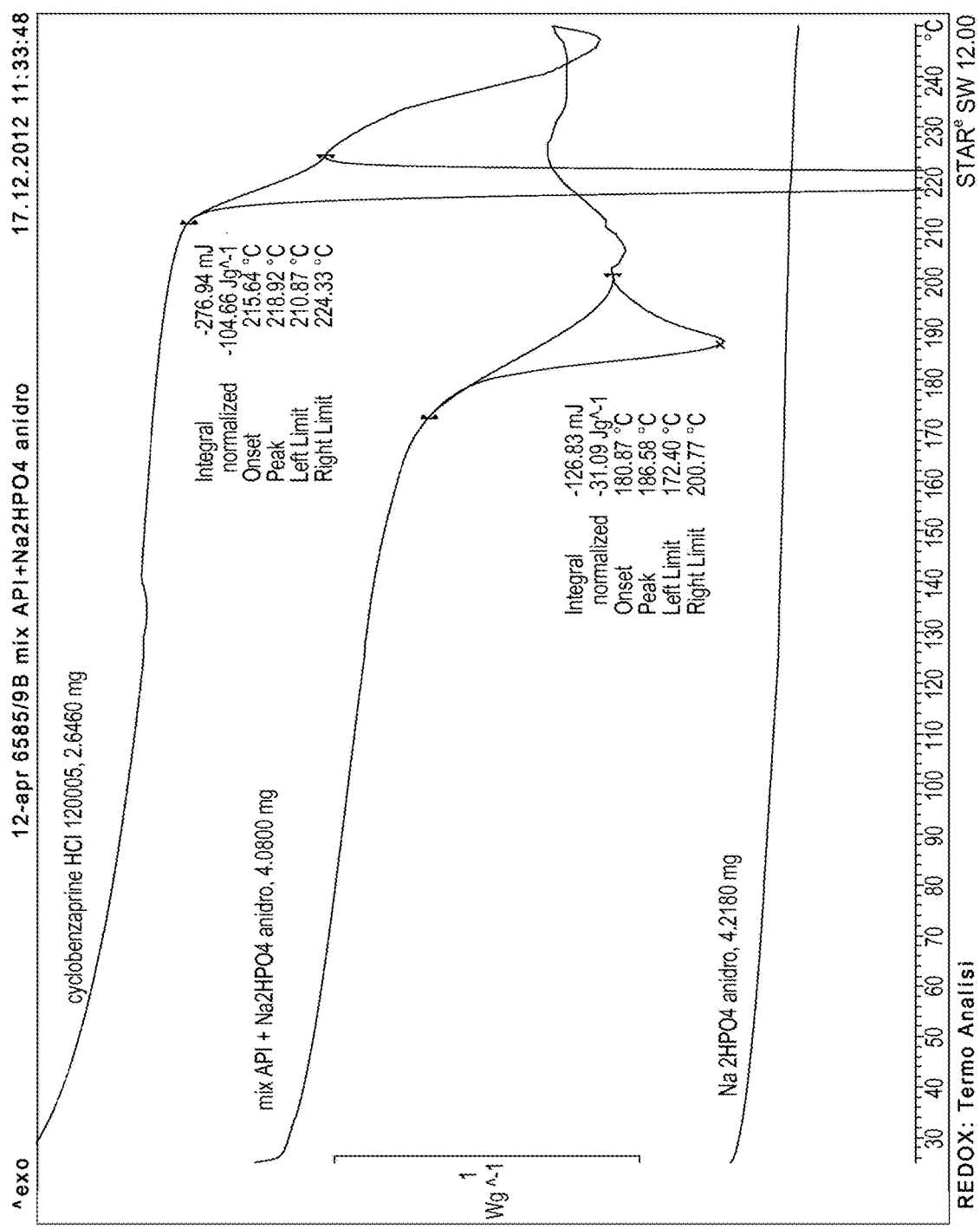
FIG. 18: DSC heating curve of Cyclobenzaprine HCl+ Sodium phosphate anhydrous 1:1 (mixture B).
Figure 19:
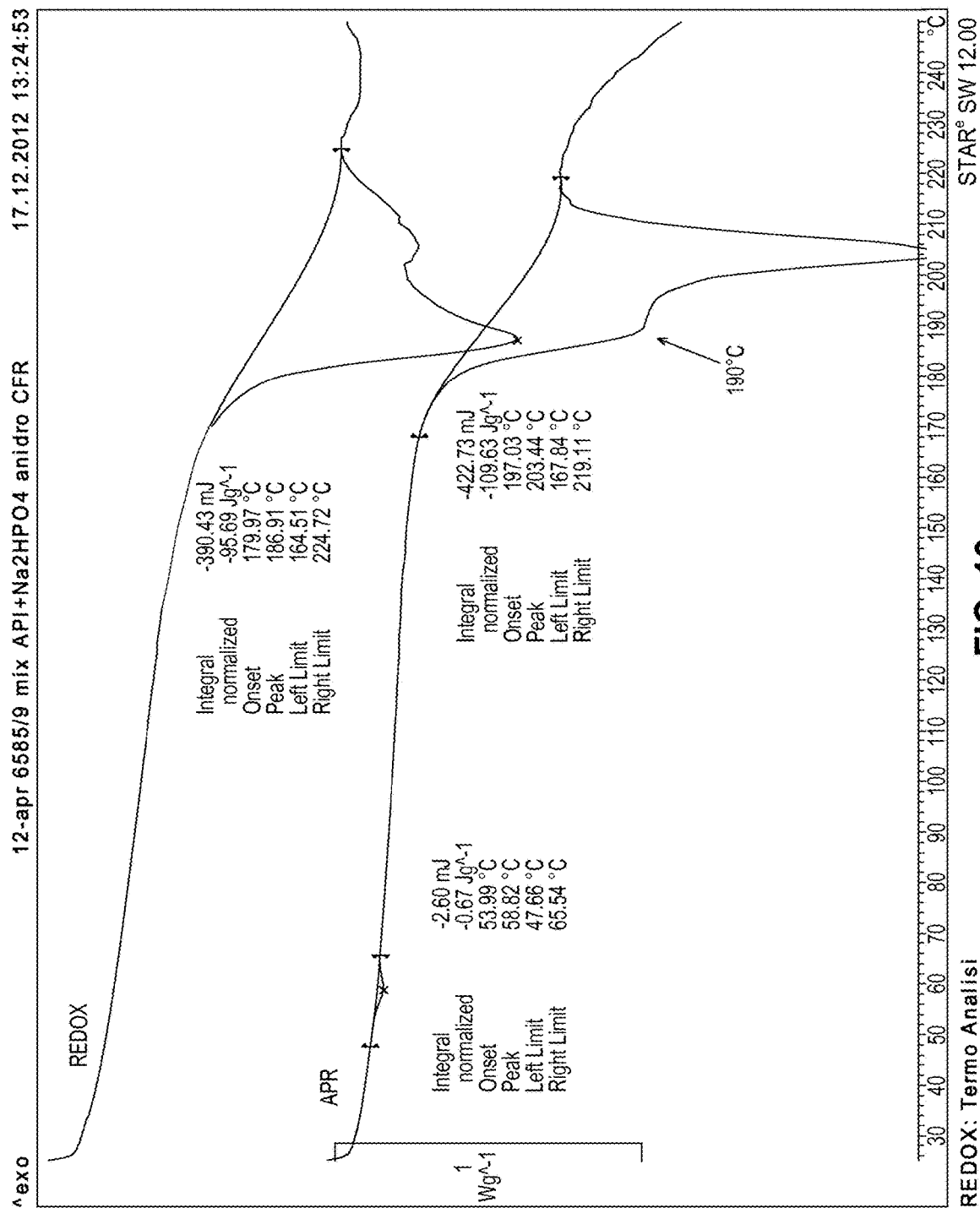
FIG. 19: Comparison of DSC heating curves of Cyclobenzaprine HCl+Sodium phosphate anhydrous 1:1 (mixture A & B).

Decomposition of Cyclobenzaprine HCl with melting was detected between 210° C. and 225° C. (onset at 215.6° C., ΔH=−105.0 J/g) (FIG. 16). The DSC heating curves of the mixtures in comparison with the API and excipients (mixtures A and B) were then analyzed. The interaction peak for a 1:1 Cyclobenzaprine HCl—sodium phosphate anhydrous mixture (mixture A) was recorded in the range of 167° C. to 220° C. (onset at 197.0° C., ΔH =−109.6 J/g). A physical interaction was observed and characterized by the lowering of API melting (FIG. 17). The interaction peak for a 1:1 Cyclobenzaprine HCl—sodium phosphate anhydrous mixture (mixture B) was recorded in the range of 172° C. to 201° C. (onset at 180.9° C., ΔH=−31.1 J/g). A physical interaction was observed (FIG. 18). By comparing the mixtures A and B, it is evident that the interaction is presented more in the milled mixture (FIG. 19).

Figure 20:
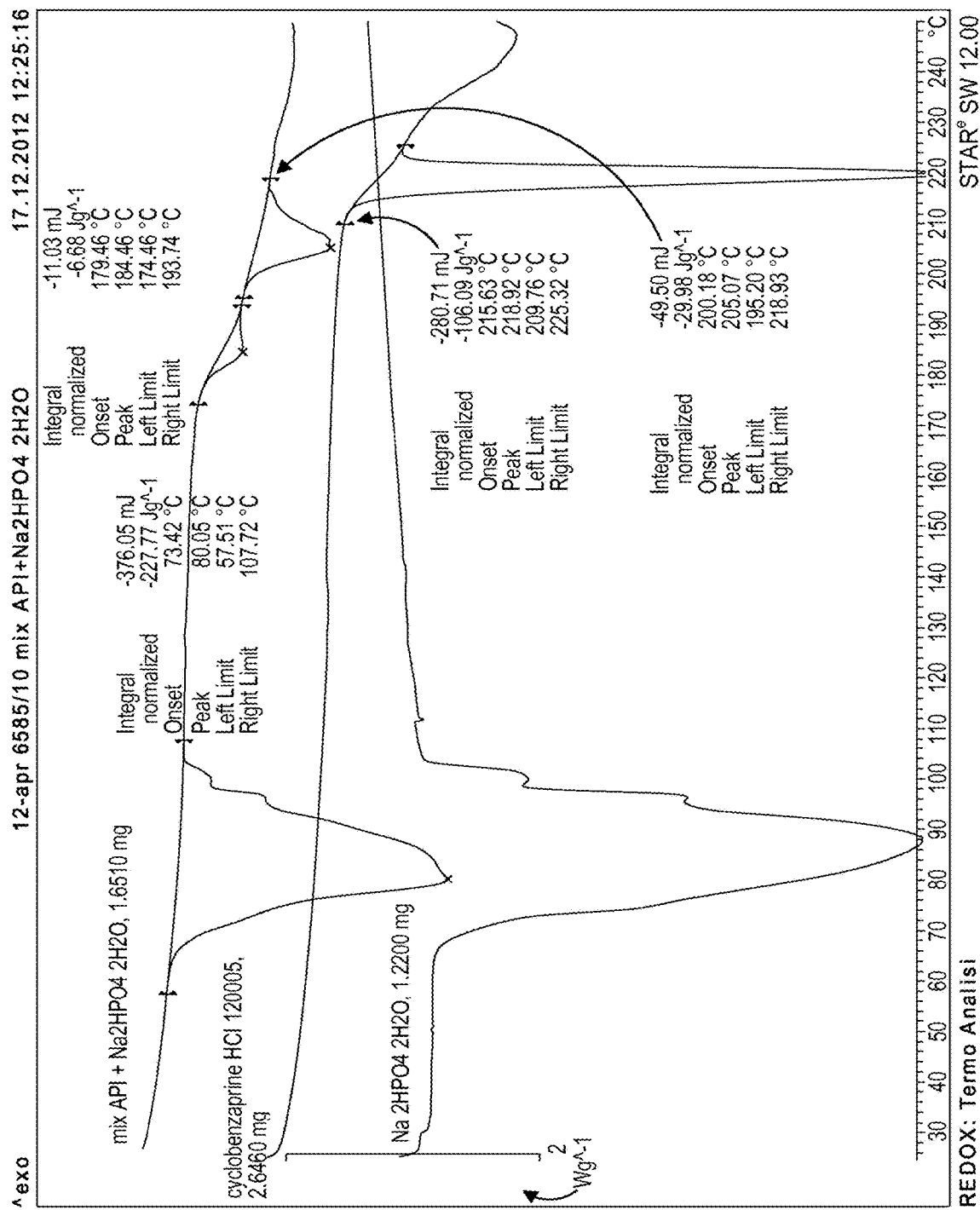
FIG. 20: DSC heating curve of Cyclobenzaprine HCl+Sodium phosphate dihydrate 1:1 (mixture A).
Figure 21:
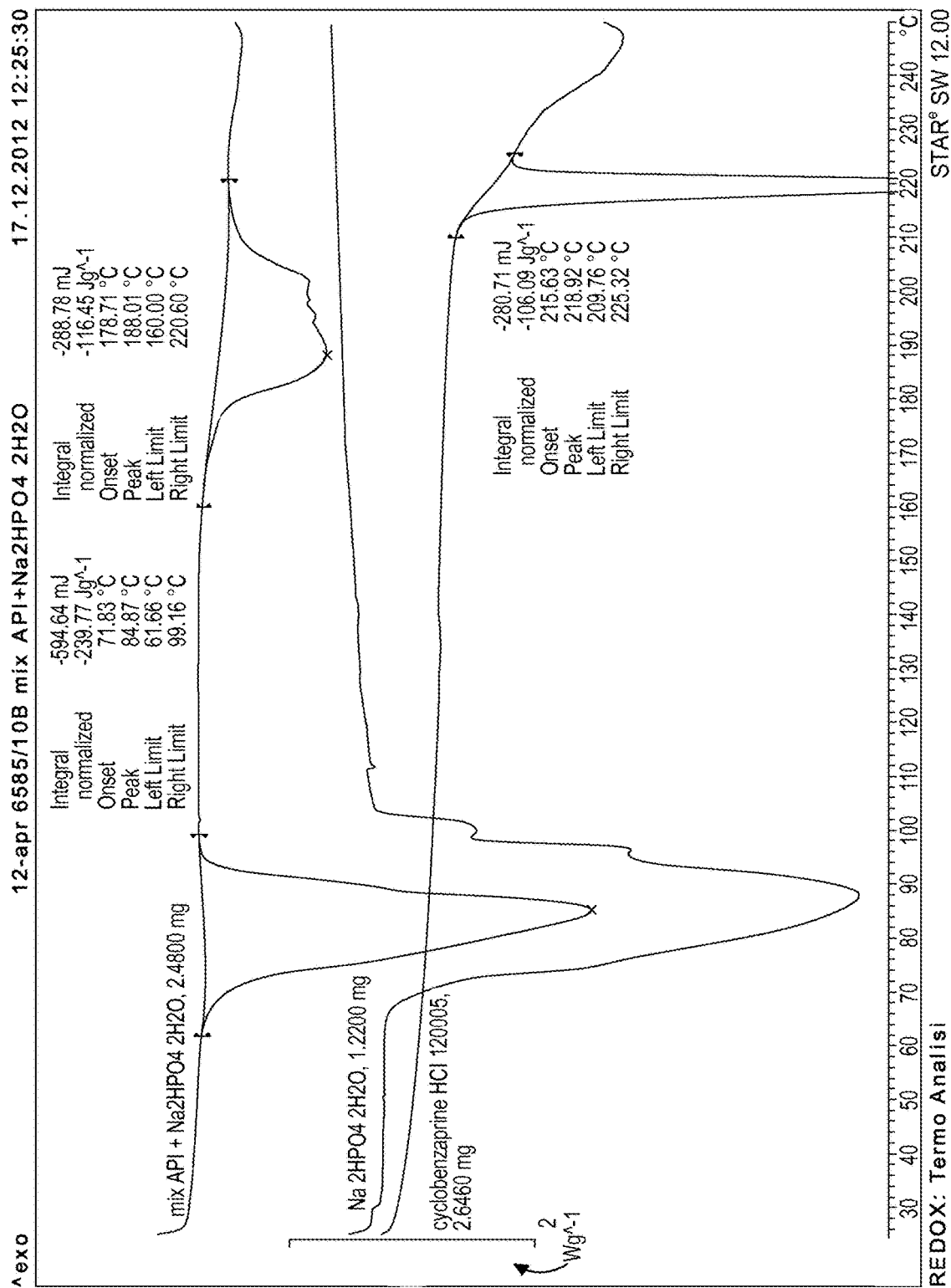
FIG. 21: DSC heating curve of Cyclobenzaprine HCl+Sodium phosphate dihydrate 1:1 (mixture B).
Figure 22:
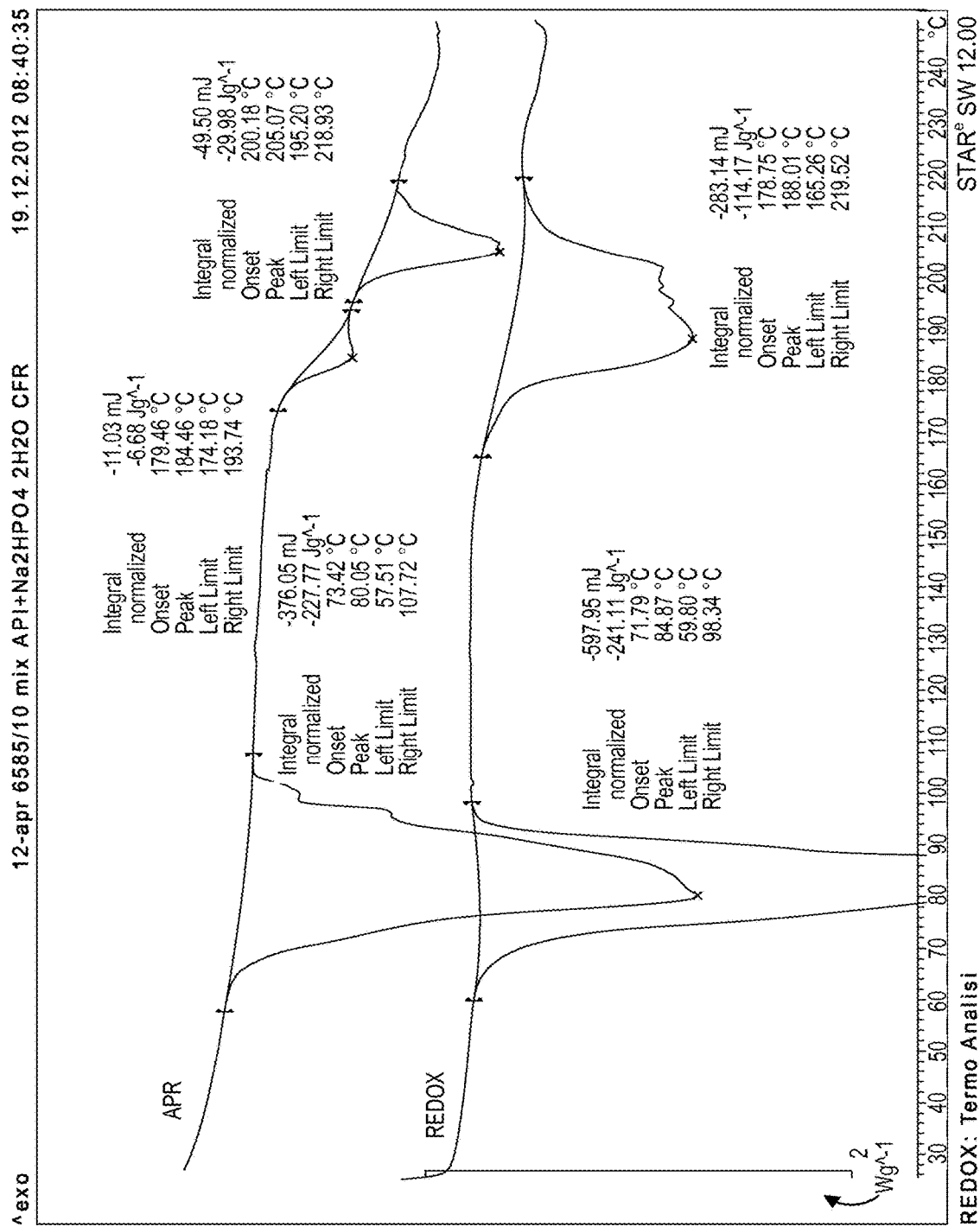
FIG. 22: Comparison of DSC heating curves of Cyclobenzaprine HCl+Sodium phosphate dihydrate 1:1 (mixture A & B).

The release of crystallization water from sodium phosphate in a 1:1 mixture of Cyclobenzaprine HCl and sodium phosphate dihydrate (mixture A) was observed between 57° C. and 108° C. (onset at 73.4° C., ΔH=−227.8 J/g), followed by the interaction peak in the range of 174° C. to 220° C. (FIG. 20). This effect was composed by two small effects: a physical interaction and partial solubilization. Few peaks on the plot were observed, likely due to release of small amount of water in a melted matrix. The release of crystallization water in a 1:1 mixture of Cyclobenzaprine HCl and sodium phosphate dihydrate (mixture B) was recorded between 61° C. and 100° C. (onset at 71.8° C., ΔH=−239.8 J/g), followed by the interaction peak in the range of 160° C. to 221° C. (onset at 178.7° C., ΔH=−116.5 J/g) (FIG. 21). A physical interaction was observed. FIG. 22 shows a comparison between mixtures A and B. The interaction is more evident in the milled mixture. The water present in the excipient can modify the mixture and reduce the API stability.

Figure 23:
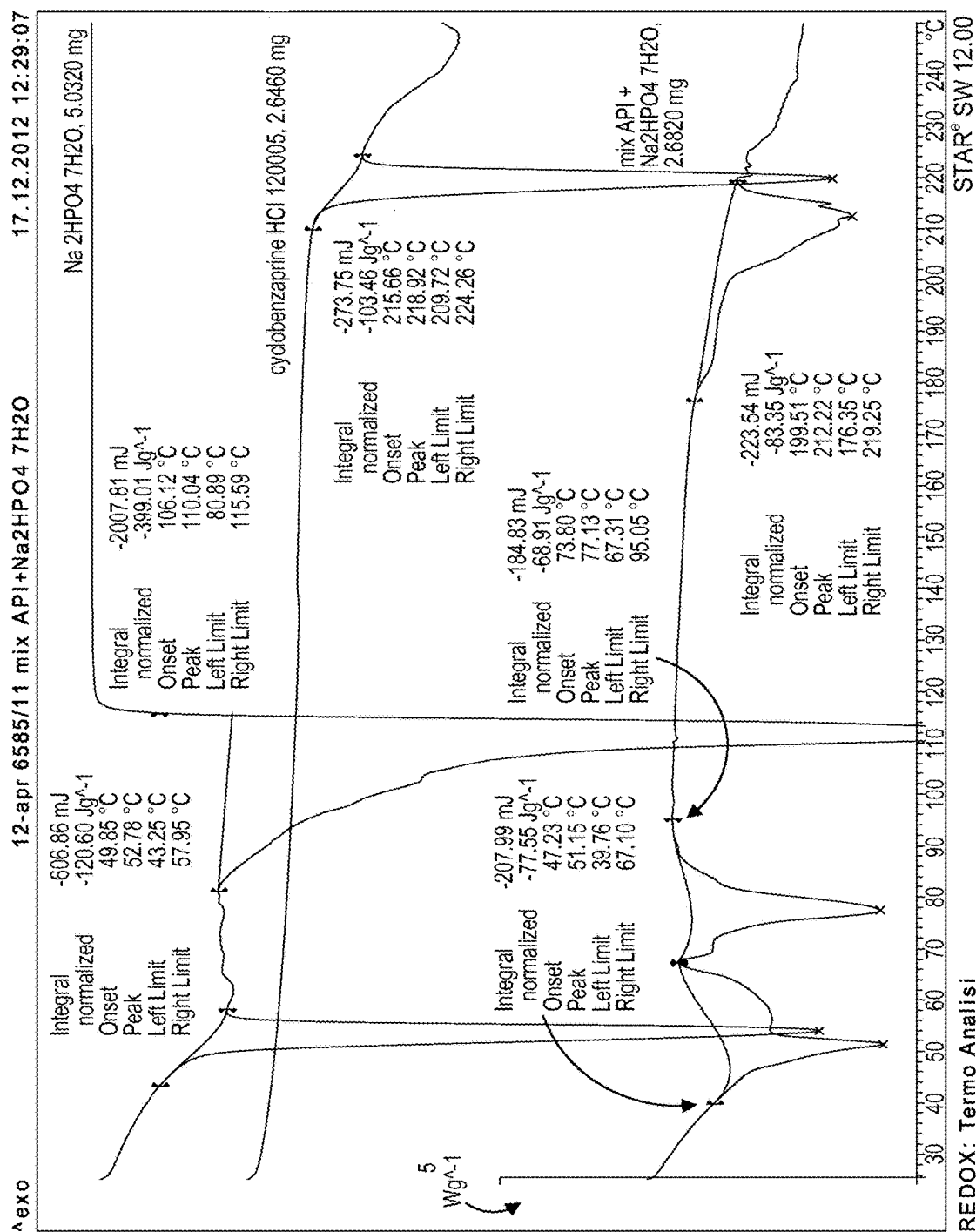
FIG. 23: DSC heating curve of Cyclobenzaprine HCl+Sodium phosphate heptahydrate 1:1 (mixture A).

The release of crystallization water in a 1:1 mixture of Cyclobenzaprine HCland sodium phosphate heptahydrate (mixture A) (in two different steps) was recorded between 39° C. and 68° C. (onset at 47.2° C., ΔH=−77.6 J/g) and between 67° C. and 96° C. (onset at 73.8° C., H=−68.9 J/g), followed by the interaction peak in the range of 176° C. to 220° C. (onset at 199.5° C., ΔH=−83.4 J/g) (FIG. 23). With mixture B, crystallization water was released (in two different steps) between 43° C. to 54° C. (onset at 45.9° C., ΔH=−49.6J/g) and between 73° C. and 98° C. (onset at 77.8° C., ΔH=−151.7 J/g), followed by the interaction peak in the range of 174° C. to 215° C. (onset at 174.5° C., ΔH=−55.4

Figure 24:
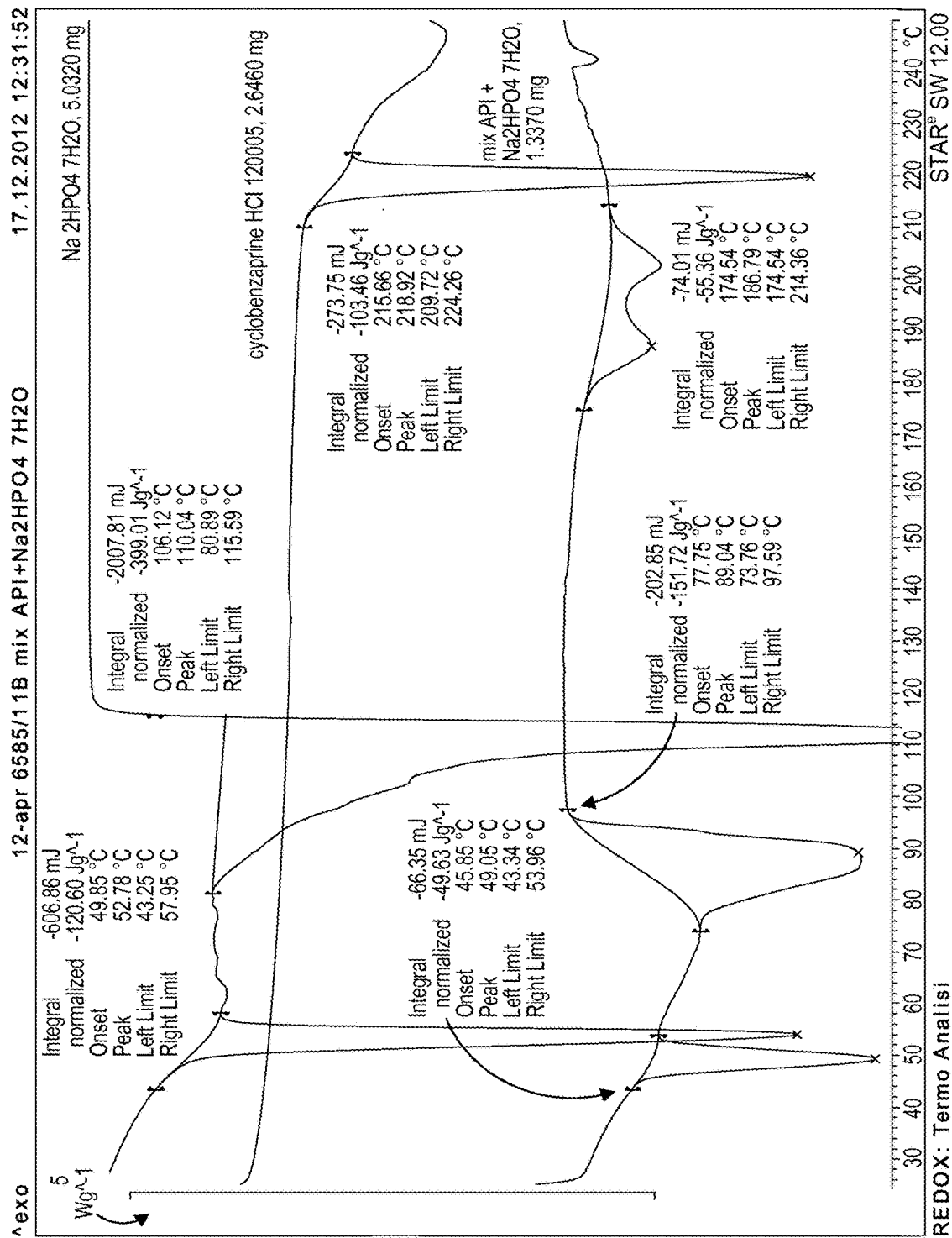
FIG. 24: DSC heating curve of Cyclobenzaprine HCl+Sodium phosphate heptahydrate 1:1 (mixture B).
Figure 25:
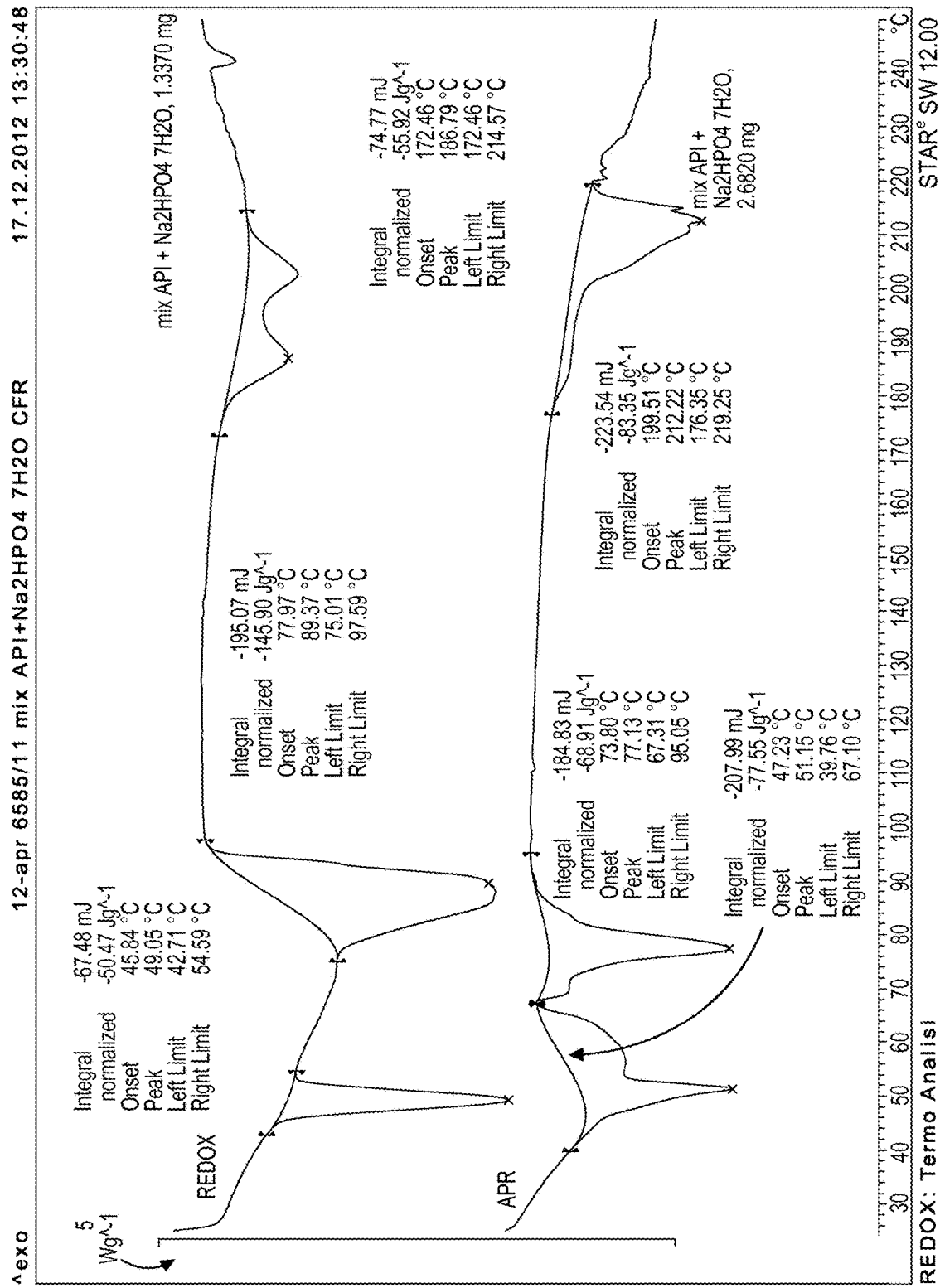
FIG. 25: Comparison of DSC heating curves of Cyclobenzaprine HCl+Sodium phosphate heptahydrate 1:1 (mixture A & B).

J/g) (FIG. 24). FIG. 25 shows a comparison between mixtures A and B. The interaction was anticipated in the milled mixture and showed two events, relating to the interaction peak and to a residual of API. The water present in the excipient induced physical changes of the API, even at low temperatures.

Figure 26:
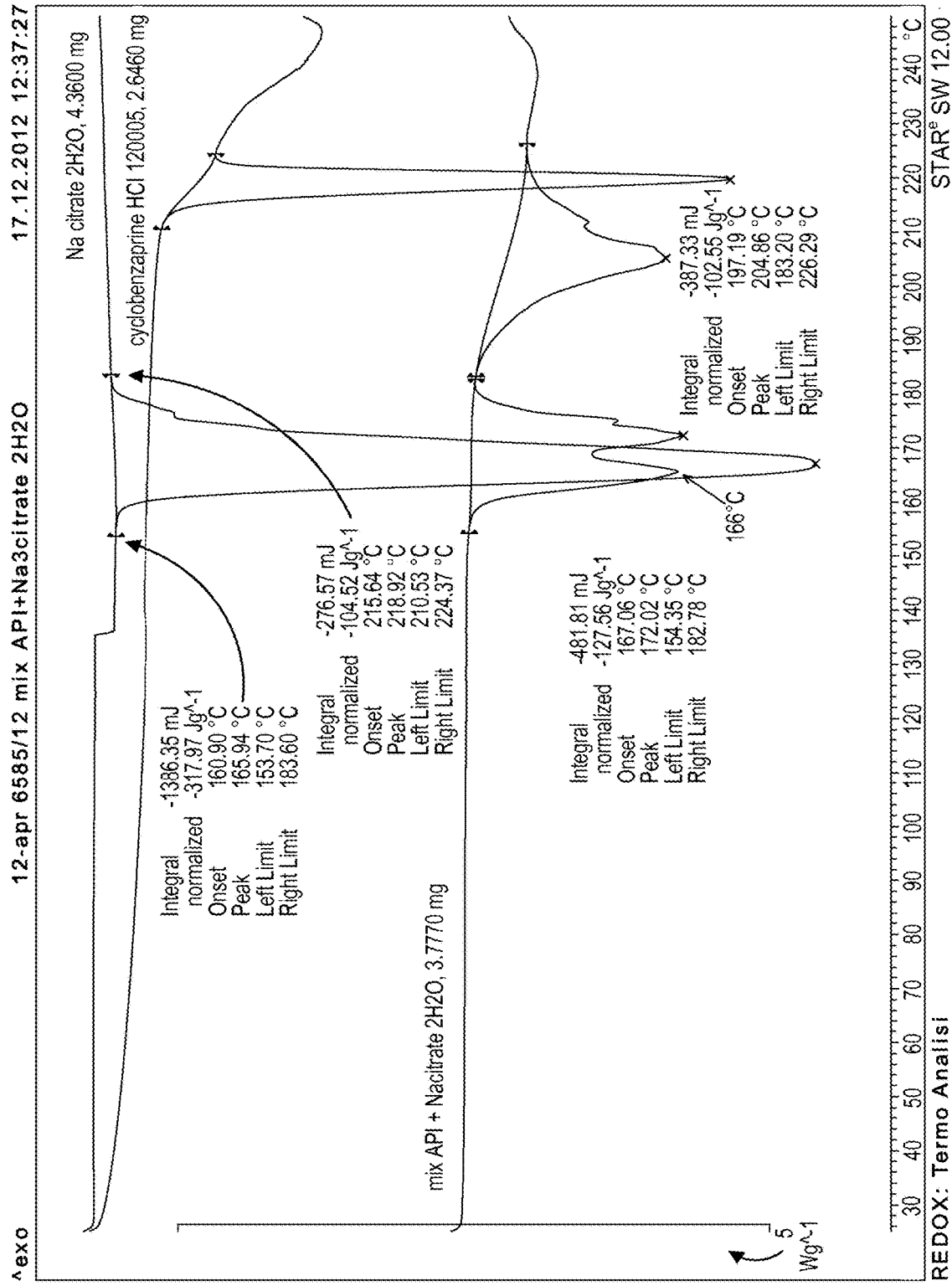
FIG. 26: DSC heating curve of Cyclobenzaprine HCl+Sodium citrate dihydrate 1:1 (mixture A).
Figure 27:
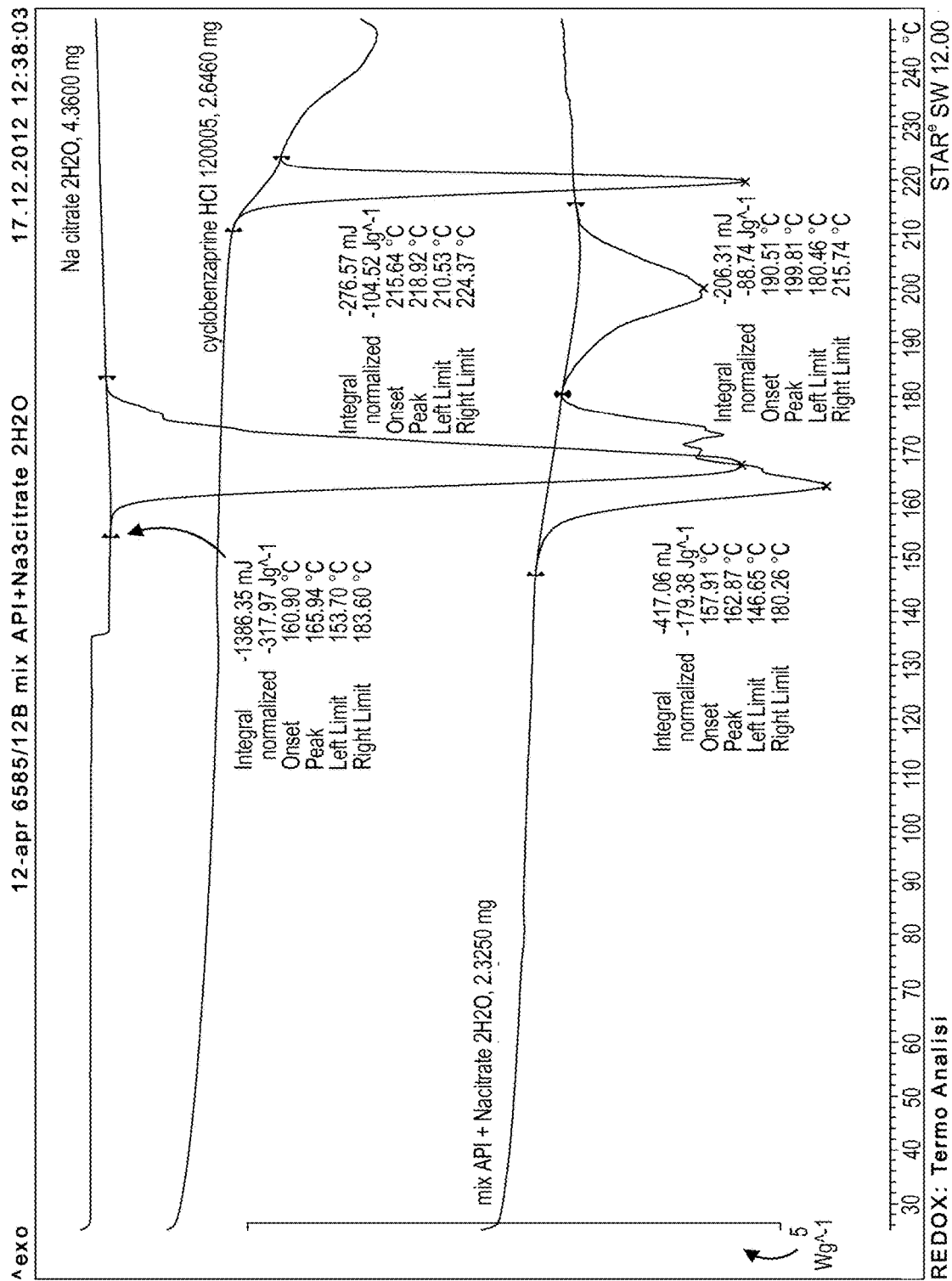
FIG. 27: DSC heating curve of Cyclobenzaprine HCl+Sodium citrate dihydrate 1:1 (mixture B).
Figure 28:
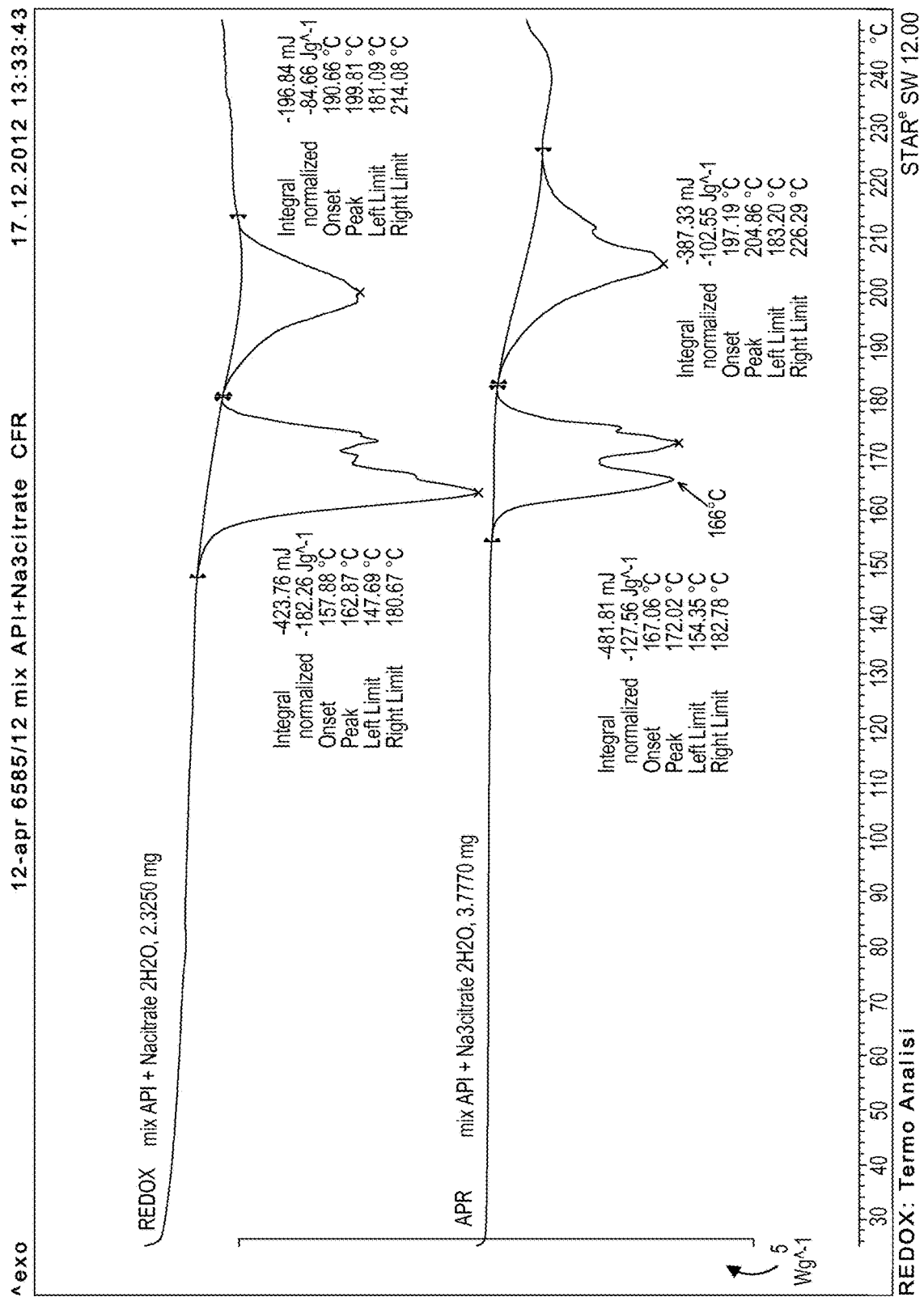
FIG. 28: Comparison of DSC heating curves of Cyclobenzaprine HCl+Sodium citrate dihydrate 1:1 (mixture A & B).

Crystallization water was released and decomposition (complex peak) of a 1:1 mixture of Cyclobenzaprine HCl and trisodium citrate dihydrate (mixture A). was recorded between 154° C. and 183° C. (onset at 167.1° C., ΔH=−127.6J/g), followed by the interaction peak in the range of 186° C. to 227° C. (onset at 197.2° C., ΔH=−102.6 J/g) (FIG. 26). A physico-chemical interaction was observed. The release of crystallization water and excipient decomposition (complex peak) in mixture B were recorded between 146° C. and 181° C. (onset at 157.9° C., ΔH=−179.4J/g), followed by the interaction peak in the range of 180° C. to 216° C. (onset at 190.5° C., ΔH=−88.7 J/g). A physico-chemical interaction was observed (FIG. 27). The decomposition of trisodium citrate was similar in mixtures A and B (FIG. 28).

Figure 29:
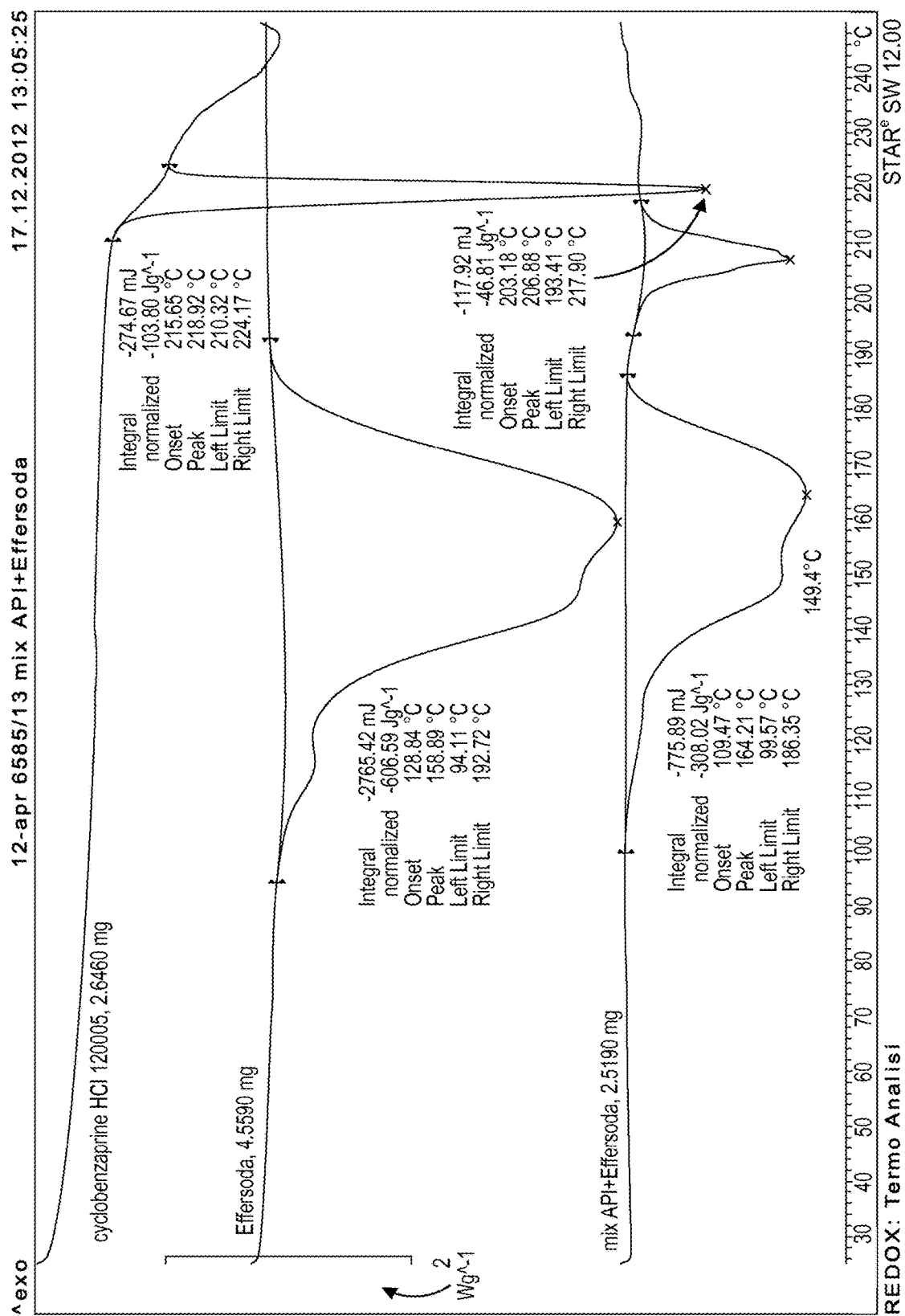
FIG. 29: DSC heating curve of Cyclobenzaprine HCl+Effersoda®Effersoda®® 1:1 (mixture A).
Figure 30:
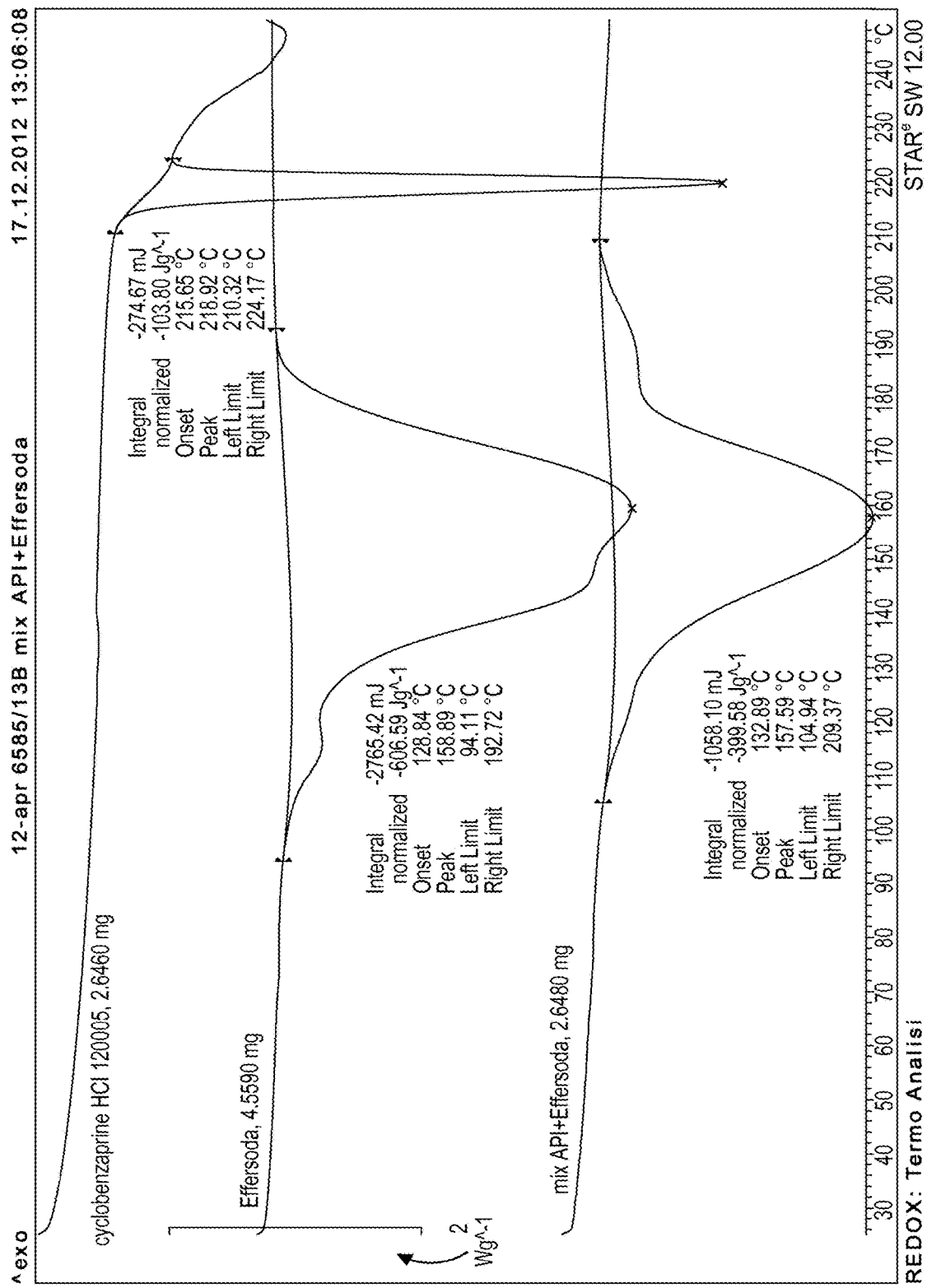
FIG. 30: DSC heating curve of Cyclobenzaprine HCl+Effersoda®Effersoda®® 1:1 (mixture B).
Figure 31:
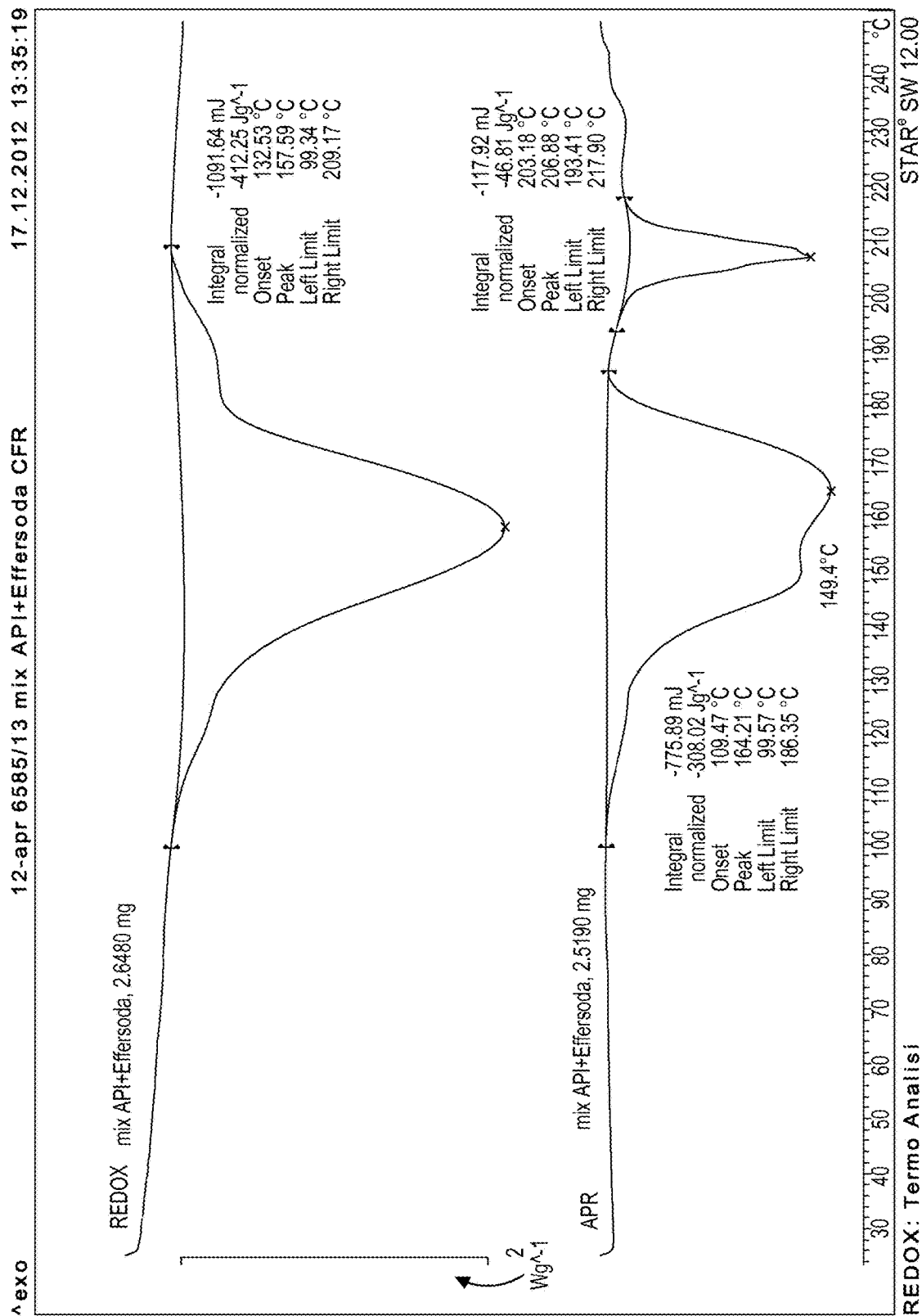
FIG. 31: Comparison of DSC heating curves of Cyclobenzaprine HCl+Effersoda® 1:1 (mixture A & B).

A release of $CO_2$ was recorded in a 1:1 Cyclobenzaprine HCl—Effersoda® mixture (mixture A) between 99° C. and 187° C. (onset at 109.5° C., ΔH =−308.0 J/g), followed by the melting of API in the range of 193° C. to 218° C. (onset at 203.2° C., ΔH=−46.8 J/g) (FIG. 29). The physical interaction observed was small, but due to excipient instability; the API melting peak was anticipated and interaction occurred. Mixture B resulted in a release of $CO_2$ between 104° C. and 210° C. (onset at 132.9° C., ΔH=−399.6 J/g) and disappearance of the API peak (FIG. 30). A physico-chemical interaction was observed. In comparing mixtures A and B, the interaction of mechanical mixture was lower, while the milled mixture was higher. Also, the release of CO, by Effersoda® covered the APT behavior, due to possible interactions (FIG. 31).

Figure 32:
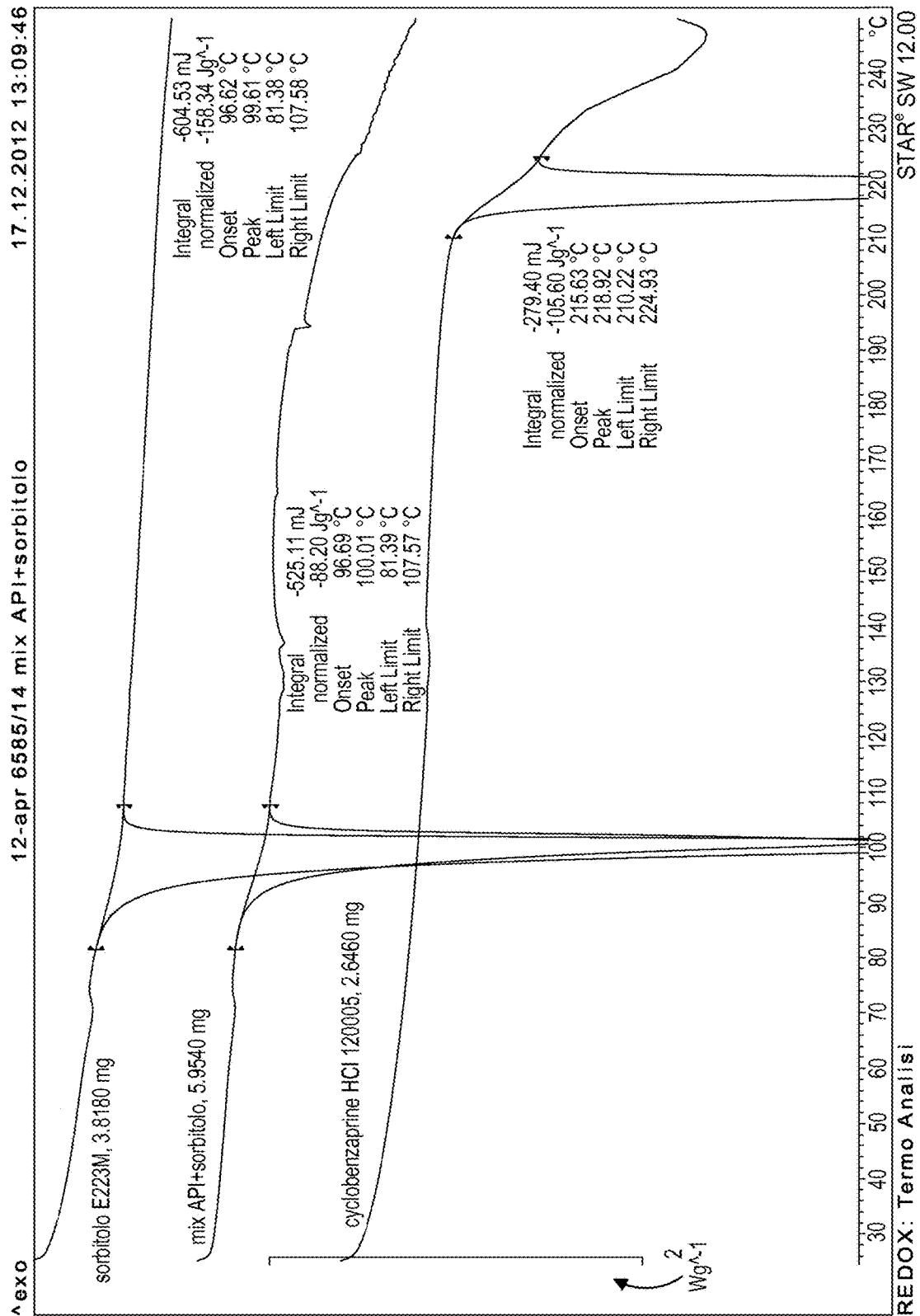
FIG. 32: DSC heating curve of Cyclobenzaprine HCl+Sorbitol 1:1 (mixture A).
Figure 33:
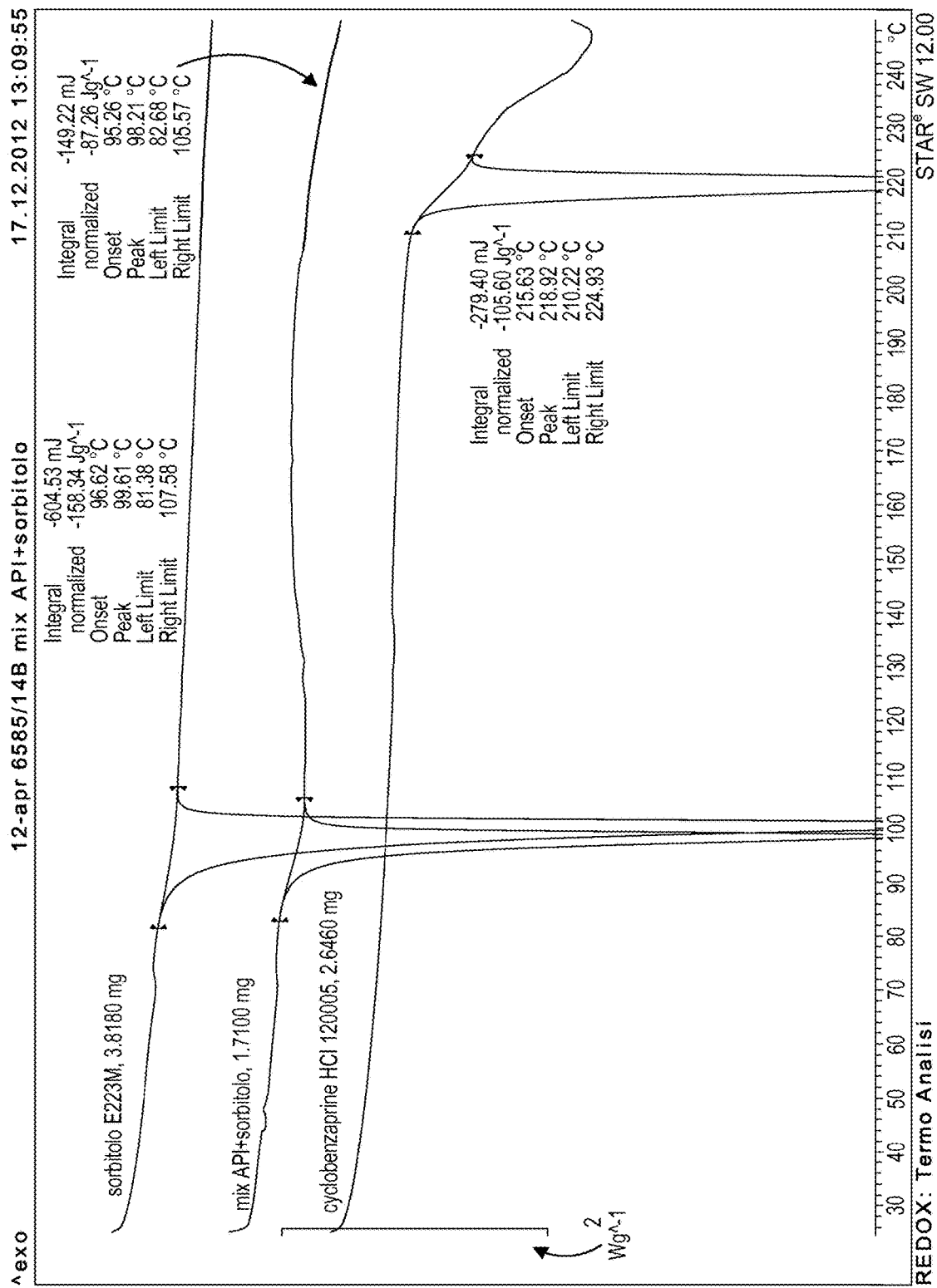
FIG. 33: DSC heating curve of Cyclobenzaprine HCl+Sorbitol 1:1 (mixture B).
Figure 34:
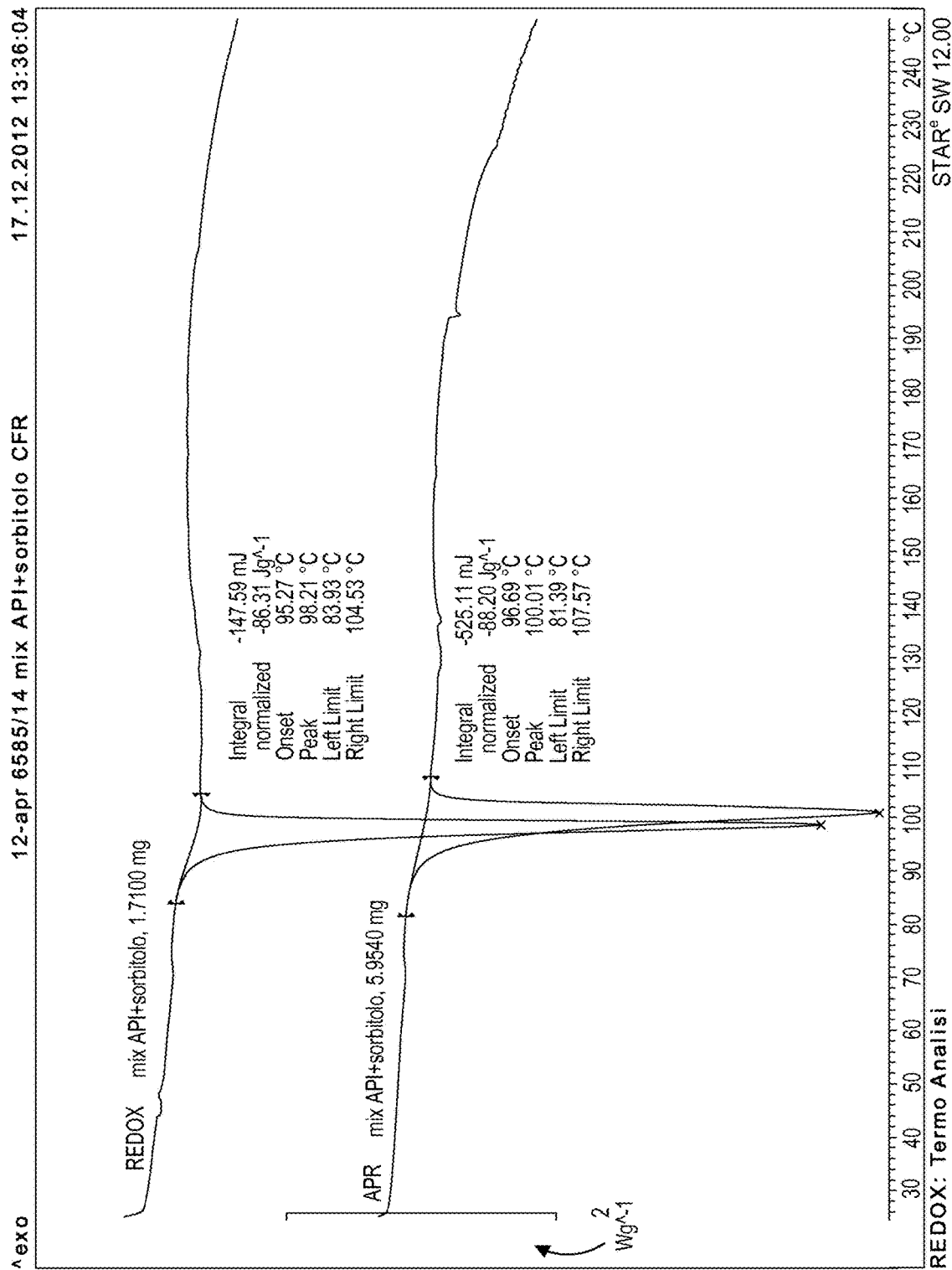
FIG. 34: Comparison of DSC heating curves of Cyclobenzaprine HCl+Sorbitol 1:1 (mixture A & B).
Figure 35:
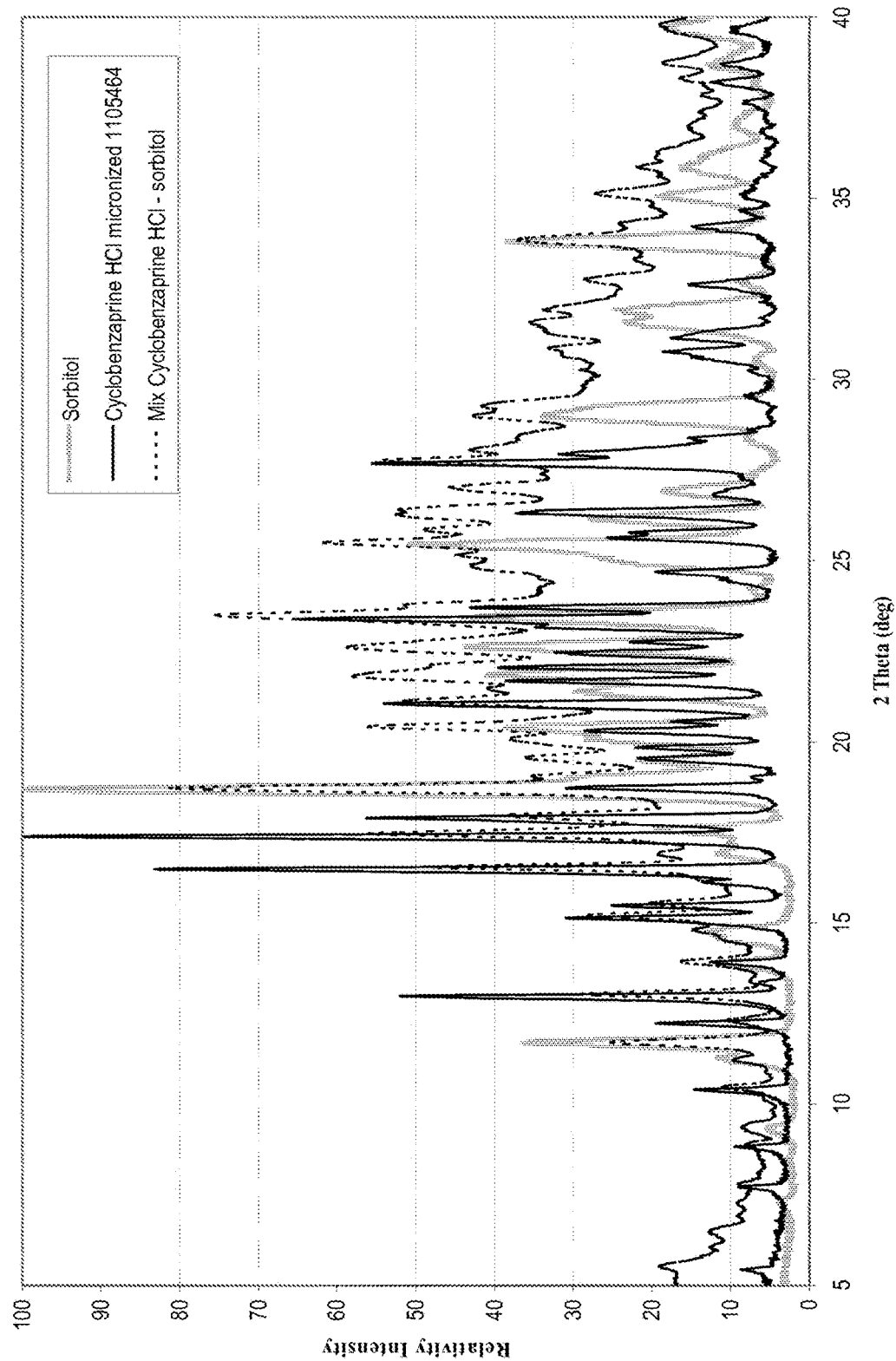
FIG. 35: Stacking of XRPD patterns of Cyclobenzaprine HCl+Sorbitol 1:1 (mixture B).

In a 1:1 mixture of Cyclobenzaprine HCl and sorbitol (mixture A), the melting of sorbitol covered the API melting peak. The event was recorded between 81° C. and 108° C. (onset at 96.7° C., ΔH=−88.2 J/g) (FIG. 32). An interaction was observed, due to the solubilization of API by sorbitol. With mixture B, the melting of sorbitol also covered the API melting peak. The event was recorded between 82° C. and 107° C. (onset at 95.3° C., ΔH=−87.3 J/g) (FIG. 33). An interaction was observed, due to the solubilization of API by sorbitol. The interaction was comparable in both mixtures A and B (FIG. 34). To confirm that sorbitol, during the mixture, solubilized the API, an XRPD investigation was carried out (FIG. 35). The mixture presented several peaks of sorbitol and very few of Cyclobenzaprine HCl . The broadening of the baseline was indicative of amorphous phases, due to the matrix melting.

Figure 36:
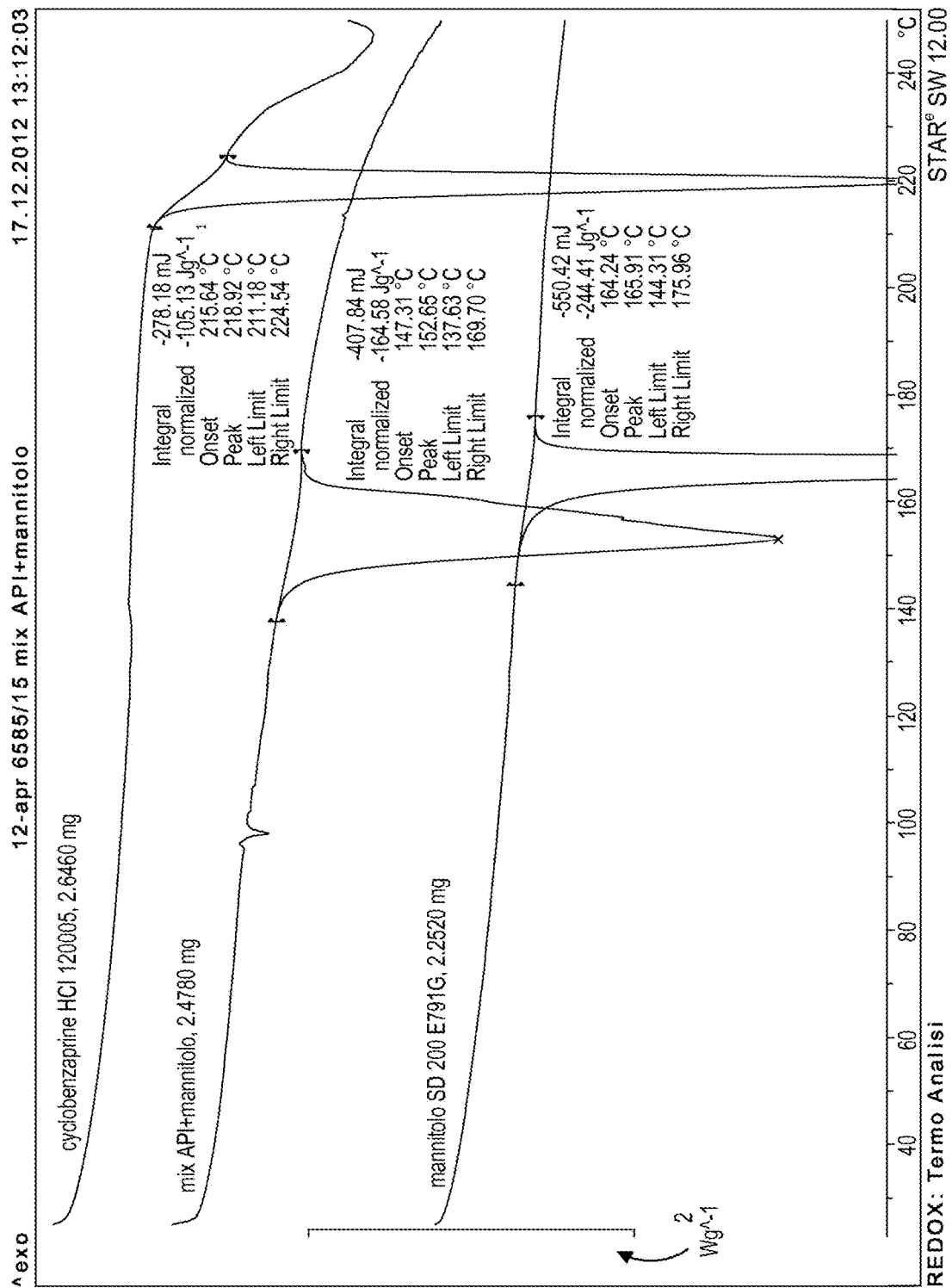
FIG. 36: DSC heating curve of Cyclobenzaprine HCl+Mannitol 1:1 (mixture A).
Figure 37:
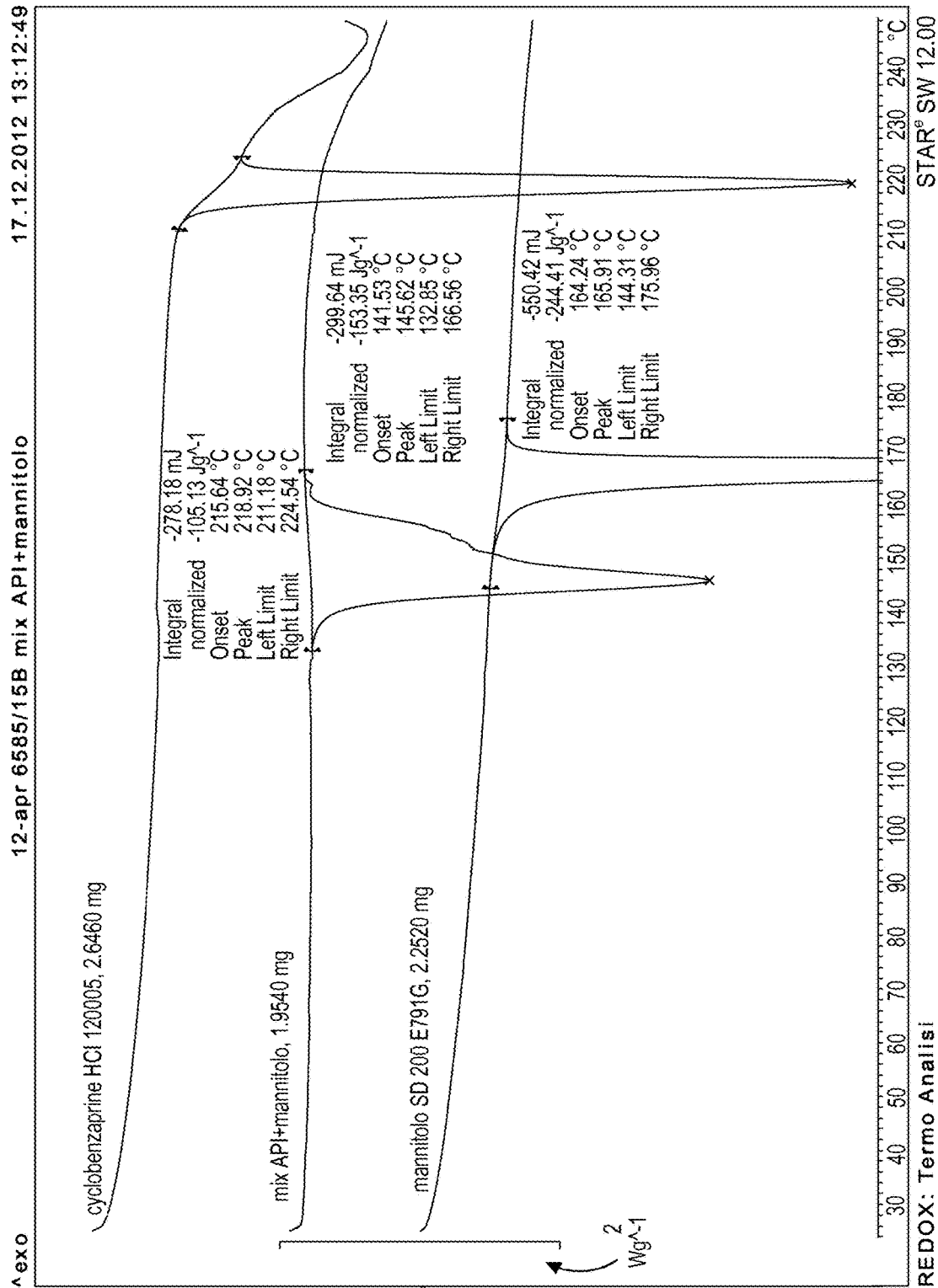
FIG. 37: DSC heating curve of Cyclobenzaprine HCl+Mannitol 1:1 (mixture B).
Figure 38:
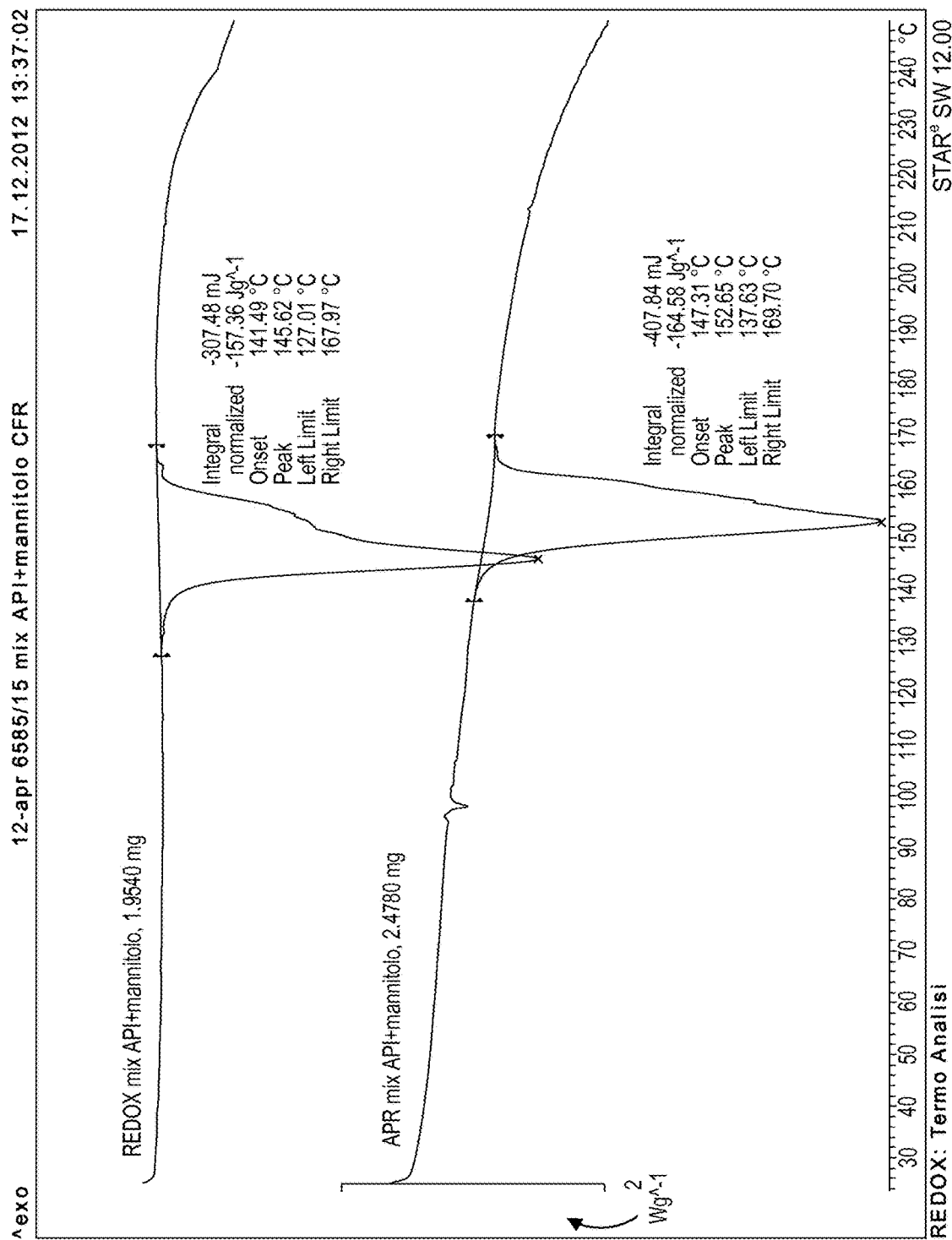
FIG. 38: Comparison of DSC heating curves of Cyclobenzaprine HCl+Mannitol 1:1 (mixture A & B).

Surprisingly, a physical complex interaction peak (eutectic) was observed in the range of 137° C. to 170° C. (onset at 147.3° C., ΔH=−164.6 J/g) in a 1:1 Cyclobenzaprine HCl—mannitol mixture (mixture A) (FIG. 36). No API transition melting was detected, only the melting of a eutectic at a lower temperature. With mixture B, a physical complex interaction peak (eutectic) also was observed in the range of 132° C. to 167° C. (onset at 141.5° C., H=−153.4 J/g) (FIG. 37). No API transition melting was detected, only the melting of eutectic at a lower temperature. The interaction was comparable in both the mixtures (FIG. 38).

Figure 39:
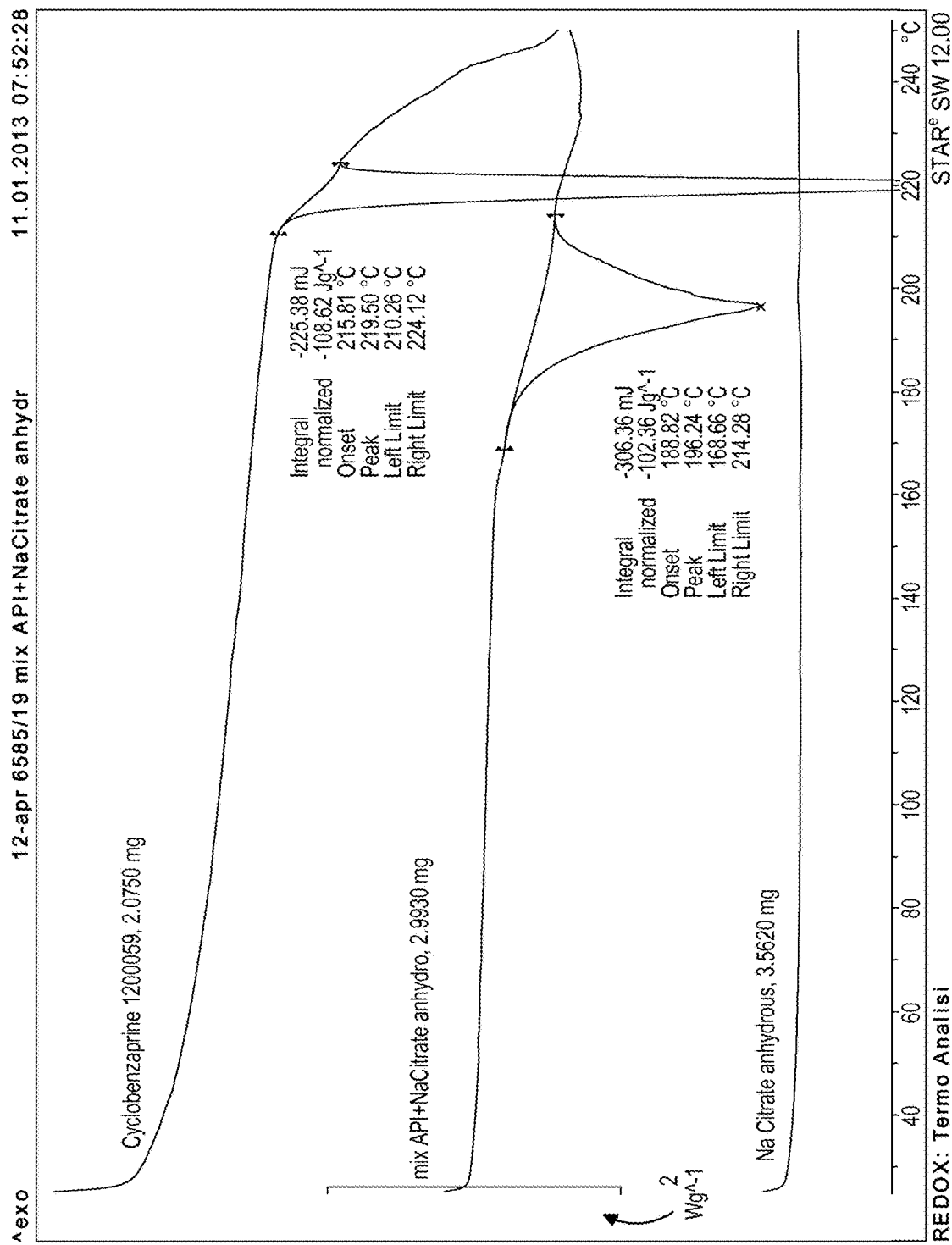
FIG. 39: DSC heating curve of Cyclobenzaprine HCl+Trisodium citrate anhydrous 1:1 (mixture A).
Figure 40:
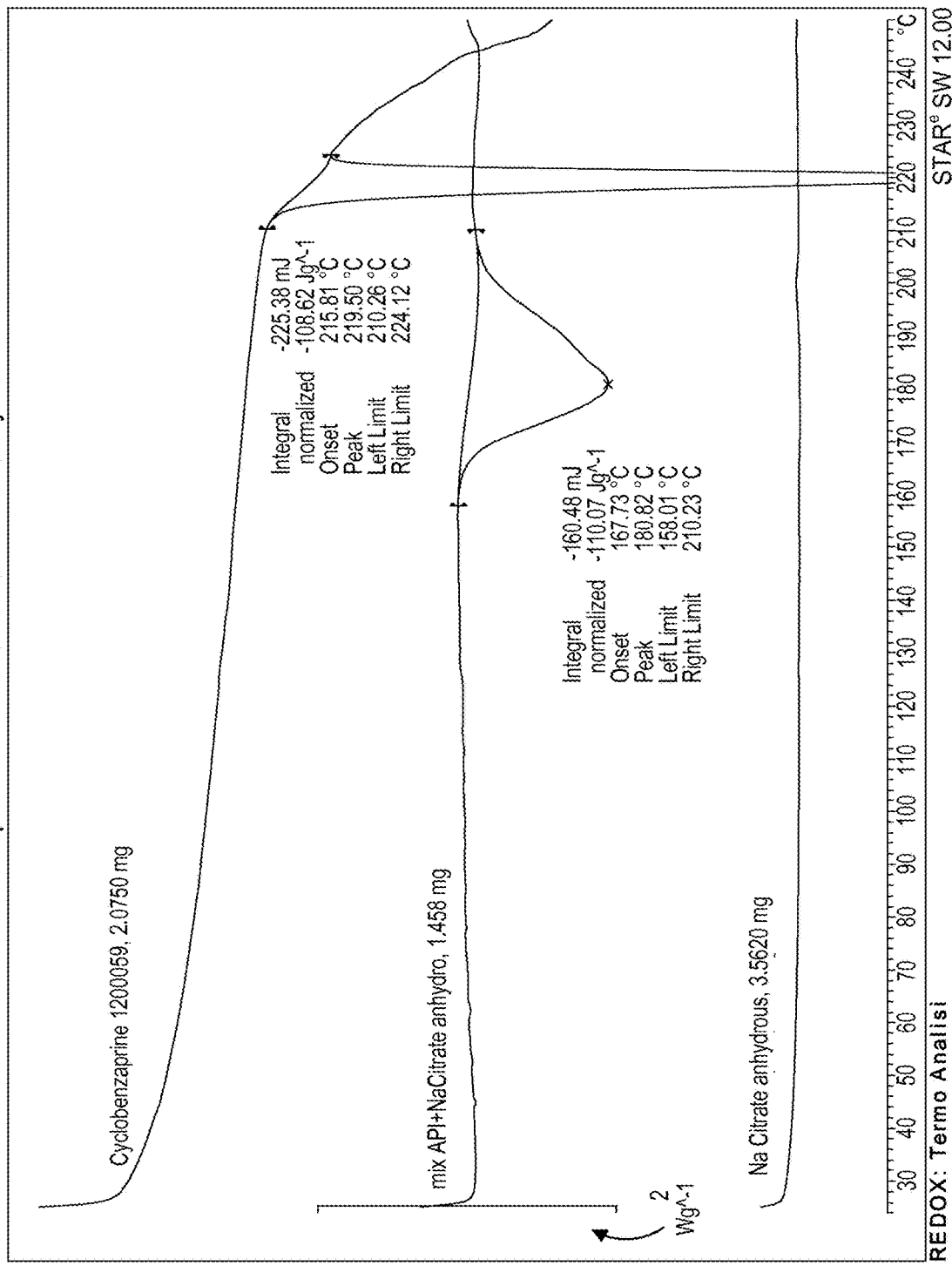
FIG. 40: DSC heating curve of Cyclobenzaprine HCl+Trisodium citrate anhydrous 1:1 (mixture A).
Figure 41:
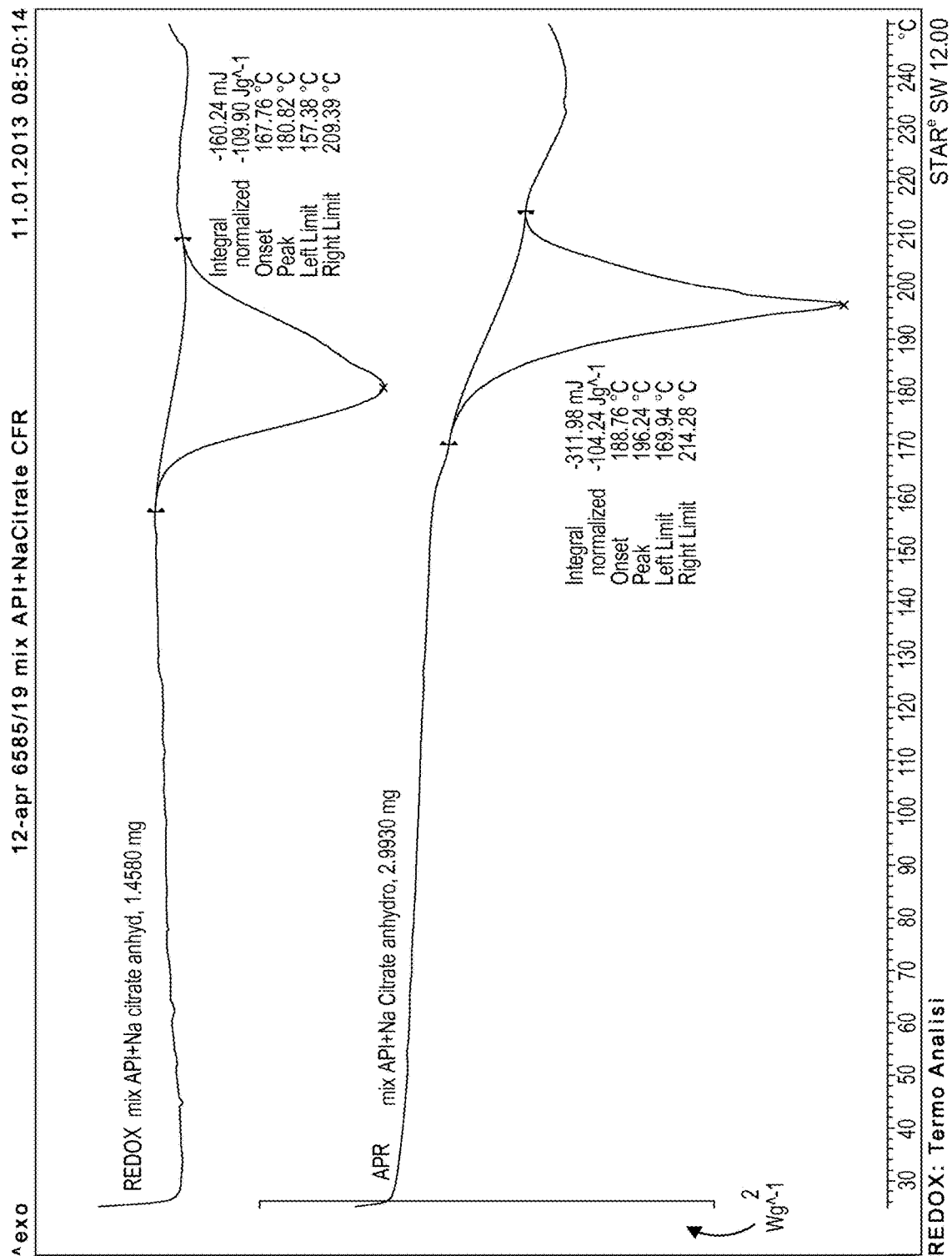
FIG. 41: Comparison of DSC heating curves of Cyclobenzaprine HCl+Trisodium citrate anhydrous 1:1 (mixture A & B).

In a 1:1 mixture of Cyclobenzaprine HCl and Trisodium Citrate anhydrous (mixture A), the interaction peak was observed in the range of 168° C. to 215° C. (onset at 188.8° C., ΔH=−102.4 J/g) (FIG. 39). No API transition melting was detected, only a physical complex melting at a lower temperature. The interaction peak was observed in the range of 158 ° C. to 211° C. (onset at 167.7° C., H=−110.1 J/g) in mixture B (FIG. 40). No API transition melting was detected, only a physical complex melting at lower temperature. In comparing the milled and mixed mixtures, the interaction was more evident in the milled mixture (FIG. 41).

Figure 42:
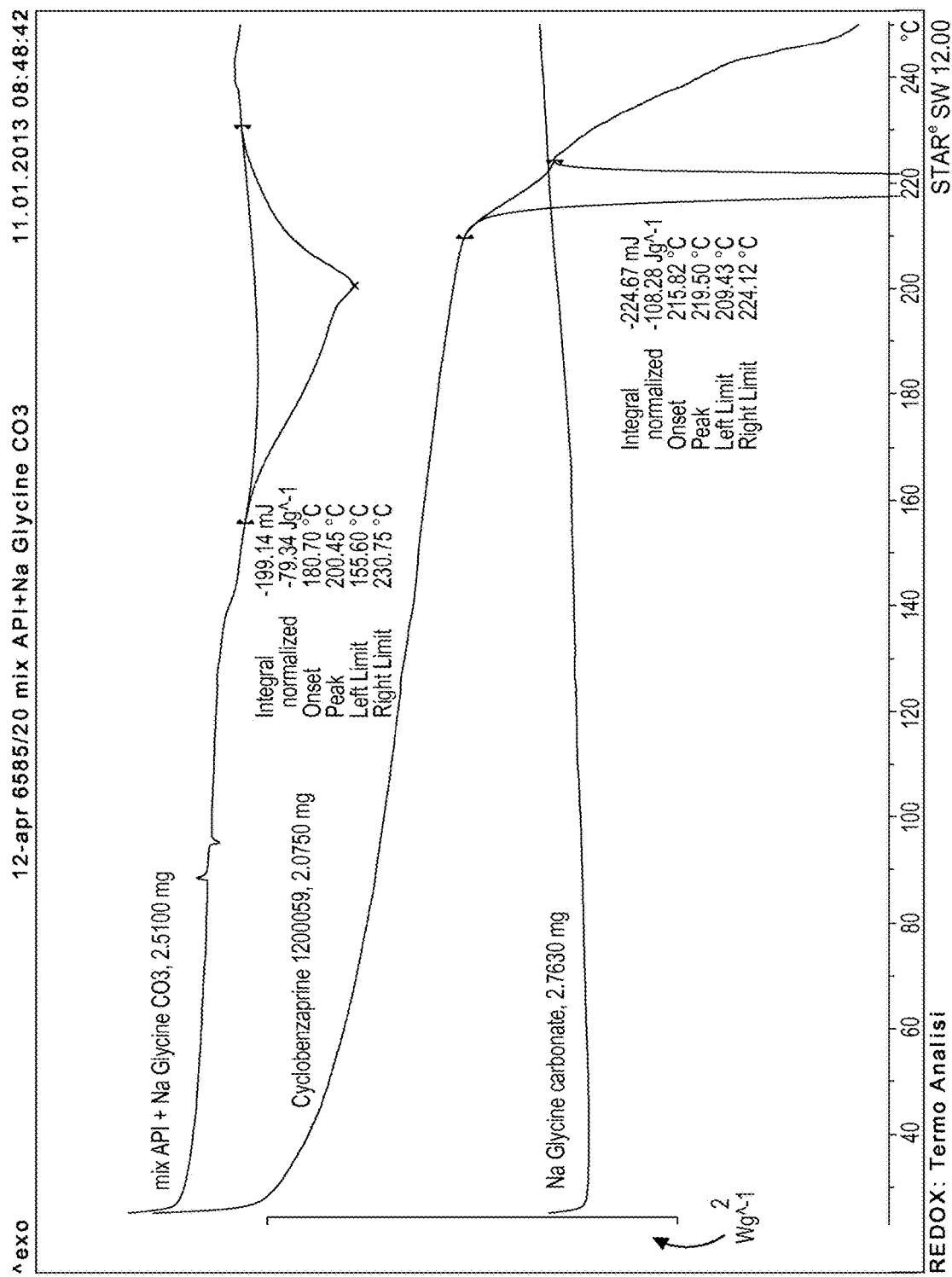
FIG. 42: DSC heating curve of Cyclobenzaprine HCl+Disodium glycine carbonate 1:1 (mixture A).
Figure 43:
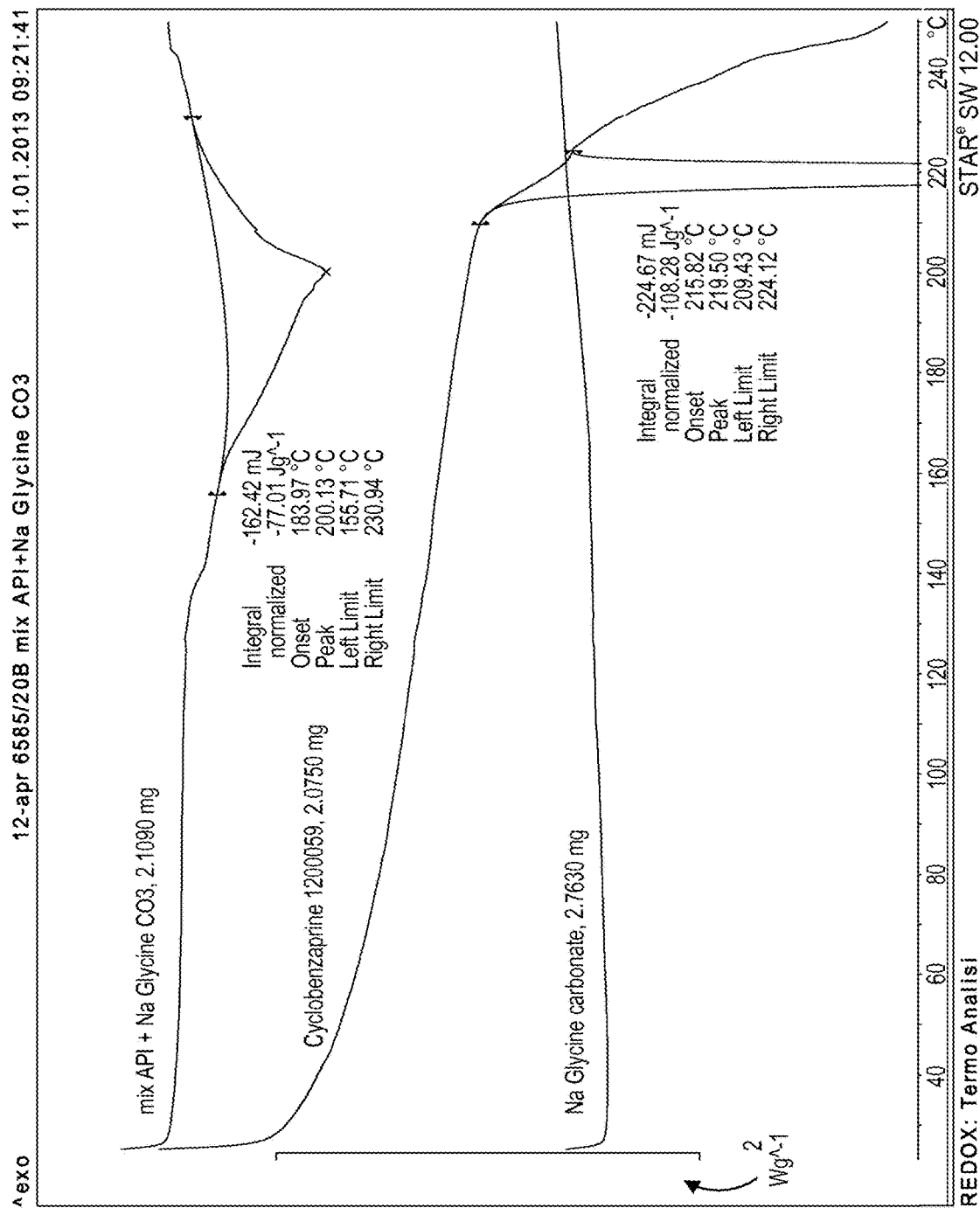
FIG. 43: DSC heating curve of Cyclobenzaprine HCl+Disodium glycine carbonate 1:1 (mixture B).
Figure 44:
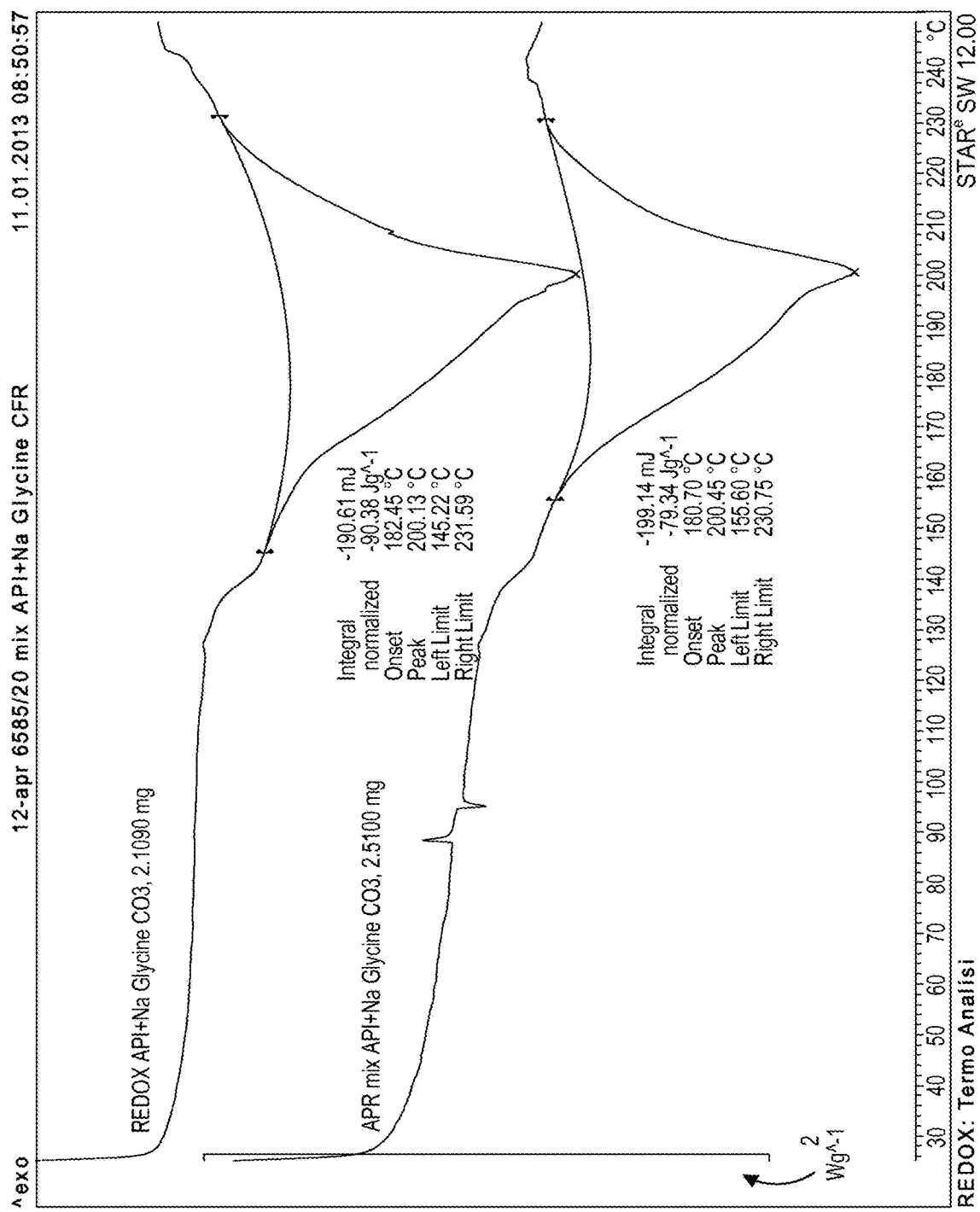
FIG. 44: Comparison of DSC heating curve of Cyclobenzaprine HCl+Disodium glycine carbonate 1:1 (mixture A & B).

In a 1:1 mixture of Cyclobenzaprine HCl and Disodium Glycine carbonate (Mixture A), a broad interaction peak was observed in the range of 155° C. to 231° C. (onset at 180.7° C., H=−79.3 J/g) (FIG. 42). No API transition melting was detected, only a physical complex melting at a lower temperature. Mixture B produced an interaction peak in the range of 155° C. to 231° C. (onset at 184.0° C., H=−77.0 J/g) (FIG. 43). No API transition melting was detected, only a physical complex melting at a lower temperature. The interaction was comparable in both the mixtures (FIG. 44)

FT-IR/ATR

Figure 45:
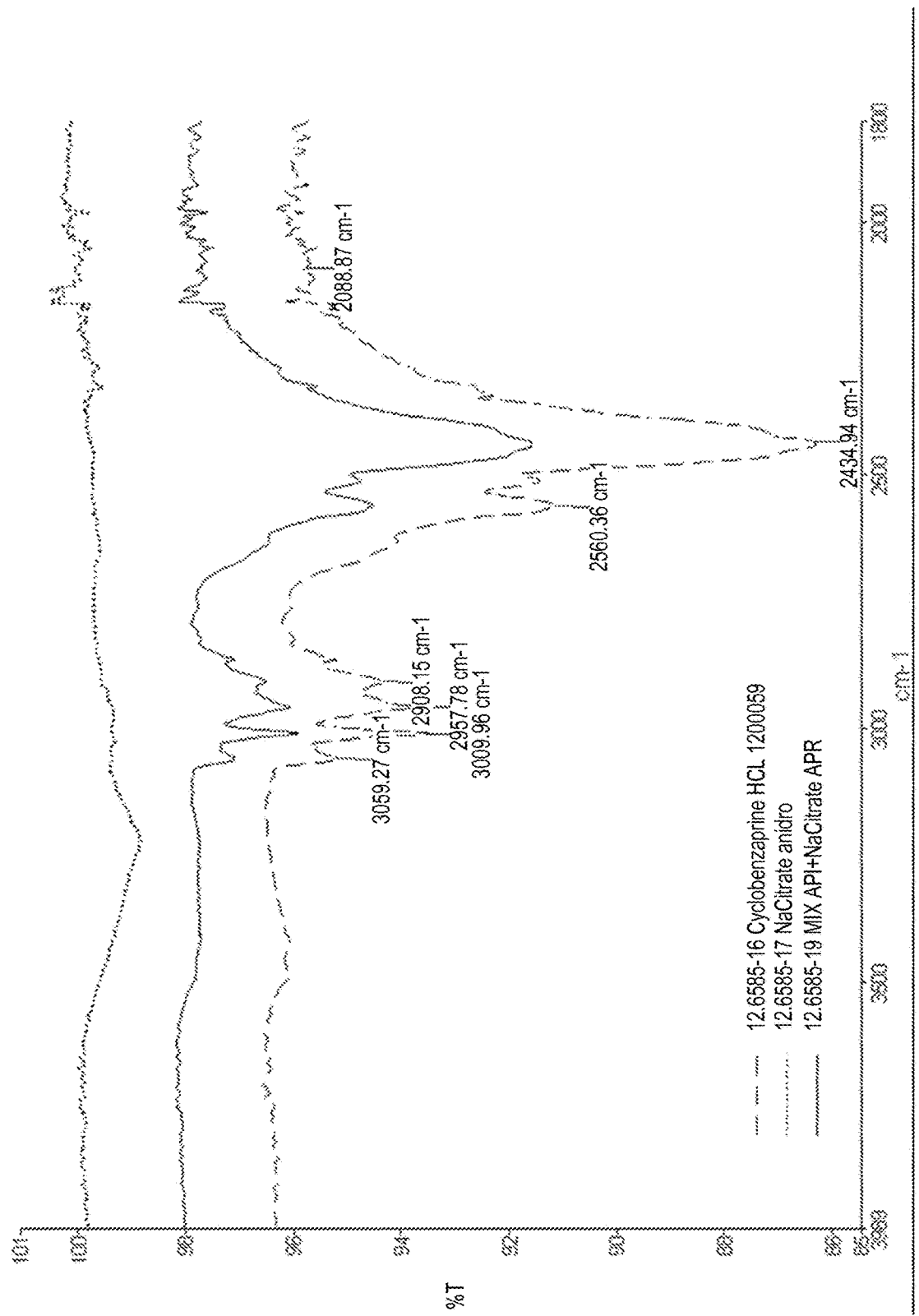
FIG. 45: FT-IR/ATR spectra stacking of Cyclobenzaprine HCl+Trisodium citrate anhydrous 1:1 (mixture A).
Figure 46:
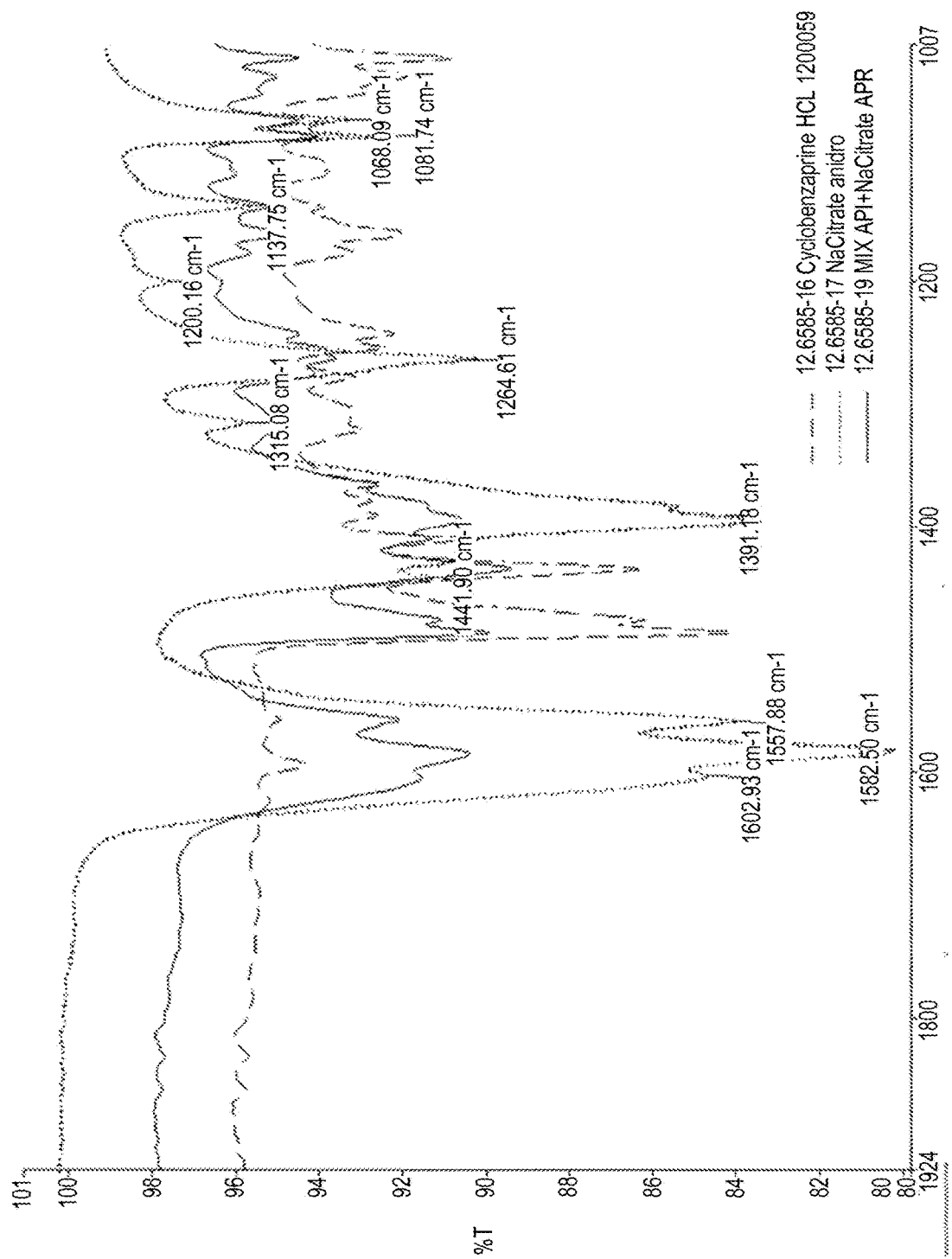
FIG. 46: FT-IR/ATR spectra stacking of Cyclobenzaprine HCl+Trisodium citrate anhydrous 1:1 (mixture A).
Figure 47:
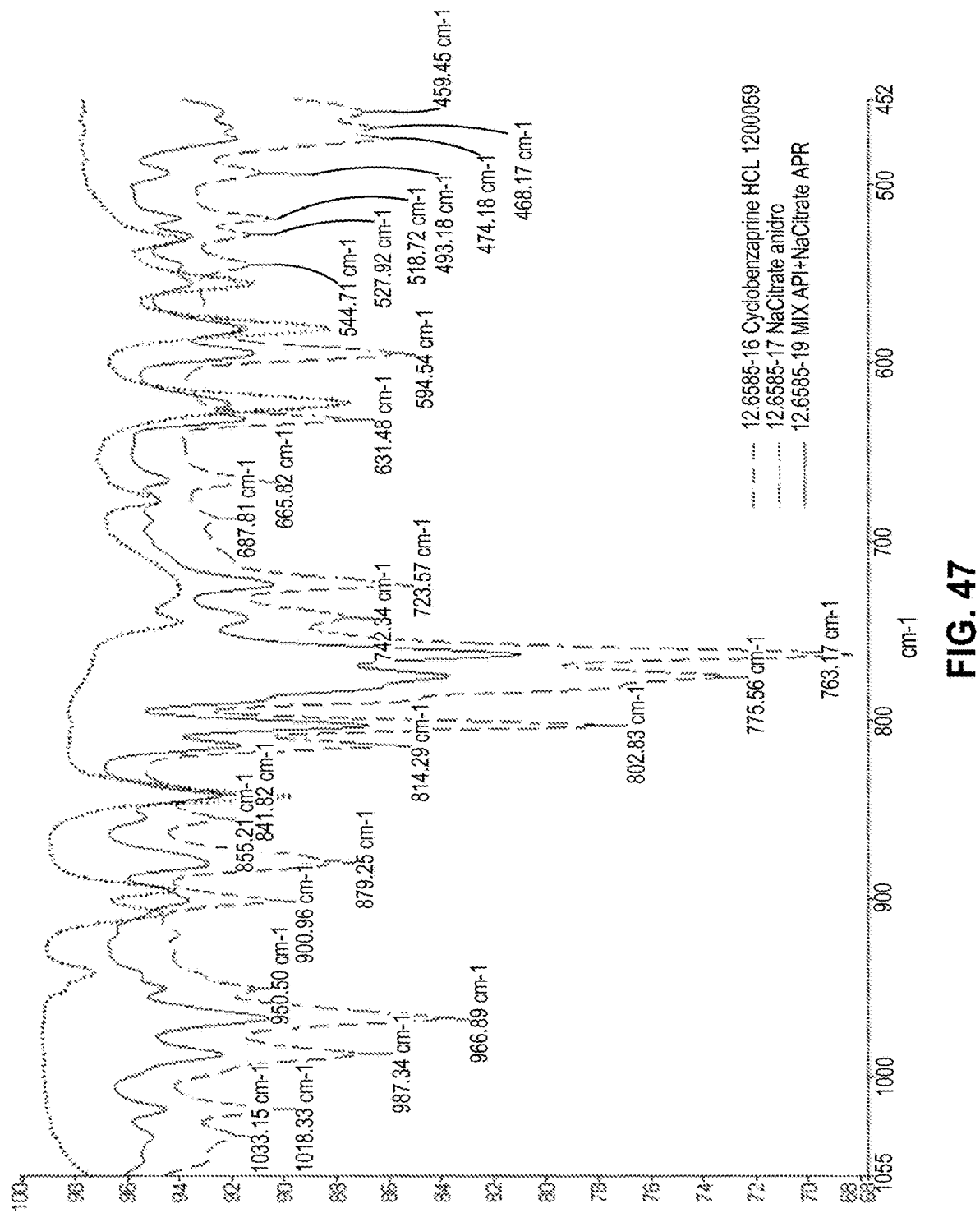
FIG. 47: FT-IR/ATR spectra stacking of Cyclobenzaprine HCl+Trisodium citrate anhydrous 1:1 (mixture A).
Figure 48:
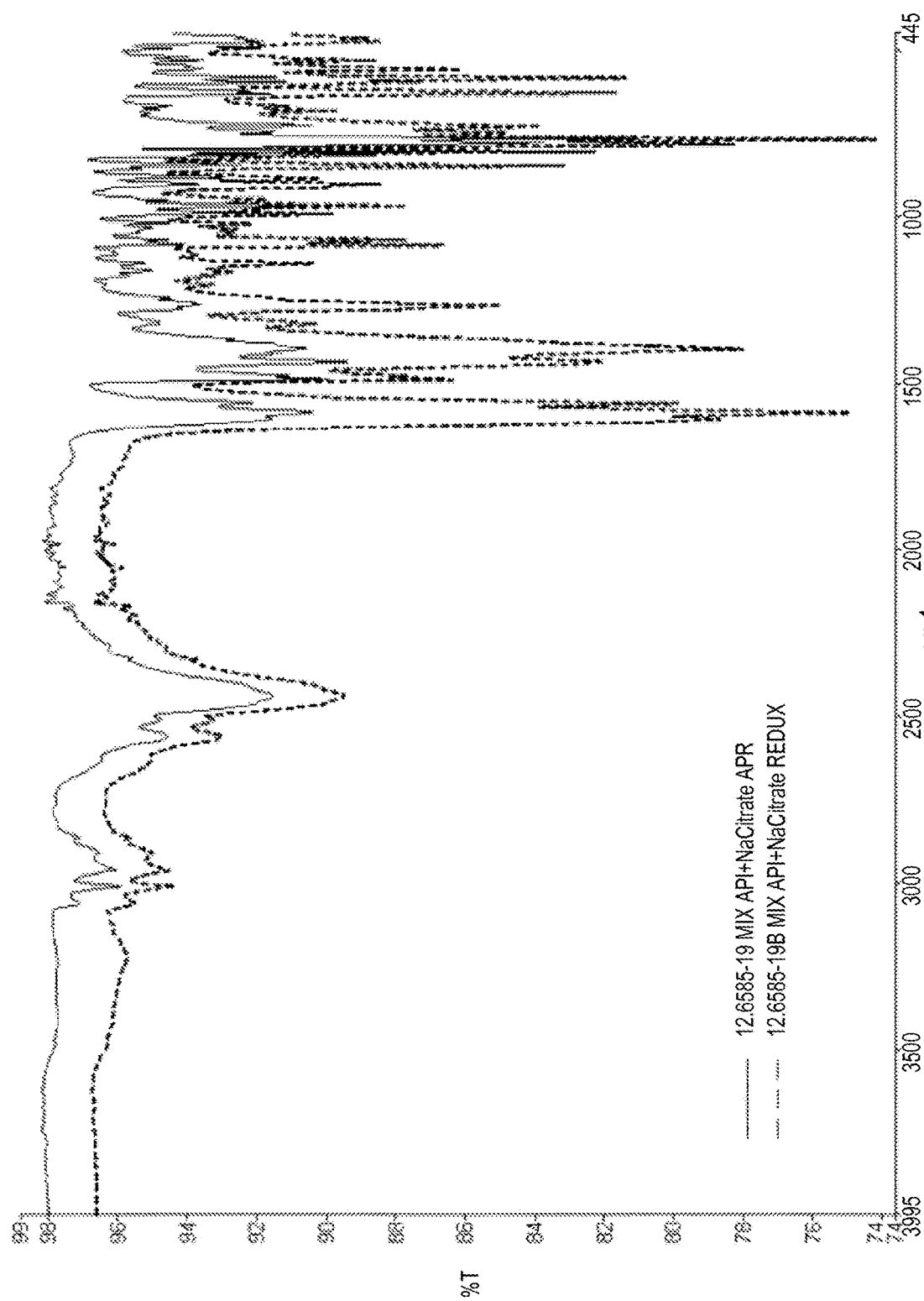
FIG. 48: FT-IR/ATR spectra stacking of Cyclobenzaprine HCl+Trisodium citrate anhydrous 1:1 (mixture A & B).

To define the nature of the interactions observed by DSC and understand if the thermal treatment, during the temperature rise, was the root cause of the different DSC profiles, FT-IR/ATR spectroscopy investigation was carried out. In FIGS. 45-47, the FT-IR/ATR spectra of Cyclobenzaprine HCl and Trisodium Citrate anhydrous (mixture A) are shown in superimposition, in different regions. In the mixture, the presence of all the bands of both API and excipient were observed. In particular, in the 3000-2000 $cm^{-1}$ region (FIG. 45), the band of chlorohydrate was still well visible, as a sign that no chemical acid-base reaction had occurred. In FIG. 48, the superimposition of mixtures A and B shows that no substantial modifications were observed.

Figure 49:
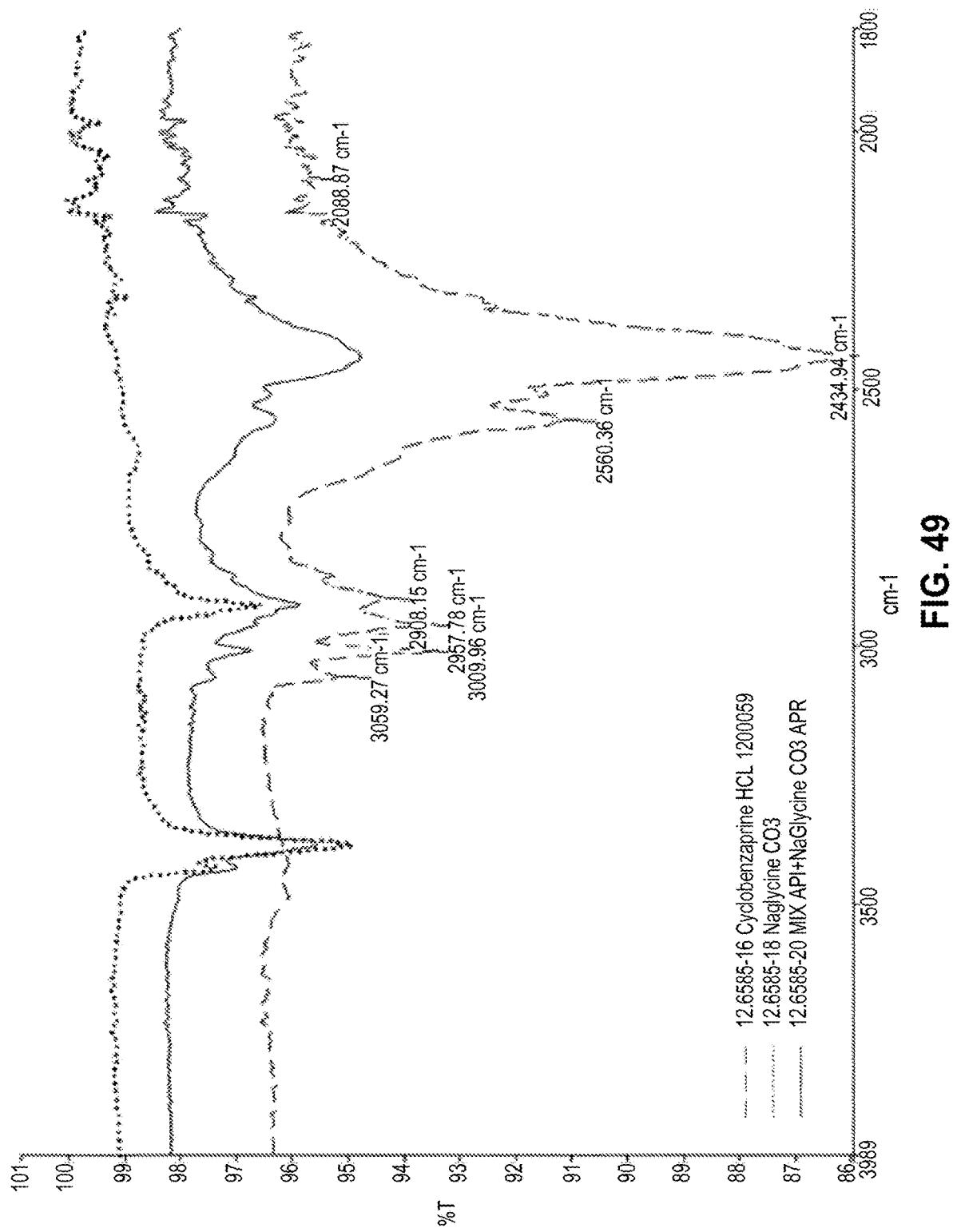
FIG. 49: FT-IR/ATR spectra stacking of Cyclobenzaprine HCl+Disodium Glycine carbonate 1:1 (mixture A).
Figure 50:
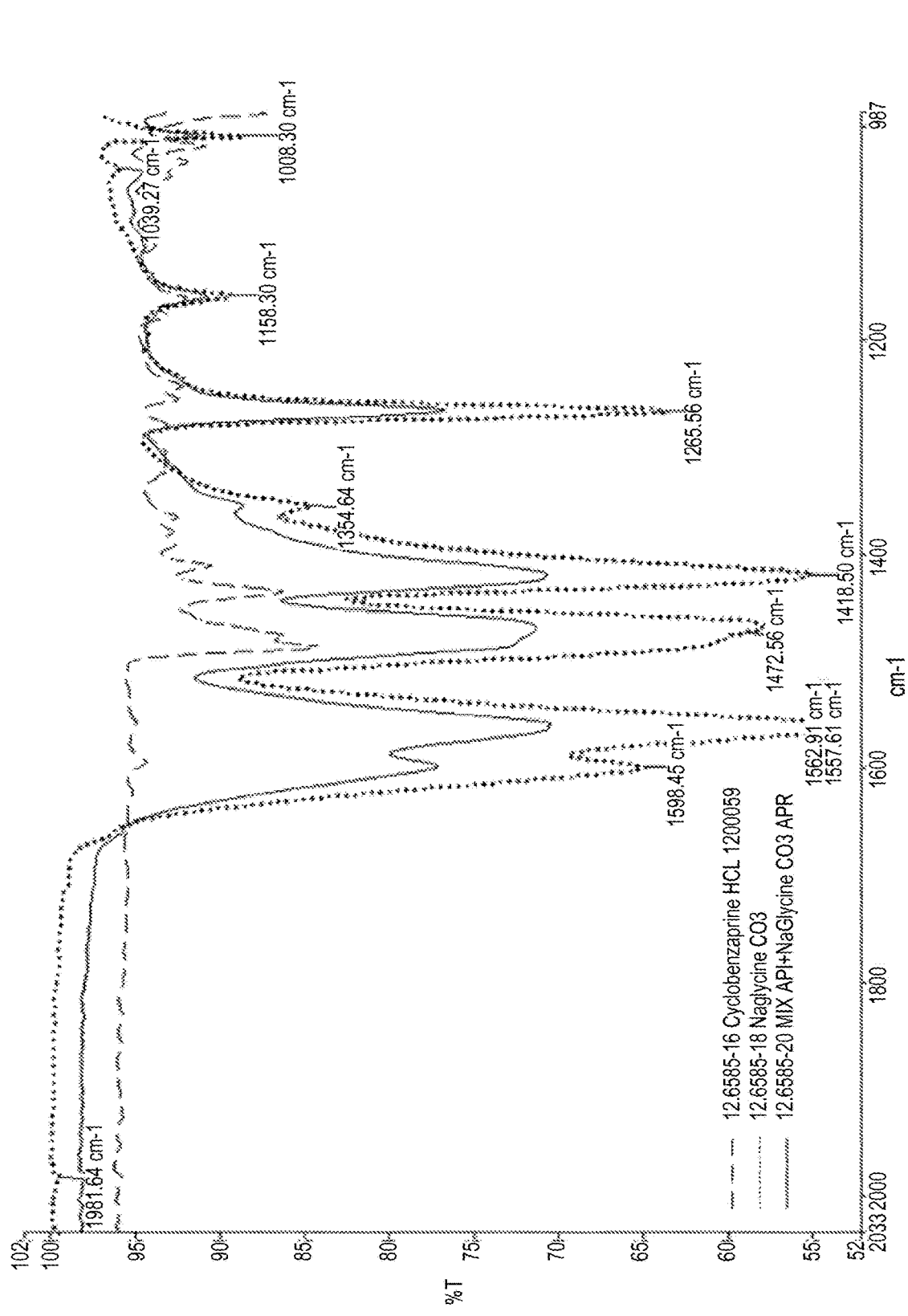
FIG. 50: FT-IR/ATR spectra stacking of Cyclobenzaprine HCl+Disodium Glycine carbonate 1:1 (mixture A).
Figure 51:
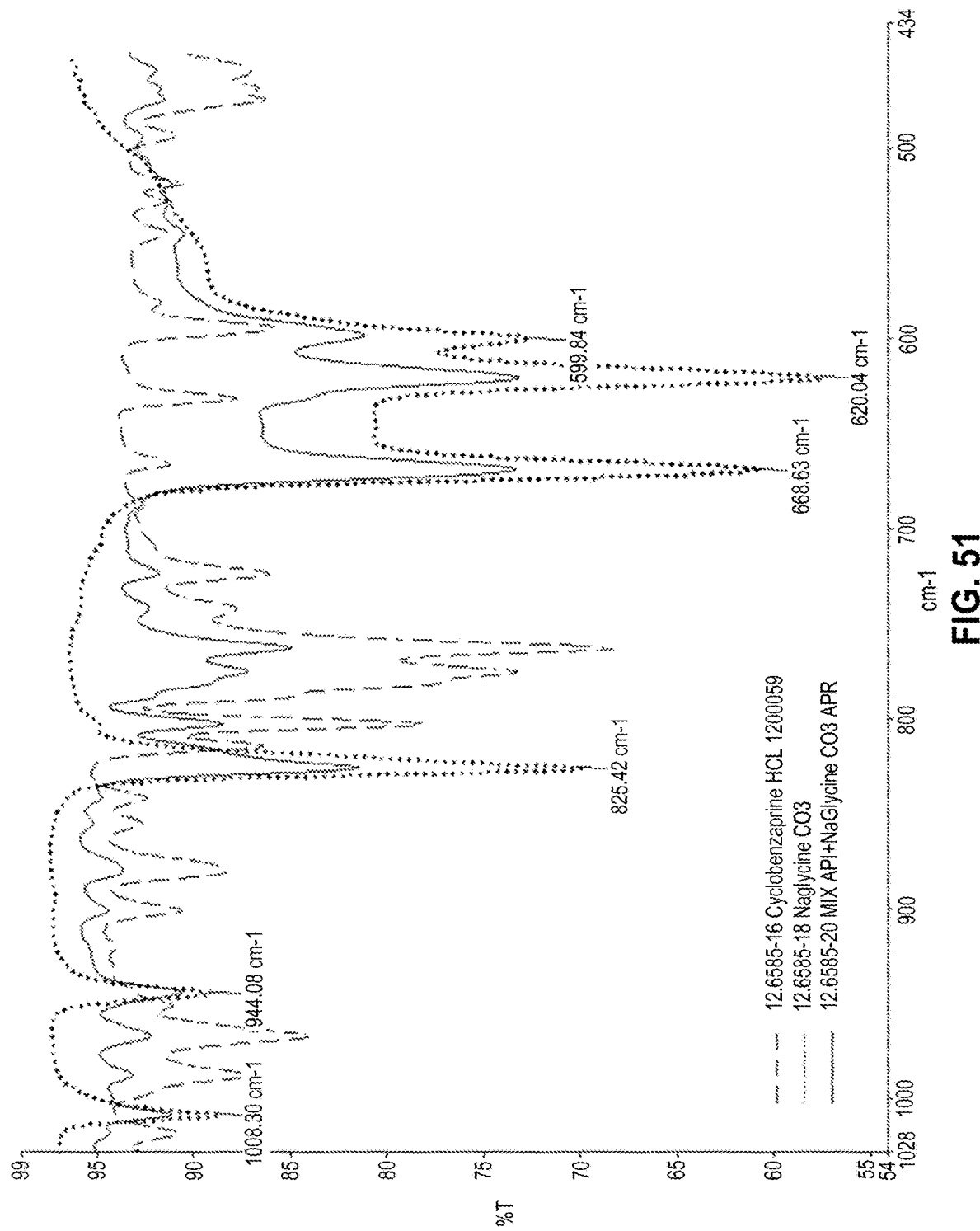
FIG. 51: FT-IR/ATR spectra stacking of Cyclobenzaprine HCl+Disodium Glycine carbonate 1:1 (mixture A).
Figure 52:
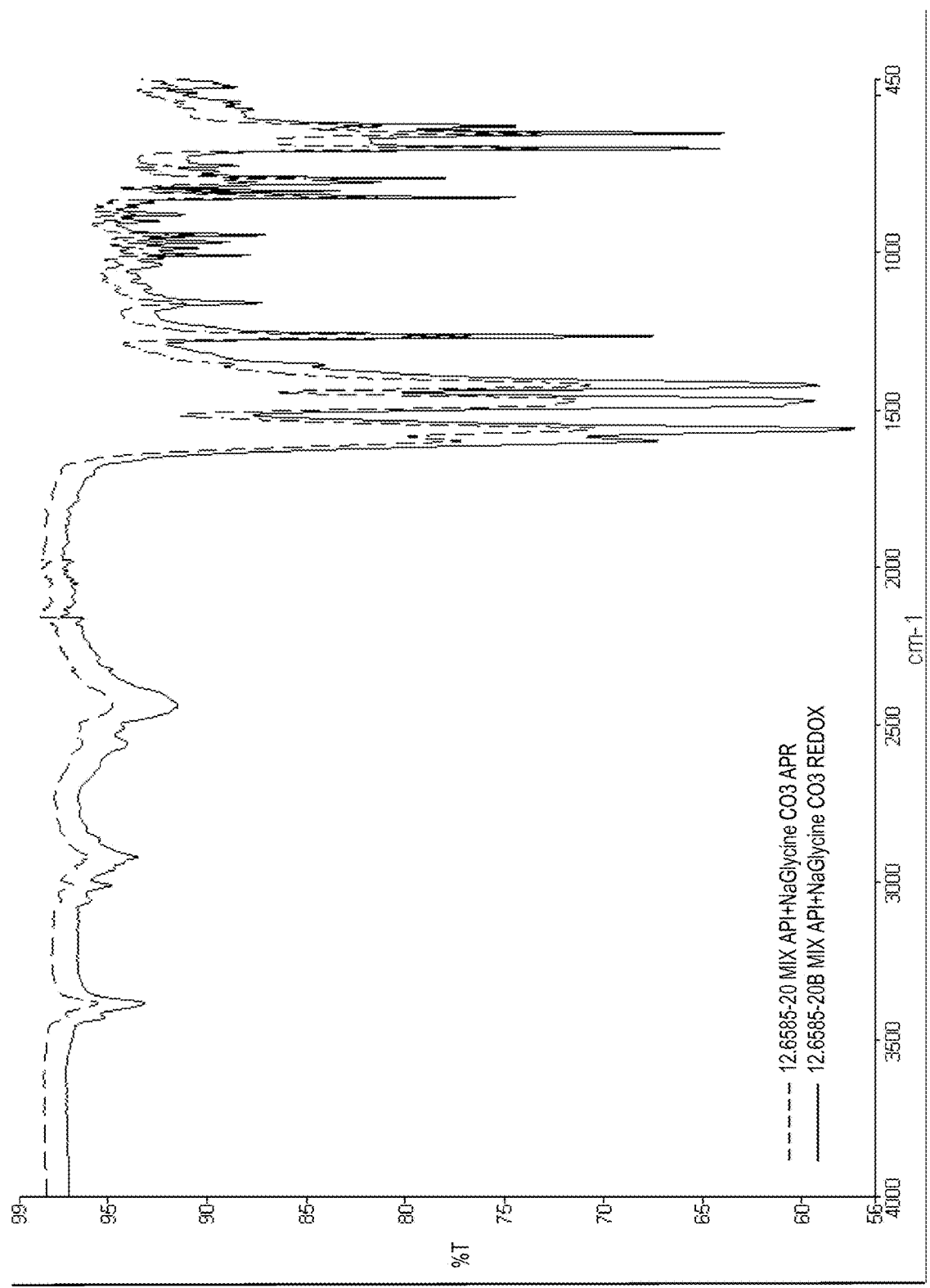
FIG. 52: FT-IR/ATR spectra stacking of Cyclobenzaprine HCl+Disodium Glycine carbonate 1:1 (mixture A & B).

FIGS. 49-51 show the FT-TR/ATR spectra of Cyclobenzaprine HCl and Disodium Glycine Carbonate (mixture A) in superimposition, in different regions. In the mixture, all bands of both API and excipient were observed. In particular, in the 3000-2000 $cm^{-1}$ region (FIG. 49), the band of chlorohydrate was still visible, as a sign that no chemical acid-basis reaction occurred. FIG. 52 depicts the superimposition of mixtures A and B. No substantial modifications were observed. From the FT-IR/ATR spectra, the thermal transitions recorded originated from the heating of the mixtures, but, at room temperature, the two components were stable and did not interact.

In summary, different types of interaction were observed among the excipients and the API. With all the basic excipients investigated (especially the hydrates), interactions were observed. The interactions seemed to be acid/base type reactions, possibly between the cation Na and the HCl of the drug substance. The interaction was more evident in milled mixtures, because the contact between API and excipient particles was deeper and closer. With sorbitol, a physical interaction was observed, due to the solubilization of the API in the melted excipient, while with mannitol, the formation of a eutectic was surprisingly observed. The interaction with trisodium citrate anhydrous and disodium glycine carbonate was only physical and occurred at high temperatures as shown by FT-IR/ATR spectroscopy. Table 2 shows a summary of the interactions between the API and excipients for the mixed and milled mixtures.

TABLE 2

Interactions between Cyclobenzaprine HCl and excipients

| Excipient | Mixture 1:1 (mixed) | Mixture 1:1 (milled) |
| --- | --- | --- |
| Di Sodium phosphate anhydrous | Low chemical | Low chemical |

TABLE 2-continued

Interactions between Cyclobenzaprine HCl and excipients

| Excipient | Mixture 1:1 (mixed) | Mixture 1:1 (milled) |
|---|---|---|
| Di Sodium phosphate di hydrate | Chemical | Chemical |
| Di Sodium phosphate heptahydrate | Chemical | Chemical |
| Trisodium citrate dihydrate | Chemical | Chemical |
| Effersoda ® | Low chemical | Chemical |
| Sorbitol | Chemical | Chemical |
| Mannitol | Eutectic | Eutectic |
| Tri Sodium Citrate anhydrous | Physical | Physical |
| Di Sodium Glycine carbonate | Physical | Physical |

Example 3

The compatibility of mannitol with Cyclobenzaprine HCl was investigated by differential scanning calorimetry (DSC), and the resulting interactions were assessed. In particular, the formation of a eutectic between the mannitol and the Cyclobenzaprine HCl during mixing improved the cohesion between the particles and provided better physical bonding between the Cyclobenzaprine HCl active pharmaceutical ingredient (API) and the mannitol excipient. Additionally, the physical state prevents the erosion of a dosage form for Cyclobenzaprine administration.

The interaction between Cyclobenzaprine HCl and Pearlitol Flash® (an excipient containing mannitol) is an invariant physical interaction because it is in thermal equilibrium in which the two components are well mixed and stabilized. Physically, this means that the melted eutectic, solid eutectic, and solid mannitol all coexist at the same time and are in chemical equilibrium. The resulting solid macrostructure from the eutectic reaction depends on a few factors, including that the two solid solutions nucleate and grow together during a mechanical mixture.

Because mannitol is a common excipient in solid drug formulations, it was examined for compatibility with Cyclobenzaprine HCl was investigated using DSC and interactions occurring were assessed. Surprisingly, the formation of a eutectic during mechanical mixing was discovered. To confirm the formation of a eutectic and to characterize its physical properties, several binary mixtures at different ratios of API and excipient were prepared and analyzed by DSC and by XRPD. The eutectic formation improved the cohesion between the API and excipient particles and assured better physical linking between the two.

In order to confirm the eutectic formation and to characterize its physical properties, several binary mixtures at different ratios of API-excipient were prepared and analyzed by DSC and by X-ray powder diffraction (XRPD). The mixtures were obtained by gently milling in agate mortar of micronized Cyclobenzaprine HCl and mannitol, in order to obtain homogeneous distribution of the particles. For each DSC heating curve, the onset temperature and the enthalpy were evaluated both for the eutectic contribute and for the excess of component. The recorded values were plotted and a phase diagram between the two components was obtained with a characteristic profile of phase diagrams of eutectic mixtures.

Mixtures also were investigated by XRPD and compared with the patterns of pure components. These analyses were carried out to confirm that the eutectic compound is only a physical interaction between the two products and not a formation of a new entity with different chemical properties. The XRPD patterns obtained in the mixtures, compared with pure components, were plotted in order to confirm the linearity of the peak intensities (cpf) of mannitol and Cyclobenzaprine HCl, and a proportional peak height at characteristic 2θ angles.

Aliquots of Cyclobenzaprine HCl API and Mannitol were weighed in the ratios described below and ground in an agate mortar, and the homogeneous mixtures subsequently analyzed.

| Mixture | API amount (%) |
|---|---|
| 1 | 15 |
| 2 | 30 |
| 3 | 40 |
| 4 | 45 |
| 5 | 50 |
| 6 | 65 |
| 7 | 75 |
| 8 | 80 |
| 9 | 90 |
| 10 | 95 |

Differential Scanning Calorimetry (DSC)

DSC heating curves were obtained using a TA 821 DSC Mettler instrument under the following conditions:

| | |
|---|---|
| Heating rate | 10° C./min |
| Ambient | Nitrogen 30 mL/min |
| Sample order | Normal open aluminum pan |
| Temperature range | From 25° C. to 250° C. |
| Instrument calibration | Indium sample purity 99.999% |

X-Ray powder Diffraction (XRPD)

X-ray powder diffraction (XRPD) tests were performed with a ULTIMA IV (Rigaku) instrument, laying the sample on a static sample holder. The X-ray focusing slit had a variable width, interlocked with the θ value. The X-ray tube had a Copper target, with a current intensity of 40 mA and a voltage of 50 kV. The radiation generated by the Cockcroft-Walton method is constituted by $K_{\alpha 1}$ 1.540562 Å) and $K_{\alpha 2}$ (1.544398 Å). The analytical conditions were as follows:

Fixed Time: Sampling width, 0.02 deg; Scanning rate, 1.0 s/step

2 θ range: 3/50 deg.

Sample holder: amorphous glass—equiangular 9200/2G, 0.2 mm deep. The sample was pressed with a glass plate.

Figure 53:
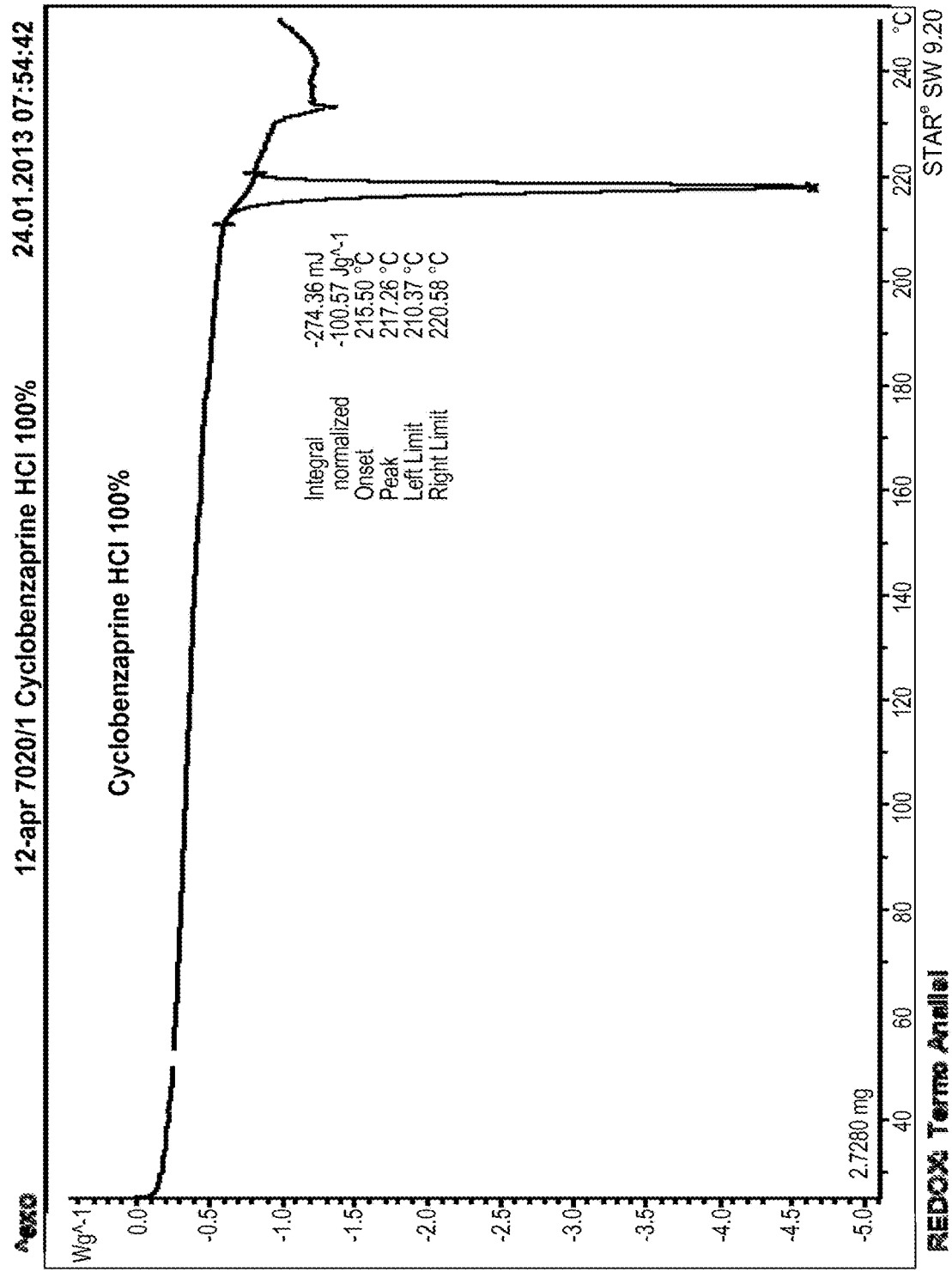
FIG. 53: DSC heating curve of Cyclobenzaprine HCl.
Figure 54:
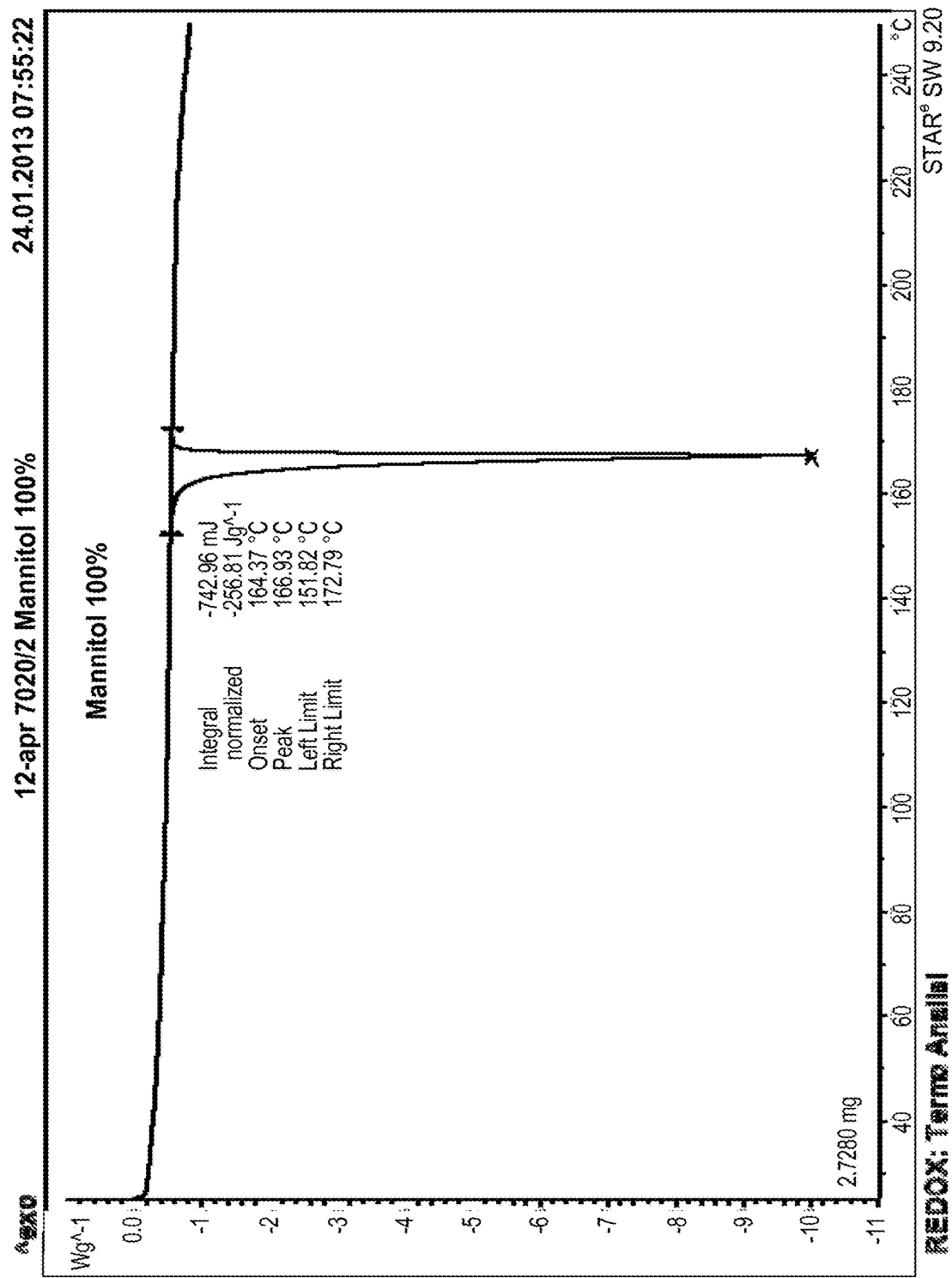
FIG. 54: DSC heating curve of Mannitol, beta form.

Pure components of Cyclobenzaprine HCl and mannitol, as well as mixtures of the two, were analyzed with DSC (Table 1). FIG. 53 depicts the melting curve with 100% Cyclobenzaprine HCl. Melting with decomposition was detected between 210° C. and 221° C. (onset at 215.5° C., ΔH=−100.6 J/g). FIG. 54 depicts the melting curve with 100% mannitol. Melting was detected between 151° C. and 173° C. (onset at 164.4° C., ΔH=−256.8 J/g). FIGS. C-L depict the various mixtures. Table 3 summarizes the data.

TABLE 3

Summary of DSC data

Figure 55:
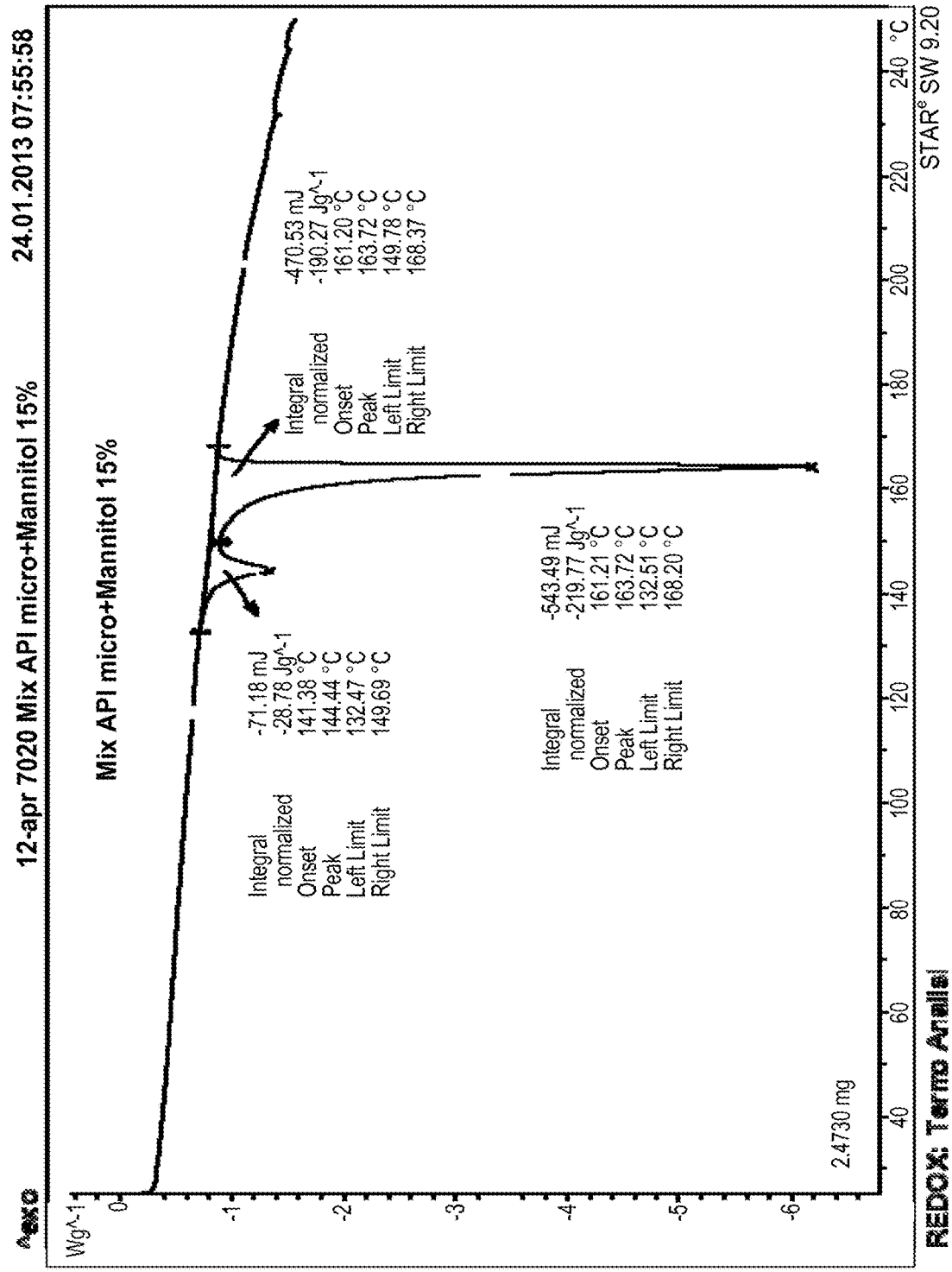
FIG. 55: DSC heating curve of a mixture of Cyclobenzaprine HCl and Mannitol at 15% of API.44
Figure 56:
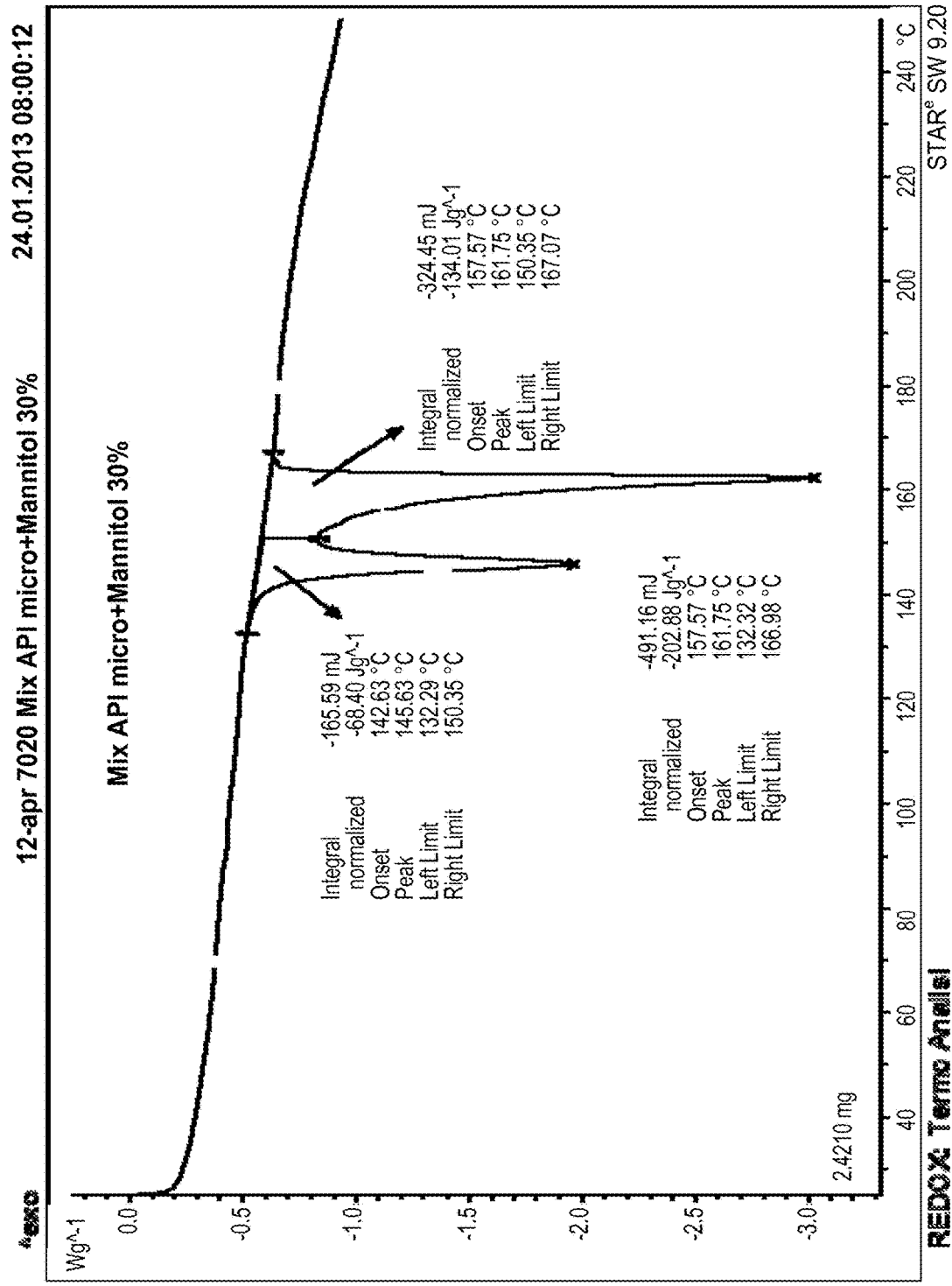
FIG. 56: DSC heating curve of a mixture of Cyclobenzaprine HCl and Mannitol at 30% of API.
Figure 57:
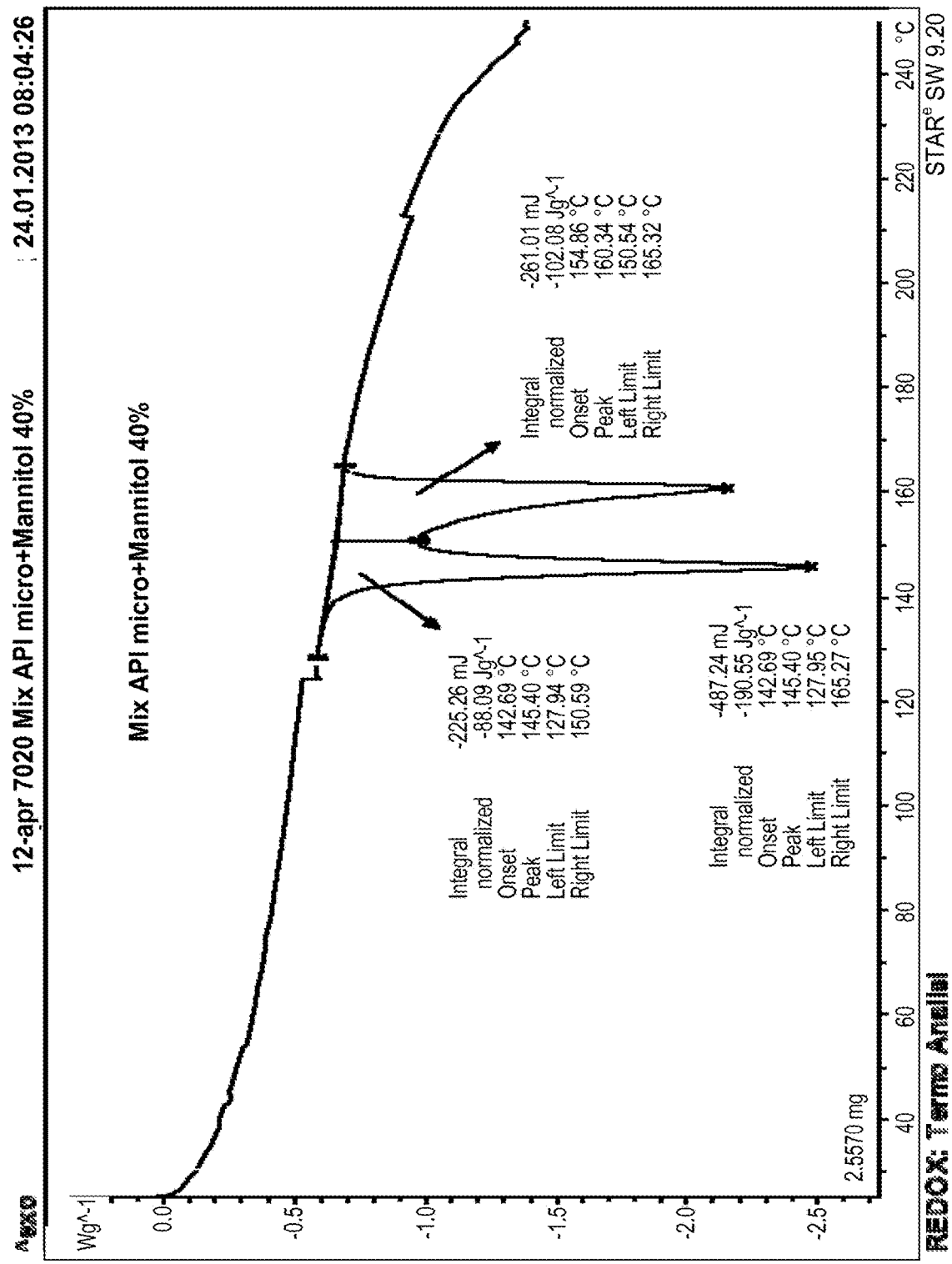
FIG. 57: DSC heating curve of a mixture of Cyclobenzaprine HCl and Mannitol at 40% of API.44
Figure 58:
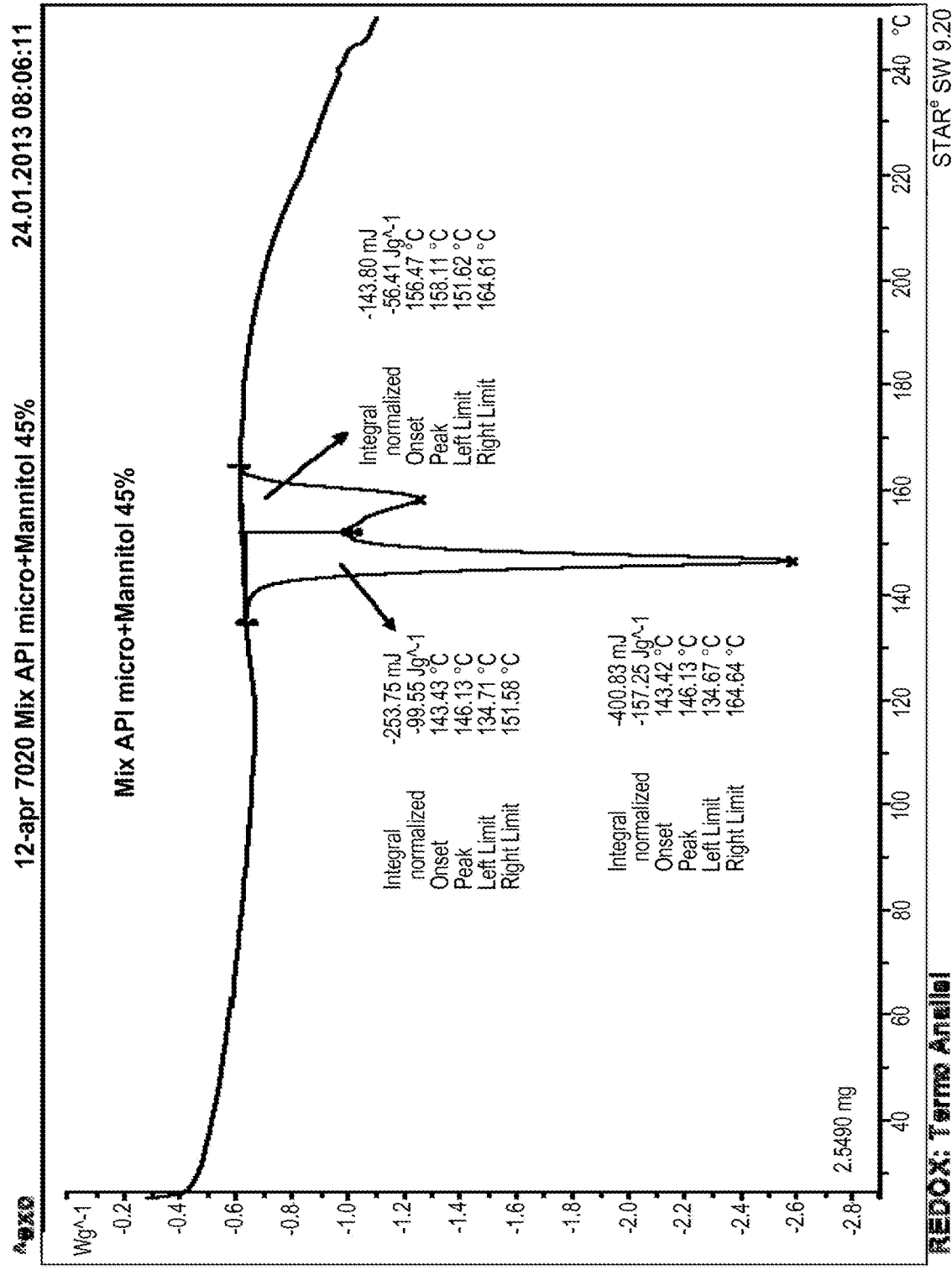
FIG. 58: DSC heating curve of a mixture of Cyclobenzaprine HCl and Mannitol at 45% of API.
Figure 59:
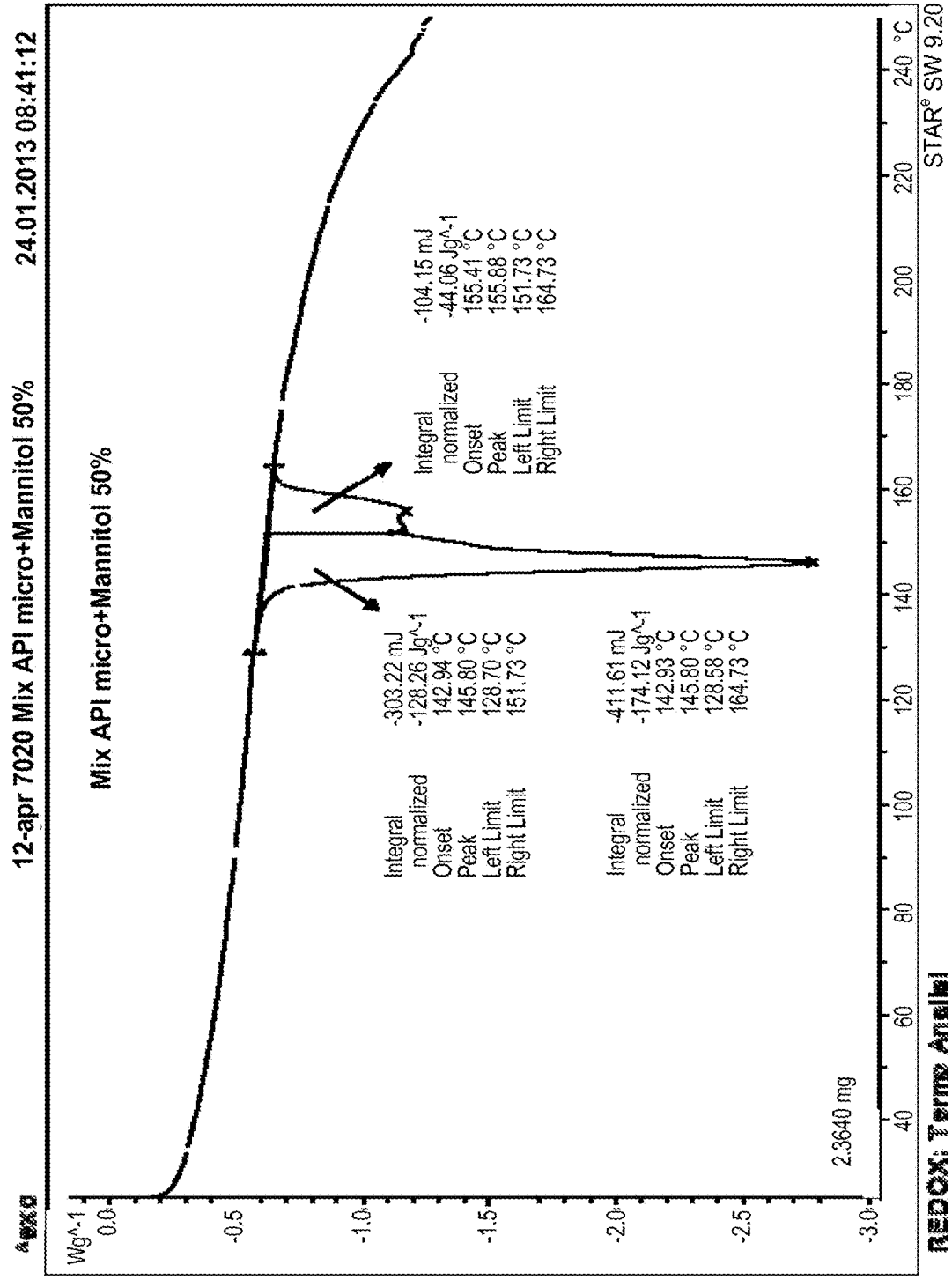
FIG. 59: DSC heating curve of a mixture of Cyclobenzaprine HCl and Mannitol at 50% of API.
Figure 60:
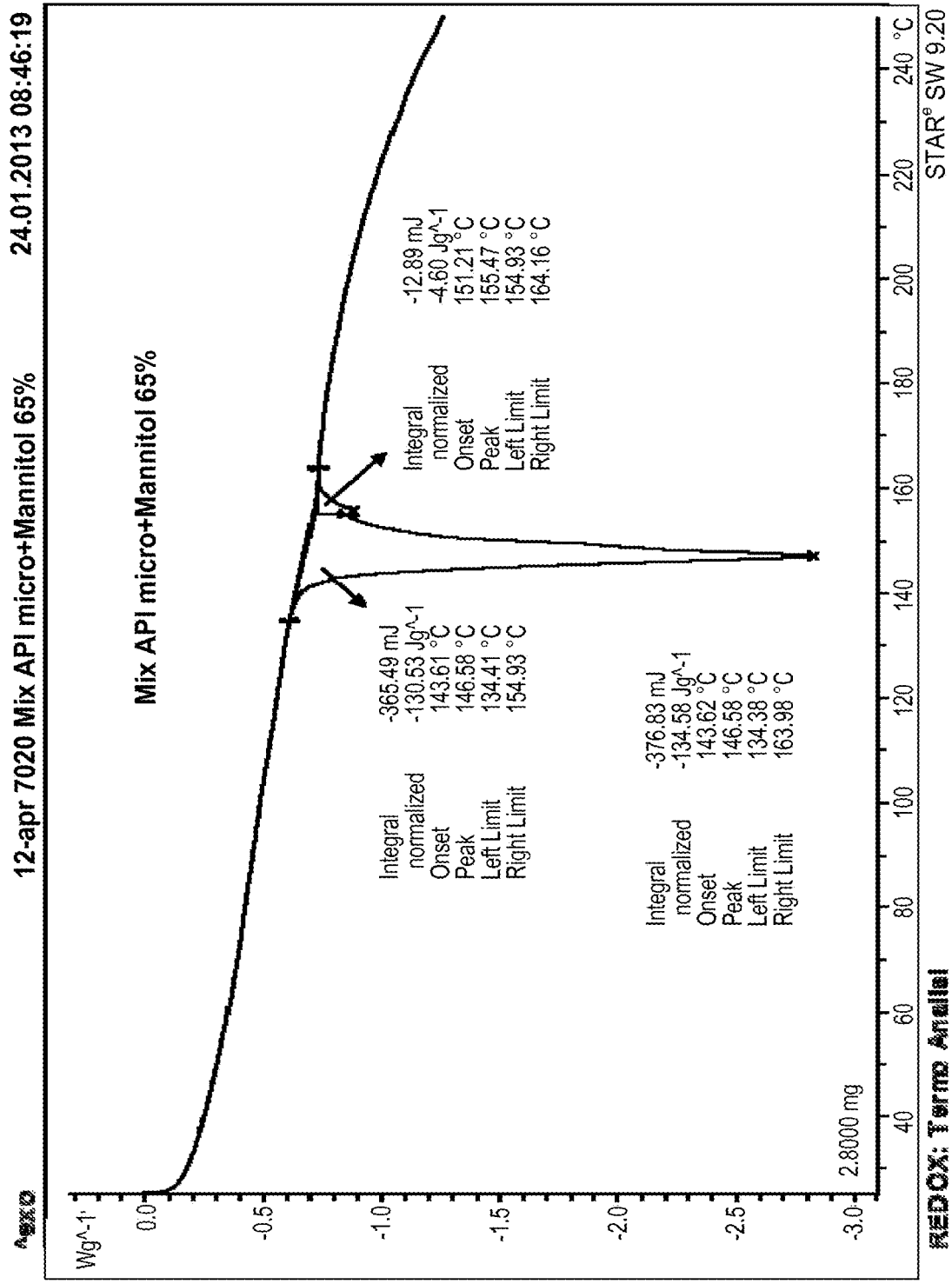
FIG. 60: DSC heating curve of a mixture of Cyclobenzaprine HCl and Mannitol at 65% of API.
Figure 61:
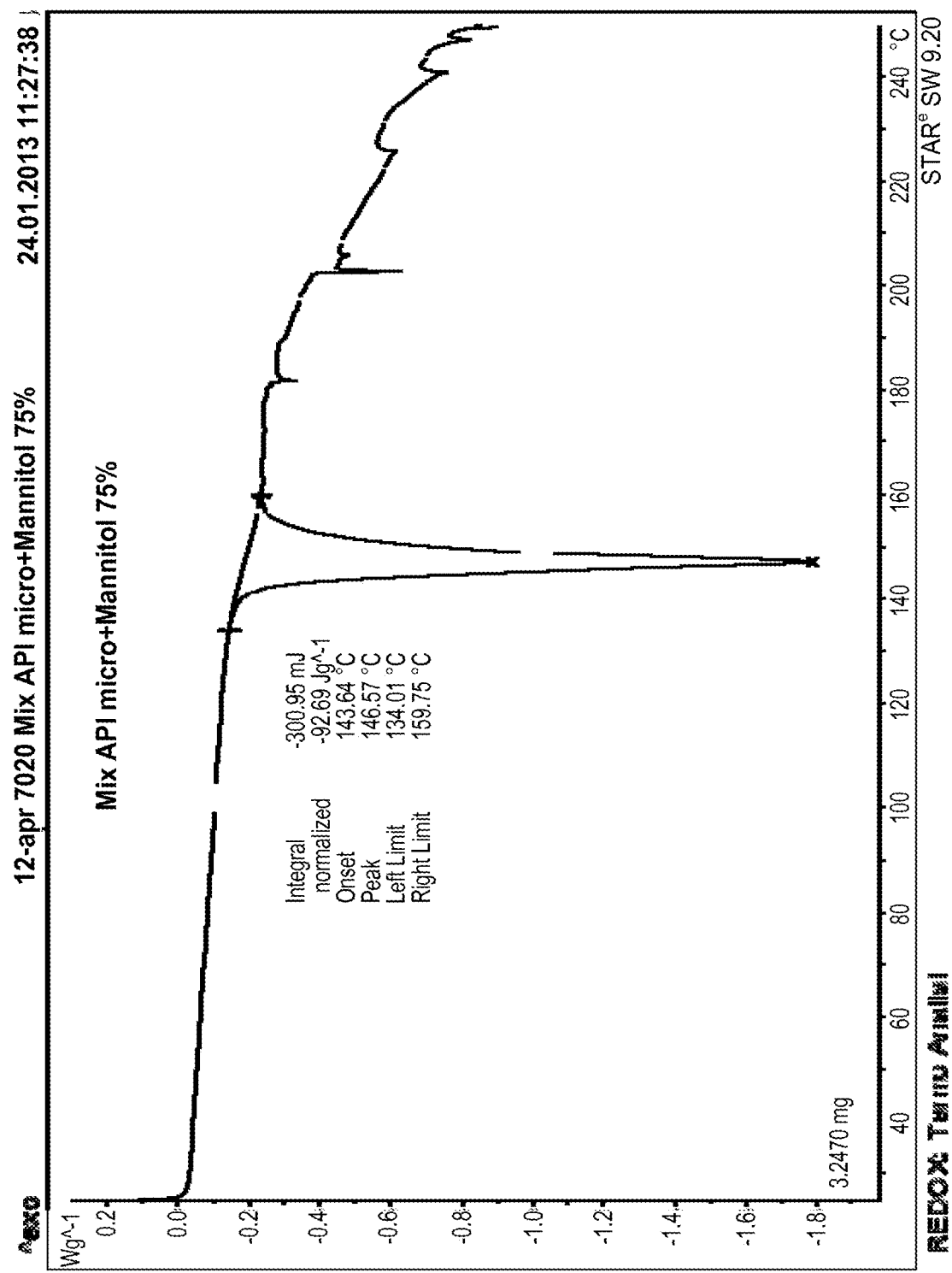
FIG. 61: DSC heating curve of a mixture of Cyclobenzaprine HCl and Mannitol at 75% of API.
Figure 62:
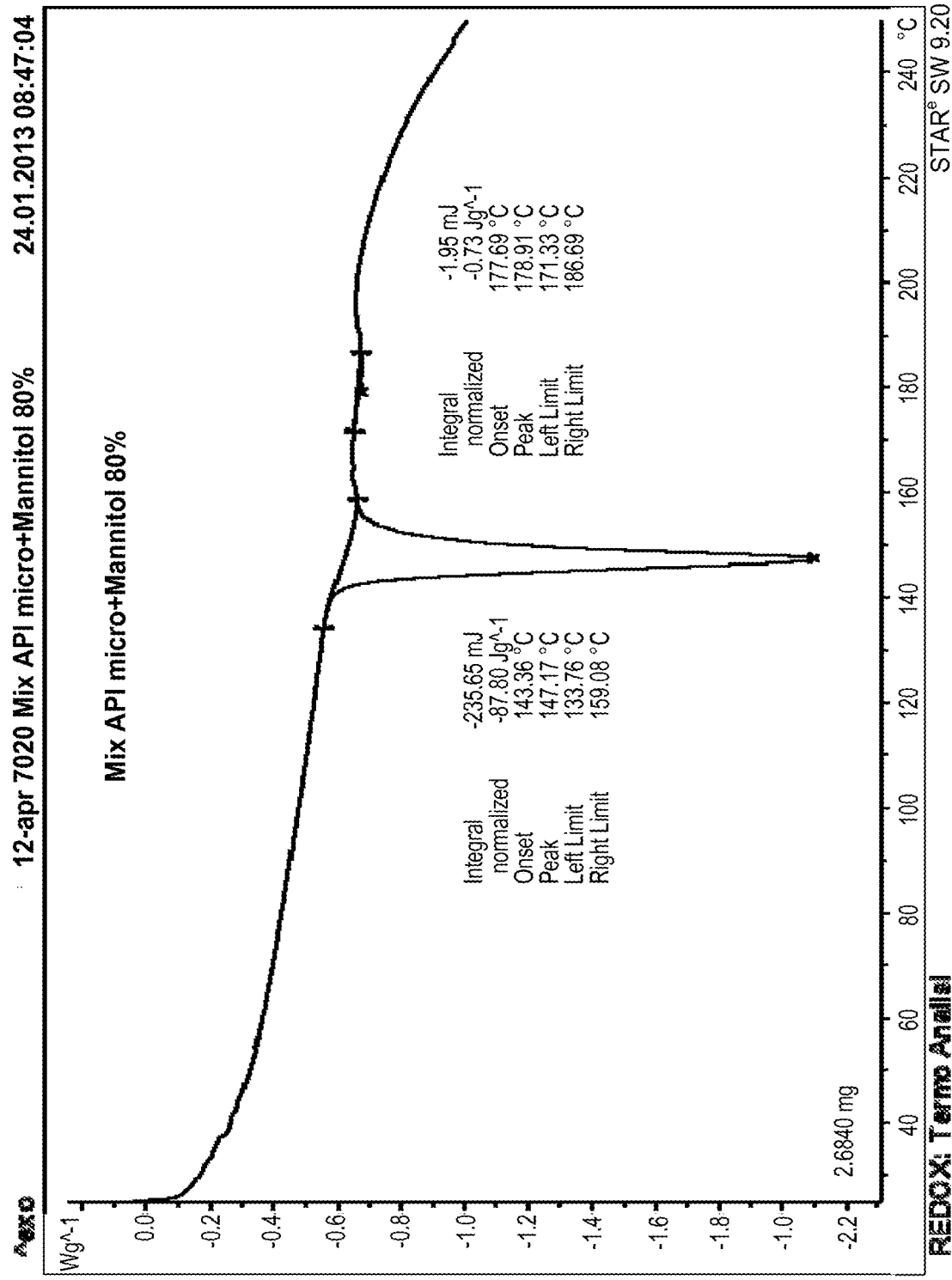
FIG. 62: DSC heating curve of a mixture of Cyclobenzaprine HCl and Mannitol at 80% of API.
Figure 63:
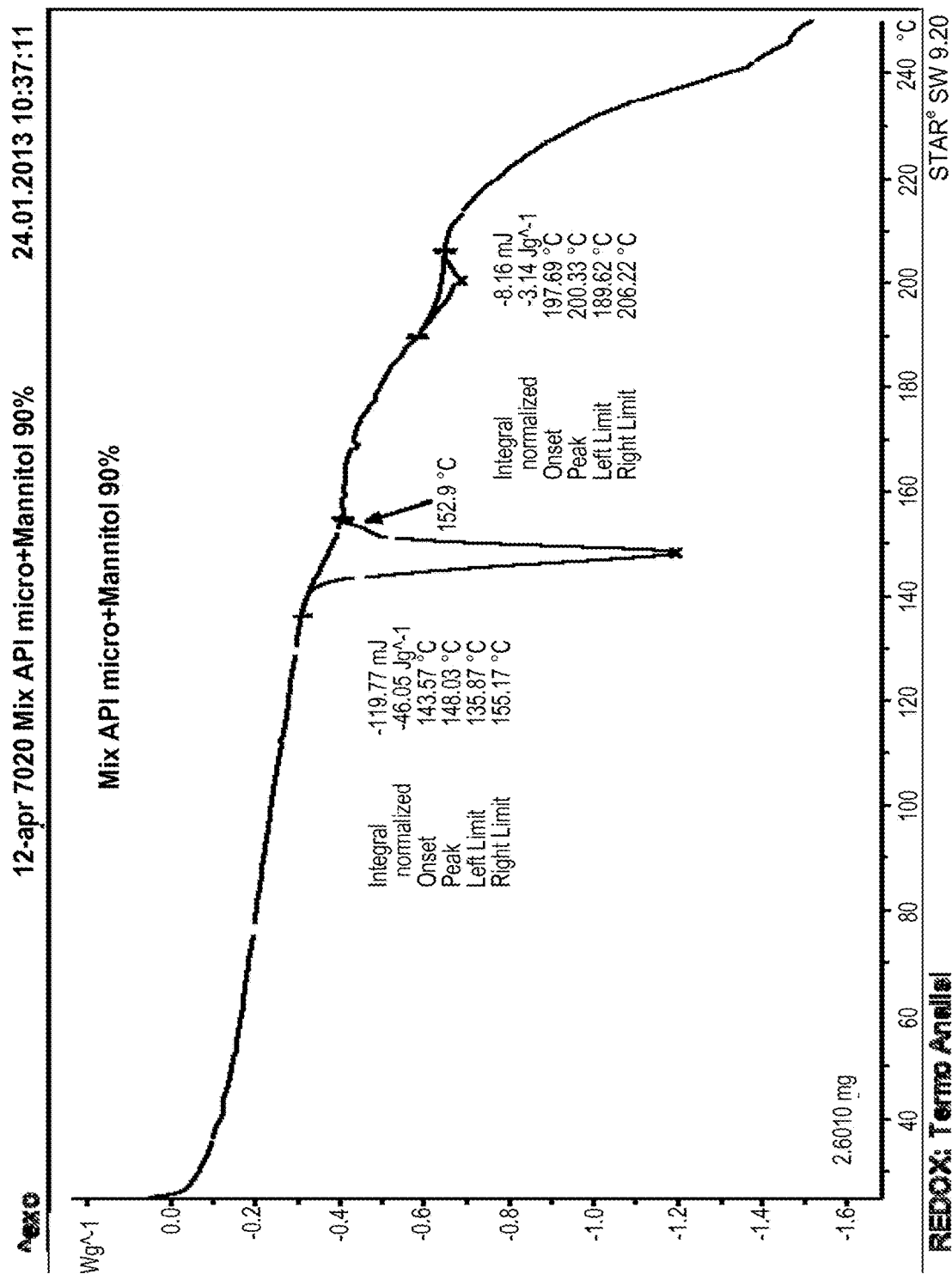
FIG. 63: DSC heating curve of a mixture of Cyclobenzaprine HCl and Mannitol at 90% of API.
Figure 64:
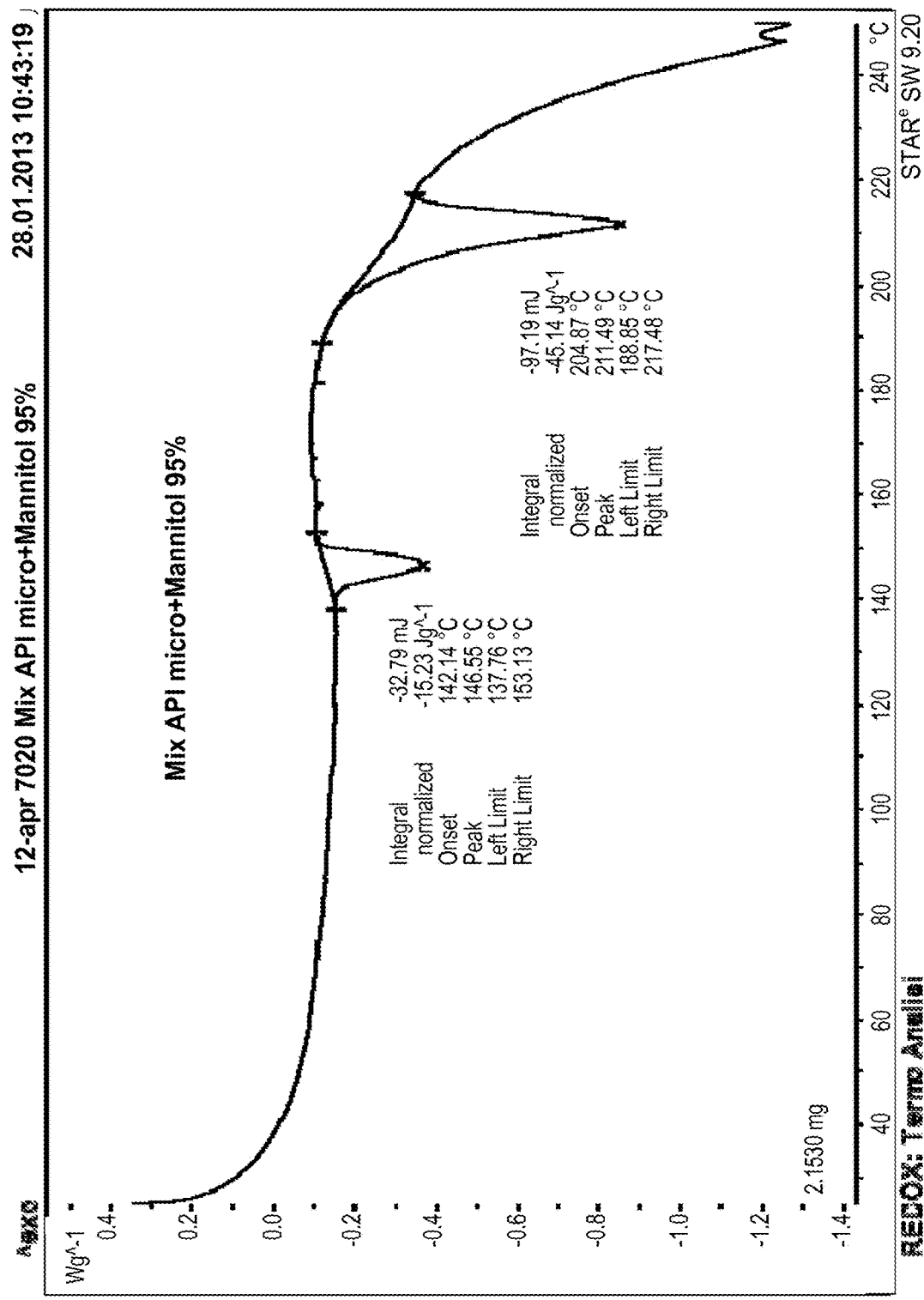
FIG. 64: DSC heating curve of a mixture of Cyclobenzaprine HCl and Mannitol at 95% of API.

| % API | % Mannitol | T onset eutectic (° C.) | T onset 2nd effect (° C.) | ΔH eutectic (J/g) | ΔH 2nd effect (J/g) | ΔH global (J/g) | Plot |
|---|---|---|---|---|---|---|---|
| 100 | 0 | — | 215.5 | — | 100.57 | — | FIG. 53 |
| 0 | 100 | — | 164.37 | — | — | 256.81 | FIG. 54 |
| 15 | 85 | 141.38 | 161.21 | 28.78 | 190.27 | 219.77 | FIG. 55 |
| 30 | 70 | 142.63 | 157.57 | 68.4 | 134.01 | 202.88 | FIG. 56 |
| 40 | 60 | 142.69 | 154.86 | 88.09 | 102.08 | 190.55 | FIG. 57 |
| 45 | 55 | 143.43 | 156.47 | 99.55 | 56.41 | 157.25 | FIG. 58 |
| 50 | 50 | 142.94 | 155.41 | 109.8 | 44.06 | 174.12 | FIG. 59 |
| 65 | 35 | 143.61 | 151.21 | 130.53 | 4.6 | 134.58 | FIG. 60 |
| 75 | 25 | 143.64 | 143.64 | 92.7 | — | — | FIG. 61 |
| 80 | 20 | 143.36 | 177.69 | 87.8 | 0.73 | — | FIG. 62 |
| 90 | 10 | 143.57 | 197.69 | 46.05 | 3.14 | — | FIG. 63 |
| 95 | 5 | 142.1 | 204.9 | 15.23 | 45.14 | — | FIG. 64 |

Figure 65:
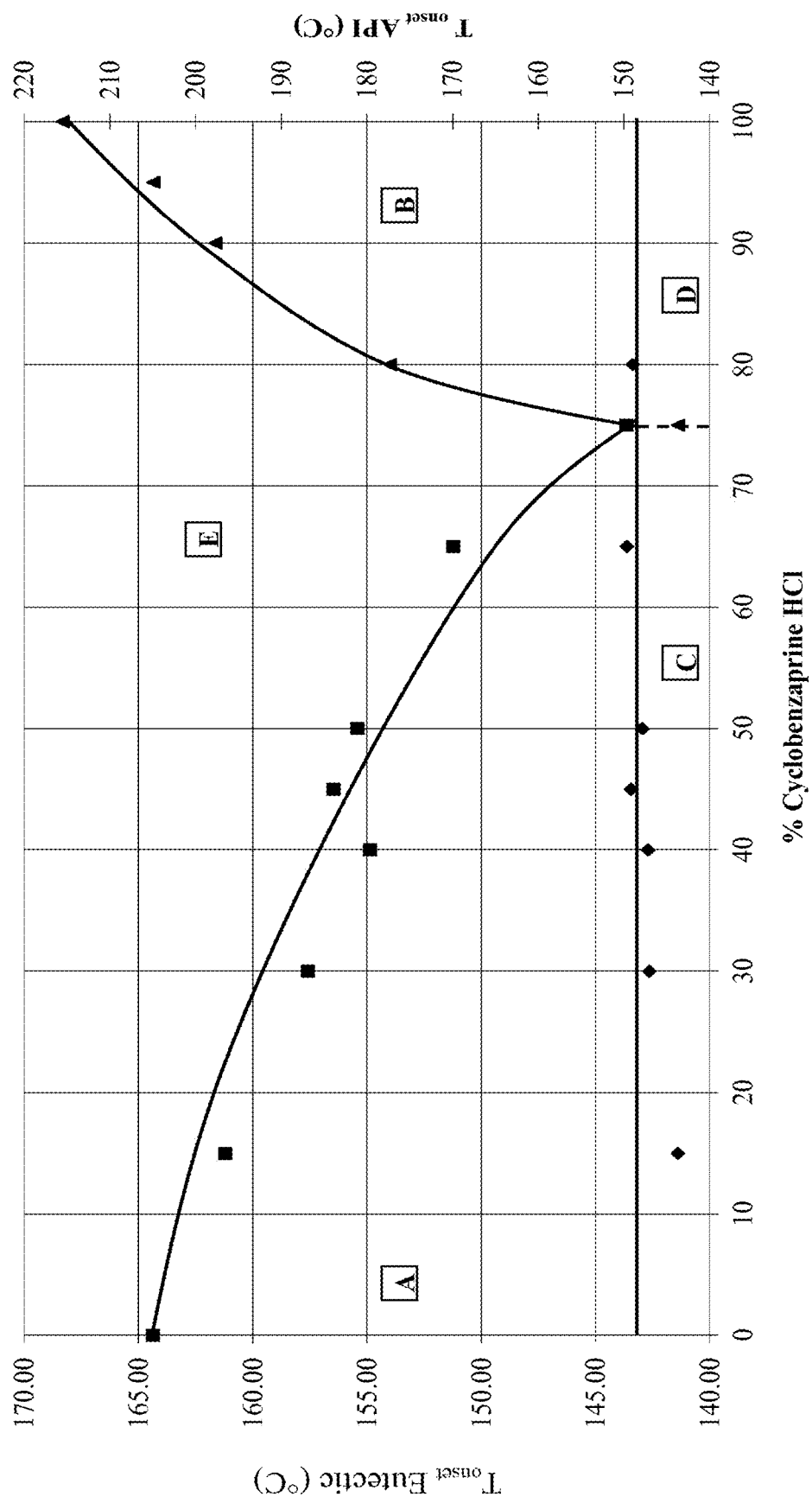
FIG. 65: Phase diagram of binary mixtures between Cyclobenzaprine HCl and Mannitol.

The above results demonstrated that the eutectic composition formed at approximately 75% Cyclobenzaprine HCl (API) and 25% mannitol. Under 75%, two distinct melting peaks were observed from the melting of the eutectic fraction and the excess of the individual components. FIG. 65 shows a phase diagram depicting the onset melting temperatures of the eutectic fraction and the excess components, plotted as function of API percentage. Five distinct zones are present in the diagram:
  Zone A: Excess of Mannitol (liquid eutectic+solid mannitol)
  Zone B: Excess of Cyclobenzaprine HCl (liquid eutectic +solid Cyclobenzaprine HCl)
  Zone C: Solid eutectic with mannitol
  Zone D: Solid eutectic with Cyclobenzaprine HCl
  Zone E: Liquid phase with mannitol and Cyclobenzaprine HCl In Zone A, when the percentage of API increased, the onset temperature of the excess of mannitol decreased while the temperature of eutectic fraction remained constant around 143° C. Above the eutectic composition, the excess of API led to an increase in the temperature (Zone B). In addition, there was a good correlation between mixtures and temperature. A few small deviations from the trend curve were due to an incompletely homogeneous powder mixture.

Figure 66:
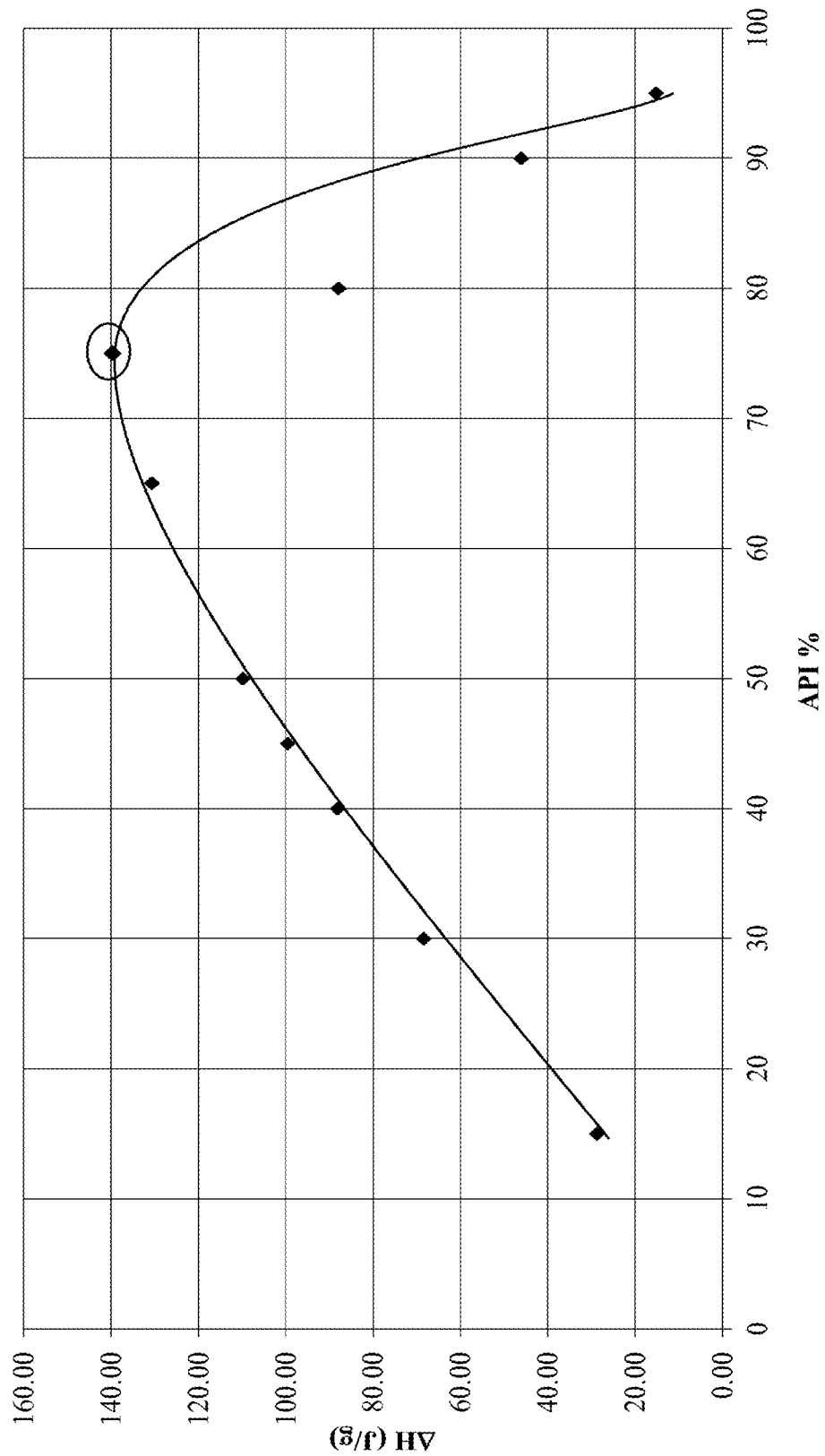
FIG. 66: Plot of melting enthalpy as function of API percentage.
Figure 67:
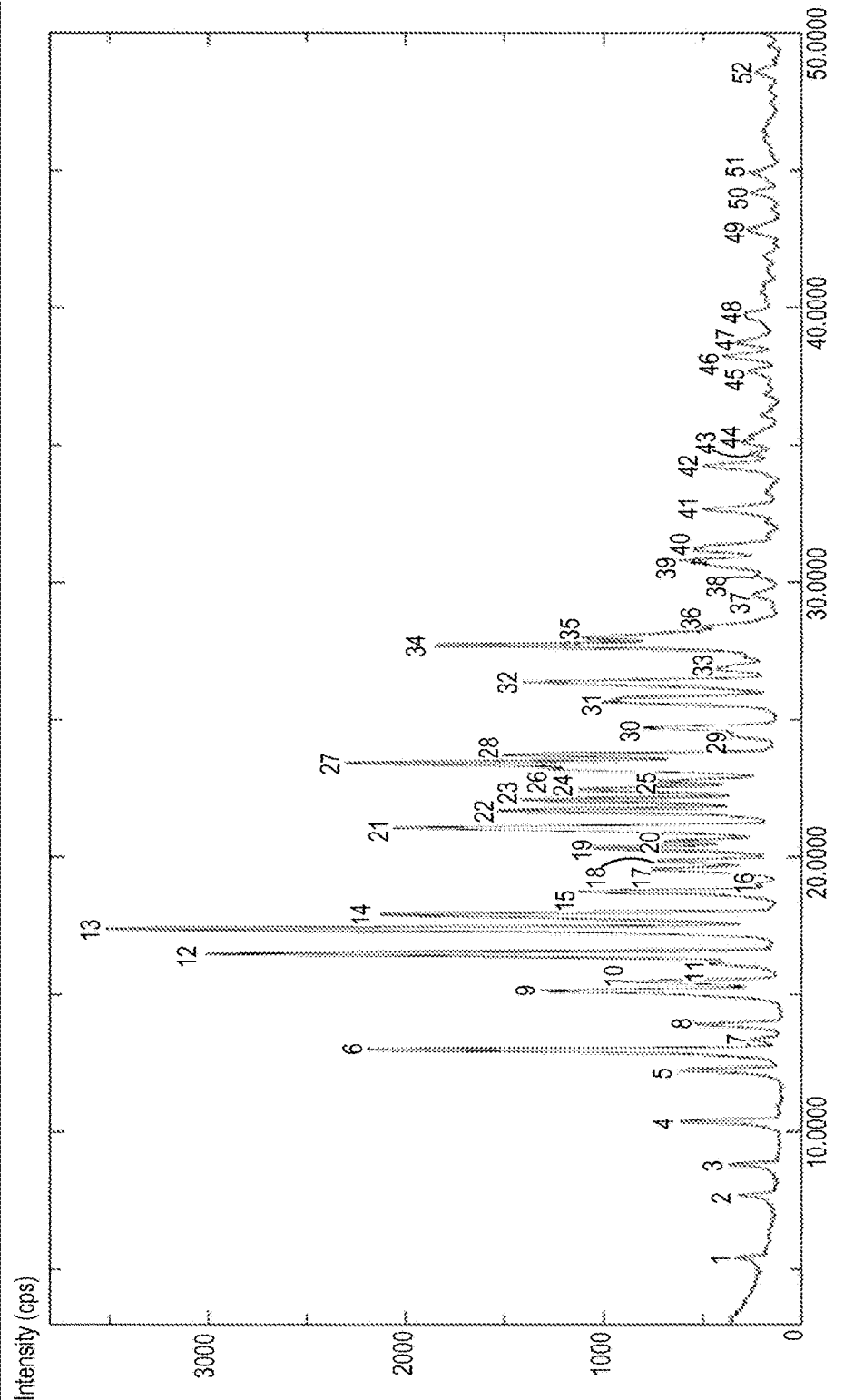
FIG. 67: XRPD pattern of Cyclobenzaprine HCl.
Figure 69:
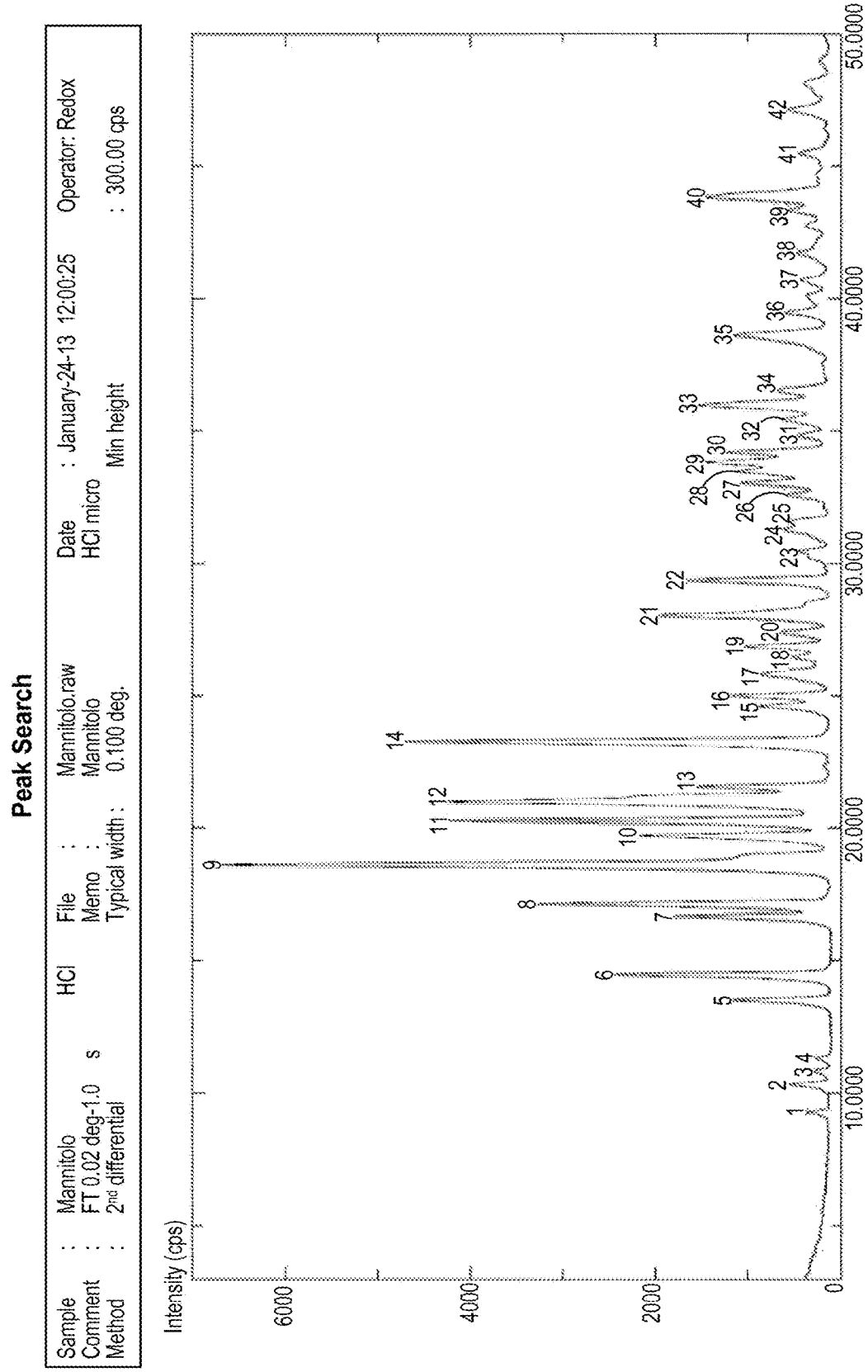
FIG. 69: XRPD pattern of Mannitol, beta form.
Figure 71:
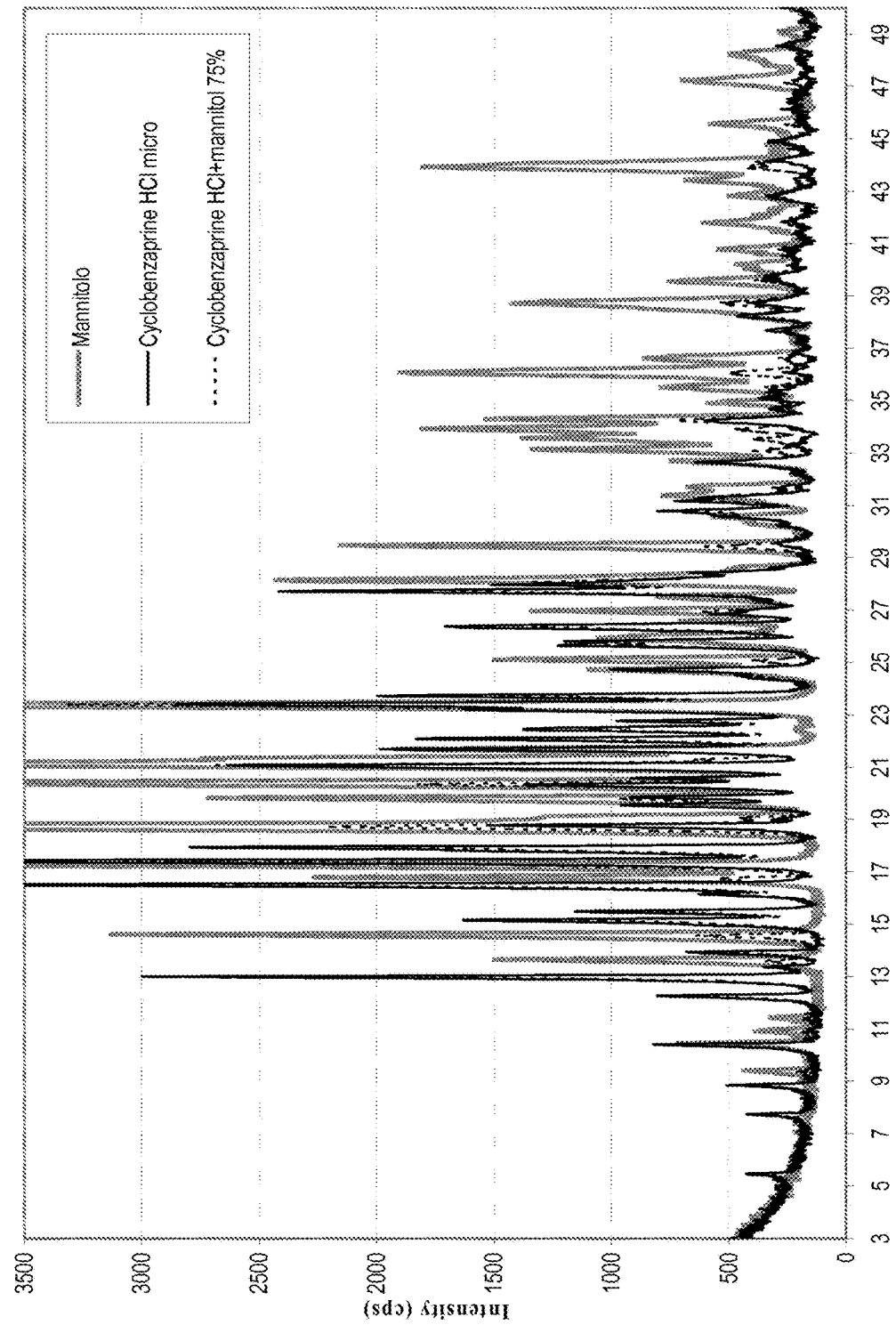
FIG. 71: Stacking of XRPD patterns of pure compounds and eutectic mixture.

FIG. 66 shows eutectic melting enthalpy as function of the API percentage. The eutectic melting enthalpy increases until the eutectic composition is attained. At the eutectic composition, the maximum value should be reached, but, due to partial decomposition of the product, it was not possible to correctly evaluate the melting heat. Instead, the plot shows the theoretical value, obtained on the basis of the melting enthalpy of the pure compounds. The eutectic composition corresponds to 75% API, 25 Mannitol, by weight. The theoretical ratio between the molecular weights (311.38 mw/182.17 mw) was 1.71, while the ratio from the weight percentage [(0.75/311.38 mw)/(0.25/182.17 mw)] gives a molar ratio for the eutectic of 1.76 (i.e., 1.76 moles of Cyclobenzaprine HCl to 1 mole of Mannitol in the eutectic).

XRPD

Figure 72:
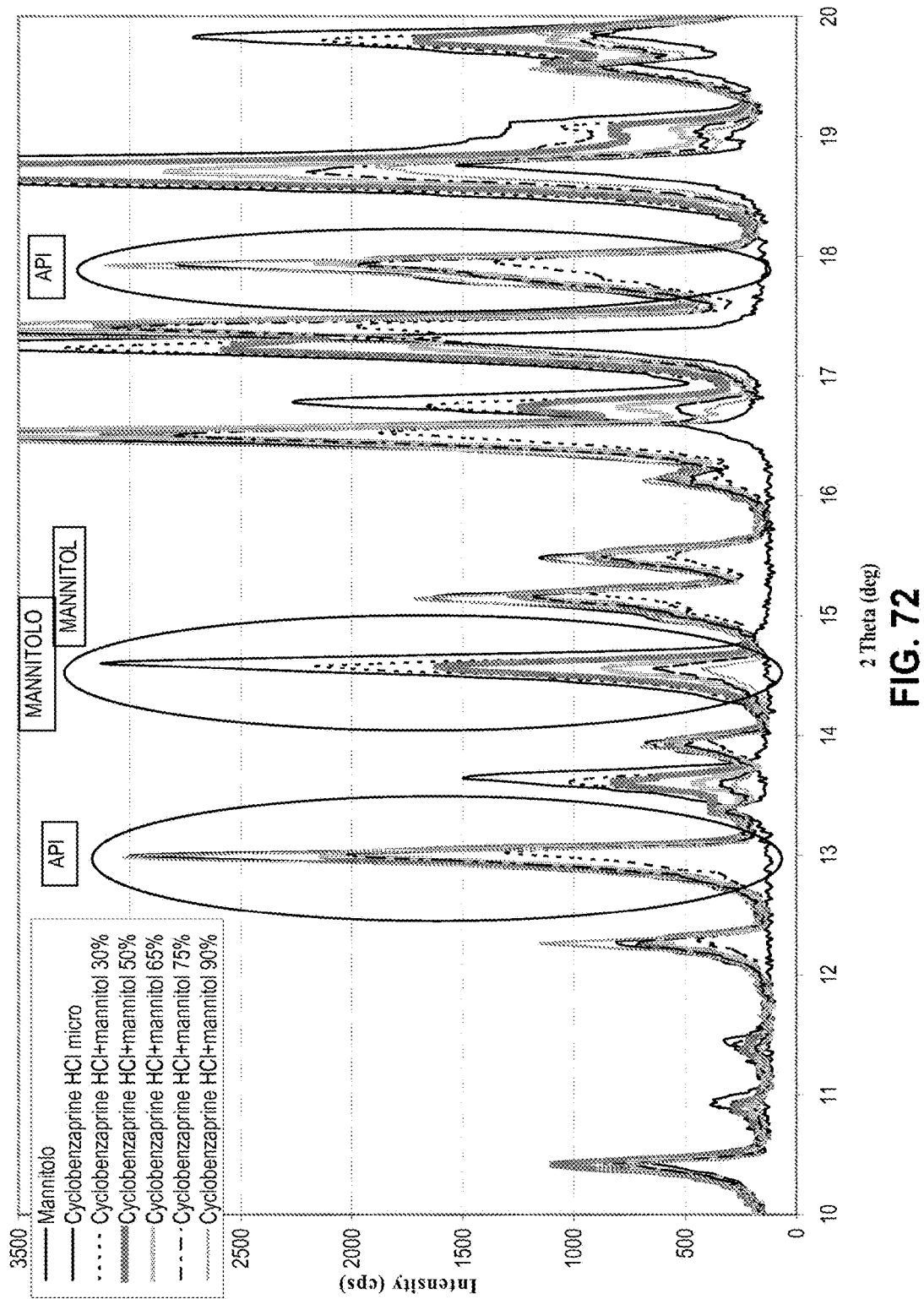
FIG. 72: Stacking of XRPD patterns of pure compounds and mixtures.
Figure 73:
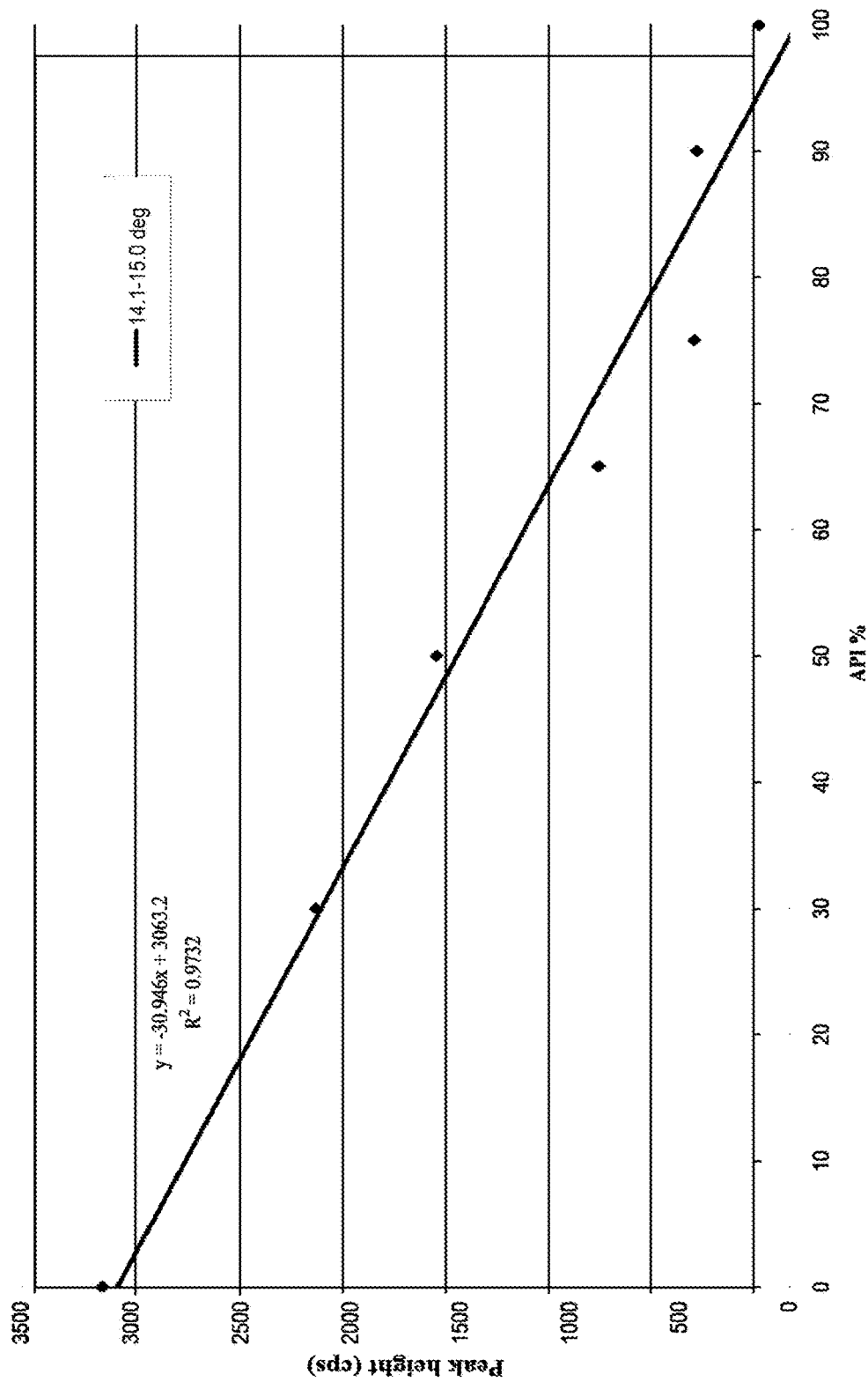
FIG. 73: Linearity of Mannitol peaks in the range of 14.1-15° 2θ.
Figure 74:
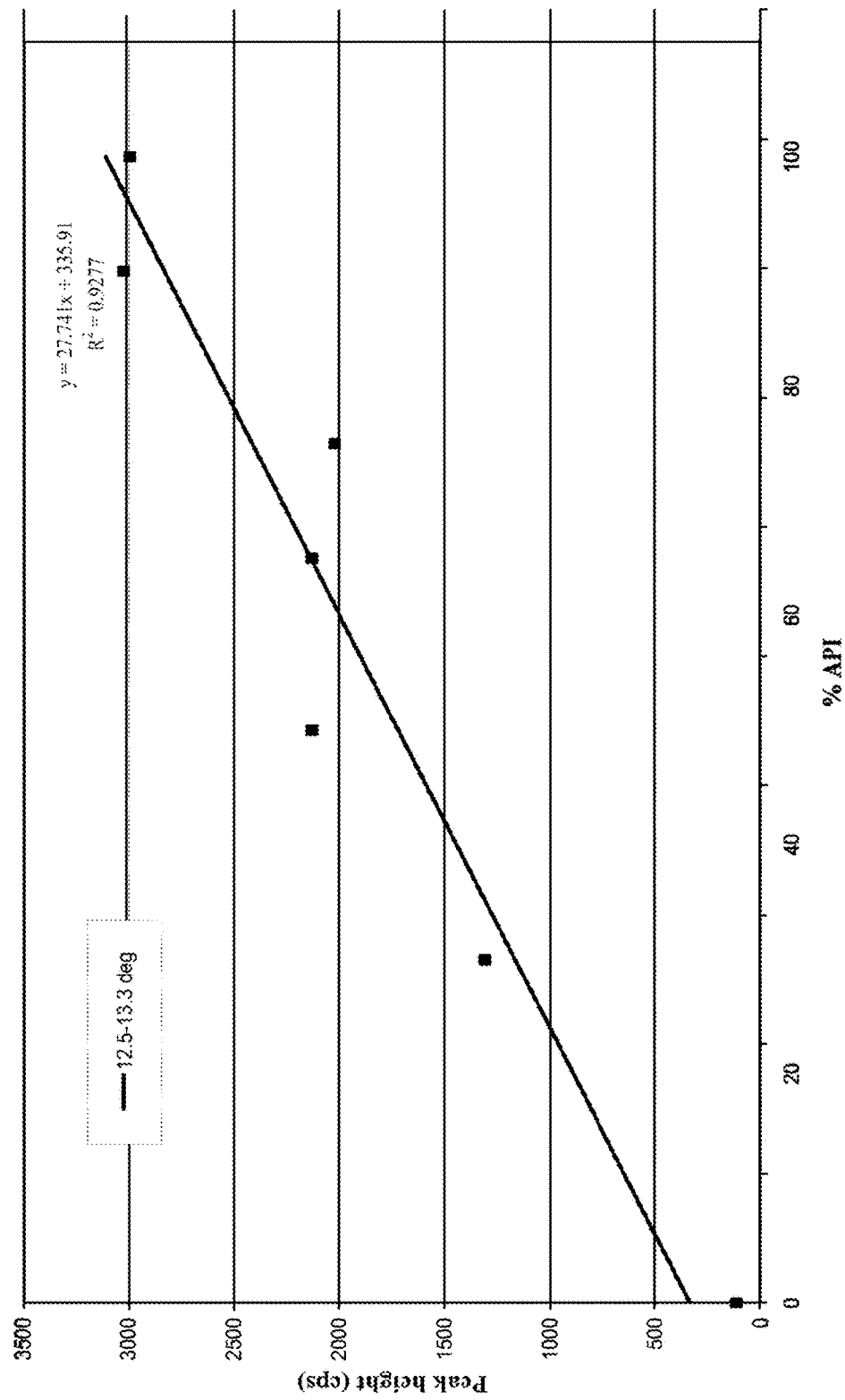
FIG. 74: Linearity of API peaks in the range of 12.5-13.3° 2θ.

To confirm that the eutectic composition was only a physical mixture and that a new entity or adduct was not formed, the mixtures were analyzed by X-ray Powder Diffraction, where no thermal treatments were applied (pure Cyclobenzaprine HCl, FIGS. O-P; pure mannitol, FIGS. Q-R). Fig S depicts the stacking of pure mannitol, API, and the eutectic mixture at 75%, showing different diffraction zones where no peaks of the pure components were distinguishable and no interferences were detected. FIG. 72 shows the stacking of pure mannitol and API and mixtures thereof, where it was possible to point out three distinct diffraction ranges: Mannitol 14.1-15.0° 2θ, API 12.5-13.3° 2θ and 17.5-18.2° 2θ.

Within these ranges, an evaluation was carried out for each mixture analyzed (30, 50, 65, 75 and 90%). Each peak height was plotted as function of API % and linearity coefficient was obtained (FIGS. U-V). Good correlations between concentration and peak heights were obtained. API and mannitol, when mixed, resulted in no adduct formation, only a physical eutectic formation.

In summary, the data show that thermal behavior of the mixtures presents two endotherms, relating to the eutectic and to the melting of the excess of the main component. Thermal entities recorded for the mixtures agreed with the percentage of API/Mannitol ratio present in the eutectic mixture. At the eutectic composition, only one melting peak was visible. The eutectic composition was reached at about 75% API and 25% Mannitol. The eutectic composition confirmed the molar stoichiometry (ratio between the two components: 1.76). The melting temperature of the eutectic was about 143.6° C. and was recorded for all the investigated mixtures. By XRPD, no adduct interaction occurred between API and mannitol, only a physical eutectic formation.

Example 4

Thermal analytical techniques were used to assess the compatibility of the drug product Amitriptyline HCl. The compatibility assessment was carried out between the APT and the excipients in a 1:1 ratio. On the basis of thermal events recorded for each component and for the mixtures, the analyses were carried out by investigating the peaks recorded by DSC in mixtures between API and the excipients. Differences in thermal profiles between the single compound and the related mixtures were obtained after milling the products in an agate mortar.

DSC was performed substantially as described in Examples 1 and 2. The following raw materials were used:
  Amitriptyline HCl
  Sodium stearyl fumarate
  Stearic acid
  Glycerol dibehenate
  Magnesium stearate
  Pearlitol flash
  Pearlitol 200 SO/Mannitol
  Unipure DW/Com starch pregelatinized
  Crospovidone—Kollidon CL
  Silicon Colloidal/ Aerosil 200
  Sodium phosphate dibasic
  Sodium bicarbonate
  Sodium carbonate
  Sodium Phosphate dodecahydrate
  Sodium Phosphate anhydrous.

Figure 75:
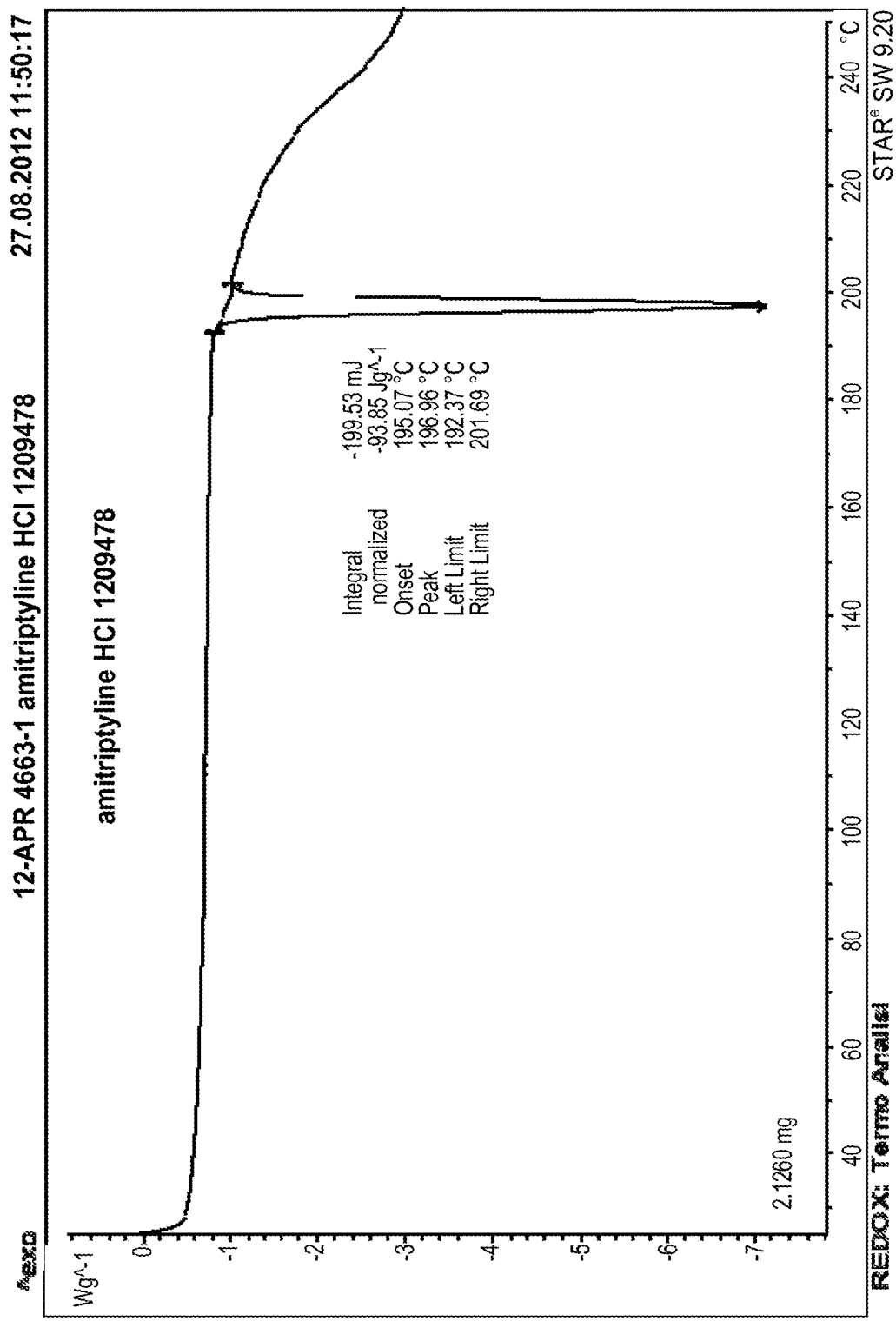
FIG. 75: DSC heating curve of Amitriptyline HCl.

The melting and decomposition of 100% Amitriptyline HCl was detected between 192° C. and 202° C. (onset at 195.1° C., ΔH=−93.9 J/g) (FIG. 75).

Figure 76:
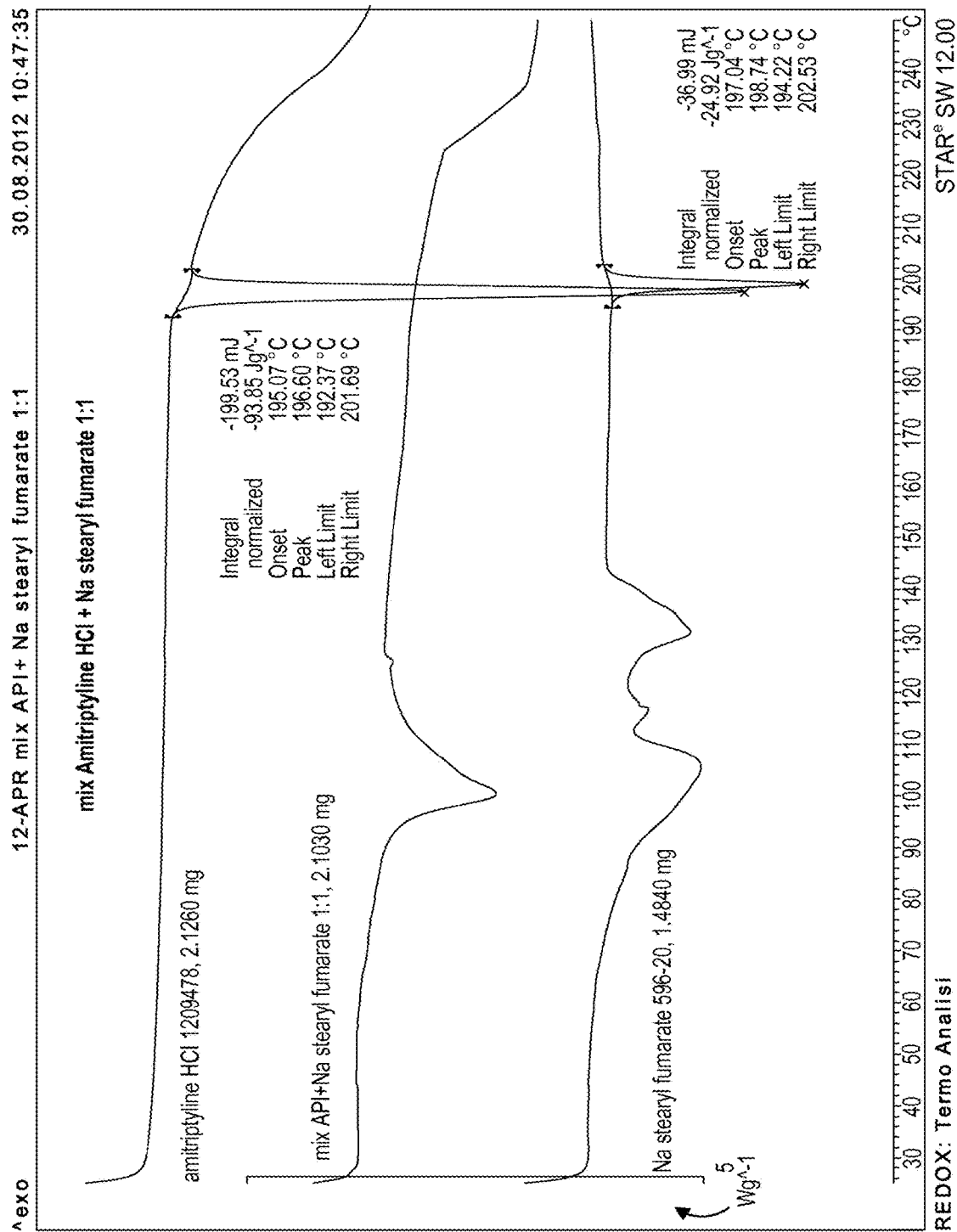
FIG. 76: DSC heating curve of Amitriptyline HCl+Sodium stearyl Fumarate 1:1.

In a 1:1 mixture of Amitriptyline HCl and Sodium Stearyl fumarate, the endothermic transitions of sodium stearyl fumarate were recorded in the range of 90° C. to 120° C. (FIG. 76). No API transition peak was detected, and a physical interaction was observed.

Figure 77:
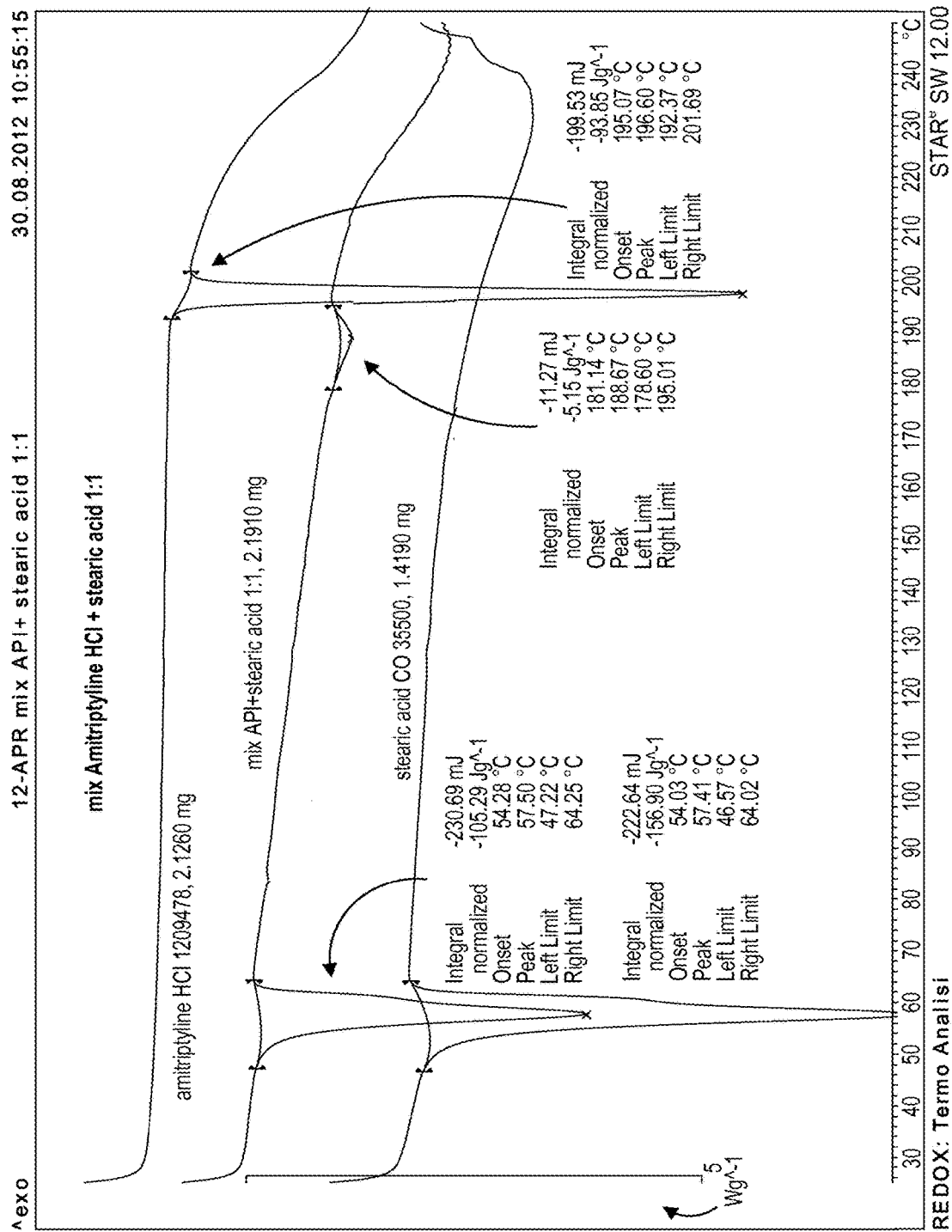
FIG. 77: DSC heating curve of Amitriptyline HCl+Stearic acid 1:1.

The endothermic transitions of stearic acid in a 1:1 mixture of Amitriptyline HCland Stearic acid were recorded in the range of 47° C. to 64° C. The API transition peak was detected between 179° C. and 195° C. (onset at 181.1 ° C., ΔH=−5.15 J/g) (FIG. 77). A small physical interaction was observed.

Figure 78:
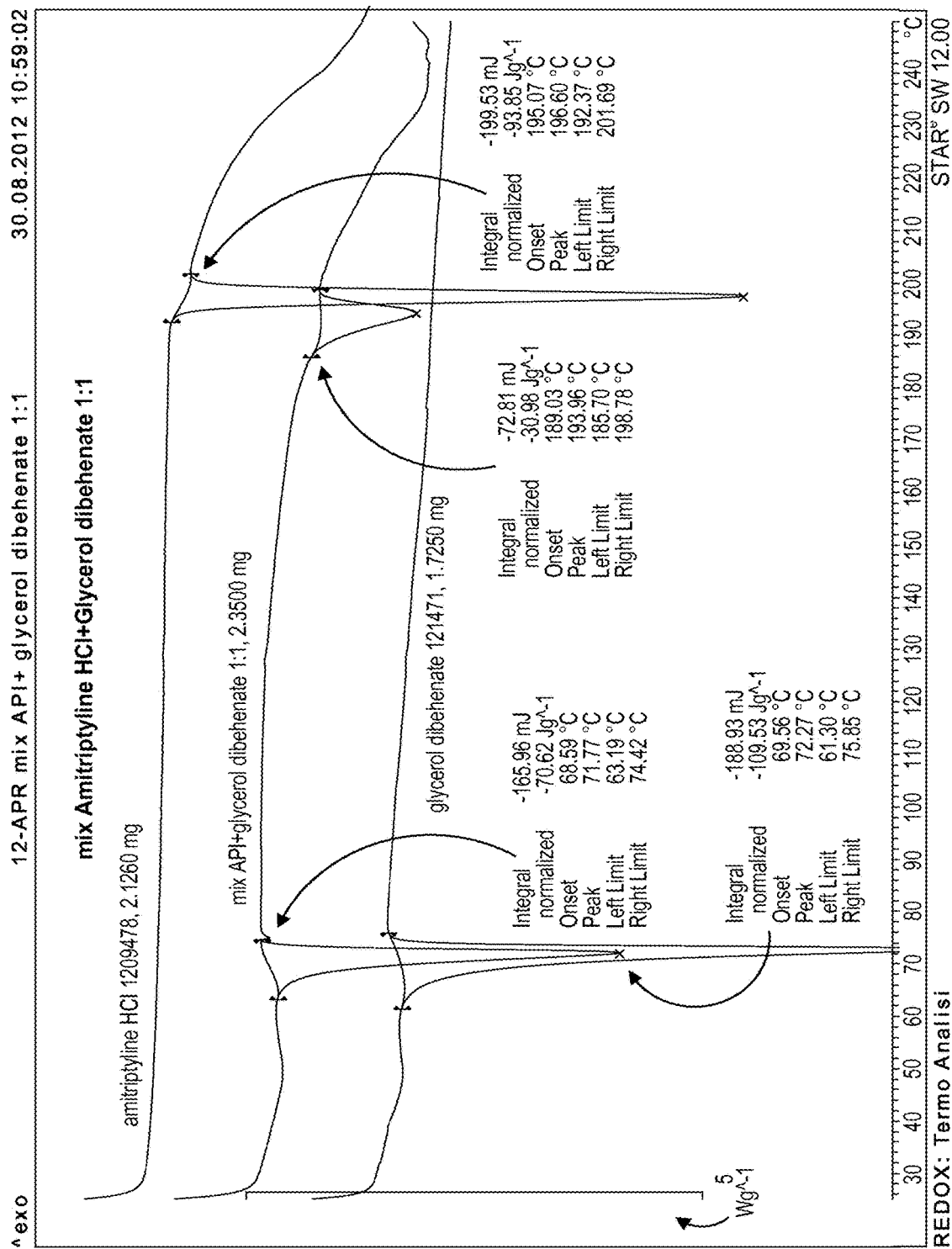
FIG. 78: DSC heating curve of Amitriptyline HCl+Glycerol dibehenate 1:1.

In a 1:1 mixture of Amitriptyline HCl and glycerol dibehenate (or glycerol behenate), the endothermic transitions of glycerol dibehenate were recorded in the range of 63° C. to 74° C. The API transition peak was detected between 186° C. and 199° C. (onset at 189.0° C., ΔH=−31.0 J/g) (FIG. 78). A small physical interaction was observed.

Figure 79:
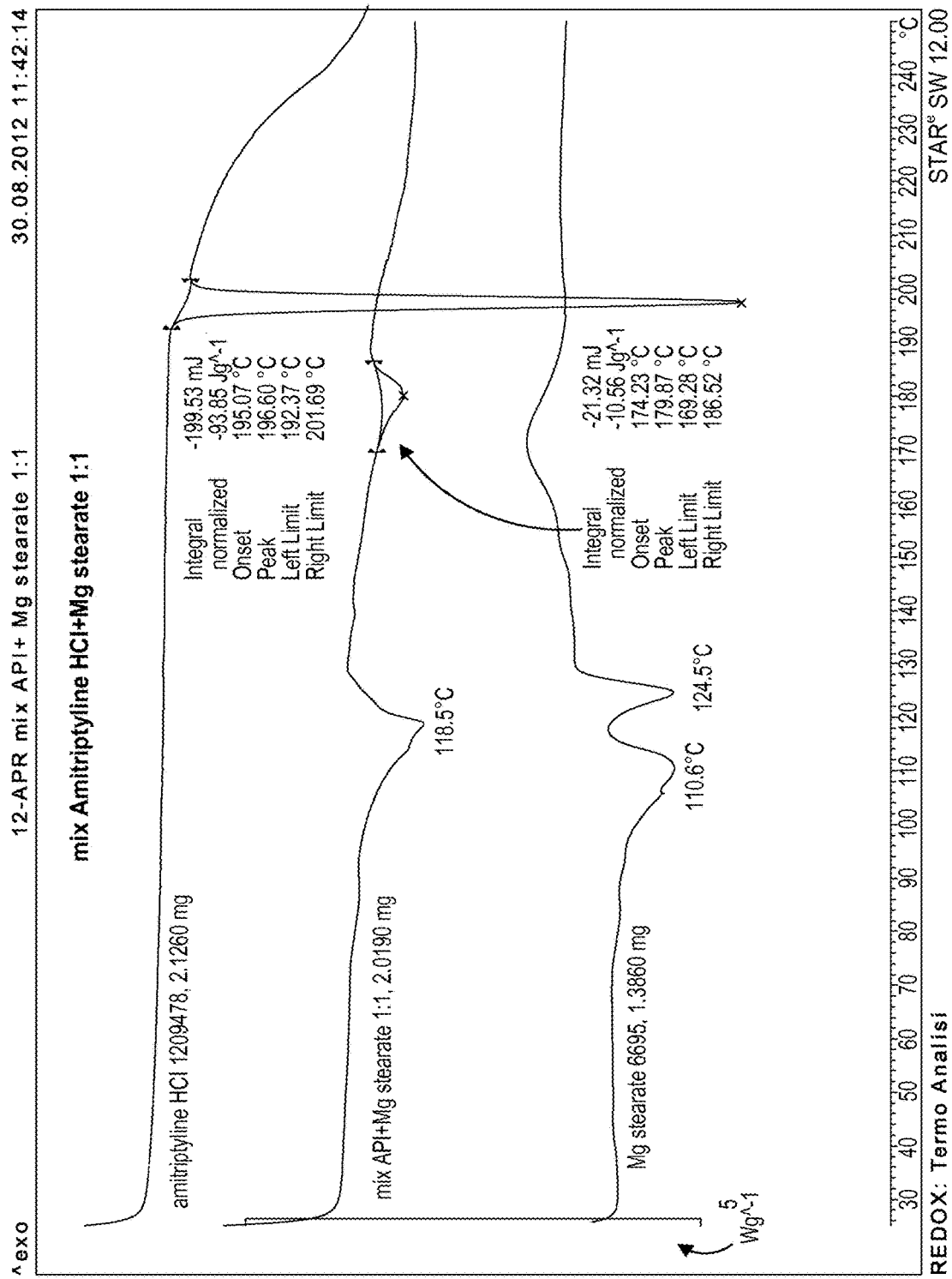
FIG. 79: DSC heating curve of Amitriptyline HCl+Magnesium stearate 1:1.

In a 1:1 mixture of Amitriptyline HCland Magnesium stearate, the endothermic transitions of magnesium stearate were recorded in the range of 100° C. to 120° C. The APT transition peak was detected between 169° C. and 187° C. (onset at 174.0° C., ΔH=−10.6 J/g) (FIG. 79). A small physical interaction was observed.

Figure 80:
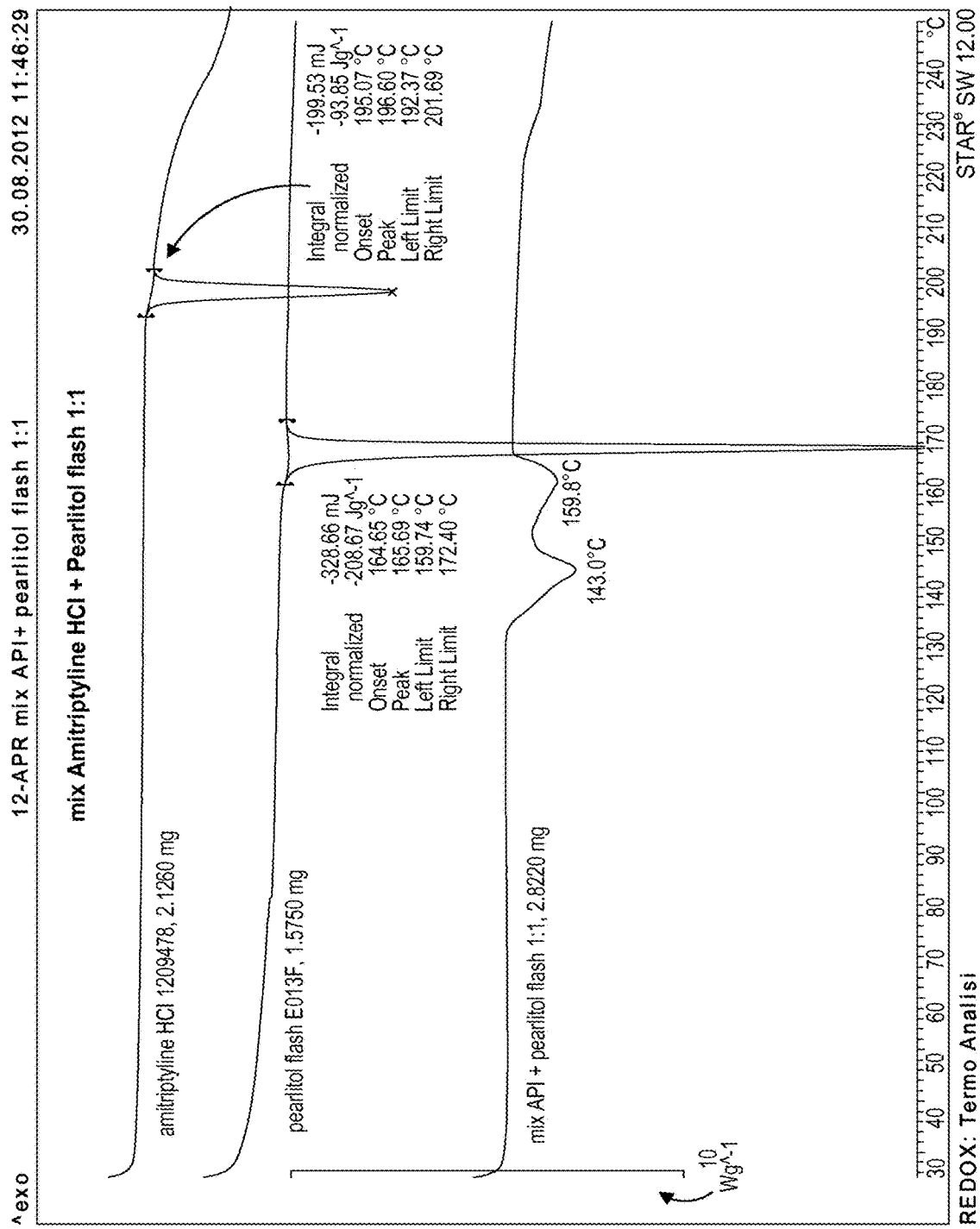
FIG. 80: DSC heating curve of Amitriptyline HCl+Pearlitol flash 1:1.
Figure 81:
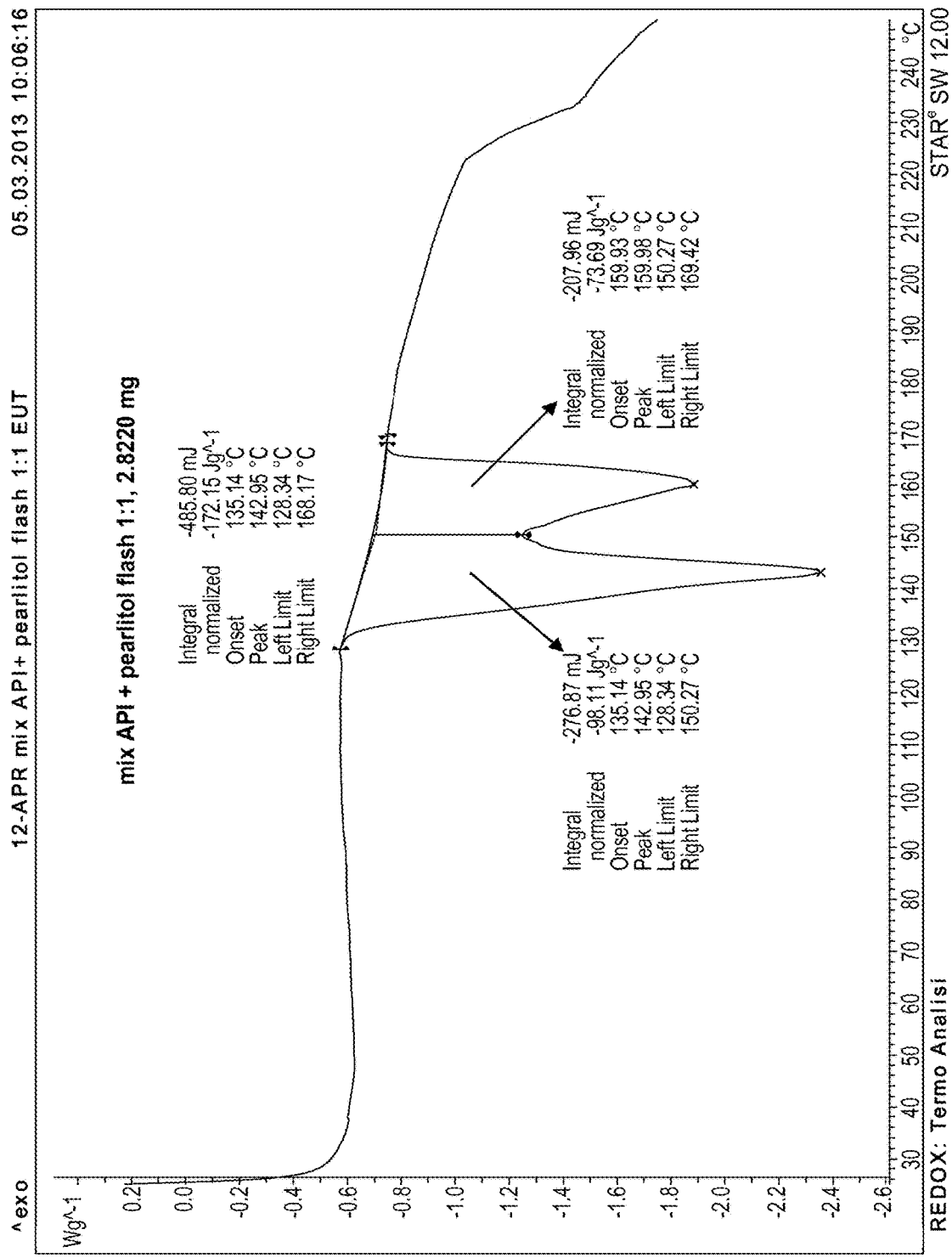
FIG. 81: Eutectic evaluation of DSC heating curve of API+Pearlitol 1:1.

In a 1:1 mixture of Amitriptyline HCland Pearlitol Flash®, a mannitol-containing excipient, a physical complex interaction peak (eutectic) was observed in the range of 130° C. to 170° C. (FIG. 80). No API transition melting was detected, only a physical complex fusion at lower temperature. The eutectic melting point corresponds to 135.1° C. (the onset value) (FIG. 81).

Figure 82:
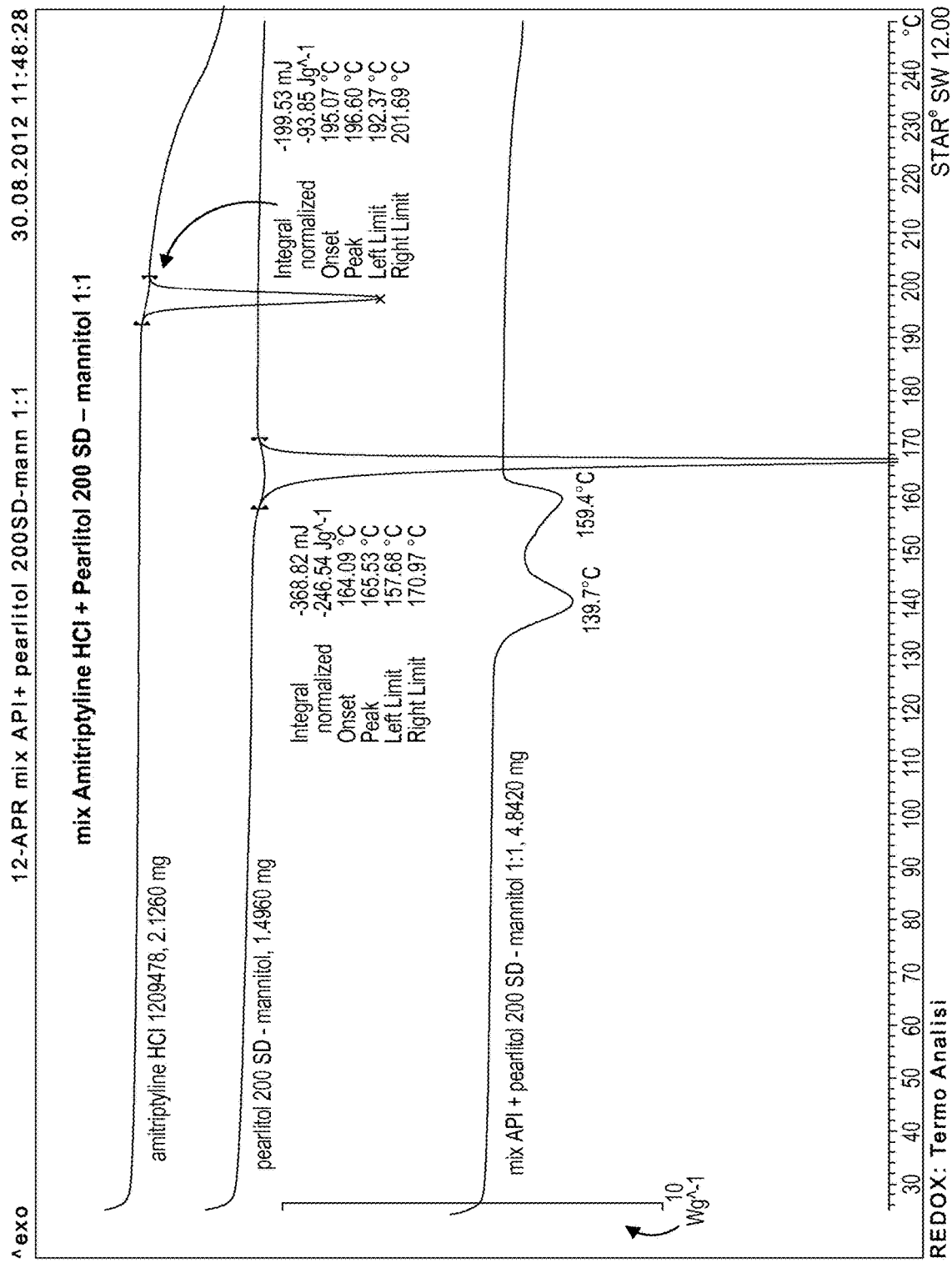
FIG. 82: DSC heating curve of Amitriptyline HCl+Pearlitol 200 SD/Mannitol 1:1.
Figure 83:
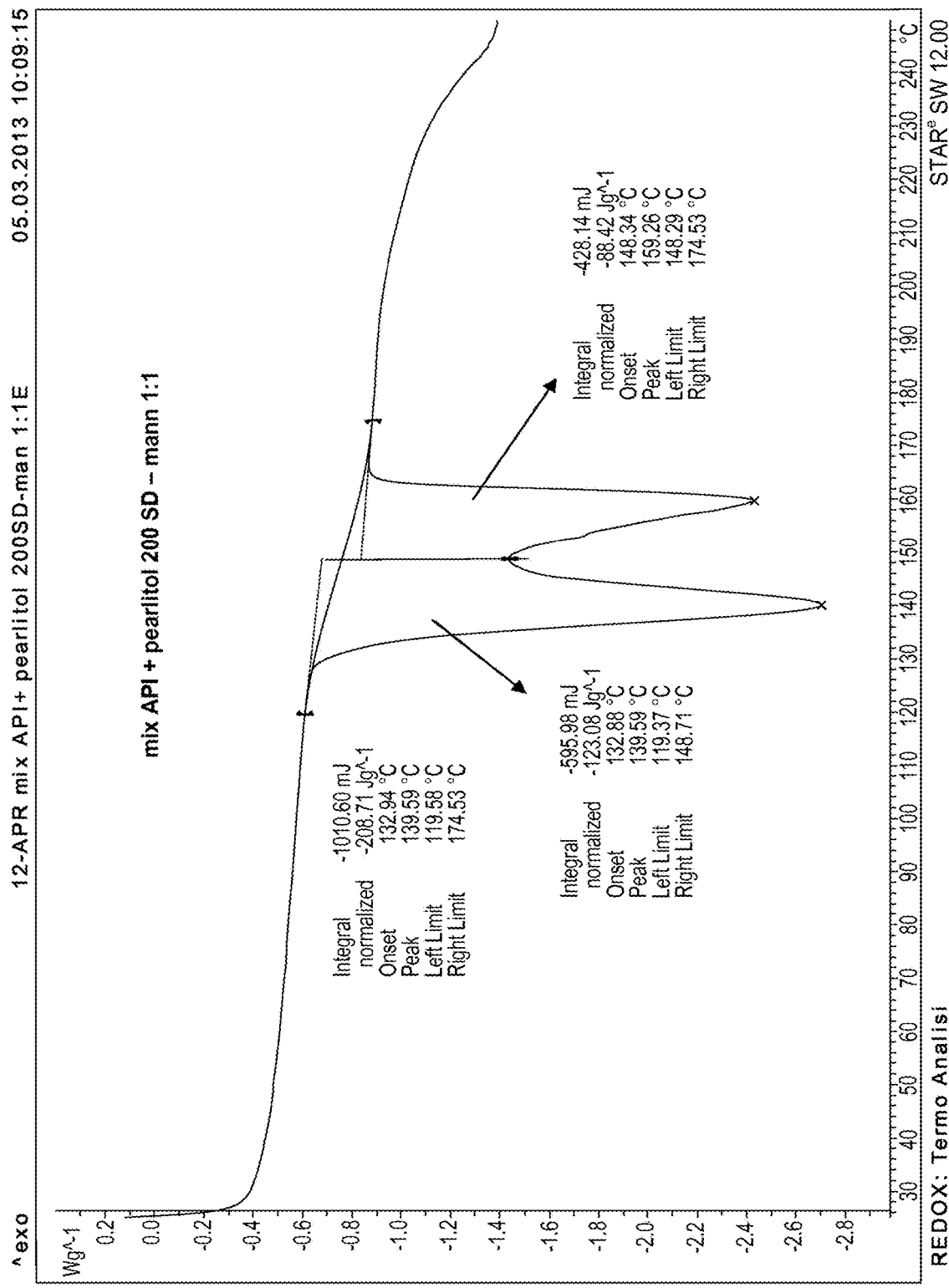
FIG. 83: Eutectic evaluation of DSC heating curve of API+Pearlitol/mannitol 1:1.

In a 1:1 mixture of Amitriptyline HCland Pearlitol 200 SD/Mannitol, a physical complex interaction peak (eutectic) was observed in the range of 130° C. to 170° C. (FIG. 82). No API transition melting was detected, only a physical complex fusion at lower temperature. The eutectic melting point corresponds to 132.8° C. (the onset value) (FIG. 83). The difference in melting temperatures of about 2° C., as compared to the mixture with only Pearlitol flash, is due to the presence of additional mannitol in this mixture.

The release of imbibition water in a 1:1 mixture of Amitriptyline HCland

Figure 84:
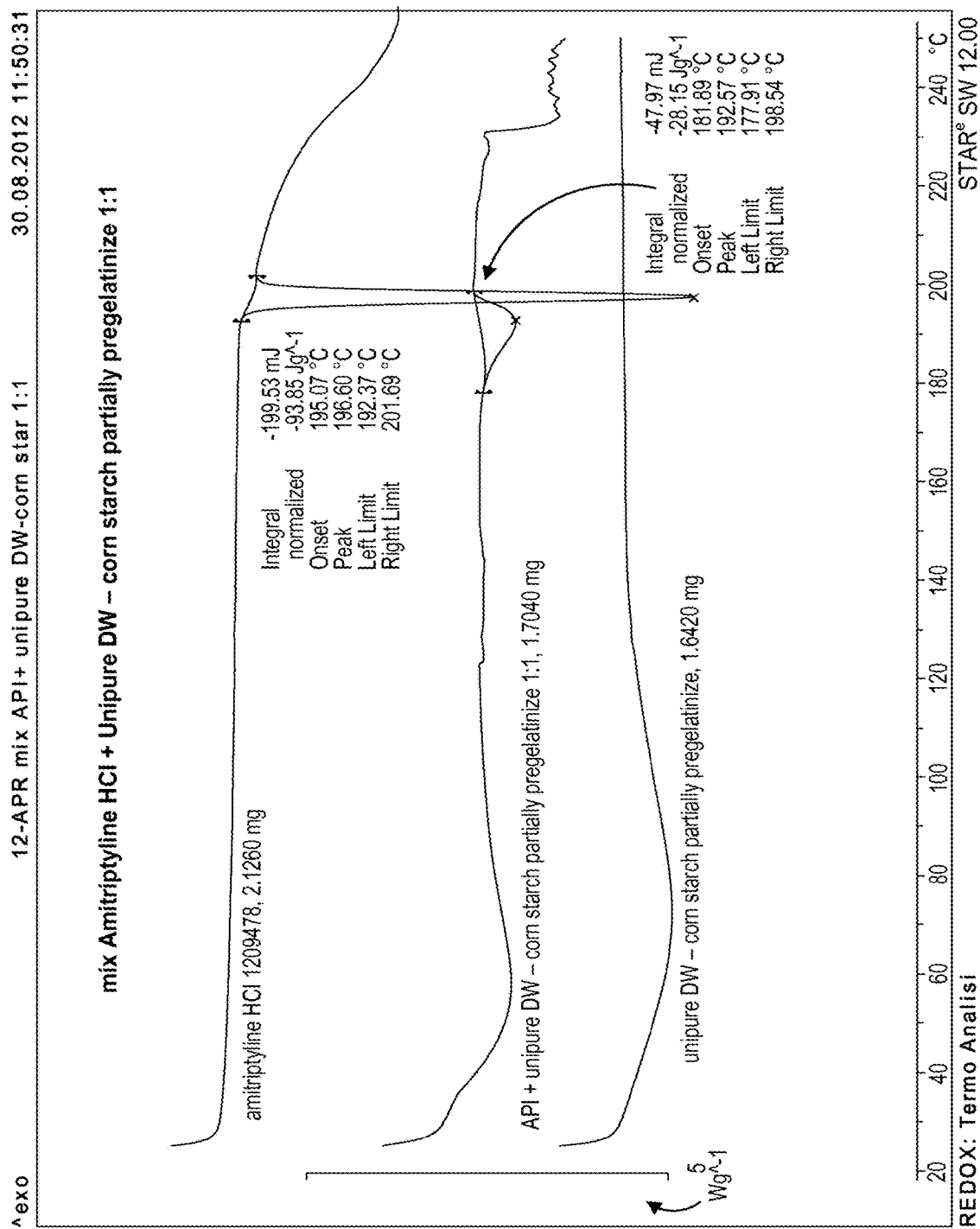
FIG. 84: DSC heating curve of Amitriptyline HCl+Unipure DW/Corn starch partially pregelatinized 1:1.
Figure 85:
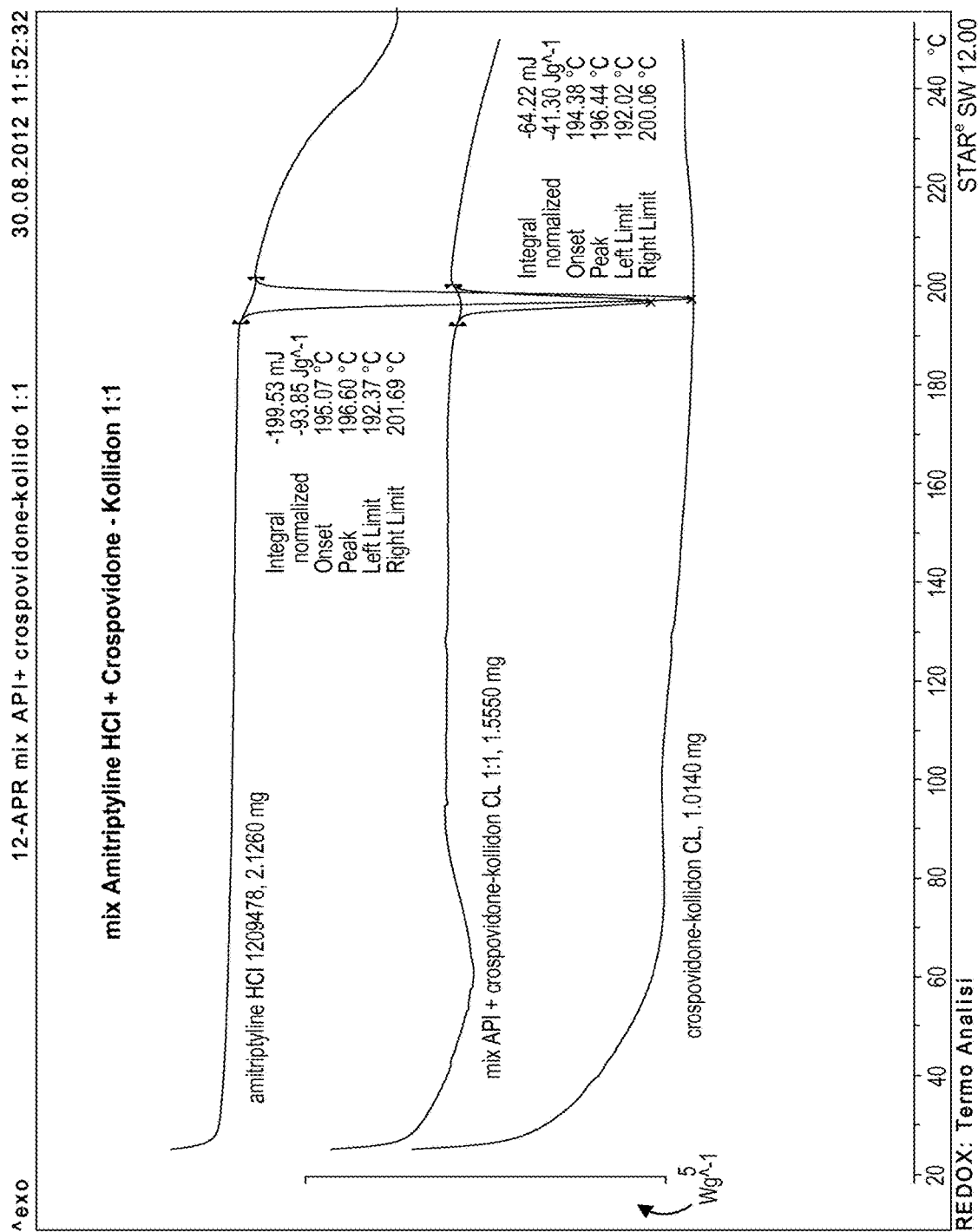
FIG. 85: DSC heating curve of Amitriptyline HCl+Crospovidone Kollidon CL 1:1.

Unipure DW/Corn starch (partially pregelatinized) was recorded between 30° C. and 110° C., followed by the melting of API between 178° C. and 199° C. (onset at 181.9° C., ΔH=−28.2 J/g) (FIG. 84). No interaction was detected In a 1:1 mixture of Amitriptyline HCl and Crospovidone (Kollidon CL), the release of imbibition water was recorded between 30° C. and 100° C., followed by the melting/decomposition of API between 192° C. and 200° C. (onset at 194.4° C., ΔH=−41.3 J/g) (FIG. 85). No interaction was detected.

Figure 86:
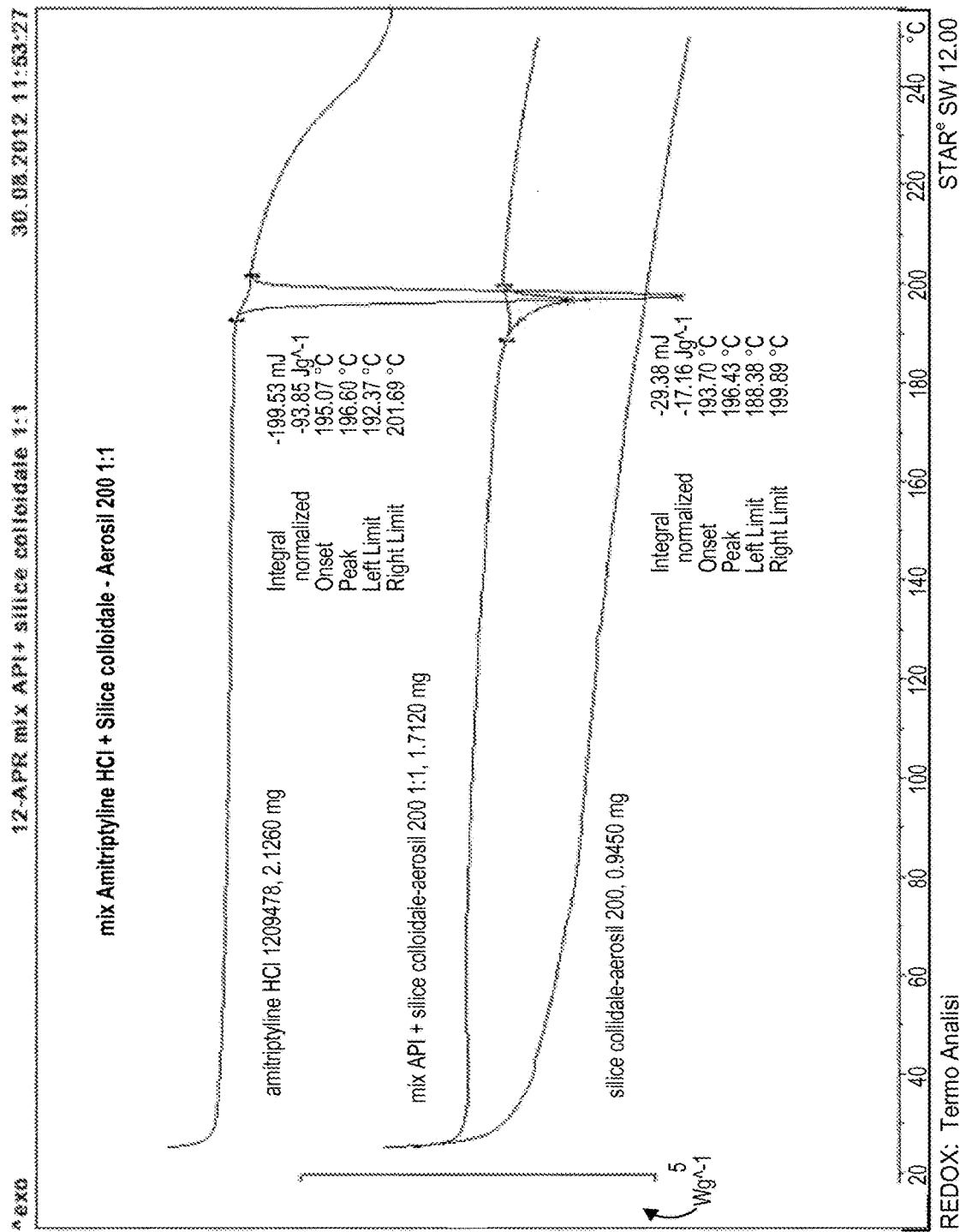
FIG. 86: DSC heating curve of Amitriptyline HCl+Silicon Colloidal/Aerosil 200 1:1.

In a 1:1 mixture of Amitriptyline HCl and Silicon (colloidal), the API melting peak was recorded between 188° C. and 200c° C. (onset at 193.7c° C., ΔH=−17.2 J/g) (FIG. 86). No interaction was detected, only a lowering of the degree of crystalline Amitriptyline HCl.

Figure 87:
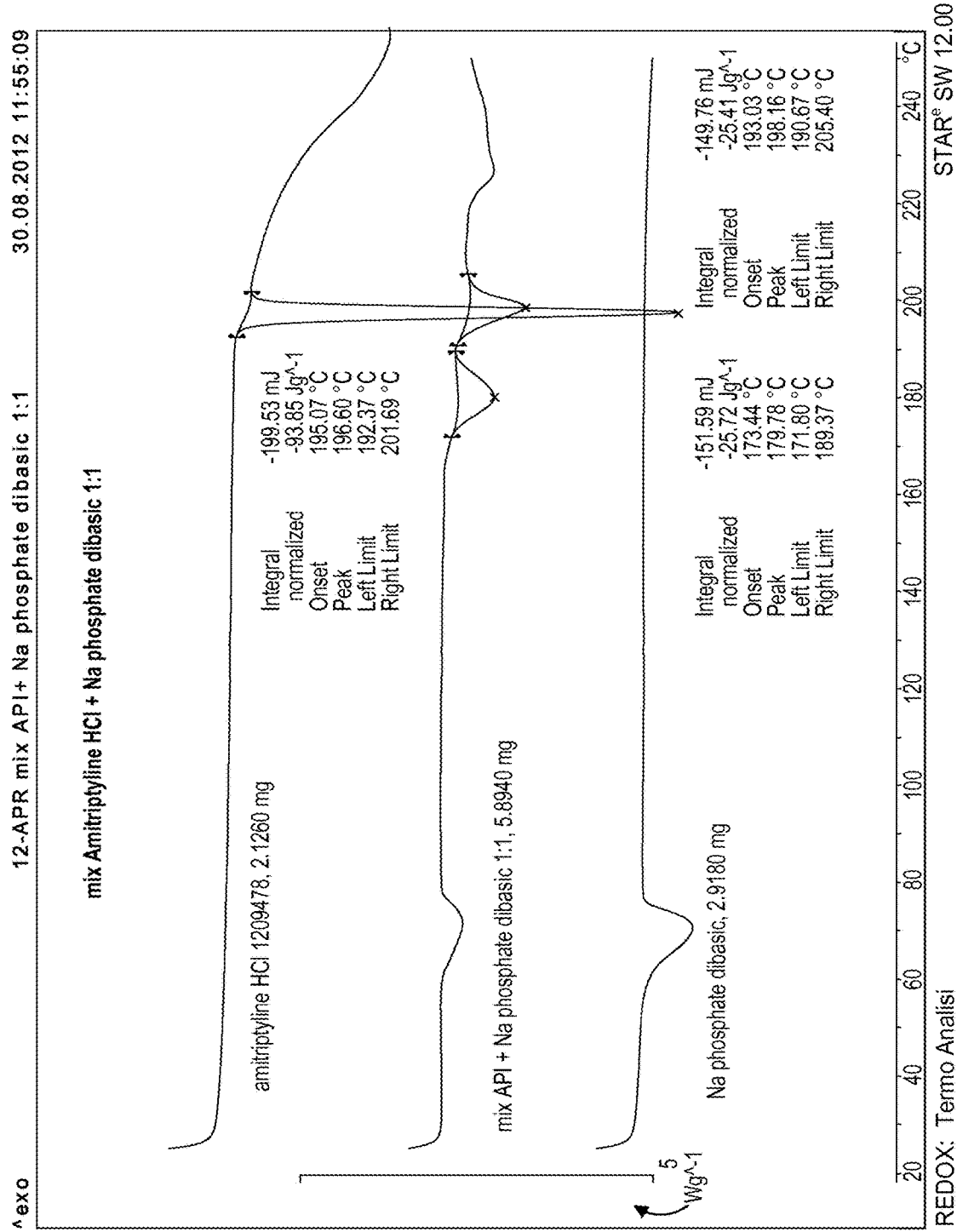
FIG. 87: DSC heating curve of Amitriptyline HCl+Sodium phosphate dibasic 1:1.

The endothermic transitions of sodium phosphate dibasic in a 1:1 mixture of Amitriptyline HCland Sodium phosphate dibasic were recorded in the range of 60° C. and 80° C. API transition peaks were detected at 180° C. and 193° C. (FIG. 87).

Figure 88:
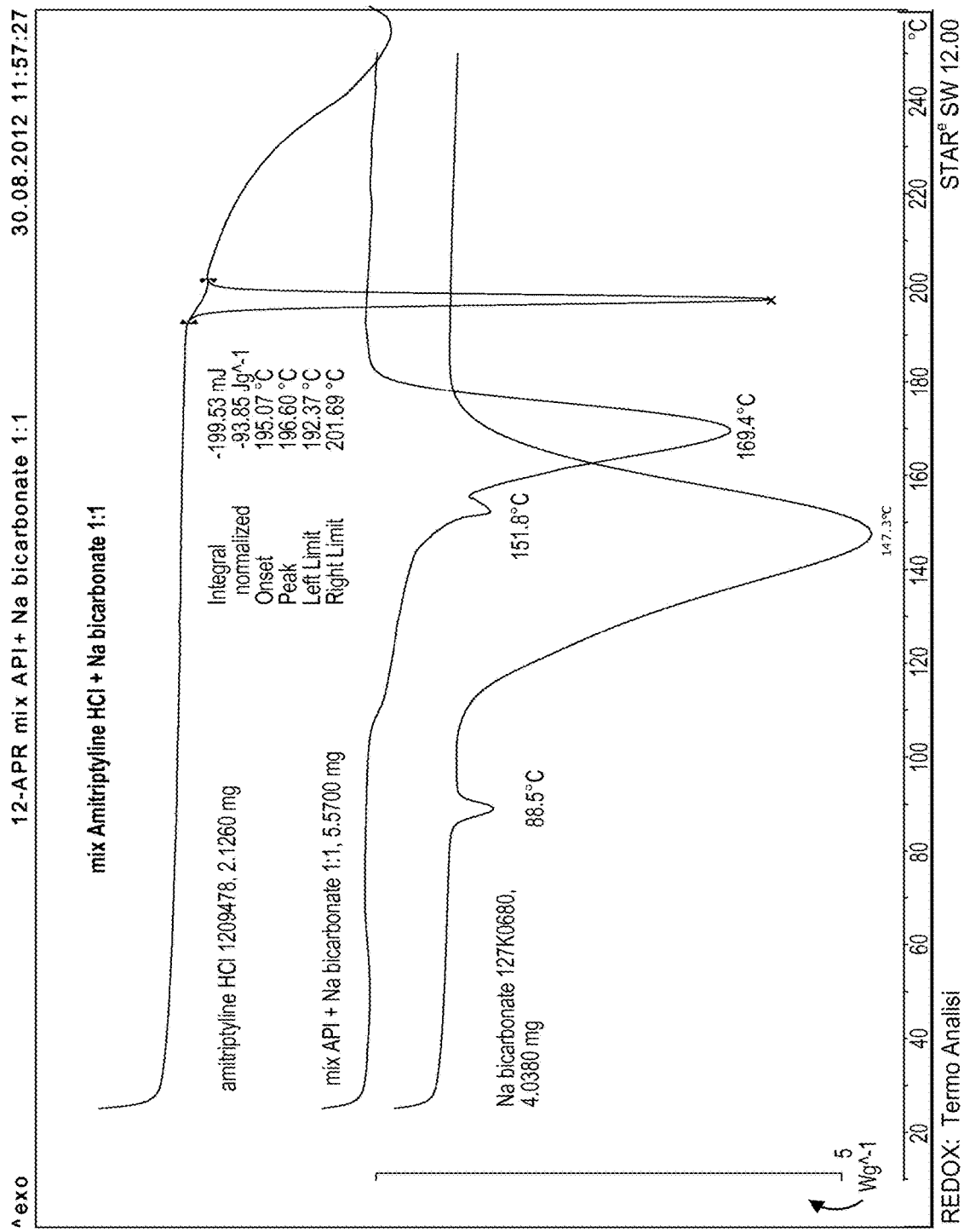
FIG. 88: DSC heating curve of Amitriptyline HCl+Sodium bicarbonate 1:1.

In a 1:1 mixture of Amitriptyline HCl and Sodium bicarbonate, the endothermic transitions of sodium bicarbonate were recorded in the range of 150° C. to 180° C. (FIG. 88). No API transition peak was detected. A physical interaction was observed.

Figure 89:
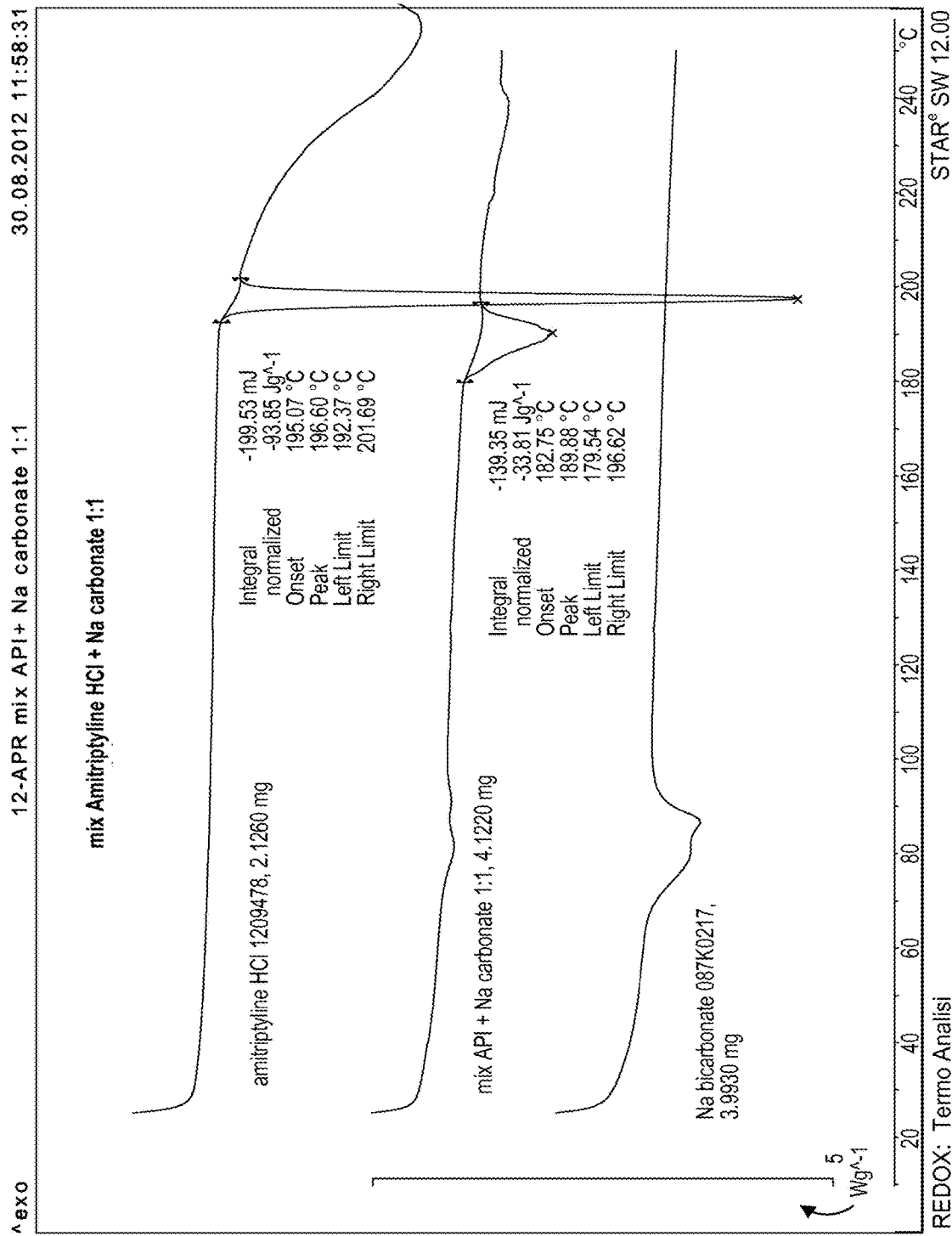
FIG. 89: DSC heating curve of Amitriptyline HCl+Sodium carbonate 1:1.

In a 1:1 mixture of Amitriptyline HCland Sodium carbonate, the endothermic transitions of sodium carbonate were recorded in the range of 70° C. to 90 ° C. (FIG. 89). The API transition peak was detected between 180° C. and 197 ° C. (onset at 182.8° C., ΔH=−33.8 J/g). A small physical interaction was observed.

Figure 90:
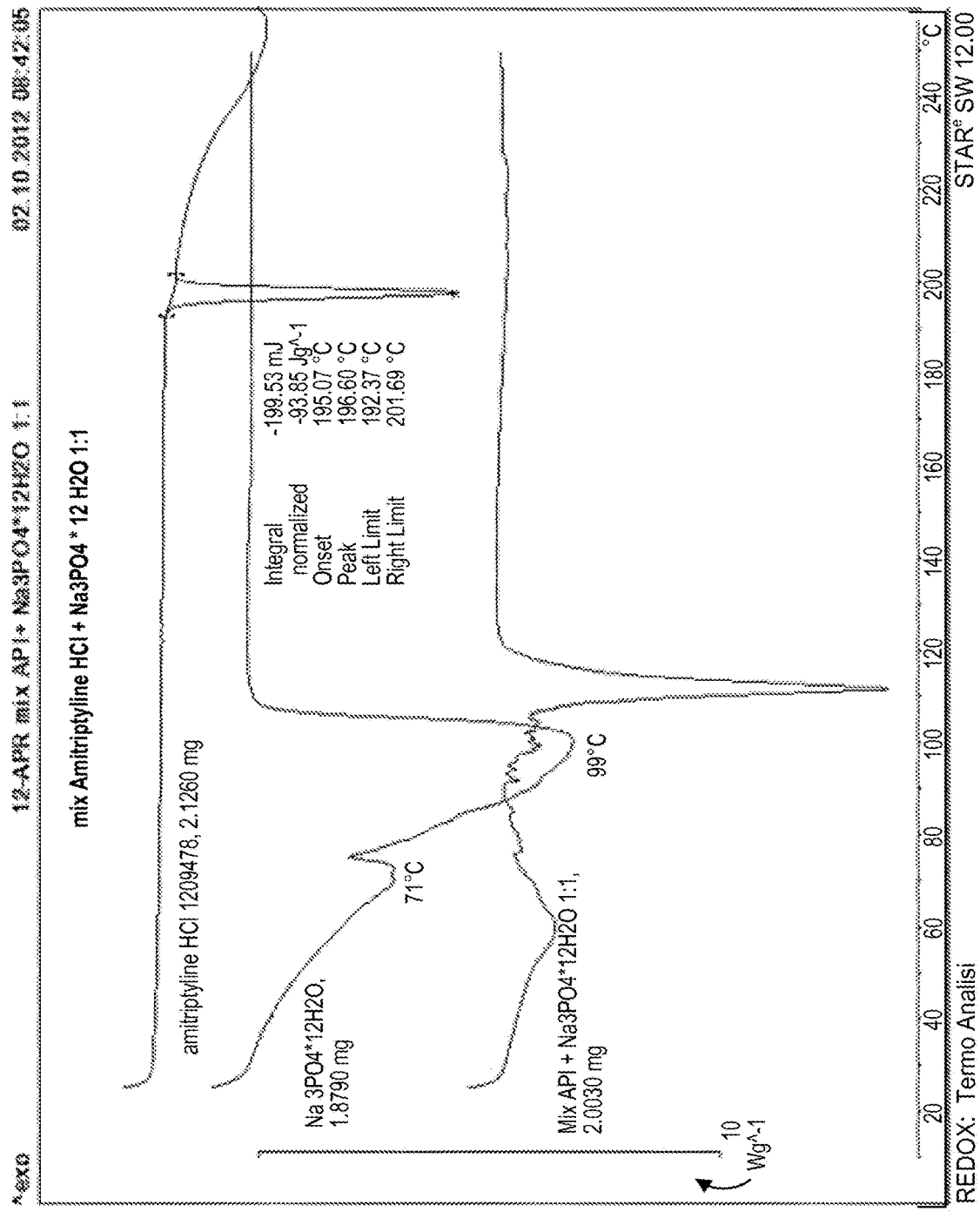
FIG. 90: DSC heating curve of Amitriptyline HCl+Sodium phosphate dodecahydrate 1:1.

In a 1:1 mixture of Amitriptyline HCland Sodium phosphate dodecahydrate, the endothermic transitions were recorded in the range of 40° C. to 112° C. (FIG. 90). No API transition peak was detected. A physical/chemical interaction was observed.

Figure 91:
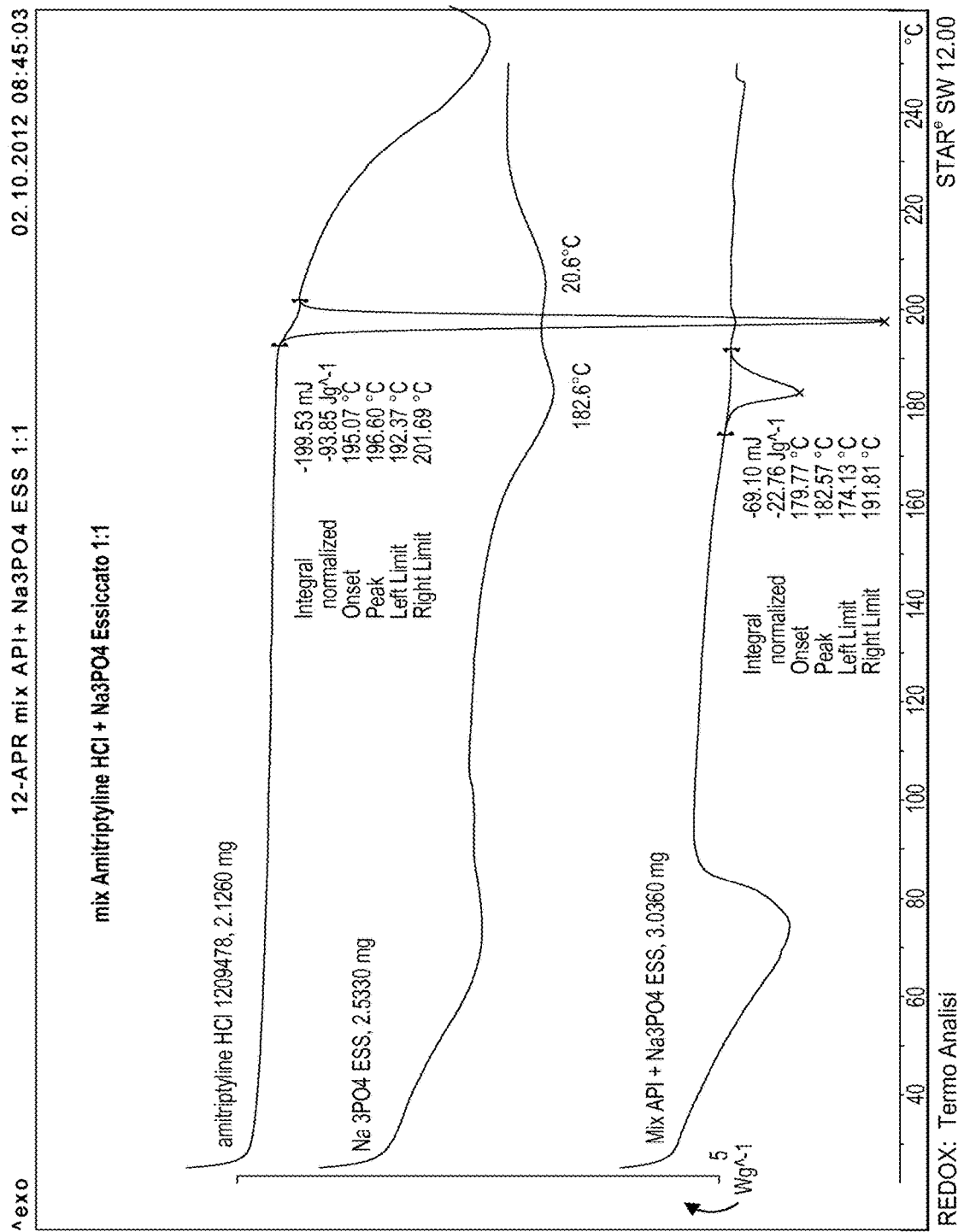
FIG. 91: DSC heating curve of Amitriptyline HCl+Sodium phosphate anhydrous 1:1.

The endothermic transition of sodium phosphate in a 1:1 mixture of Amitriptyline HCland Sodium phosphate anhydrous was recorded in the range of 40° C. to 90° C. The API transition peak was detected between 174° C. and 192° C. (onset at 179.8° C., ΔH=−222.8 J/g) (FIG. 91). No physical interaction was observed.

In summary, different types of interaction were observed among the excipients and the API. A physical interaction was observed with Magnesium stearate and Sodium phosphate dibasic, probably because of partial API solubilization. A eutectic interaction was observed with Pearlitol flash and Pearlitol 200 SO/Mannitol, due to the presence of mannitol. The thermal transition of the API is completely shifted by excipient complex formation of a eutectic. A physical interaction was observed with Sodium Stearyl fumarate, likely because of partial API solubilization or reactions at the particles' surfaces between the HCl and Na counter ions. A physical interaction was observed with Sodium Phosphate dodecahydrate, also likely because of partial API solubilization. No interaction was observed with Stearic acid, Glycerol dibehenate, Unipure DW/Cornstarch partially pregelatinized, Silicon (colloidal), Crospovidone/Kollidon CL, Sodium carbonate, Sodium bicarbonate, or Sodium Phosphate anhydrous. Table 4 summarizes the data observed.

TABLE 4

Interactions between API and excipients

| Excipient | Mixture in formulation (1:1 ratio) |
| --- | --- |
| Sodium stearyl fumarate | Physical interaction |
| Stearic acid | No interaction |
| Glycerol dibehenate | No interaction |
| Magnesium stearate | Physical interaction |
| Pearlitol flash | Eutectic interaction |
| Pearlitol 200 SO/Mannitol | Eutectic interaction |
| Unipure DW/Corn starch Pregelatinized | Partially no interaction |
| Crospovidone-Kollidon CL | No interaction |
| Silicon Colloidal/Aerosil 200 | No interaction |
| Sodium phosphate dibasic | Physical interaction |
| Sodium bicarbonate | No interaction |
| Sodium carbonate | No interaction |
| Sodium phosphate dodecahydrate | Physical interaction |
| Sodium phosphate anhydrous | No interaction |

Example 4

To test whether wet mixing of Cyclobenzaprine and mannitol changes the eutectic, 10 g of the eutectic mixture (75% API and 25% Mannitol) were put in a mortar with 1 mL of water and mixed until reaching a paste consistency. This paste was left to dry at room temperature while being ground in the mortar. The ground powder was sieved in 500 μm sieve. Sample morphology was assessed by a Scanning Electron Microscope (SEM) FEI S50 instrument with an electron beam accelerated by a voltage of 25 kV, supported on an adhesive graphite plate and coated with a gold layer. The Specific Surface Area (SSA) and Powder Porosity was assessed by the BET method (nitrogen), by degassing the samples at 40° C. under nitrogen for 2 hours in a Micromeritics Tristar II 3020 instrument. DSC heating curves were obtained by TA 821 DSC Mettler instrument under the following conditions:

Heating rate: 10° C./min

Ambient: Nitrogen 30 ml/min

Sample older: normal open aluminium pan

Temperature range: from 25 to 250° C.

Instrument calibration: Indium sample purity 99.999%

X-ray powder diffraction (XRPD) tests were performed with an ULTIMA IV instrument (Rigaku), laying the sample on a static sample holder. The X-ray focusing slit had a variable width, interlocked with the θ value. The X-ray tube had a Copper target, with a current intensity of 40 mA and a voltage of 50 kV, and the radiation generated by the Cockcroft-Walton method is constituted by $K_{\alpha 1}$ (1.540562 Å) and $K_{\alpha 2}$ (1.544398 Å). The analytical conditions were the following:

Fixed Time

Sampling width: 0.02 deg

Scanning rate: 1.0 s/step

2 θ range: 3÷50 deg.

Sample holder: amorphous glass—equiangular 9200/2G, 0.2 mm deep. The sample was pressed with a glass plate.

Figure 92:
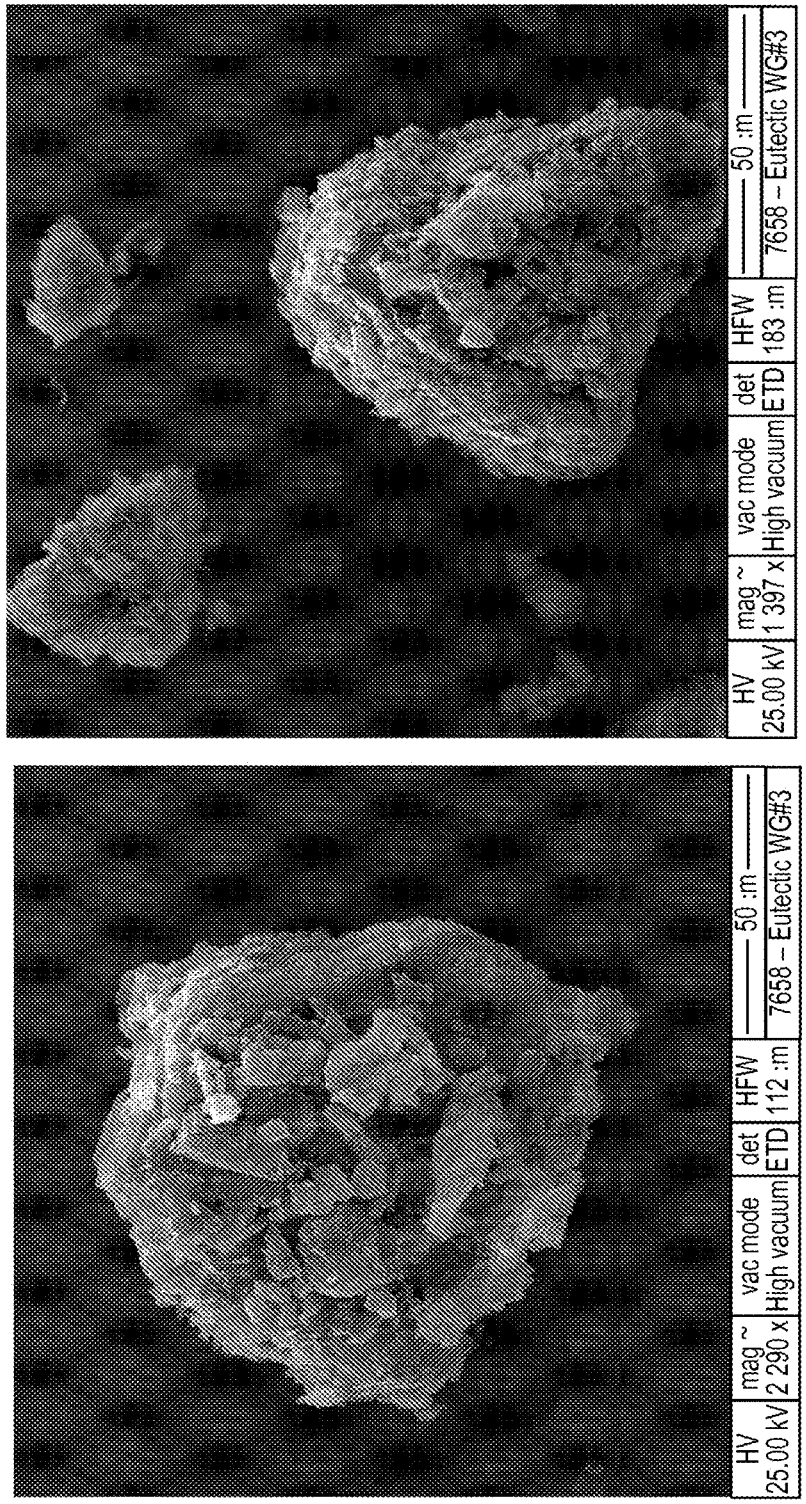
FIG. 92: SEM of particles formed by wet granulation.
Figure 93:
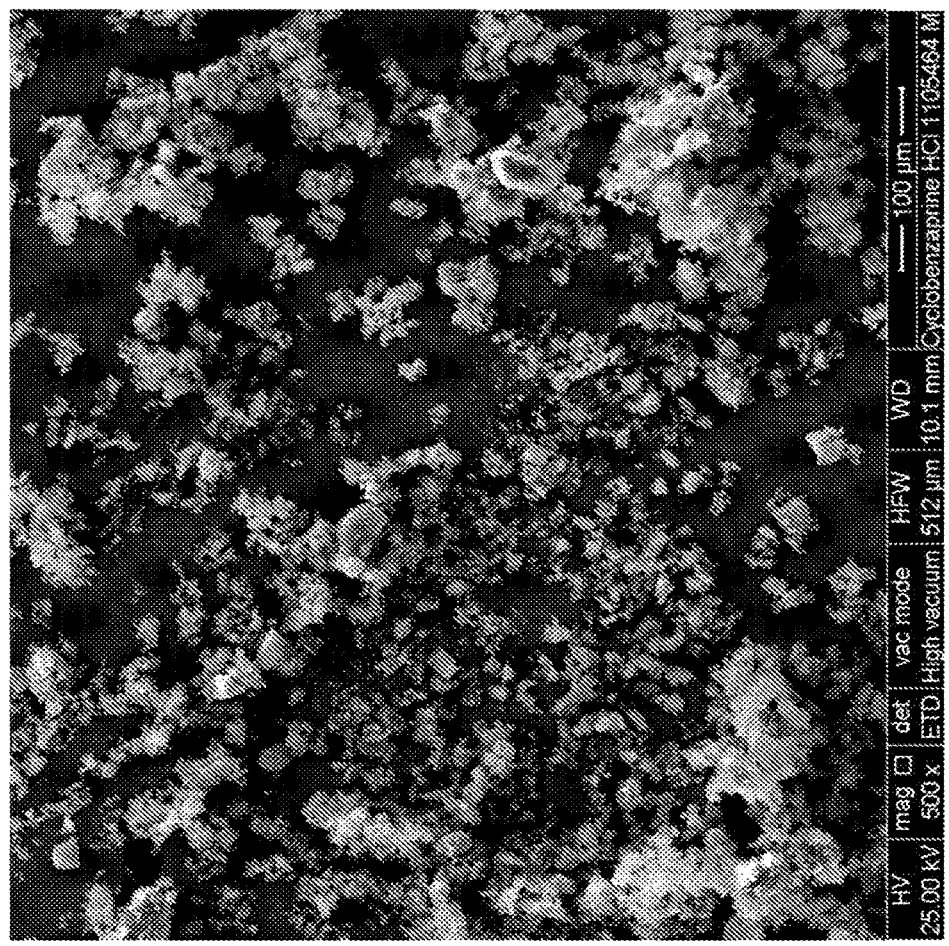
FIG. 93: SEM of pure Cyclobenzaprine HCl.
Figure 94:
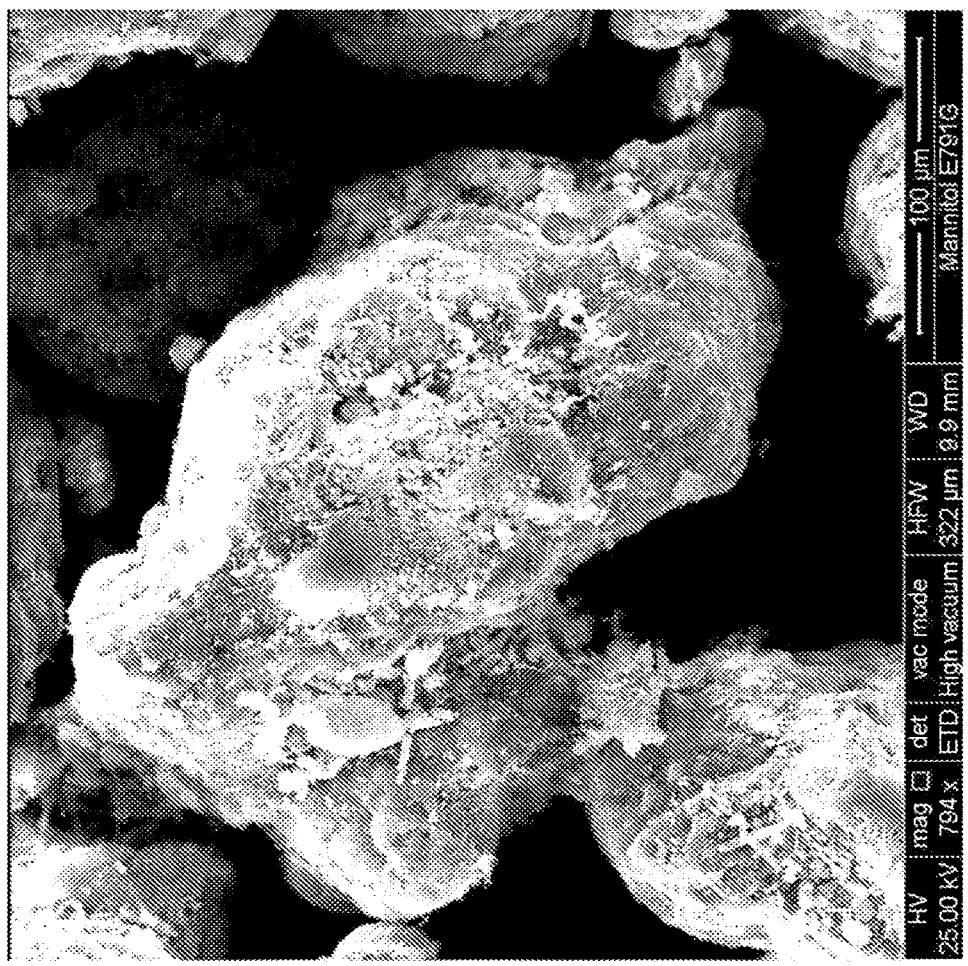
FIG. 94: SEM of pure mannitol.
Figure 95:
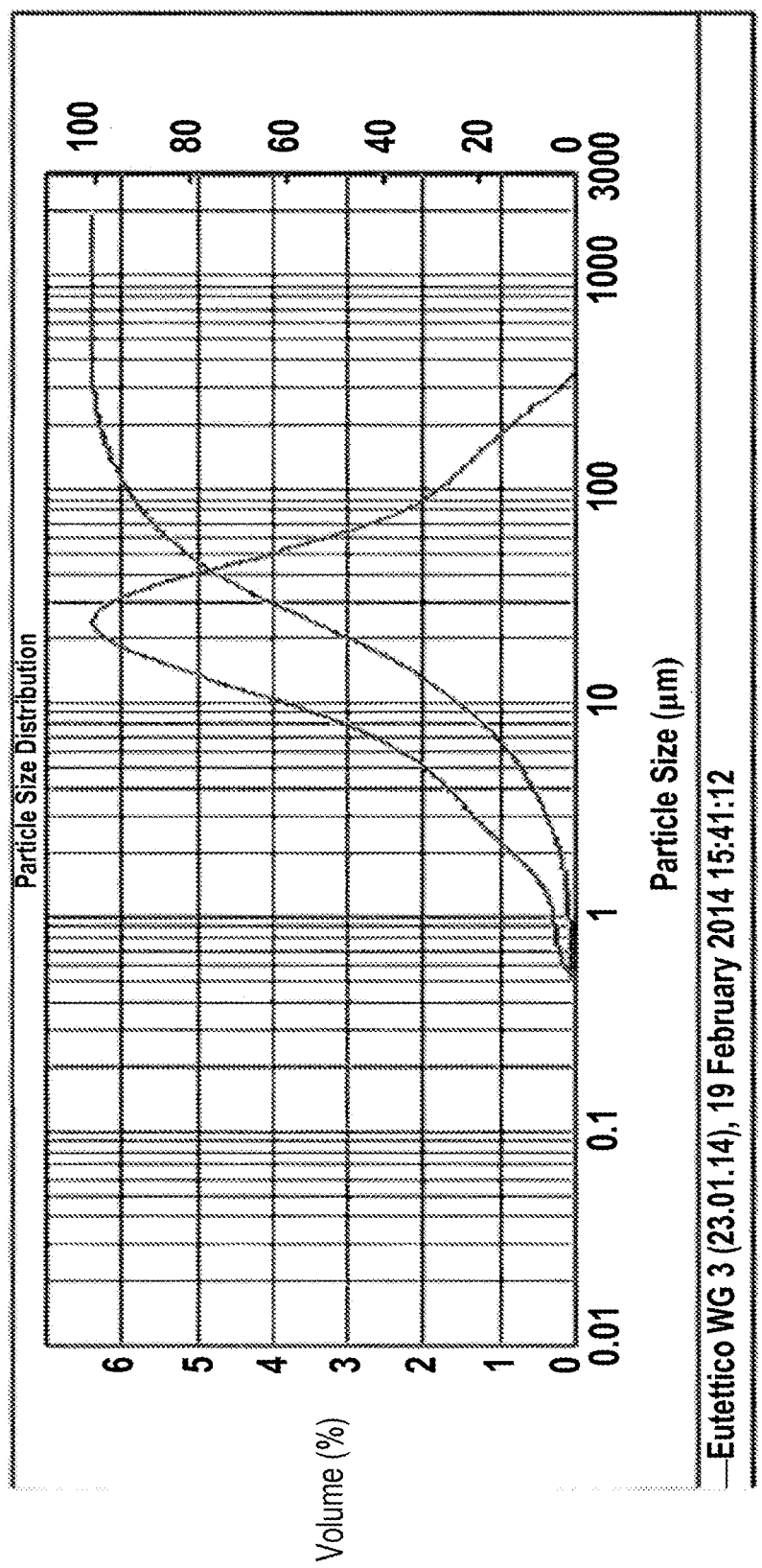
FIG. 95: wet granulated eutectic particle size distribution.
Figure 96:
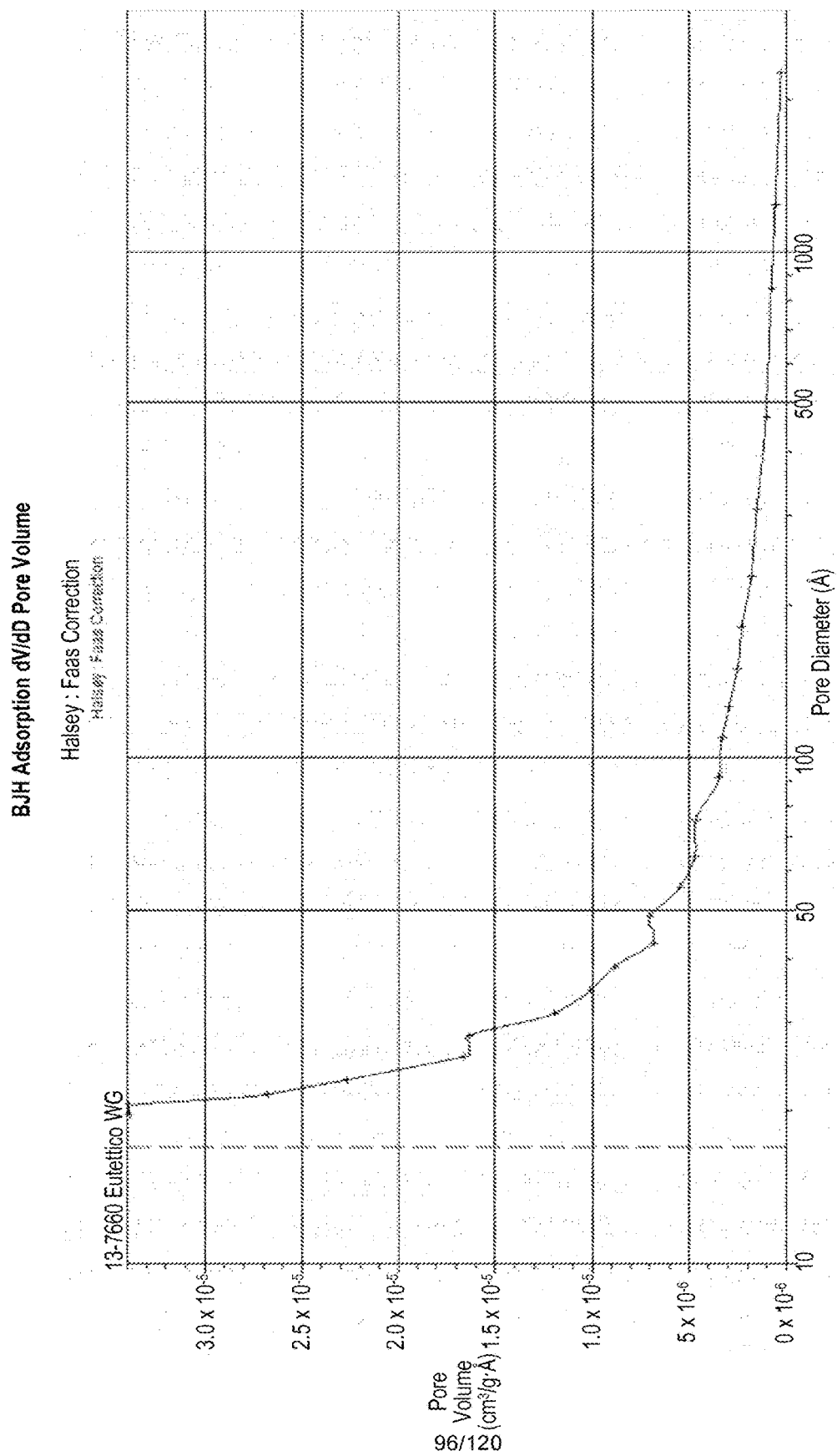
FIG. 96: wet granulated eutectic pore volume over diameter.
Figure 97:
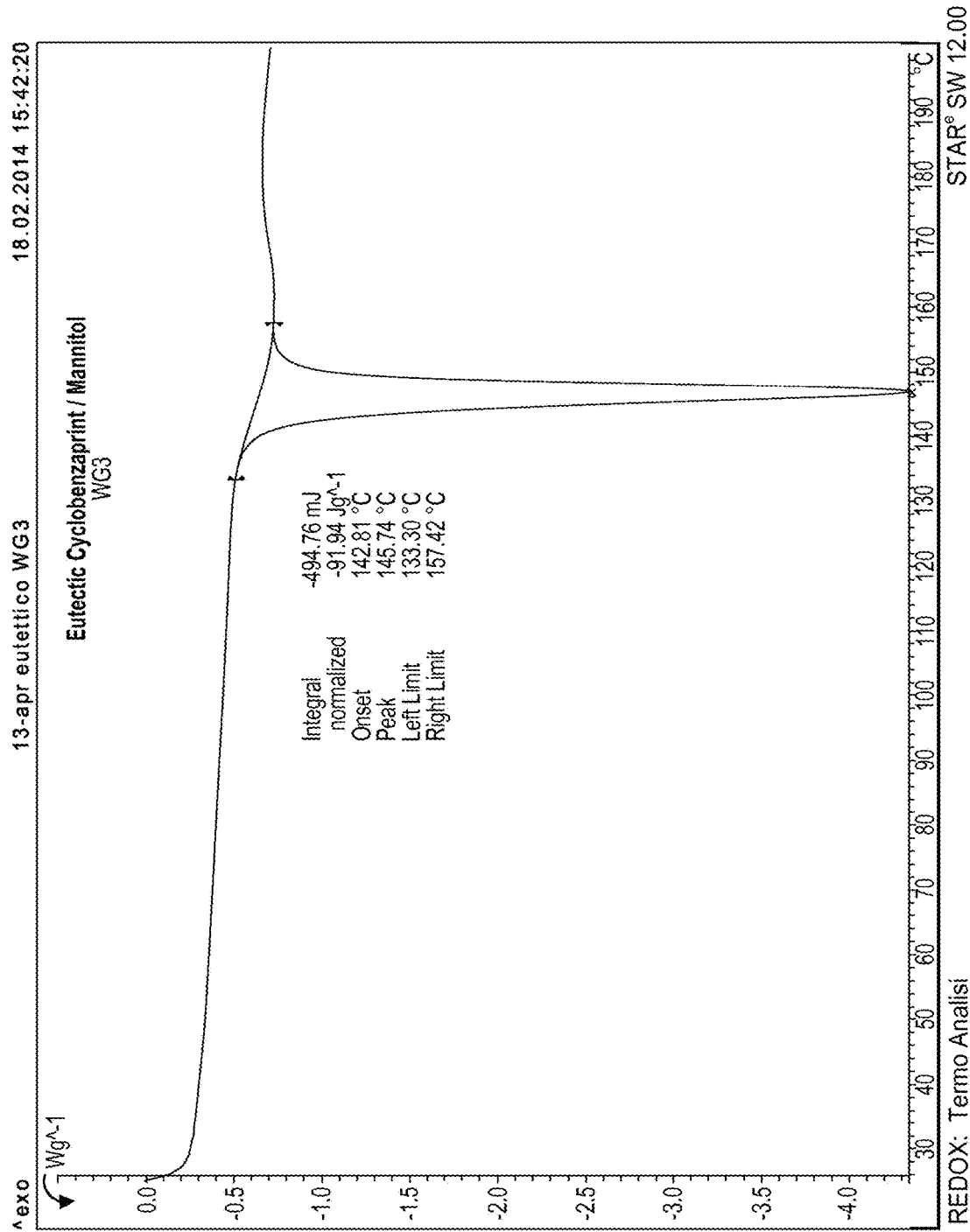
FIG. 97: DSC heating curve of the Cyclobenzaprine HCl/mannitol eutectic.
Figure 98:
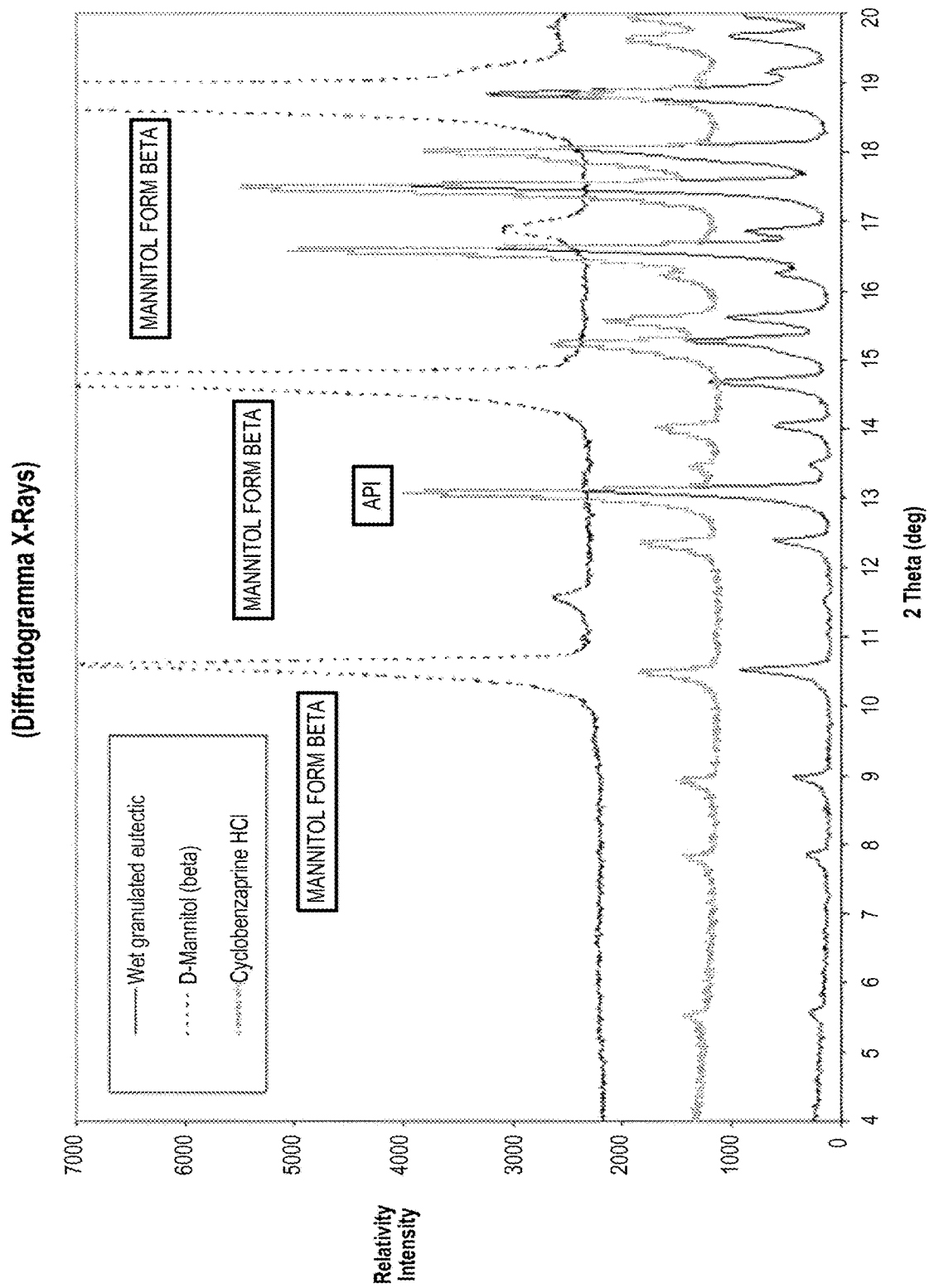
FIG. 98: XRPD pattern of the Cyclobenzaprine HCl/mannitol eutectic.

SEM shows that the eutectic formed by wet granulation has particles with hard surfaces as seen in FIG. 92. These particles can be compared to particles observed by SEM of pure Cyclobenzaprine HCl (FIG. 93) and pure mannitol (FIG. 94). The physical characteristics were measured and are summarized in Table 5 (SSA: specific surface area; D10: 10% of the particles are smaller than this measurement; D50: 50% of the particles are smaller than this measurement; D90: 90% of the particles are smaller than this measurement). FIG. 95 depicts wet granulated eutectic particle size distribution and FIG. 96 depicts wet granulated eutectic pore volume over diameter. Moreover, both DSC and X-ray powder diffraction show complete incorporation of mannitol into the eutectic composition (FIG. 97 and FIG. 98, respectively).

TABLE 5

Physical characteristics of eutectic formed by wet granulation

| | |
|---|---|
| SSA (m²/g) | 0.9148 |
| Pore Volume (cm³/g) | 0.001599 |
| Pore size (Å) | 69.91 |
| D10 (um) | 4.629 |
| D50 (um) | 22.046 |
| D90 (um) | 82.096 |

Example 5

In addition to wet mixing, spray drying also can he used to mix ingredients to make pharmaceutical compositions. Five mixtures (10 g) of mannitol and Cyclobenzaprine HCl, in different ratios, were dissolved in 500 ml of water for spray drying. The total solid concentration was 2% w/v, although 15% w/v also worked in earlier tests (data not shown). The solutions were spray-dried using a Büchi Spray Dryer B-290 (Bëchi Labortechnik, Flawil, Switzerland) under the conditions reported in Table 6. Soft micro-particles were obtained in case of the first two hatches created, while the other batches had slightly yellow scales and crystals. The yield obtained decreased with the increase of the Cyclobenzaprine HCl percentage in the solution to be spray dried.

TABLE 6

Spray Drying Process Parameters

| Batch | T Inlet (° C.) | T Outlet (° C.) | Feed rate (ml/min) | Flow Rate (L/h) | Aspiration (100%) | delta Pressure (mbar) |
|---|---|---|---|---|---|---|
| 1) 100% Mannitol, 0% API | 120 | 74 | 4 | 600 | 100 | 10 |
| 2) 75% Mannitol, 25% API | 120 | 74 | 4 | 600 | 100 | 5 |
| 3) 50% Mannitol, 50% API | 120 | 76 | 4 | 600 | 100 | 5 |
| 4) 25% Mannitol, 75% API | 120 | 73 | 4 | 600 | 100 | 5 |
| 5) 10% Mannitol, 90% API | 120 | 74 | 4 | 600 | 100 | 2 |

Figure 99:
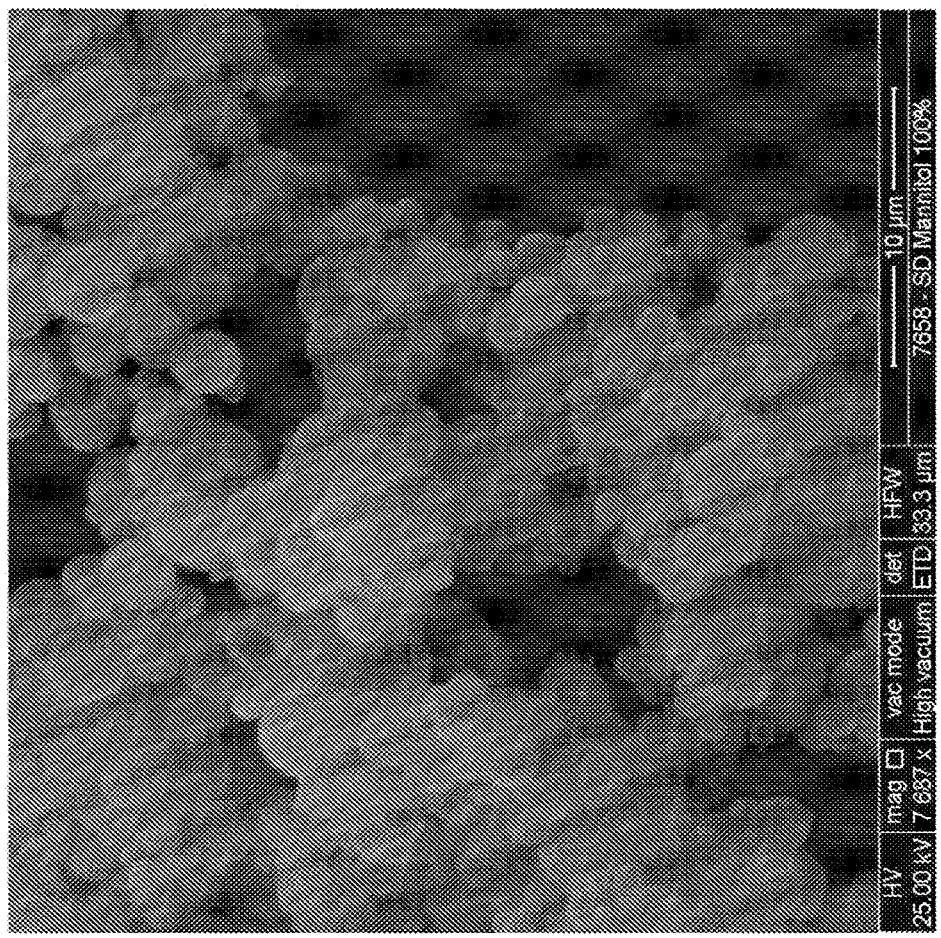
FIG. 99: SEM of spray dried mannitol.
Figure 100:
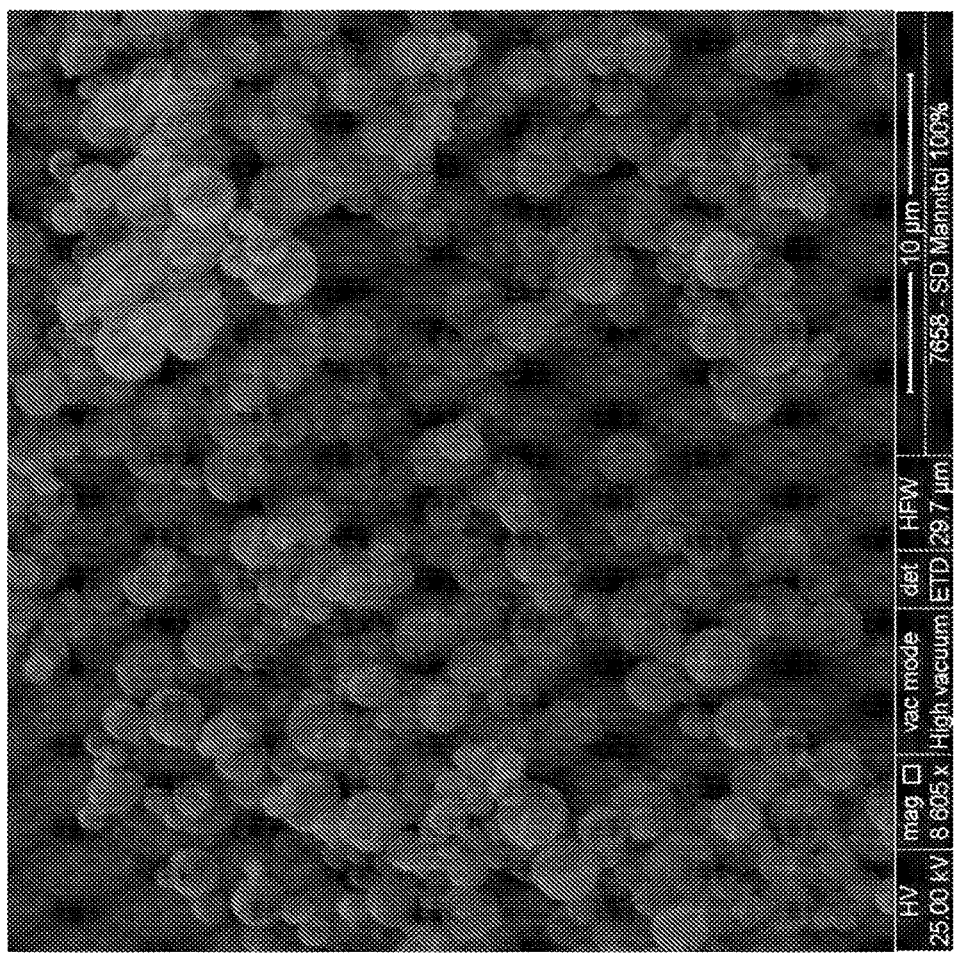
FIG. 100: SEM of spray dried mannitol.
Figure 101:
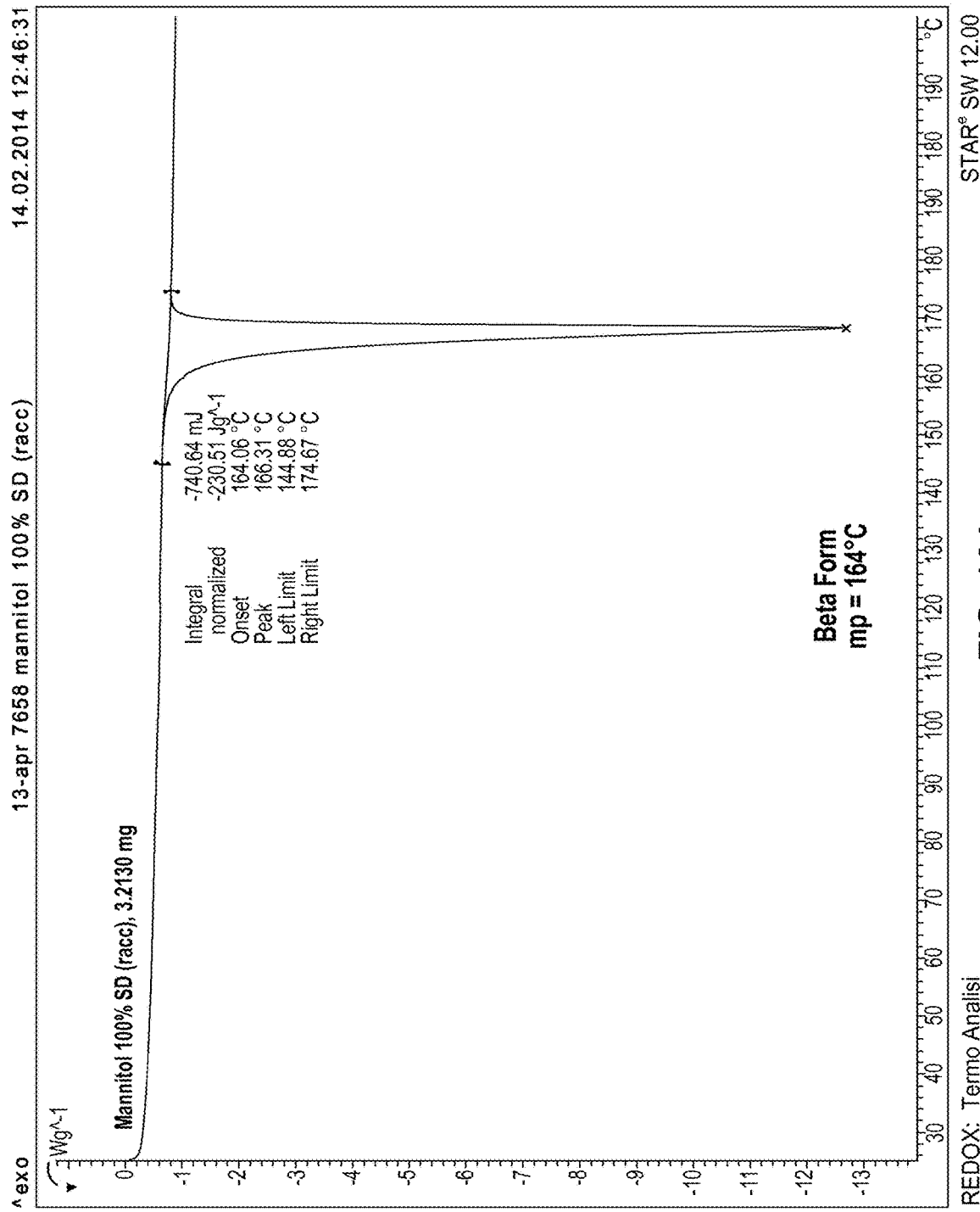
FIG. 101: DSC heating curve of spray dried mannitol.
Figure 102:
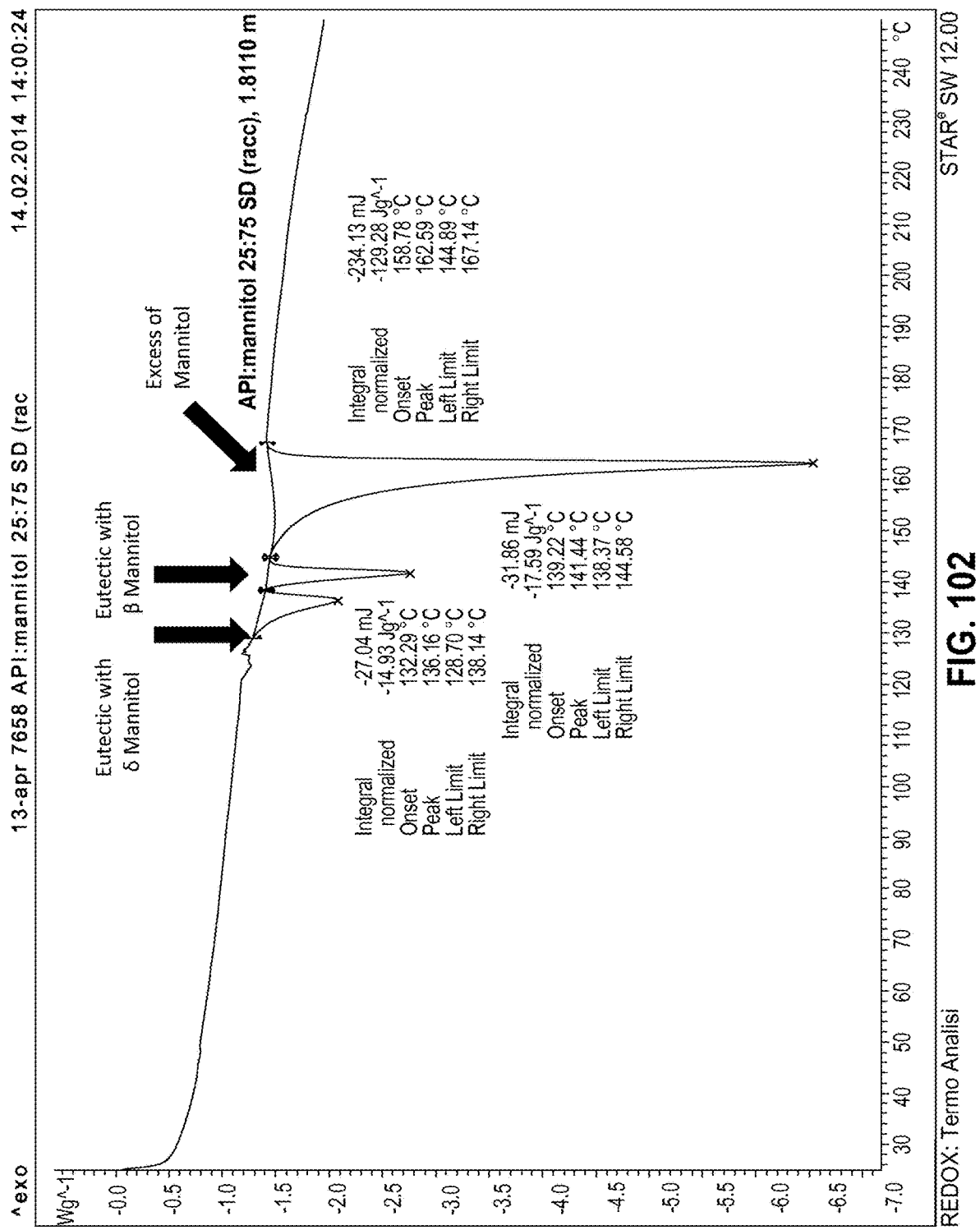
FIG. 102: DSC heating curve of 25% Cyclobenzaprine HCl by weight ±75% mannitol by weight, spray dried.
Figure 103:
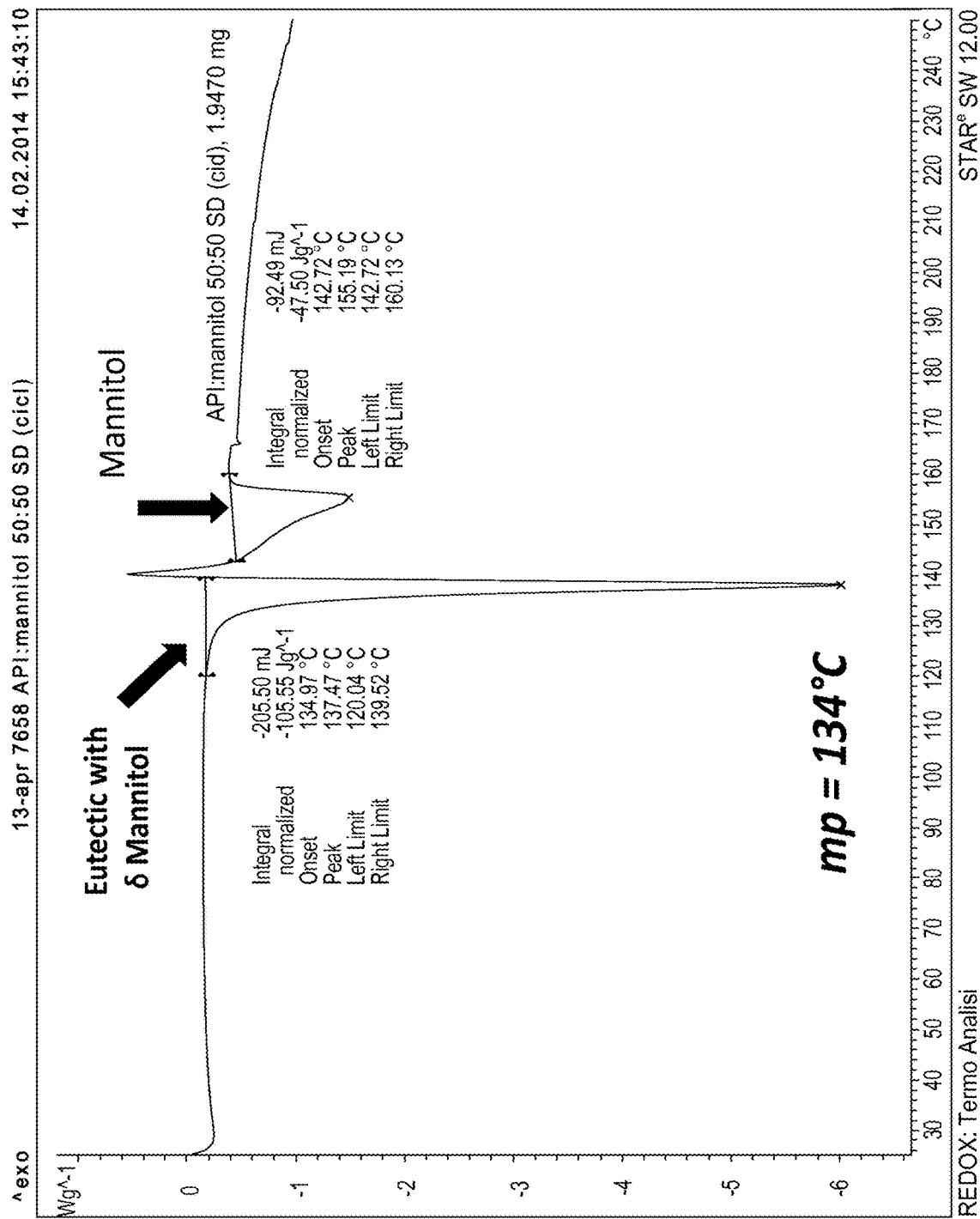
FIG. 103: DSC heating curve of 50% Cyclobenzaprine HCl by weight ±50% mannitol by weight, spray dried.
Figure 104:
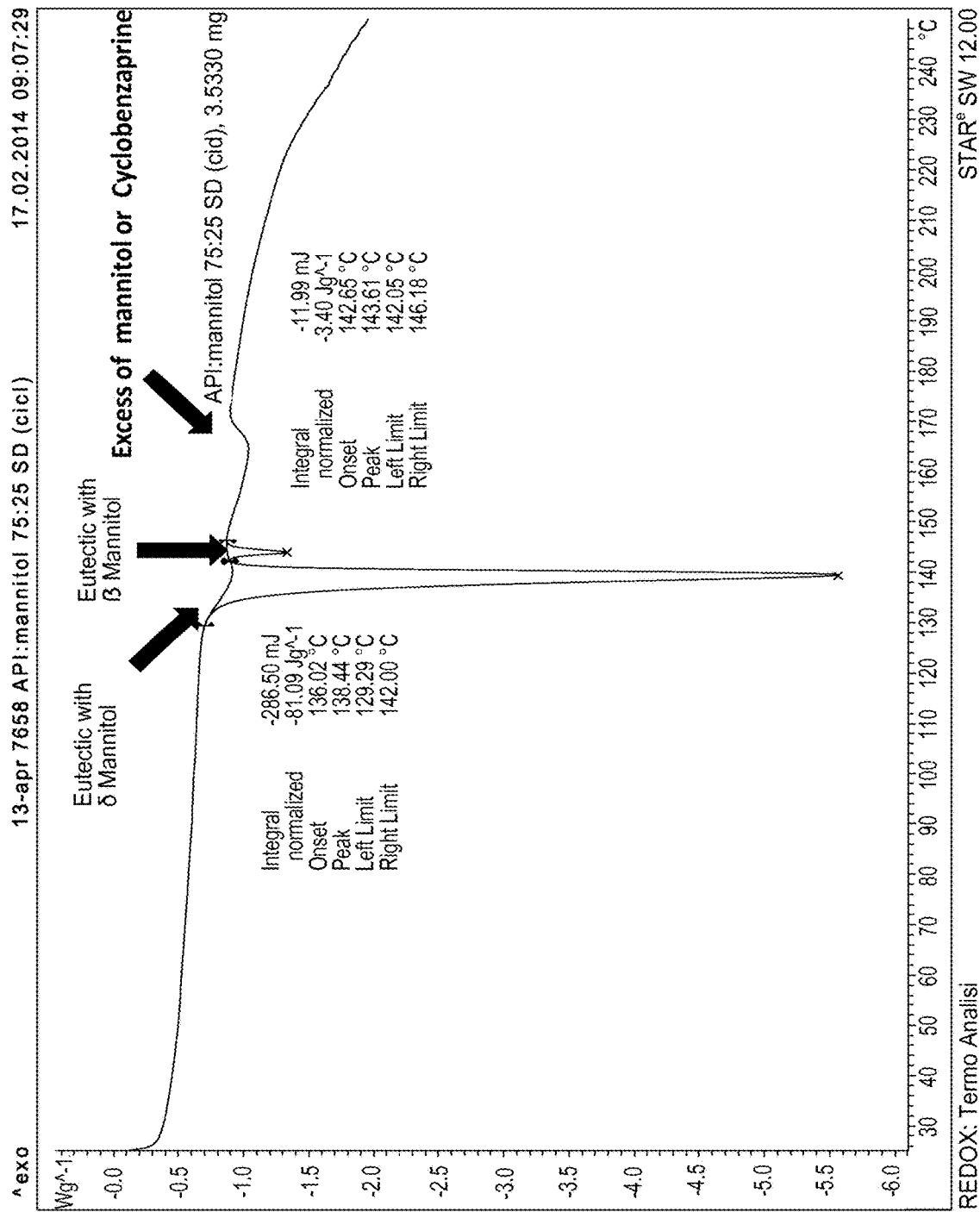
FIG. 104: DSC heating curve of 75% Cyclobenzaprine HCl by weight ±25% mannitol by weight, spray dried.
Figure 105:
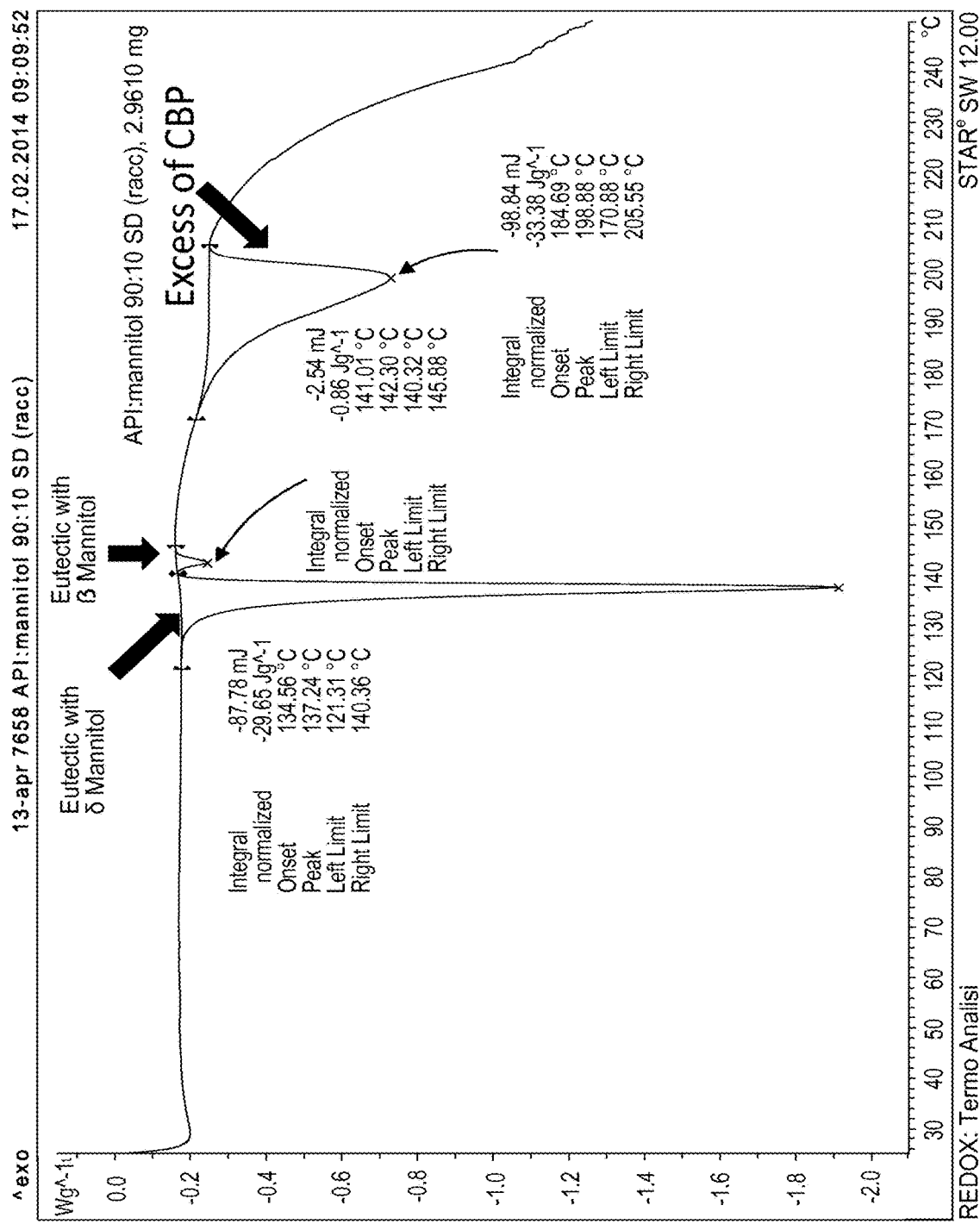
FIG. 105: DSC heating curve of 90% Cyclobenzaprine HCl by weight ±10% mannitol by weight, spray dried.
Figure 106:
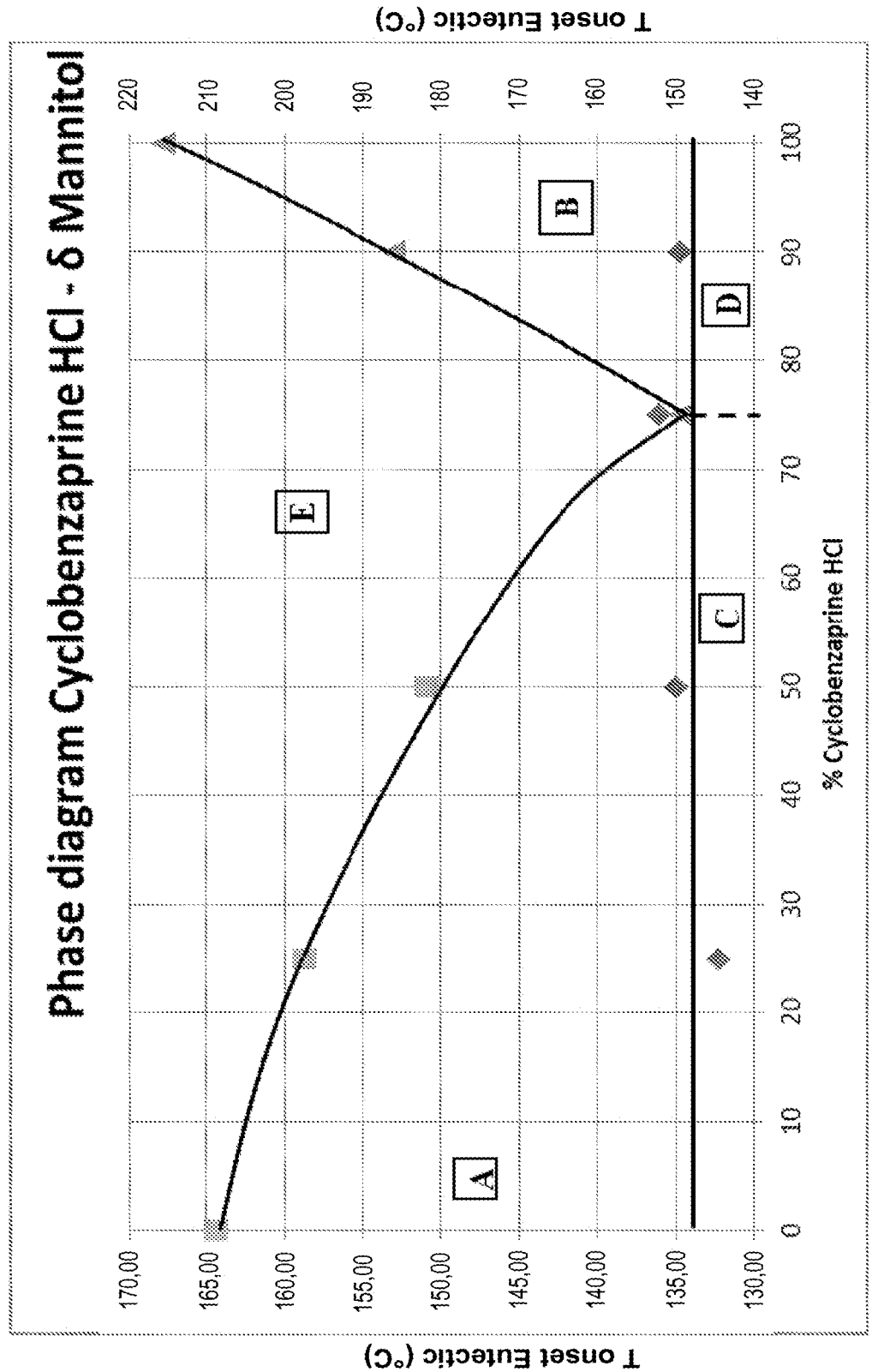
FIG. 106: Phase diagram of the eutectic formed between Cyclobenzaprine HCl and δ mannitol after spray drying.
Figure 107:
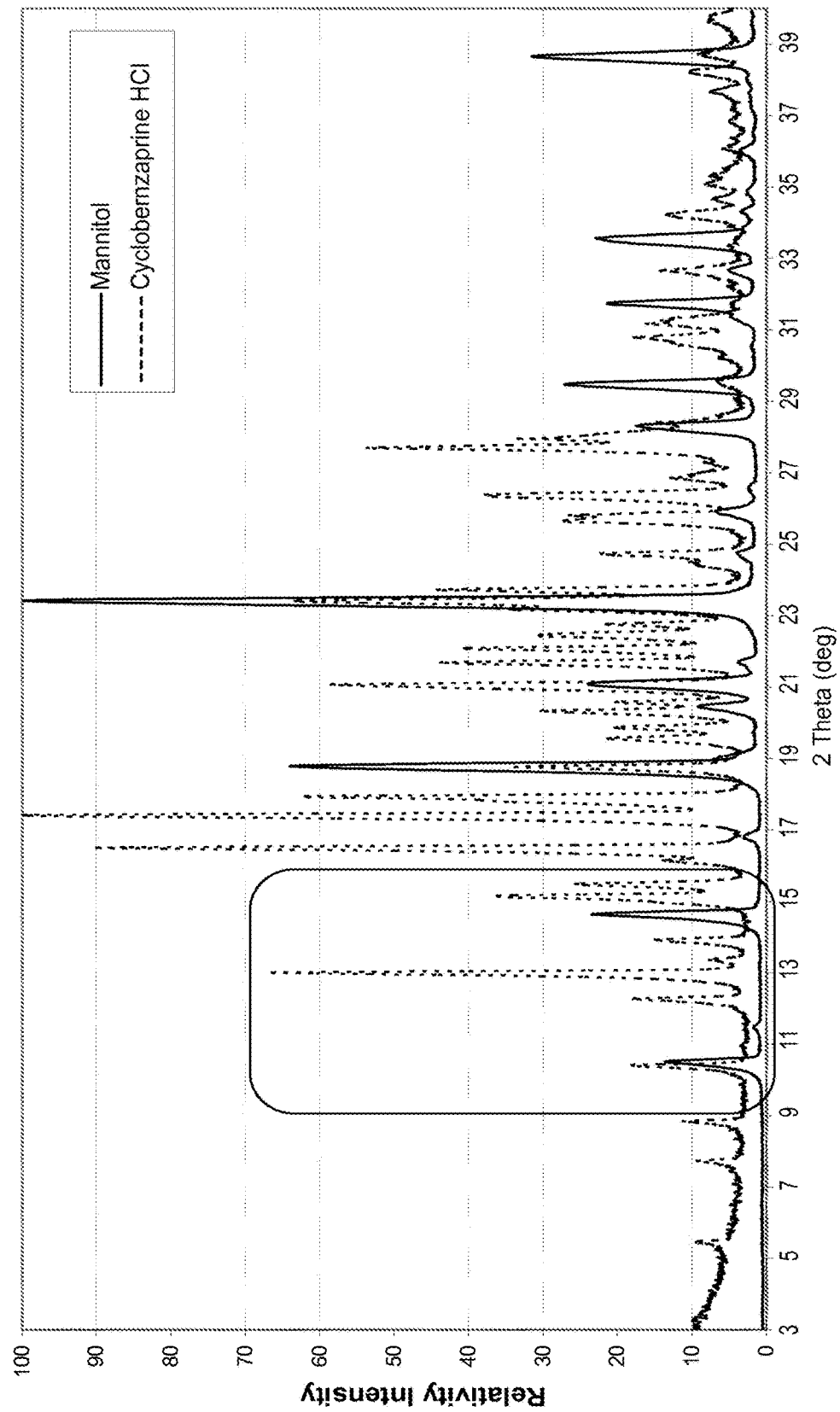
FIG. 107: XRPD pattern of Cyclobenzaprine HCl and spray dried mannitol.
Figure 108:
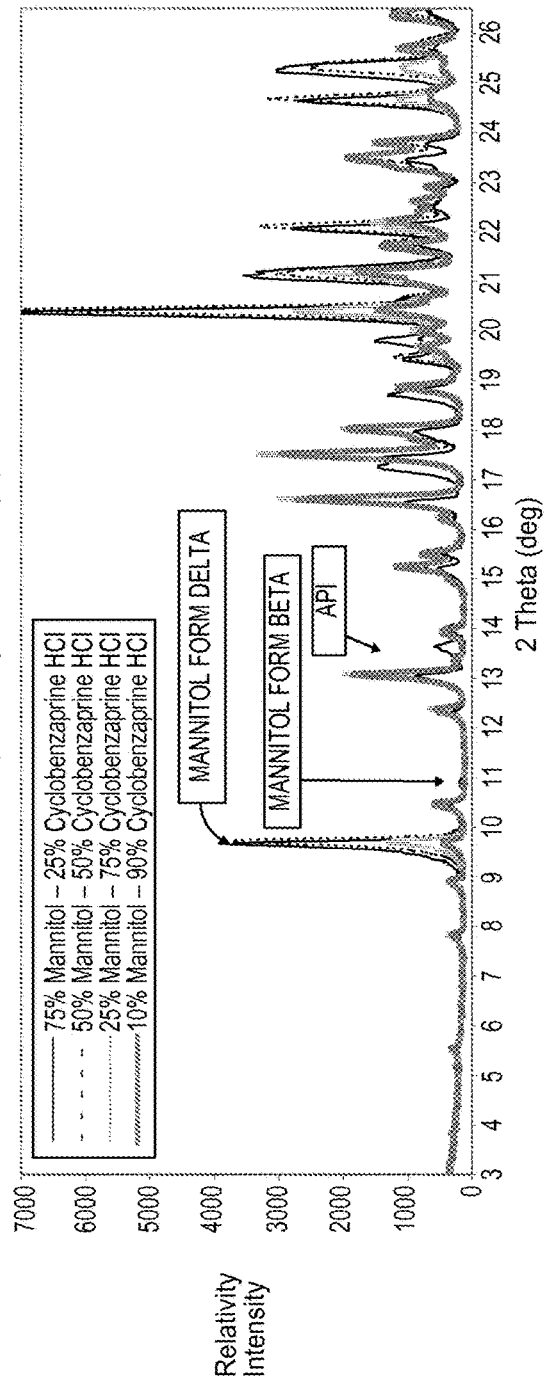
FIG. 108: Overlaid XRPD patterns from 25% Cyclobenzaprine HCl by weight ±75% mannitol by weight, spray dried; 50% Cyclobenzaprine HCl by weight ±50% mannitol by weight, spray dried; 75% Cyclobenzaprine HCl by weight ±25% mannitol by weight, spray dried; and 90% Cyclobenzaprine HCl by weight ±10% mannitol by weight, spray dried.
Figure 108:
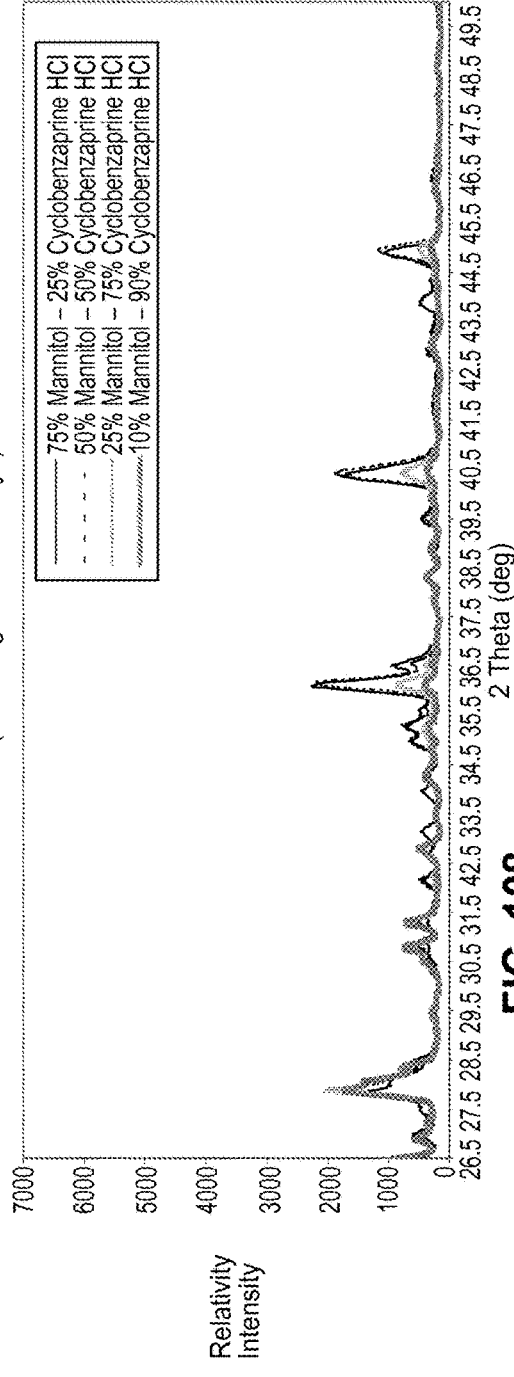

DSC shows that spray drying the Cyclobenzaprine HCl-mannitol mixture unexpectedly converts the mannitol in the eutectic from its β form to its δ form. Mannitol is capable of crystallizing in three polymorphic states: α, β, and δ. These three forms can be distinguished by X-ray powder diffraction and based on different melting points for each polymorph. See, e.g., Sharma and Kalonia, AAPS PharmaSciTech 5(1):E10 (2004). In the above Examples, the mannitol used was β polymorphic mannitol. To test whether the spray drying process itself was sufficient to convert the mannitol from β mannitol to δ mannitol, SEM and DSC were performed on spray dried β mannitol. FIG. 99 and FIG. 100 show that spray dried mannitol appears different than the pure mannitol, but DSC revealed that that spray drying alone was not able to convert β mannitol to δ mannitol (FIG. 101). This is consistent with earlier studies of spray dried mannitol. See, e.g., Hulse et al., Drug Development and Industrial Pharmacy 35(6):712-718 (2009). Without wishing to be bound by theory, the change in mannitol's polymorphic state seems to be due to the combination of spray drying and the addition of Cyclobenzaprine. This may be because spray drying, unlike wet or dry mixing, involves dissolving the components and then allowing them to co-crystallize together. The mixtures tested by DSC were 25% Cyclobenzaprine:75% mannitol (by weight) (FIG. 102), 50% Cyclobenzaprine:50% mannitol (by weight) (FIG. 103), 75% Cyclobenzaprine:25% mannitol (by weight) (FIGS. 104), and 90% Cyclobenzaprine:10% mannitol (by weight) (FIG. 105). These measurements were used to calculate a melting point of 134° C. and to generate a phase diagram for the eutectic composition (FIG. 106). When the phase diagram obtained after spray drying (δ polymorph) is compared to the phase diagram after mixing (β polymorph, FIG. 65), the differences between the melting points can clearly be observed. The melting point for the β polymorph is 143° C., while the melting point for the δ polymorph is 134° C. This lower melting point is beneficial because it aids in dissolution, as described below. XRPD of the pure mannitol and Cyclobenzaprine HCl (FIG. 107) as compared to XRPD of the eutectics formed by spray drying (FIG. 108) also confirm that spray drying results in the formation of S mannitol. Indeed, the XRPD pattern shows that even at 10% mannitol, all of the mannitol is present in the S polymorph.

Figure 109:
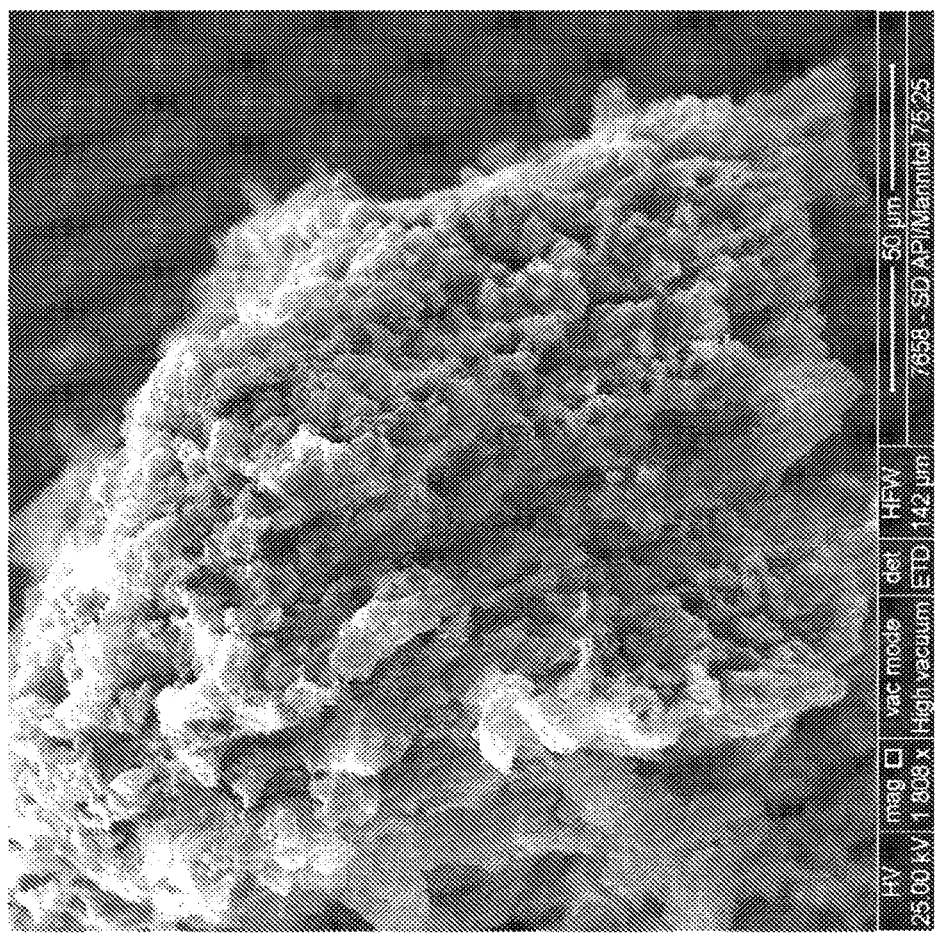
FIG. 109: SEM of the Cyclobenzaprine HCl/δ mannitol eutectic.
Figure 110:
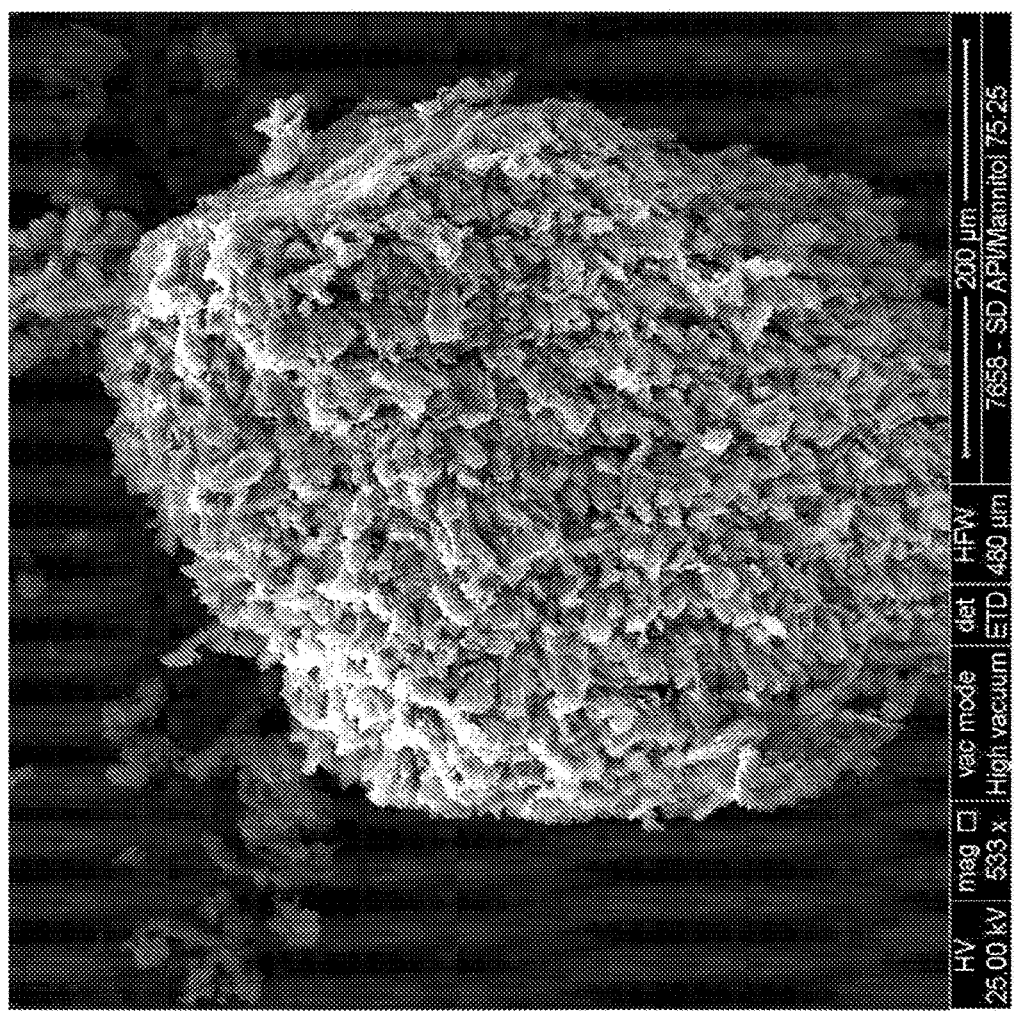
FIG. 110: SEM of the Cyclobenzaprine HCl/δ mannitol eutectic.
Figure 111:
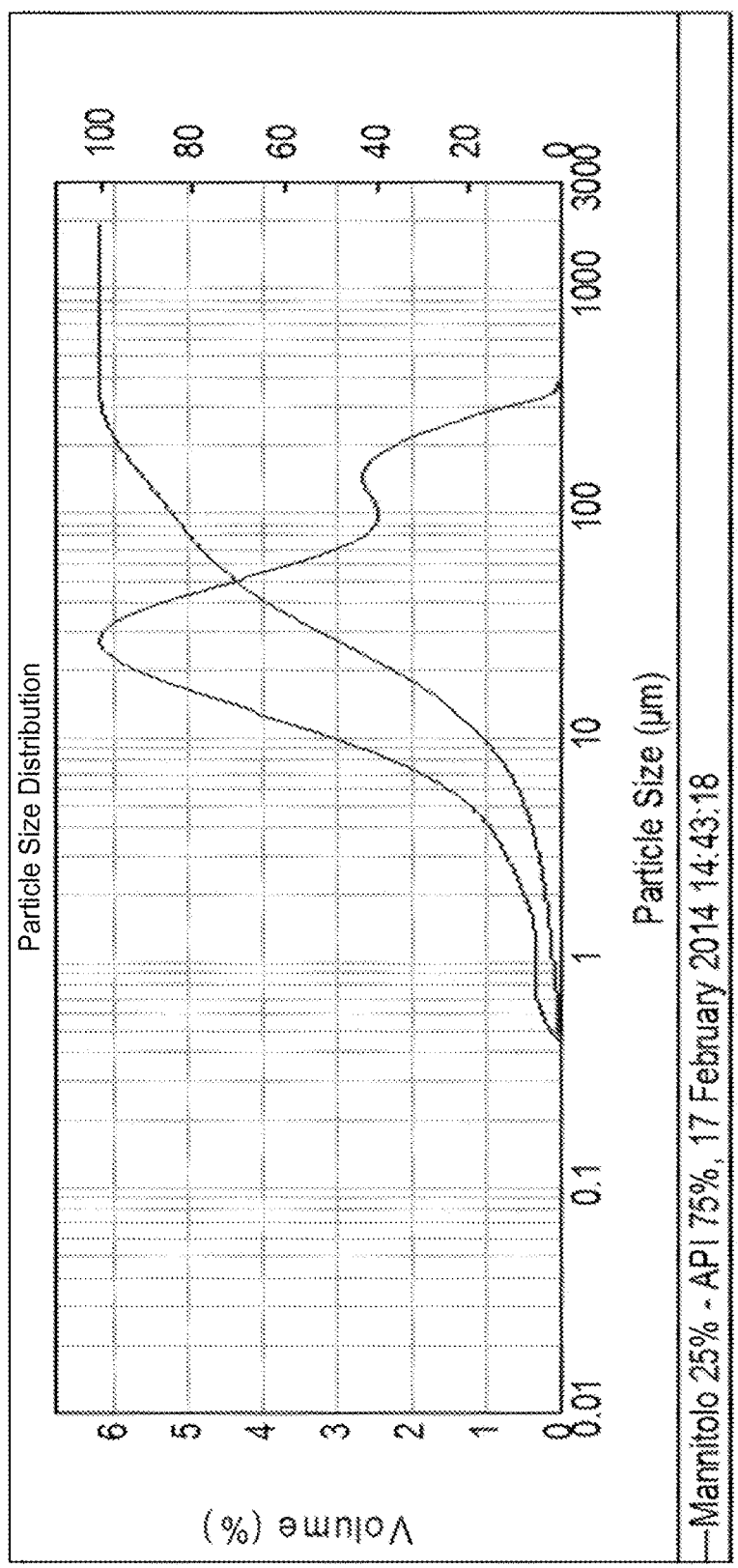
FIG. 111: Spray dried eutectic particle size distribution.
Figure 112:
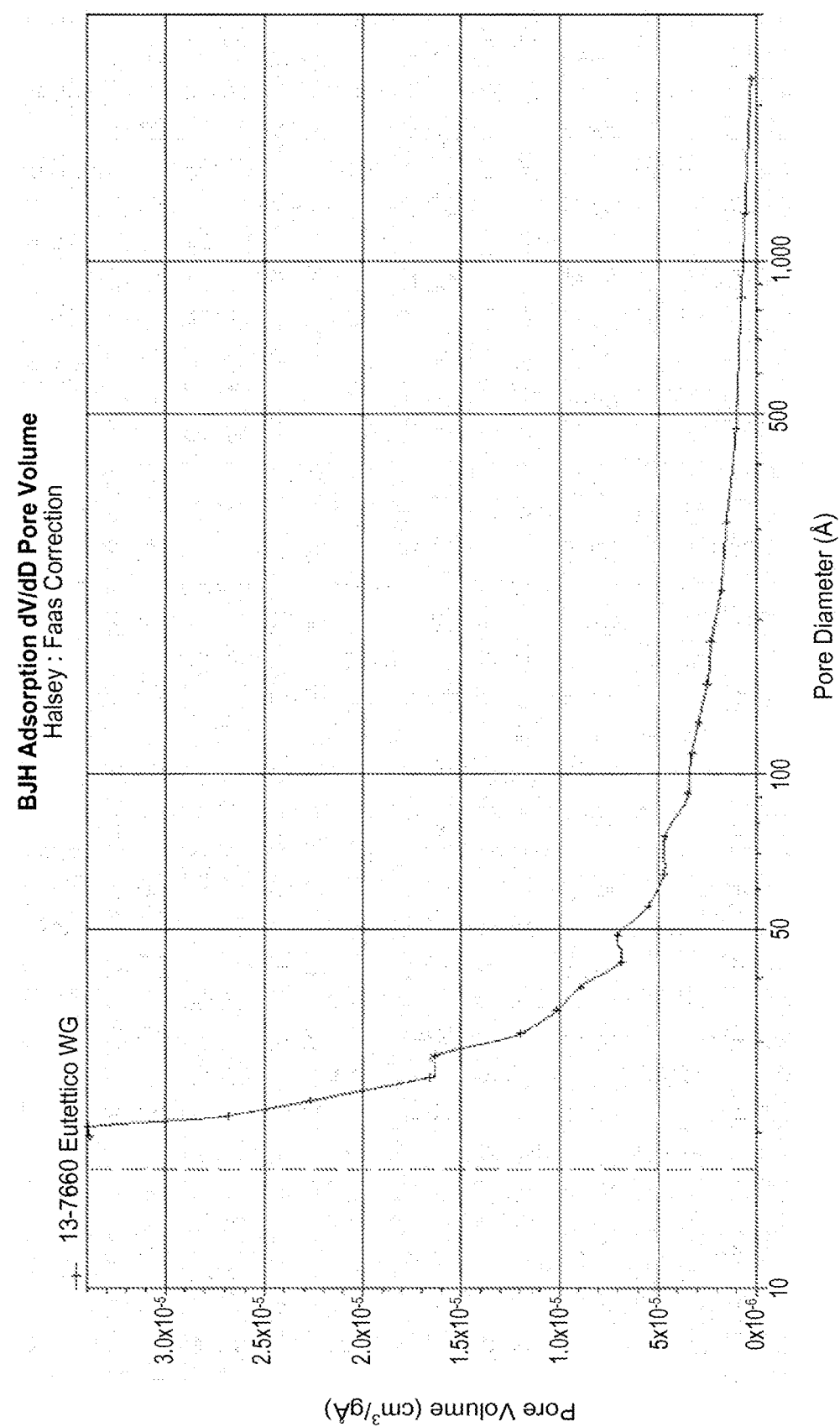
FIG. 112: Spray dried eutectic pore volume over diameter.
Figure 113:
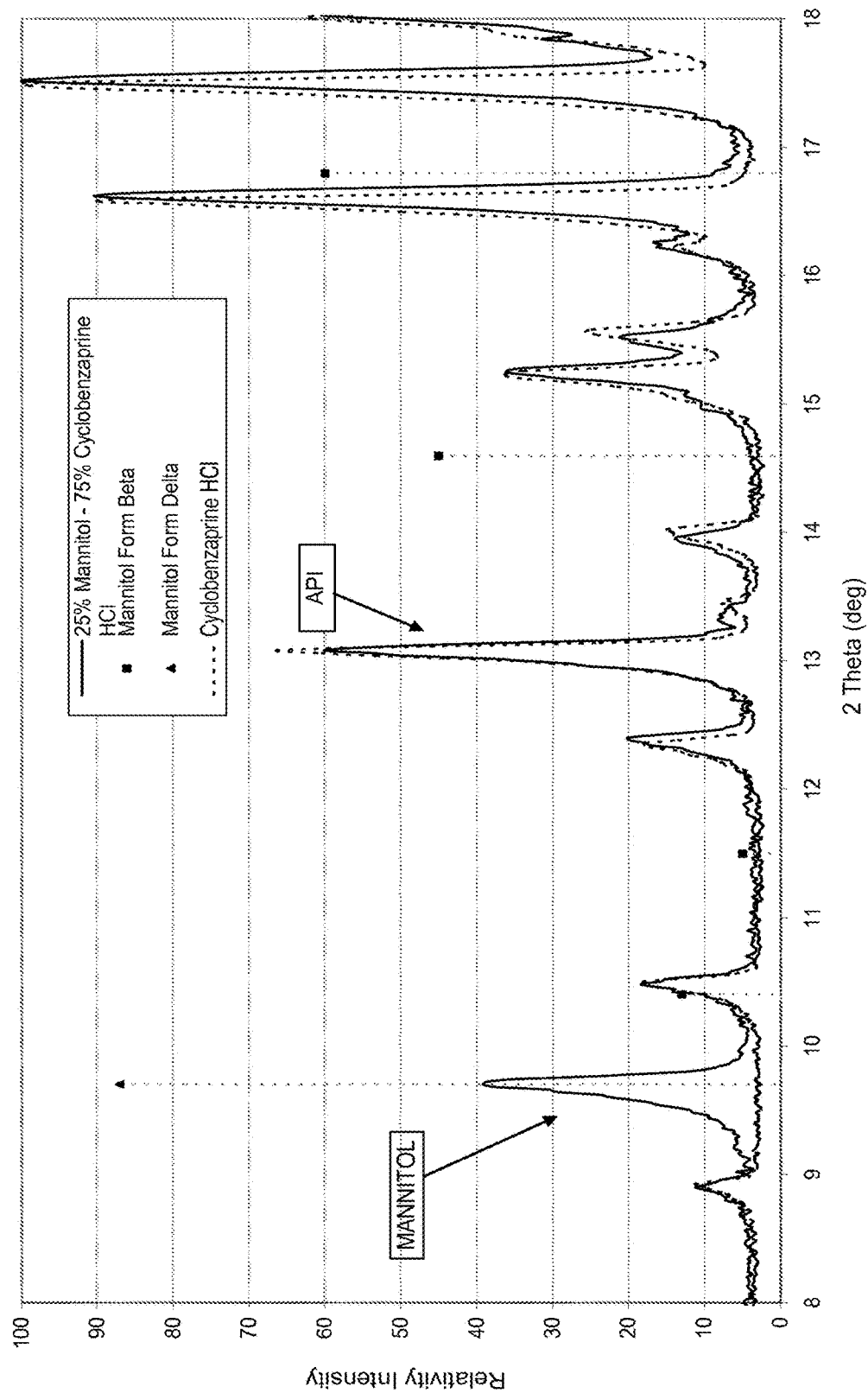
FIG. 113: XRPD patterns of 25% mannitol+75% Cyclobenzaprine HCl, spray dried; and Cyclobenzaprine HCl.
Figure 114:
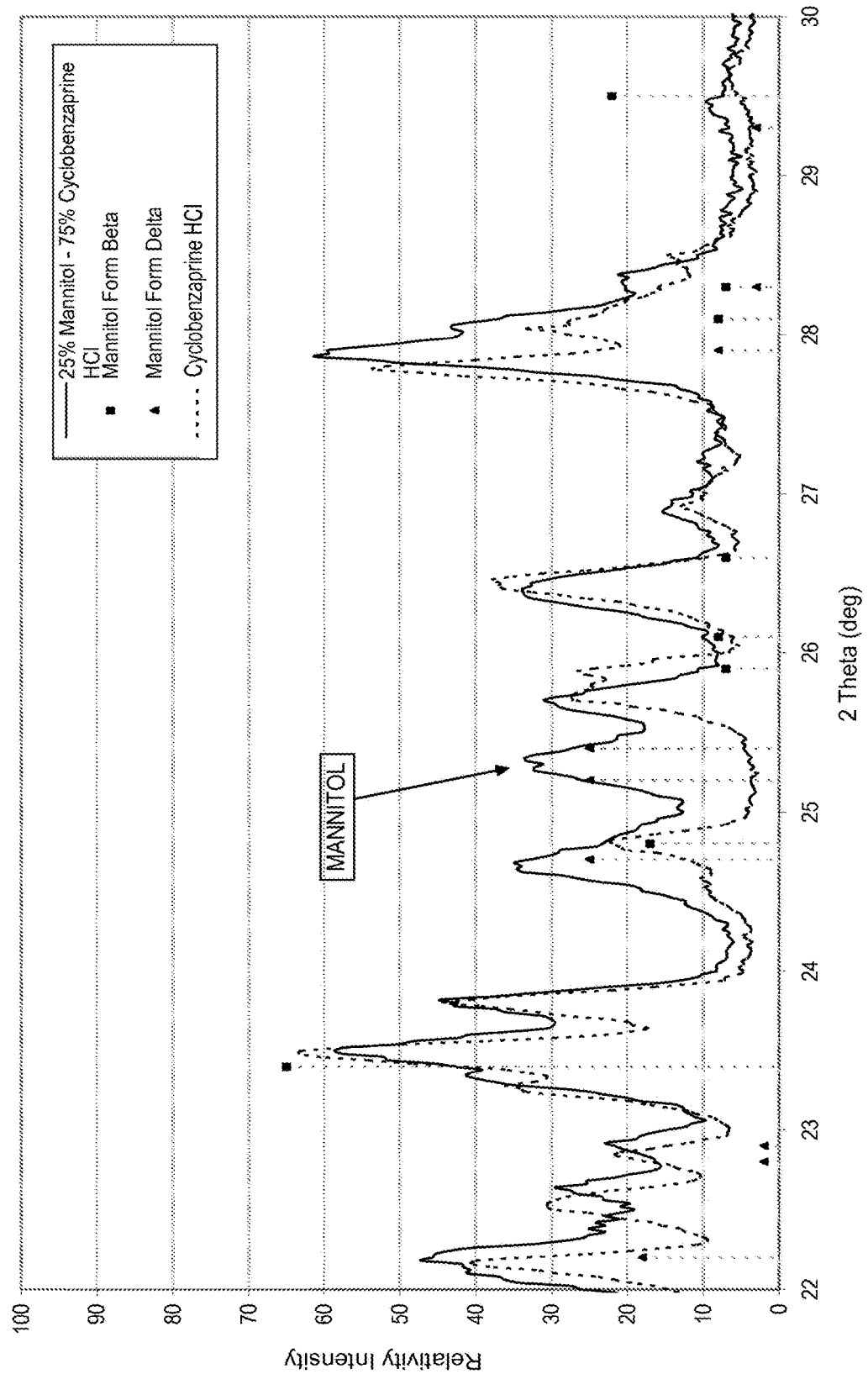
FIG. 114: XRPD patterns of 25% mannitol+75% Cyclobenzaprine HCl, spray dried; and Cyclobenzaprine HCl.
Figure 115:
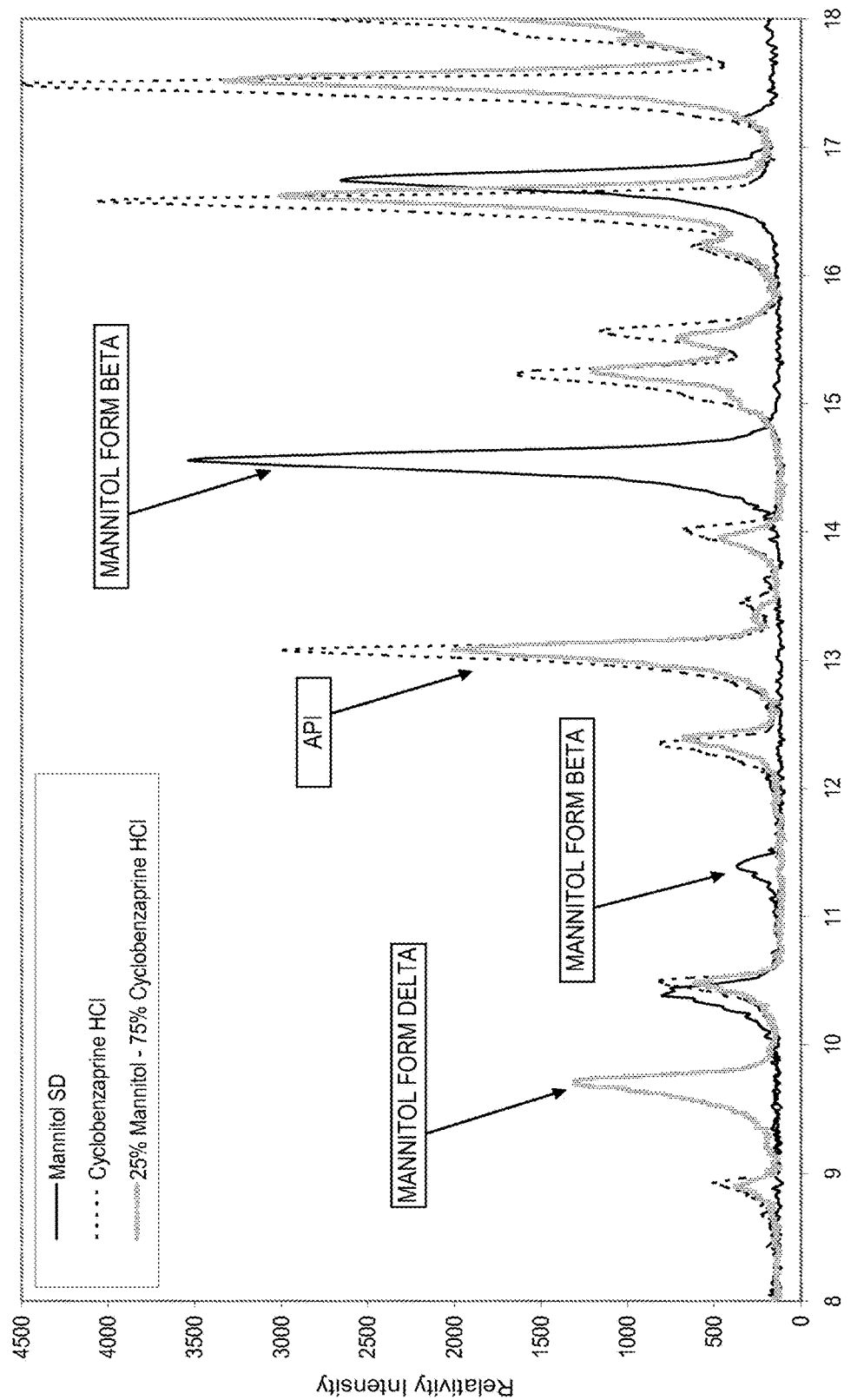
FIG. 115: XRPD patterns of 25% mannitol+75% Cyclobenzaprine HCl, spray dried; Cyclobenzaprine HCl; and spray dried mannitol.
Figure 116:
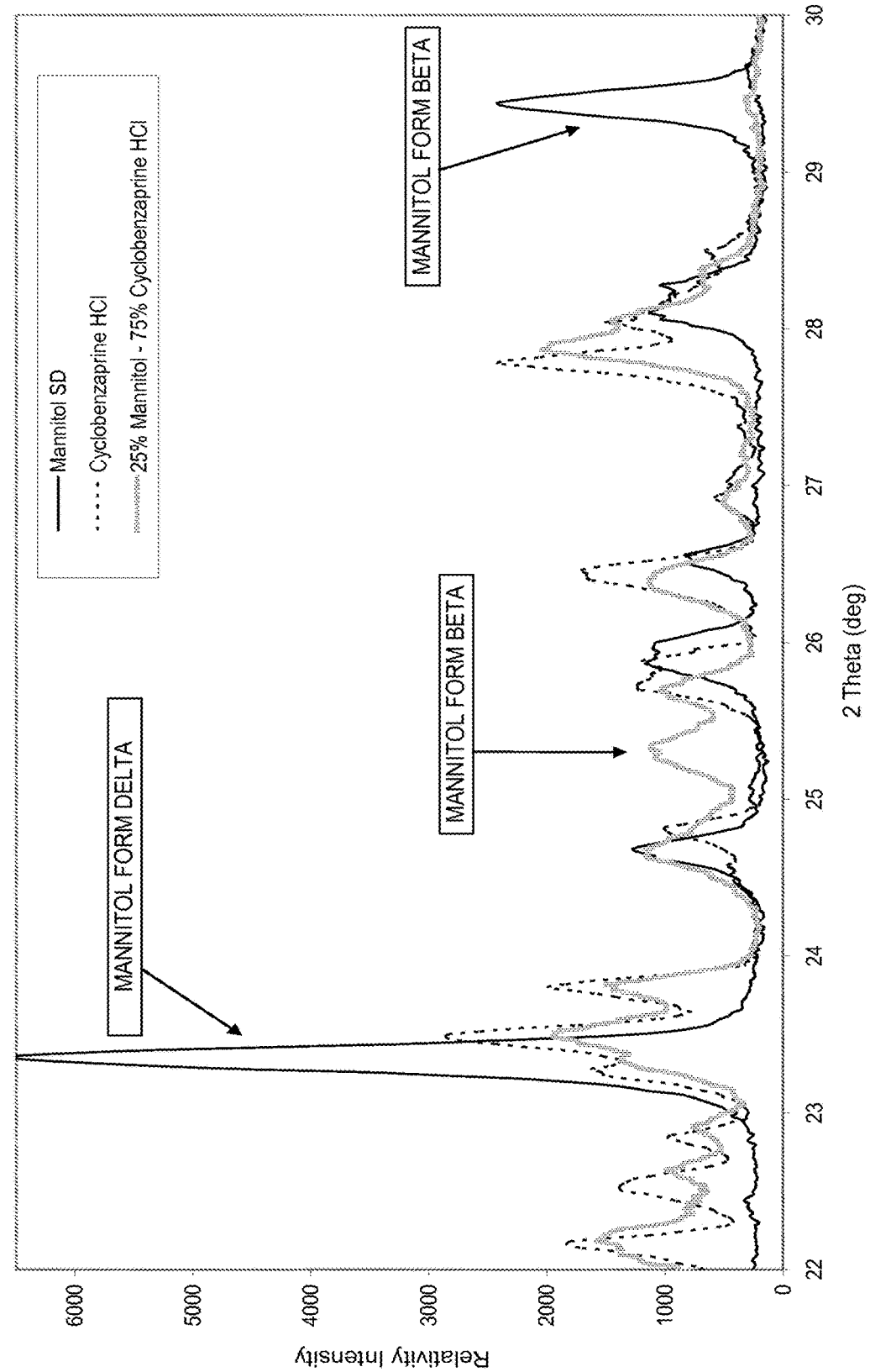
FIG. 116: XRPD patterns of 25% mannitol+75% Cyclobenzaprine HCl, spray dried; Cyclobenzaprine HCl; and spray dried mannitol.

The physical properties of the S mannitol eutectic also were measured, and are described in Table 7 (SSA: specific surface area; D10: 10% of the particles are smaller than this measurement; D50: 50% of the particles arc smaller than this measurement; D90: 90% of the particles are smaller than this measurement). SEM reveals that the particles formed by spray drying are much more porous than those formed from wet granulation (FIG. 109 and FIG. 110). FIG. 111 depicts spray dried eutectic particle size distribution and FIG. 112 depicts spray dried eutectic pore volume over diameter. FIGS. 113-116 depict X-ray powder diffraction data. In particular, FIG. 113 depicts X-ray powder diffraction (2θ from 8-18 degrees) on a 25%:75% solution of mannitol:Cyclobenzaprine HCl (by weight) from the spray dry experiment and from cyclobenzaprine HCl. The locations of expected peaks from the mannitol β polymorph ("form beta") and δ polymorph ("form delta") are marked. FIG. 114 depicts X-ray powder diffraction (2θ from 22-30 degrees) on the 25%:75% solution of mannitol:Cyclobenzaprine HCl (by weight) from the spray dry experiment and from cyclobenzaprine HCl. The locations of expected peaks from the mannitol β polymorph ("form beta") and δ polymorph ("form delta") are marked. FIG. 115 depicts X-ray powder diffraction (2θ from 8-19 degrees) on 25%:75% solution of mannitol:Cyclobenzaprine HCl (by weight) from the spray dry experiment, Cyclobenzaprine HCl, and the mannitol β polymorph ("form beta"). FIG. 116 depicts X-ray powder diffraction (2θ from 22-30 degrees) on the 25%:75% solution of mannitol-Cyclobenzaprine HCl (by weight) from the spray dry experiment, cyclobenzaprine HCl, and the mannitol β polymorph ("form beta").

TABLE 7

Physical properties of δ mannitol eutectic

| | |
|---|---|
| SSA (m²/g) | 0.5398 |
| Pore Volume (cm³/g) | 0.000654 |
| Pore size (Å) | 48.46 |
| D10 (um) | 6.653 |
| D50 (um) | 28.834 |
| D90 (um) | 143.74 |

To test the dissolution properties of the δ mannitol eutectic, dissolution tests were carried out with a Copley DIS 6000 instrument under the following conditions:
Apparatus: USP Paddle
RPM: 50
Medium: Pyrophosphate buffer 0.5% pH=4.5±0.05
Additive: Methocel 0.3%
Vessel volume: 300 mL
Temperature: 37±0.5° C.
Sampling time: 1, 2, 5, 10, 20, 30, and 60 min, then each hour until 6 hours.
The sampling solutions were diluted 1 to 50 mL and then 1 to 50 mL with medium and submitted to UV analysis with UV (GBC Cintral 10e) under the following conditions:

λ max: 224 nm
Cuvette: Quartz 1 cm
Blank: medium

Figure 117:
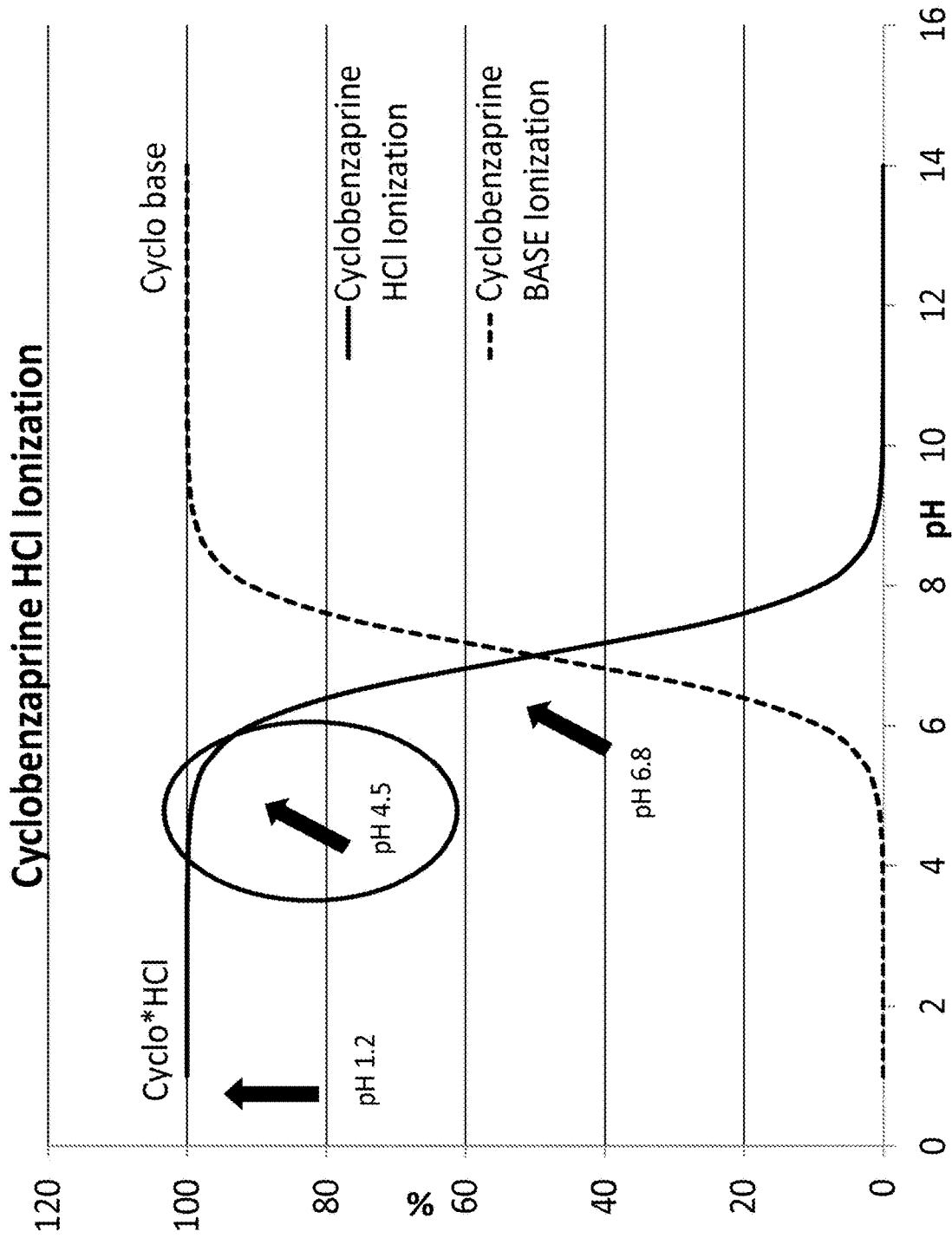
FIG. 117: Theoretical Ionization of Cyclobenzaprine HCl at different pHs.
Figure 118:
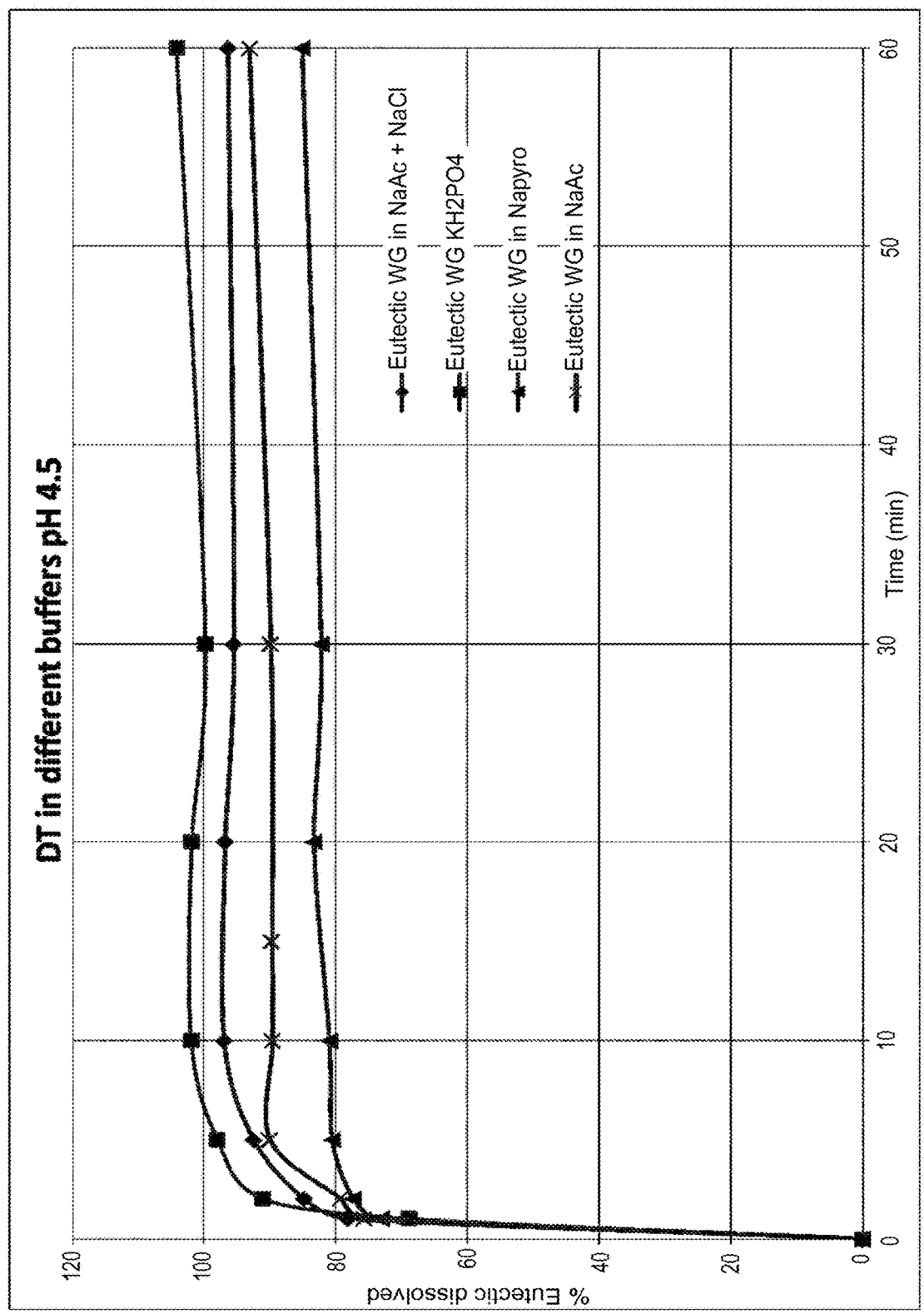
FIG. 118: Dissolution test of the wet granulated (WG) Cyclobenzaprine eutectic in 1) sodium acetate and sodium chloride; 2) potassium phosphate monobasic; 3) sodium pyrophosphate, and 4) sodium acetate at pH 4.5 over 60 minutes.
Figure 119:
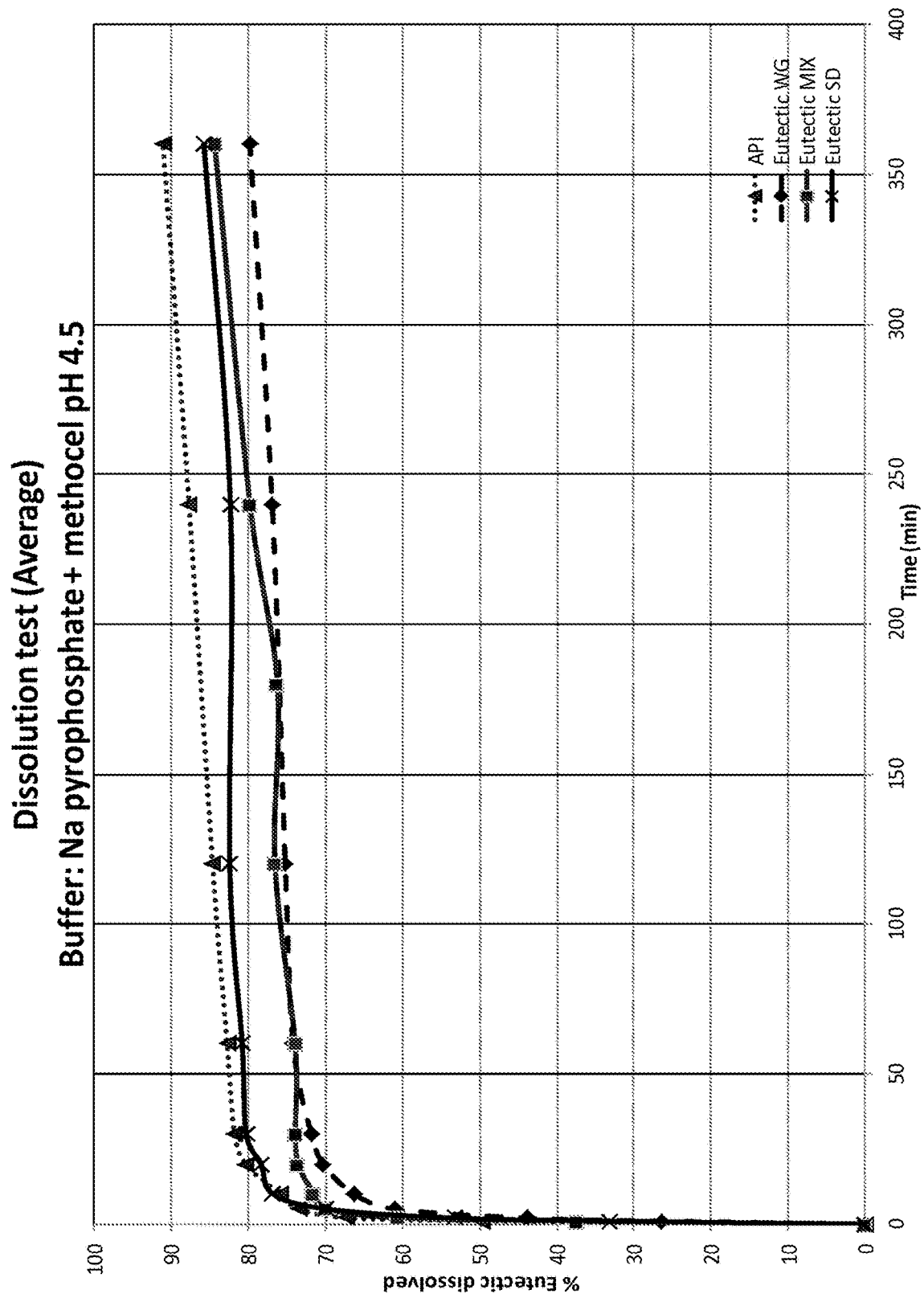
FIG. 119: Dissolution test of the Cyclobenzaprine HCl (API); the Cyclobenzaprine HCl/mannitol eutectic formed from wet granulation (WG); the Cyclobenzaprine HCl/mannitol eutectic formed from dry mixing (MIX); and the Cyclobenzaprine HCl/mannitol eutectic formed from spray drying (SD) in sodium pyrophosphate and methocel at pH 4.5 over 6 hours.
Figure 120:
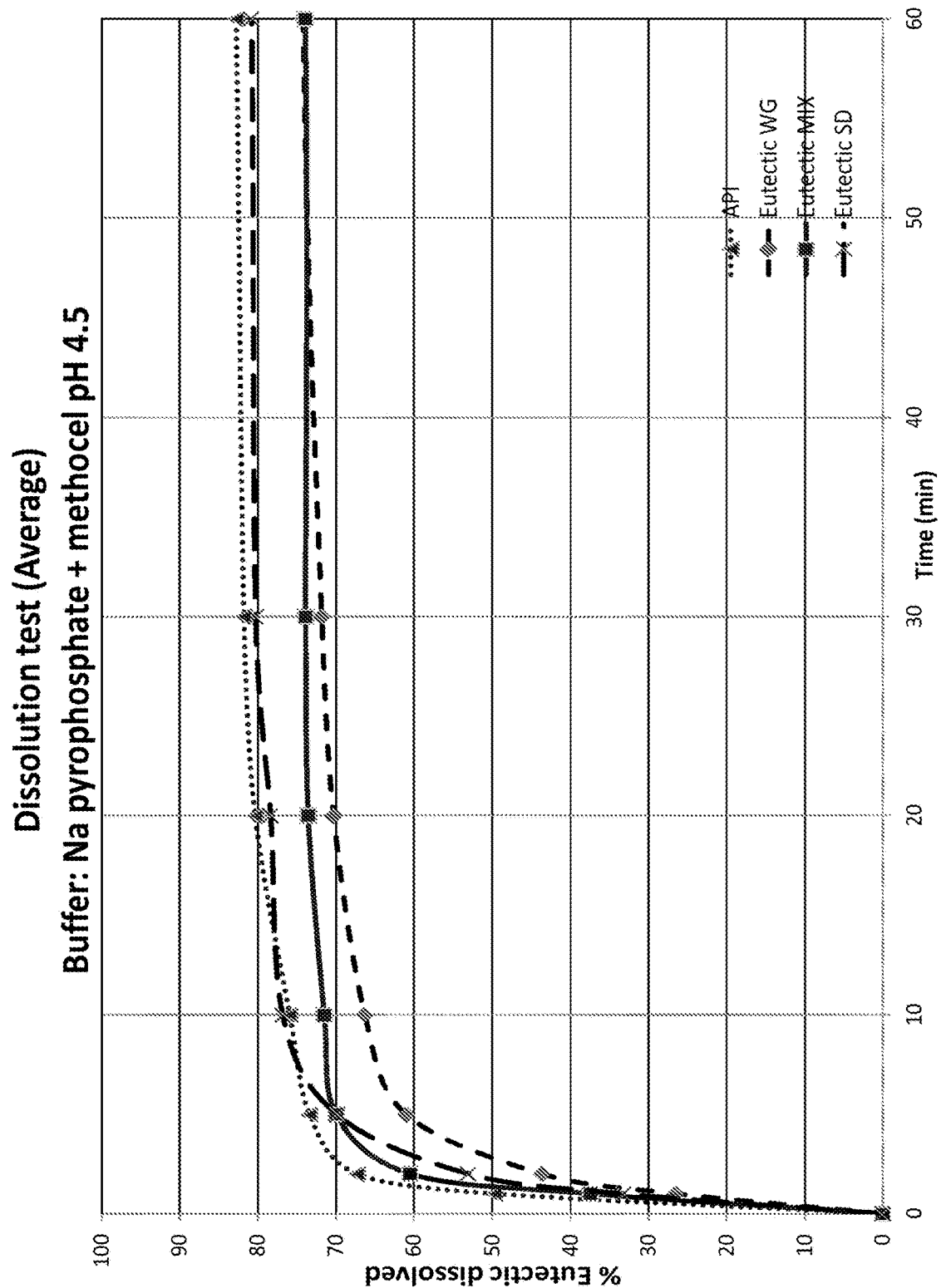
FIG. 120: Closeup of the dissolution test of FIG. 119 over the first 60 minutes.

FIG. 117 shows the ionization of Cyclobenzaprine at different pHs. Notably, at pH 4.5, there still is free base present. The free base does not go into solution, so the Cyclobenzaprine dissolution does not reach 100%. Dissolution tests were performed on the wet granulated mixture (FIG. 118) and the spray dried mixture (FIGS. 119 and 120) to test whether the δ mannitol eutectic had different dissolution properties than the β mannitol dissolution product. FIG. 119 depicts comparisons between the wet granulated (WG), dry mixed (MIX), and spray dried (SD) mixtures, as well as Cyclobenzaprine HCl alone (API), over 6 hours. These experiments show that, especially during the first hour (FIG. 120), the spray dried composition dissolves faster than both the wet granulated and dry mixed compositions, demonstrating the benefits of the δ mannitol eutectic. This enhanced dissolution is beneficial because it will increase the rate of absorption of Cyclobenzaprine in both oral and sublingual formulations. The δ mannitol eutectic also is stable even after three weeks of accelerating stability tests when stored at 50° C. in an oven. In these tests, the δ form remained unchanged and no transformation into the β form was observed (data not shown).

Based on the surprising observation of δ mannitol in the Cyclobenzaprine eutectic, spray drying also may be used to create a δ mannitol eutectic with Amitriptyline.

What is claimed is:
1. A method of manufacturing a eutectic of Cyclobenzaprine HCl and β-mannitol comprising 75%±2% Cyclobenzaprine HCl and 25±2% β-mannitol by weight, the method comprising mixing Cyclobenzaprine HCl and (β-mannitol or milling Cyclobenzaprine HCl and β-mannitol.
2. The method of claim 1, comprising milling the Cyclobenzaprine HCl and β-mannitol.
3. The method of claim 2, wherein, the Cyclobenzaprine HCl and β-mannitol are milled in a high shear granulator.
4. The method of claim 1, comprising mixing the Cyclobenzaprine HCl and β-mannitol.
5. The method of claim 4, wherein the Cyclobenzaprine HCl and β-mannitol are mixed via compression.
6. The method of claim 5, wherein the Cyclobenzaprine HCl and β-mannitol are compressed via roller compaction.
7. The method of any one of claims 1-6, wherein the Cyclobenzaprine HCl is micronized Cyclobenzaprine HCl.

* * * * *

UNITED STATES PATENT AND TRADEMARK OFFICE
CERTIFICATE OF CORRECTION

PATENT NO. : 11,839,594 B2
APPLICATION NO. : 17/082949
DATED : December 12, 2023
INVENTOR(S) : Marino Nebuloni and Patrizia Colombo It is certified that error appears in the above-identified patent and that said Letters Patent is hereby corrected as shown below:

In the Claims

Claim 1, Column 38, Line 32, please delete "25±2%" and replace with --25%±2%--.

Claim 1, Column 38, Line 33, please delete "and (β-mannitol" and replace with --and β-mannitol--.

Signed and Sealed this
Thirteenth Day of February, 2024

*Katherine Kelly Vidal*

Katherine Kelly Vidal
*Director of the United States Patent and Trademark Office*